US007208161B1

(12) United States Patent
Murphy et al.

(10) Patent No.: US 7,208,161 B1
(45) Date of Patent: *Apr. 24, 2007

(54) PRODUCTION OF ATTENUATED PARAINFLUENZA VIRUS VACCINES FROM CLONED NUCLEOTIDE SEQUENCES

(75) Inventors: Brian R. Murphy, Bethesda, MD (US); Peter L. Collins, Rockville, MD (US); Anna P. Durbin, Germantown, MD (US); Mario H. Skiadopoulos, Potomac, MD (US); Tao Tao, Bethesda, MD (US)

(73) Assignee: The United States of America, represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/083,793

(22) Filed: May 22, 1998

Related U.S. Application Data

(60) Provisional application No. 60/059,385, filed on Sep. 19, 1997, provisional application No. 60/047,575, filed on May 23, 1997.

(51) Int. Cl.
*A61K 39/155* (2006.01)
*C12N 7/00* (2006.01)

(52) U.S. Cl. ................................ 424/211.1; 424/199.1; 435/235.1; 435/325; 435/320.1; 536/23.72

(58) Field of Classification Search ............ 536/23.72; 424/199.1, 211.1; 435/235.1, 320.1, 325, 435/471, 472
See application file for complete search history.

(56) References Cited

U.S. PATENT DOCUMENTS

| | | | | |
|---|---|---|---|---|
| 5,716,821 A | | 2/1998 | Wertz et al. | 435/235.1 |
| 5,789,229 A | | 8/1998 | Wertz et al. | 435/235.1 |
| 5,869,036 A | * | 2/1999 | Belshe et al. | 424/93.2 |
| 6,033,886 A | | 3/2000 | Conzelmann | |

FOREIGN PATENT DOCUMENTS

| | | |
|---|---|---|
| EP | 0 440 219 A1 | 8/1991 |
| EP | 0 702 085 A1 | 3/1996 |
| WO | WO 97/06270 | 2/1997 |
| WO | WO 97/11093 | 3/1997 |
| WO | WO 97/20468 | 6/1997 |
| WO | 99/02657 | 1/1999 |

OTHER PUBLICATIONS

Kato et al, Genes to Cells 1:569-579, Jun. 1996.*
Conzelmann, "Genetic manipulation of non-segmented negative-strand RNA viruses," *J. Gen. Virol.* 77:381-89 (1996).

Cook et al., "In Vivo antigenic Studies of Parainfluenza Viruses," *Amer. Jour. Hyg. 77*:150, 1963.

Cook et al., "Antigenic Relationships Among the "Newer" Myxoviruses (Parainfluenza)," *Amer. Jour. Hyg. 69*:250, 1959.

Dimock and Collins, "Rescue of Synthetic Analogs of Genomic RNA and Replicative-Intermediate RNA of Human Parainfluenza Virus Type 3," *J. Virol.* :2772-2778, 1993.

Durbin et al., "Recovery of Infectious Human Parainfluenza Virus Type 3 from cDNA," *Virology 235*:323-332, 1997.

Durbin et al., "Minimum protein Requirements for Transcription and RNA Replication of a Minigenome of Human Parainfluenza Virus Type 3 and Evaluation of the Rule of Six," *Virology* 234:74-78 (1997).
Flexner et al., "Prevention of vaccinia virus infection in immunodeficient mice by vector-directed IL-2 expression," *Nature* 33:259-262, 1987.
Frank et al. "Comparison of Different Tissue Cultures for Isolation and Quantitation of Influenza and Parainfluenza Viruses," *J. Clin. Microbiol.* 10:32-6 (1979).
Fuerst et al., "Eukaryotic transient-expression system based on recombinant vaccinia virus that synthesizes bacteriophage T7 RNA polymerase," *Proc. Natl. Acad. Sci. USA* 83:8122-8126, 1986.

Galinski et al., "Molecular cloning and Sequence Analysis of the Human parainfluenza 3 Virus Gene Encoding the L Protein," *Virology 165*: 499-510, (1988).

Galinski et al., "RNA Editing in the Phosphoprotein Gene of the Human Parainfluenza Virus Type 3," *Virology 186*: 543-50 (1992).

Garcin et al., "A highly recombinogenic system for the recovery of infectious Sendai paramyxovirus from cDNA: generation of a novel copy-back nondefective interfering virus," *EMBO J.* 14(24) :6087-6094 (1995).

Grosfeld et al., "RNA Replication by Respiratory Syncytial Virus (RSV) Is Directed by the N, P, and L Proteins; Transcription Also Occurs under These Conditions but Requires RSV Superinfection for Efficient Synthesis of Full-Length mRNA," *J. Virol. 69*: 5677-5686 (1995).

(Continued)

*Primary Examiner*—Stacy B. Chen
(74) *Attorney, Agent, or Firm*—Birch, Stewart, Kolasch & Birch, LLP

(57) ABSTRACT

Isolated polynucleotide molecules provide recombinant PIV genomes and antigenomes for production of recombinant PIV vaccines. The recombinant genome or antigenome can be expressed with a nucleoprotein (N), phosphoprotein (P), and a large (L) polymerase protein to produce isolated infectious PIV particles. The recombinant PIV genome and antigenome can be modified to produce desired changes, for example to incorporate attenuating mutations from biologically derived PIV mutants or to create chimeric PIV clones, to generate attenuated, immunogenic viruses for vaccine use.

70 Claims, 20 Drawing Sheets

OTHER PUBLICATIONS

Hall et al., "Cold-passaged human parainfluenza type 3 viruses contain *ts* and non-*ts* mutations leading to attenuation in rhesus monkeys," *Virus Res.* 22 (3) :173-184, 1992.

Karron et al., "A Live Attenuated Bovine Parainfluenza Virus Type 3 Vaccine Is Safe, Infectious, Immunogenic, and Phenotypically Stable in Infants and Children," *J. Infect. Dis.* 171:1107-1114, 1995.

Kast et al., "Protection against lethal Sendai virus infection by *in vivo* priming of virus-specific cytotoxic T lymphocytes with a free synthetic peptide," *Proc. Natl. Acad. Sci. USA* 88:2283-2287, 1991.

Kunkel et al., "Rapid and Efficient Site-Specific Mutagenesis without Phenotypic Selection," *Methods Enzymol.* 154: 367-382, (1987).

Lawson et al., "Recombinant vesicular stomatitis viruses from DNA," *Proc. Natl. Acad. Sci. U.S.A.* 92:4477-81 (1995).

Murphy et al., "Failure of Attenuated Temperature-Sensitive Influenza A (H3N2) Virus to Induce Heterologous Interference in Humans to Parainfluenza Type 1 Virus," *Infect. Immun.* 12:62-8, 1975.

Murphy et al., "Current approaches to the development of vaccines effective against parainfluenza and respiratory syncytial viruses," *Virus Res.* 11:1-15 (1988).

Murphy et al., "Enhanced pulmonary histopathology is observed in cotton rats immunized with formalin-inactivated respiratory syncytial virus (RSV) or purified F glycoprotein and challenged with RSV 3-6 months after immunization," *Vaccine* 8 (5) :497-502, 1990.

Palese et al., "Negative-strand RNA viruses: Genetic engineering and application," *Proc. Natl. Acad. Sci. U.S.A.* 93:11354-58, (1996).

Pelet et al., "The P gene of bovine parainfluenza virus 3 expresses all three reading frames from a single mRNA editing site," *EMBO J.* 10:443-448 (1991).

Radecke et al., "Rescue of measles viruses from cloned DNA," *EMBO J.* 14:5773-5784 (1995).

Ray et al., "Human Parainfluenza virus Induces a Type-Specific Protective Immune Response," *J. Infect. Dis.* 162:746, 1990.

Ray et al., "Temperature-Sensitive Phenotype of the Human Parainfluenza virus Type 3 Candidate Vaccine Strain (cp45) Correlates with a Defect in the L Gene," *J. Virol.* 70:580-584 (1996).

Sakaguchi et al., "Expression of the HN, F, NP and M proteins of Sendai virus by recombinant vaccinia viruses and their contribution to protective immunity against Sendai virus infections in mice," *J. Gen. Virol.* 74:479-484, 1993.

Schnell et al., "Infectious rabies viruses from cloned cDNA," *EMBO J.* 13:4195-203 (1994).

Skiadopoulos et al., "Three Amino Acid Substitutions in the L Protein of the Human Parainfluenza Virus Type 3 cp45 Live Attenuated Vaccine Candidate Contribute to Its Temperature-Sensitive and Attenuation Phenotypes," *J. Virol* 72(3) :1762-1768, 1998.

Spriggs and Collins, "Sequence analysis of the P and C Protein Genes of Human parainfluenza Virus Type 3: Patterns of Amino Acid Sequence Homology among Paramyxovirus Proteins," *J. Gen. Virol.* 67 2705-2719, (1986).

Stokes et al., "The complete nucleotide sequence of the JS strain of human parainfluenza virus type 3: comparison with the Wash/47885/57 prototype strain," *Virus Res.* 25:91-103 1992.

Stokes et al., "The complete nucleotide sequence of two cold-adapted, temperature-sensitive attenuated mutant vaccine viruses (cp 12 and cp 45) derived from the JS strain and human parainfluenza virus type 3 (PIV3)," *Virus Res.* 30 (1) :43-52, 1993.

Tanabayashi, K. and Compans, R.W., "Functional Interaction of Paramyxovirus Glycoproteins: identification of a Domain in Sendai Virus HN Which Promotes Cell Fusion," *J. Virol.* 70:6112-18 (1996).

Tao et al., "Recovery of a Fully Viable Chimeric Human Parainfluenza Virus (PIV) Type 3 in Which the Hemagglutinin-Neuraminidase and Fusion Glycoproteins Have Been Replaced by Those of PIV Type 1," *J. Virol.* 72:2955-2961, 1998.

Thomson et al., "Recombinant Polyepitope Vaccines for the Delivery of Multiple CD8 Cytotoxic T Cell Epitopes," *J. Immunol.* 157:822, 1996.

van Wyke Coelingh et al., "Antigenic and Structural Properties of the Hemagglutinin-Neuraminidase glycoprotein of Human Parainfluenza Virus Type 3: Sequence analysis of Variants Selected with Monoclonal antibodies Which Inhibit Infectivity, Hemagglutination, and Neuraminidase Activities," *J. Virol.* 61:1473-1477, (1987).

van Wyke Coelingh et al., "Antigenic Variation in the Hemagglutinin-Neuraminidase Protein of Human Parainfluenza Type 3 Virus," *Virology* 143 (2) :569-582, 1985.

Whelan et al., "Efficient recovery of infectious vesicular stomatitis virus entirely from cDNA clones," *Proc. Natl. Acad. Sci. USA* 92:8388-8392 (1995).

Baron et al., "Rescue of Rinderpest Virus from Cloned cDNA," *J. Virol.* 71:1265-1271, 1997.

Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," *J. Virol.* 73:251-259, 1999.

Bukreyev, et al., "Recovery of Infectious Respiratory Syncytial Virus Expressing an Additional, Foreign Gene," *J. Virol.* 70:6634-41, 1996.

Bukreyev, et al., "Interferon γ Expressed by a Recombinant Respiratory Syncytial Virus Attenuates Virus Replication in Mice Without Compromising Immunogenicity," *Proc. Nat. Acad. Sci. USA* 96:2367-2372, 1999.

Cadd et al., "The Sendai Paramyxovirus Accessory C Proteins Inhibit Viral Genome Amplification in Promoter-Specific Fashion," *J. Virol.* 70:5067-74, 1996.

Curran, et al., "Sendai Virus P Gene Produces Multiple Proteins from Overlapping Open Reading Frames," *Enzyme* 44:244-249, 1990.

Curran, et al., "The Sendai Virus Nonstructural C Proteins Specifically Inhibit Viral mRNA Synthesis," *Virology* 189:647-656, 1992.

Delenda, et al., "Normal Cellular Replication of Sendai Virus Without the *trans*-Frame, Nonstructural V Protein," *Virology* 228:55-62, 1997.

Delenda et al., "Sendai Viruses with Altered P, V, and W Protein Expression," *Virology* 242:327-337, 1998.

Finke et al. "Ambisense Gene Expression for Recombinant Rabies Virus: Random Packaging of Positive- and Negative-Strand Ribonucleoprotein Complexes into Rabies Virions," *J. Virol.* 71:7281-7288, 1997.

Galinski et al., "Molecular Cloning and Sequence Analysis of the Human Parainfluenza 3 Virus mRNA Encoding the P and C Proteins," *Virology* 155:46-60, 1986.

Garcin et al., "A Point Mutation in the Sendai Virus Accessory C Proteins Attenuates Virulence for Mice, But Not Virus Growth in Cell Culture," *Virology* 238:424-431, 1997.

Hasan et al., "Creation of an Infectious Recombinant Sendai Virus Expressing the Firefly Luciferase Gene from the 3' Proximal First Locus," *J. Gen. Virol.* 78:2813-20, 1997.

He et al., "Recovery of Infectious SV5 from Cloned DNA and Expression of a Foreign Gene," *Virology* 237:249-260, 1997.

Hoffman et al., "An Infectious Clone of Human Parainfluenza Virus Type 3," *J. Virol.* 71:4272-4277, 1997.

Itoh et al., "Isolation of an Avirulent Mutant of Sendai Virus with Two Amino Acid Mutations from a Highly Virulent Field Strain Through Adaption to LLC-MK$_2$ Cells," *J. Gen. Virol.* 78:3207-3215, 1997.

Jin et al., "Recombinant Human Respiratory Syncytial Virus (RSV) from cDNA and Construction of Subgroup A and B Chimeric RSV," *Virology* 251:206-214, 1998.

Johnson et al., "Specific Targeting to CD4+ Cells of Recombinant Vesicular Stomatitis Viruses Encoding Human Immunodeficiency Virus Envelope Proteins," *J. Virol.* 71:5060-5068, 1997.

Juhasz et al., "The Temperature-Sensitive (*ts*) Phenotype of a Cold-Passaged (*cp*) Live Attenuated Respiratory Syncytial Virus Vaccine Candidate, Designated *cpts*530, Results from a Single Amino Acid Substitution in the L Protein," *J. Virol.* 71:5814-5819, 1997.

Kahn et al., "Recombinant Vesicular Stomatitis Virus Expressing Respiratory Syncytial Virus (RSV) Glycoproteins: RSV Fusion Protein Can Mediate Infection and Cell Fusion," *Virology* 254

1) Introduced and Incidental Mutations in HN gene of JS cDNA [p218(131)]

```
                THR263                              HgaI                  PRO370
JSwt parent   AAT ACA GAT    CAA GCG TCT CAT AGT   CCA TGG  TTT
                    →                    →              →
JScDNA  7589  AAT A[T]A GAT  7898 CAA G[C]A TCT CAT AGT  A[C]T TGG  TTT
                  ILE263                              ScaI THR370
```

2) Incidental mutations in the L gene of JScDNA [p218(131)]

```
                THR595                        ASN618                   ILE2221
JSwt parent   GCT ACA CAA    AAG AAC ATT     TTG ATT  GGT
                    →                  →                →
JScDNA  10350 GCT A[C]C CAA  11328 AAG AA[T] ATT  15243 TTG AT[C] GGT
                  THR595             ASN618                   ILE2221
```

FIG.2

SCHEMATIC REPRESENTATION OF RECOMBINANT PIV3 VIRUSES BEARING MUTATIONS (*) IN THE 3' LE

FIG. 16

```
                           SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
           (A) LENGTH: 15669 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:1:

GCTGGGTACC GGGCCCGTCG ACGCGTATAT AGTTCCTCCT TTCAGCAAAA AACCCCTCAA        60

GACCCGTTTA GAGGCCCCAA GGGGTTATGC TACTGCAGGC TCTCCCTTAG CCATCCGAGT       120

GGACGTGCGT CCTCCTTCGG ATGCCCAGGT CGGACCGCGA GGAGGTGGAG ATGCCATGCC       180

GACCCACCAA ACAAGAGAAG AAACTTGTCT GGGAATATAA ATTTAACTTT AAATTAACTT       240

AGGATTAAAG ACATTGACTA GAAGGTCAAG AAAAGGGAAC TCTATAATTT CAAAAATGTT       300

GAGCCTATTT GATACATTTA ATGCACGTAG GCAAGAAAAC ATAACAAAAT CAGCCGGTGG       360

AGCTATCATT CCTGGACAGA AAAATACTGT CTCTATATTC GCCCTTGGAC CGACAATAAC       420

TGATGATAAT GAGAAAATGA CATTAGCTCT TCTATTTCTA TCTCATTCAC TAGATAATGA       480

GAAACAACAT GCACAAAGGG CAGGGTTCTT GGTGTCTTTA TTGTCAATGG CTTATGCCAA       540

TCCAGAGCTC TACCTAACAA CAAATGGAAG TAATGCAGAT GTCAAGTATG TCATATACAT       600

GATTGAGAAA GATCTAAAAC GGCAAAAGTA TGGAGGATTT GTGGTTAAGA CGAGAGAGAT       660

GATATATGAA AAGACAACTG ATTGGATATT TGGAAGTGAC CTGGATTATG ATCAGGAAAC       720

TATGTTGCAG AACGGCAGGA ACAATTCAAC AATTGAAGAC CTTGTCCACA CATTTGGGTA       780

TCCATCATGT TTAGGAGCTC TTATAATACA GATCTGGATA GTTCTGGTCA AAGCTATCAC       840

TAGTATCTCA GGGTTAAGAA AAGGCTTTTT CACCCGATTG GAAGCTTTCA GACAAGATGG       900

AACAGTGCAG GCAGGGCTGG TATTGAGCGG TGACACAGTG GATCAGATTG GGTCAATCAT       960

GCGGTCTCAA CAGAGCTTGG TAACTCTTAT GGTTGAAACA TTAATAACAA TGAATACCAG      1020

CAGAAATGAC CTCACAACCA TAGAAAAGAA TATACAAATT GTTGGCAACT ACATAAGAGA      1080

TGCAGGTCTC GCTTCATTCT TCAATACAAT CAGATATGGA ATTGAGACCA GAATGGCAGC      1140

TTTGACTCTA TCCACTCTCA GACCAGATAT CAATAGATTA AAAGCTTTGA TGGAACTGTA      1200

TTTATCAAAG GGACCACGCG CTCCTTTCAT CTGTATCCTC AGAGATCCTA TACATGGTGA      1260

GTTCGCACCA GGCAACTATC CTGCCATATG GAGCTATGCA ATGGGGGTGG CAGTTGTACA      1320

AAATAGAGCC ATGCAACAGT ATGTGACGGG AAGATCATAT CTAGACATTG ATATGTTCCA      1380

GCTAGGACAA GCAGTAGCAC GTGATGCCGA AGCTCAAATG AGCTCAACAC TGGAAGATGA      1440
```

```
ACTTGGAGTG ACACACGAAT CTAAAGAAAG CTTGAAGAGA CATATAAGGA ACATAAACAG   1500

TTCAGAGACA TCTTTCCACA AACCGACAGG TGGATCAGCC ATAGAGATGG CAATAGATGA   1560

AGAGCCAGAA CAATTCGAAC ATAGAGCAGA TCAAGAACAA AATGGAGAAC CTCAATCATC   1620

CATAATTCAA TATGCCTGGG CAGAAGGAAA TAGAAGCGAT GATCAGACTG AGCAAGCTAC   1680

AGAATCTGAC AATATCAAGA CCGAACAACA AACATCAGA GACAGACTAA ACAAGAGACT    1740

CAACGACAAG AAGAAACAAA GCAGTCAACC ACCCACTAAT CCCACAAACA GAACAAACCA   1800

GGACGAAATA GATGATCTGT TTAACGCATT TGGAAGCAAC TAATCGAATC AACATTTTAA   1860

TCTAAATCAA TAATAAATAA GAAAAACTTA GGATTAAAGA ATCCTATCAT ACCGGAATAT   1920

AGGGTGGTAA ATTTAGAGTC TGCTTGAAAC TCAATCAATA GAGAGTTGAT GGAAAGCGAT   1980

GCTAAAAACT ATCAAATCAT GGATTCTTGG GAAGAGGAAT CAAGAGATAA ATCAACTAAT   2040

ATCTCCTCGG CCCTCAACAT CATTGAATTC ATACTCAGCA CCGACCCCCA AGAAGACTTA   2100

TCGGAAAACG ACACAATCAA CACAAGAACC CAGCAACTCA GTGCCACCAT CTGTCAACCA   2160

GAAATCAAAC CAACAGAAAC AAGTGAGAAA GATAGTGGAT CAACTGACAA AAATAGACAG   2220

TCTGGGTCAT CACACGAATG TACAACAGAA GCAAAGATA GAAATATTGA TCAGGAAACT    2280

GTACAGAGAG GACCTGGGAG AAGAAGCAGC TCAGATAGTA GAGCTGAGAC TGTGGTCTCT   2340

GGAGGAATCC CCAGAAGCAT CACAGATTCT AAAAATGGAA CCCAAAACAC GGAGGATATT   2400

GATCTCAATG AAATTAGAAA GATGGATAAG GACTCTATTG AGGGAAAAT GCGACAATCT    2460

GCAAATGTTC CAAGCGAGAT ATCAGGAAGT GATGACATAT TTACAACAGA ACAAAGTAGA   2520

AACAGTGATC ATGGAAGAAG CCTGGAATCT ATCAGTACAC CTGATACAAG ATCAATAAGT   2580

GTTGTTACTG CTGCAACACC AGATGATGAA GAAGAAATAC TAATGAAAAA TAGTAGGACA   2640

AAGAAAAGTT CTTCAACACA TCAAGAAGAT GACAAAAGAA TTAAAAAAGG GGGAAAAGGG   2700

AAAGACTGGT TTAAGAAATC AAAAGATACC GACAACCAGA TACCAACATC AGACTACAGA   2760

TCCACATCAA AAGGGCAGAA GAAAATCTCA AAGACAACAA CCACCAACAC CGACACAAAG   2820

GGGCAAACAG AAATACAGAC AGAATCATCA GAAACACAAT CCTCATCATG GAATCTCATC   2880

ATCGACAACA ACACCGACCG GAACGAACAG ACAAGCACAA CTCCTCCAAC AACAACTTCC   2940

AGATCAACTT ATACAAAAGA ATCGATCCGA ACAAACTCTG AATCCAAACC CAAGACACAA   3000

AAGACAAATG GAAAGGAAAG GAAGGATACA GAAGAGAGCA ATCGATTTAC AGAGAGGGCA   3060

ATTACTCTAT TGCAGAATCT TGGTGTAATT CAATCCACAT CAAAACTAGA TTTATATCAA   3120

GACAAACGAG TTGTATGTGT AGCAAATGTA CTAAACAATG TAGATACTGC ATCAAAGATA   3180

GATTTCCTGG CAGGATTAGT CATAGGGGTT TCAATGGACA ACGACACAAA ATTAACACAG   3240

ATACAAAATG AAATGCTAAA CCTCAAAGCA GATCTAAAGA AAATGGACGA ATCACATAGA   3300

AGATTGATAG AAAATCAAAG AGAACAACTG TCATTGATCA CGTCACTAAT TTCAAATCTC   3360

AAAATTATGA CTGAGAGAGG AGGAAAGAAA GACCAAAATG AATCCAATGA GAGAGTATCC   3420

ATGATCAAAA CAAAATTGAA AGAAGAAAAG ATCAAGAAGA CCAGGTTTGA CCCACTTATG   3480

GAGGCACAAG GCATTGACAA GAATATACCC GATCTATATC GACATGCAGG AGATACACTA   3540

GAGAACGATG TACAAGTTAA ATCAGAGATA TTAAGTTCAT ACAATGAGTC AAATGCAACA   3600

AGACTAATAC CCAAAAAAGT GAGCAGTACA ATGAGATCAC TAGTTGCAGT CATCAACAAC   3660

AGCAATCTCT CACAAAGCAC AAAACAATCA TACATAAACG AACTCAAACG TTGCAAAAAT   3720

GATGAAGAAG TATCTGAATT AATGGACATG TTCAATGAAG ATGTCAACAA TTGCCAATGA   3780
```

```
TCCAACAAAG AAACGACACC GAACAAACAG ACAAGAAACA ACAGTAGATC AAAACCTGTC    3840

AACACACACA AAATCAAGCA GAATGAAACA ACAGATATCA ATCAATATAC AAATAAGAAA    3900

AACTTAGGAT TAAAGAATAA ATTAATCCTT GTCCAAAATG AGTATAACTA ACTCTGCAAT    3960

ATACACATTC CCAGAATCAT CATTCTCTGA AAATGGTCAT ATAGAACCAT TACCACTCAA    4020

AGTCAATGAA CAGAGGAAAG CAGTACCCCA CATTAGAGTT GCCAAGATCG GAAATCCACC    4080

AAAACACGGA TCCCGGTATT TAGATGTCTT CTTACTCGGC TTCTTCGAGA TGGAACGAAT    4140

CAAAGACAAA TACGGGAGTG TGAATGATCT CGACAGTGAC CCGAGTTACA AAGTTTGTGG    4200

CTCTGGATCA TTACCAATCG GATTGGCTAA GTACACTGGG AATGACCAGG AATTGTTACA    4260

AGCCGCAACC AAACTGGATA TAGAAGTGAG AAGAACAGTC AAAGCGAAAG AGATGGTTGT    4320

TTACACGGTA CAAAATATAA AACCAGAACT GTACCCATGG TCCAATAGAC TAAGAAAAGG    4380

AATGCTGTTC GATGCCAACA AAGTTGCTCT TGCTCCTCAA TGTCTTCCAC TAGATAGGAG    4440

CATAAAATTT AGAGTAATCT TCGTGAATTG TACGGCAATT GGATCAATAA CCTTGTTCAA    4500

AATTCCTAAG TCAATGGCAT CACTATCTCT ACCCAACACA ATATCAATCA ATCTGCAGGT    4560

ACACATAAAA ACAGGGGTTC AGACTGATTC TAAAGGGATA GTTCAAATTT TGGATGAGAA    4620

AGGCGAAAAA TCACTGAATT TCATGGTCCA TCTCGGATTG ATCAAAAGAA AAGTAGGCAG    4680

AATGTACTCT GTTGAATACT GTAAACAGAA AATCGAGAAA ATGAGATTGA TATTTTCTTT    4740

AGGACTAGTT GGAGGAATCA GTCTTCATGT CAATGCAACT GGGTCCATAT CAAAAACACT    4800

AGCAAGTCAG CTGGTATTCA AAAGAGAGAT TTGTTATCCT TTAATGGATC TAAATCCGCA    4860

TCTCAATCTA GTTATCTGGG CTTCATCAGT AGAGATTACA AGAGTGGATG CAATTTTCCA    4920

ACCTTCTTTA CCTGGCGAGT TCAGATACTA TCCTAATATT ATTGCAAAAG GAGTTGGGAA    4980

AATCAAACAA TGGAACTAGT AATCTCTATT TTAGTCCGGA CGTATCTATT AAGCCGAAGC    5040

AAATAAAGGA TAATCAAAAA CTTAGGACAA AAGAGGTCAA TACCAACAAC TATTAGCAGT    5100

CACACTCGCA AGAATAAGAG AGAAGGGACC AAAAAAGTCA AATAGGAGAA ATCAAAACAA    5160

AAGGTACAGA ACACCAGAAC AACAAAATCA AAACATCCAA CTCACTCAAA ACAAAAATTC    5220

CAAAAGAGAC CGGCAACACA ACAAGCACTG AACACAATGC CAACTTCAAT ACTGCTAATT    5280

ATTACAACCA TGATCATGGC ATCTTTCTGC CAAATAGATA TCACAAAACT ACAGCACGTA    5340

GGTGTATTGG TCAACAGTCC CAAAGGGATG AAGATATCAC AAAACTTTGA AACAAGATAT    5400

CTAATTTTGA GCCTCATACC AAAAATAGAA GACTCTAACT CTTGTGGTGA CCAACAGATC    5460

AAGCAATACA AGAAGTTATT GGATAGACTG ATCATCCCTT TATATGATGG ATTAAGATTA    5520

CAGAAAGATG TGATAGTAAC CAATCAAGAA TCCAATGAAA ACACTGATCC CAGAACAAAA    5580

CGATTCTTTG GAGGGGTAAT TGGAACCATT GCTCTGGGAG TAGCAACCTC AGCACAAATT    5640

ACAGCGGCAG TTGCTCTGGT TGAAGCCAAG CAGGCAAGAT CAGACATCGA AAAACTCAAA    5700

GAAGCAATTA GGGACACAAA CAAAGCAGTG CAGTCAGTTC AGAGCTCCAT AGGAAATTTA    5760

ATAGTAGCAA TTAAATCAGT CCAGGATTAT GTTAACAAAG AAATCGTGCC ATCGATTGCG    5820

AGGCTAGGTT GTGAAGCAGC AGGACTTCAA TTAGGAATTG CATTAACACA GCATTACTCA    5880

GAATTAACAA ACATATTTGG TGATAACATA GGATCGTTAC AAGAAAAAGG AATAAAATTA    5940

CAAGGTATAG CATCATTATA CCGCACAAAT ATCACAGAAA TATTCACAAC ATCAACAGTT    6000

GATAAATATG ATATCTATGA TCTGTTATTT ACAGAATCAA TAAAGGTGAG AGTTATAGAT    6060

GTTGACTTGA ATGATTACTC AATCACCCTC CAAGTCAGAC TCCCTTTATT AACTAGGCTG    6120

CTGAACACTC AGATCTACAA AGTAGATTCC ATATCATATA ACATCCAAAA CAGAGAATGG    6180
```

```
TATATCCCTC TTCCCAGCCA TATCATGACG AAAGGGGCAT TTCTAGGTGG AGCAGACGTC    6240

AAAGAATGTA TAGAAGCATT CAGCAGCTAT ATATGCCCTT CTGATCCAGG ATTTGTATTA    6300

AACCATGAAA TAGAGAGCTG CTTATCAGGA ACATATCCC AATGTCCAAG ACAACGGTC      6360

ACATCAGACA TTGTTCCAAG ATATGCATTT GTCAATGGAG GAGTGGTTGC AAACTGTATA    6420

ACAACCACCT GTACATGCAA CGGAATTGGT AATAGAATCA ATCAACCACC TGATCAAGGA    6480

GTAAAAATTA TAACACATAA AGAATGTAGT ACAATAGGTA TCAACGGAAT GCTGTTCAAT    6540

ACAAATAAAG AAGGAACTCT TGCATTCTAT ACACCAAATG ATATAACACT AAACAATTCT    6600

GTTGCACTTG ATCCAATTGA CATATCAATC GAGCTCAACA AGGCCAAATC AGATCTAGAA    6660

GAATCAAAAG AATGGATAAG AAGGTCAAAT CAAAAACTAG ATTCTATTGG AAATTGGCAT    6720

CAATCTAGCA CTACAATCAT AATTATTTTG ATAATGATCA TTATATTGTT TATAATTAAT    6780

ATAACGATAA TTACAATTGC AATTAAGTAT TACAGAATTC AAAAGAGAAA TCGAGTGGAT    6840

CAAAATGACA AGCCATATGT ACTAACAAAC AAATAACATA TCTACAGATC ATTAGATATT    6900

AAAATTATAA AAAACTTAGG AGTAAAGTTA CGCAATCCAA CTCTACTCAT ATAATTGAGG    6960

AAGGACCCAA TAGACAAATC CAAATTCGAG ATGGAATACT GGAAGCATAC CAATCACGGA    7020

AAGGATGCTG GTAATGAGCT GGAGACGTCT ATGGCTACTC ATGGCAACAA GCTCACTAAT    7080

AAGATAATAT ACATATTATG GACAATAATC CTGGTGTTAT TATCAATAGT CTTCATCATA    7140

GTGCTAATTA ATTCCATCAA AAGTGAAAAG GCCCACGAAT CATTGCTGCA AGACATAAAT    7200

AATGAGTTTA TGGAAATTAC AGAAAAGATC CAAATGGCAT CGGATAATAC CAATGATCTA    7260

ATACAGTCAG GAGTGAATAC AAGGCTTCTT ACAATTCAGA GTCATGTCCA GAATTACATA    7320

CCAATATCAT TGACACAACA GATGTCAGAT CTTAGGAAAT TCATTAGTGA AATTACAATT    7380

AGAAATGATA ATCAAGAAGT GCTGCCACAA AGAATAACAC ATGATGTAGG TATAAAACCT    7440

TTAAATCCAG ATGATTTTTG GAGATGCACG TCTGGTCTTC CATCTTTAAT GAAAACTCCA    7500

AAAATAAGGT TAATGCCAGG GCCGGGATTA TTAGCTATGC CAACGACTGT TGATGGCTGT    7560

GTTAGAACTC CGTCTTTAGT TATAAATGAT CTGATTTATG CTTATACCTC AAATCTAATT    7620

ACTCGAGGTT GTCAGGATAT AGGAAAATCA TATCAAGTCT TACAGATAGG GATAATAACT    7680

GTAAACTCAG ACTTGGTACC TGACTTAAAT CCTAGGATCT CTCATACCTT TAACATAAAT    7740

GACAATAGGA AGTCATGTTC TCTAGCACTC CTAAATATAG ATGTATATCA ACTGTGTTCA    7800

ACTCCCAAAG TTGATGAAAG ATCAGATTAT GCATCATCAG GCATAGAAGA TATTGTACTT    7860

GATATTGTCA ATTATGATGG TTCAATCTCA ACAACAAGAT TTAAGAATAA TAACATAAGC    7920

TTTGATCAAC CATATGCTGC ACTATACCCA TCTGTTGGAC CAGGGATATA CTACAAAGGC    7980

AAAATAATAT TTCTCGGGTA TGGAGGTCTT GAACATCCAA TAAATGAGAA TGTAATCTGC    8040

AACACAACTG GGTGCCCCGG GAAAACACAG AGAGACTGTA ATCAAGCATC TCATAGTACT    8100

TGGTTTTCAG ATAGGAGGAT GGTCAACTCC ATCATTGTTG TTGACAAAGG CTTAAACTCA    8160

ATTCCAAAAT TGAAAGTATG GACGATATCT ATGCGACAAA ATTACTGGGG GTCAGAAGGA    8220

AGGTTACTTC TACTAGGTAA CAAGATCTAT ATATATACAA GATCTACAAG TTGGCATAGC    8280

AAGTTACAAT TAGGAATAAT TGATATTACT GATTACAGTG ATATAAGGAT AAAATGGACA    8340

TGGCATAATG TGCTATCAAG ACCAGGAAAC AATGAATGTC CATGGGGACA TTCATGTCCA    8400

GATGGATGTA TAACAGGAGT ATATACTGAT GCATATCCAC TCAATCCCAC AGGGAGCATT    8460

GTGTCATCTG TCATATTAGA CTCACAAAAA TCGAGAGTGA ACCCAGTCAT AACTTACTCA    8520
```

```
ACAGCAACCG AAAGAGTAAA CGAGCTGGCC ATCCTAAACA GAACACTCTC AGCTGGATAT    8580

ACAACAACAA GCTGCATTAC ACACTATAAC AAAGGATATT GTTTTCATAT AGTAGAAATA    8640

AATCATAAAA GCTTAAACAC ATTTCAACCC ATGTTGTTCA AAACAGAGAT TCCAAAAAGC    8700

TGCAGTTAAT CATAATTAAC CATAATATGC ATCAATCTAT CTATAATACA AGTATATGAT    8760

AAGTAATCAG CAATCAGACA ATAGACAAAA GGGAAATATA AAAACTTAG GAGCAAAGCG     8820

TGCTCGGGAA ATGGACACTG AATCTAACAA TGGCACTGTA TCTGACATAC TCTATCCTGA    8880

GTGTCACCTT AACTCTCCTA TCGTTAAAGG TAAAATAGCA CAATTACACA CTATTATGAG    8940

TCTACCTCAG CCTTATGATA TGGATGACGA CTCAATACTA GTTATCACTA GACAGAAAAT    9000

AAAACTTAAT AAATTGGATA AAGACAACG ATCTATTAGA AGATTAAAAT TAATATTAAC     9060

TGAAAAAGTG AATGACTTAG GAAAATACAC ATTTATCAGA TATCCAGAAA TGTCAAAAGA    9120

AATGTTCAAA TTATATATAC CTGGTATTAA CAGTAAAGTG ACTGAATTAT TACTTAAAGC    9180

AGATAGAACA TATAGTCAAA TGACTGATGG ATTAAGAGAT CTATGGATTA ATGTGCTATC    9240

AAAATTAGCC TCAAAAAATG ATGGAAGCAA TTATGATCTT AATGAAGAAA TTAATAATAT    9300

ATCGAAAGTT CACACAACCT ATAAATCAGA TAAATGGTAT AATCCATTCA AAACATGGTT    9360

TACTATCAAG TATGATATGA GAAGATTACA AAAAGCTCGA AATGAGATCA CTTTTAATGT    9420

TGGGAAGGAT TATAACTTGT TAGAAGACCA GAAGAATTTC TTATTGATAC ATCCAGAATT    9480

GGTTTTGATA TTAGATAAAC AAAACTATAA TGGTTATCTA ATTACTCCTG AATTAGTATT    9540

GATGTATTGT GACGTAGTCG AAGGCCGATG GAATATAAGT GCATGTGCTA AGTTAGATCC    9600

AAAATTACAA TCTATGTATC AGAAAGGTAA TAACCTGTGG GAAGTGATAG ATAAATTGTT    9660

TCCAATTATG GGAGAAAAGA CATTTGATGT GATATCGTTA TTAGAACCAC TTGCATTATC    9720

CTTAATTCAA ACTCATGATC CTGTTAAACA ACTAAGAGGA GCTTTTTTAA ATCATGTGTT    9780

ATCCGAGATG GAATTAATAT TTGAATCTAG AGAATCGATT AAGGAATTTC TGAGTGTAGA    9840

TTACATTGAT AAAATTTTAG ATATATTTAA TAAGTCTACA ATAGATGAAA TAGCAGAGAT    9900

TTTCTCTTTT TTTAGAACAT TGGGCATCC TCCATTAGAA GCTAGTATTG CAGCAGAAAA     9960

GGTTAGAAAA TATATGTATA TTGGAAAACA ATTAAAATTT GACACTATTA ATAAATGTCA   10020

TGCTATCTTC TGTACAATAA TAATTAACGG ATATAGAGAG AGGCATGGTG GACAGTGGCC   10080

TCCTGTGACA TTACCTGATC ATGCACACGA ATTCATCATA AATGCTTACG GTTCAAACTC   10140

TGCGATATCA TATGAAAATG CTGTTGATTA TTACCAGAGC TTTATAGGAA TAAAATTCAA   10200

TAAATTCATA GAGCCTCAGT TAGATGAGGA TTTGACAATT TATATGAAAG ATAAAGCATT   10260

ATCTCCAAAA AAATCAAATT GGGACACAGT TTATCCTGCA TCTAATTTAC TGTACCGTAC   10320

TAACGCATCC AACGAATCAC GAAGATTAGT TGAAGTATTT ATAGCAGATA GTAAATTTGA   10380

TCCTCATCAG ATATTGGATT ATGTAGAATC TGGGGACTGG TTAGATGATC CAGAATTTAA   10440

TATTTCTTAT AGTCTTAAAG AAAAAGAGAT CAAACAGGAA GGTAGACTCT TTGCAAAAAT   10500

GACATACAAA ATGAGAGCTA CACAAGTTTT ATCAGAGACC CTACTTGCAA ATAACATAGG   10560

AAAATTCTTT CAAGAAATG GGATGGTGAA GGGAGAGATT GAATTACTTA AGAGATTAAC    10620

AACCATATCA ATATCAGGAG TTCCACGGTA TAATGAAGTG TACAATAATT CTAAAAGCCA   10680

TACAGATGAC CTTAAAACCT ACAATAAAAT AAGTAATCTT AATTTGTCTT CTAATCAGAA   10740

ATCAAAGAAA TTTGAATTCA AGTCAACGGA TATCTACAAT GATGGATACG AGACTGTGAG   10800

CTGTTTCCTA ACAACAGATC TCAAAAAATA CTGTCTTAAT TGGAGATATG AATCAACAGC   10860

TCTATTTGGA GAAACTTGCA ACCAAATATT TGGATTAAAT AAATTGTTTA ATTGGTTACA   10920
```

-continued

```
CCCTCGTCTT GAAGGAAGTA CAATCTATGT AGGTGATCCT TACTGTCCTC CATCAGATAA   10980

AGAACATATA TCATTAGAGG ATCACCCTGA TTCTGGTTTT TACGTTCATA ACCCAAGAGG   11040

GGGTATAGAA GGATTTTGTC AAAAATTATG GACACTCATA TCTATAAGTG CAATACATCT   11100

AGCAGCTGTT AGAATAGGCG TGAGGGTGAC TGCAATGGTT CAAGGAGACA ATCAAGCTAT   11160

AGCTGTAACC ACAAGAGTAC CCAACAATTA TGACTACAGA GTTAAGAAGG AGATAGTTTA   11220

TAAAGATGTA GTGAGATTTT TGATTCATT AAGAGAAGTG ATGGATGATC TAGGTCATGA   11280

ACTTAAATTA AATGAAACGA TTATAAGTAG CAAGATGTTC ATATATAGCA AAAGAATCTA   11340

TTATGATGGG AGAATTCTTC CTCAAGCTCT AAAAGCATTA TCTAGATGTG TCTTCTGGTC   11400

AGAGACAGTA ATAGACGAAA CAAGATCAGC ATCTTCAAAT TTGGCAACAT CATTTGCAAA   11460

AGCAATTGAG AATGGTTATT CACCTGTTCT AGGATATGCA TGCTCAATTT TAAGAATAT   11520

TCAACAACTA TATATTGCCC TTGGGATGAA TATCAATCCA ACTATAACAC AGAATATCAG   11580

AGATCAGTAT TTTAGGAATC CAAATTGGAT GCAATATGCC TCTTTAATAC CTGCTAGTGT   11640

TGGGGGATTC AATTACATGG CCATGTCAAG ATGTTTTGTA AGGAATATTG GTGATCCATC   11700

AGTTGCCGCA TTGGCTGATA TTAAAAGATT TATTAAGGCG AATCTATTAG ACCGAAGTGT   11760

TCTTTATAGG ATTATGAATC AAGAACCAGG TGAGTCATCT TTTTTGGACT GGGCTTCAGA   11820

TCCATATTCA TGCAATTTAC CACAATCTCA AAATATAACC ACCATGATAA AAATATAAC   11880

AGCAAGGAAT GTATTACAAG ATTCACCAAA TCCATTATTA TCTGGATTAT TCACAAATAC   11940

AATGATAGAA GAAGATGAAG AATTAGCTGA GTTCCTGATG GACAGGAAGG TAATTCTCCC   12000

TAGAGTTGCA CATGATATTC TAGATAATTC TCTCACAGGA ATTAGAAATG CCATAGCTGG   12060

AATGTTAGAT ACGACAAAAT CACTAATTCG GGTTGGCATA AATAGAGGAG GACTGACATA   12120

TAGTTTGTTG AGGAAAATCA GTAATTACGA TCTAGTACAA TATGAAACAC TAAGTAGGAC   12180

TTTGCGACTA ATTGTAAGTG ATAAAATCAA GTATGAAGAT ATGTGTTCGG TAGACCTTGC   12240

CATAGCATTG CGACAAAAGA TGTGGATTCA TTTATCAGGA GGAAGGATGA TAAGTGGACT   12300

TGAAACGCCT GACCCATTAG AATTACTATC TGGGGTAGTA ATAACAGGAT CAGAACATTG   12360

TAAAATATGT TATTCTTCAG ATGGCACAAA CCCATATACT TGGATGTATT TACCCGGTAA   12420

TATCAAAATA GGATCAGCAG AAACAGGTAT ATCGTCATTA AGAGTTCCTT ATTTTGGATC   12480

AGTCACTGAT GAAAGATCTG AAGCACAATT AGGATATATC AAGAATCTTA GTAAACCTGC   12540

AAAAGCCGCA ATAAGAATAG CAATGATATA TACATGGGCA TTTGGTAATG ATGAGATATC   12600

TTGGATGGAA GCCTCACAGA TAGCACAAAC ACGTGCAAAT TTTACACTAG ATAGTCTCAA   12660

AATTTTAACA CCGGTAGCTA CATCAACAAA TTTATCACAC AGATTAAAGG ATACTGCAAC   12720

TCAGATGAAA TTCTCCAGTA CATCATTGAT CAGAGTCAGC AGATTCATAA CAATGTCCAA   12780

TGATAACATG TCTATCAAAG AAGCTAATGA AACCAAAGAT ACTAATCTTA TTTATCAACA   12840

AATAATGTTA ACAGGATTAA GTGTTTTCGA ATATTTATTT AGATTAAAAG AAACCACAGG   12900

ACACAACCCT ATAGTTATGC ATCTGCACAT AGAAGATGAG TGTTGTATTA AGAAAGTTT   12960

TAATGATGAA CATATTAATC CAGAGTCTAC ATTAGAATTA ATTCGATATC CTGAAAGTAA   13020

TGAATTTATT TATGATAAAG ACCCACTCAA AGATGTGGAC TTATCAAAAC TTATGGTTAT   13080

TAAAGACCAT TCTTACACAA TTGATATGAA TTATTGGGAT GATACTGACA TCATACATGC   13140

AATTTCAATA TGTACTGCAA TTACAATAGC AGATACTATG TCACAATTAG ATCGAGATAA   13200

TTTAAAAGAG ATAATAGTTA TTGCAAATGA TGATGATATT AATAGCTTAA TCACTGAATT   13260
```

```
TTTGACTCTT GACATACTTG TATTTCTCAA GACATTTGGT GGATTATTAG TAAATCAATT    13320

TGCATACACT CTTTATAGTC TAAAAATAGA AGGTAGGGAT CTCATTTGGG ATTATATAAT    13380

GAGAACACTG AGAGATACTT CCCATTCAAT ATTAAAAGTA TTATCTAATG CATTATCTCA    13440

TCCTAAAGTA TTCAAGAGGT TCTGGGATTG TGGAGTTTTA AACCCTATTT ATGGTCCTAA    13500

TACTGCTAGT CAAGACCAGA TAAAACTTGC CCTATCTATA TGTGAATATT CACTAGATCT    13560

ATTTATGAGA GAATGGTTGA ATGGTGTATC ACTTGAAATA TACATTTGTG ACAGCGATAT    13620

GGAAGTTGCA AATGATAGGA AACAAGCCTT TATTTCTAGA CACCTTTCAT TTGTTTGTTG    13680

TTTAGCAGAA ATTGCATCTT TCGGACCTAA CCTGTTAAAC TTAACATACT TGGAGAGACT    13740

TGATCTATTG AAACAATATC TTGAATTAAA TATTAAAGAA GACCCTACTC TTAAATATGT    13800

ACAAATATCT GGATTATTAA TTAAATCGTT CCCATCAACT GTAACATACG TAAGAAAGAC    13860

TGCAATCAAA TATCTAAGGA TTCGCGGTAT TAGTCCACCT GAGGTAATTG ATGATTGGGA    13920

TCCGGTAGAA GATGAAAATA TGCTGGATAA CATTGTCAAA ACTATAAATG ATAACTGTAA    13980

TAAAGATAAT AAAGGGAATA AAATTAACAA TTTCTGGGGA CTAGCACTTA AGAACTATCA    14040

AGTCCTTAAA ATCAGATCTA TAACAAGTGA TTCTGATGAT AATGATAGAC TAGATGCTAA    14100

TACAAGTGGT TTGACACTTC CTCAAGGAGG GAATTATCTA TCGCATCAAT TGAGATTATT    14160

CGGAATCAAC AGCACTAGTT GTCTGAAAGC TCTTGAGTTA TCACAAATTT TAATGAAGGA    14220

AGTCAATAAA GACAAGGACA GGCTCTTCCT GGGAGAAGGA GCAGGAGCTA TGCTAGCATG    14280

TTATGATGCC ACATTAGGAC CTGCAGTTAA TTATTATAAT TCAGGTTTGA ATATAACAGA    14340

TGTAATTGGT CAACGAGAAT TGAAAATATT TCCTTCAGAG GTATCATTAG TAGGTAAAAA    14400

ATTAGGAAAT GTGACACAGA TTCTTAACAG GGTAAAAGTA CTGTTCAATG GAATCCTAA     14460

TTCAACATGG ATAGGAAATA TGGAATGTGA GAGCTTAATA TGGAGTGAAT TAAATGATAA    14520

GTCCATTGGA TTAGTACATT GTGATATGGA AGGAGCTATC GGTAAATCAG AAGAAACTGT    14580

TCTACATGAA CATTATAGTG TTATAAGAAT TACATACTTG ATTGGGGATG ATGATGTTGT    14640

TTTAGTTTCC AAAATTATAC CTACAATCAC TCCGAATTGG TCTAGAATAC TTTATCTATA    14700

TAAATTATAT TGGAAAGATG TAAGTATAAT ATCACTCAAA ACTTCTAATC CTGCATCAAC    14760

AGAATTATAT CTAATTTCGA AAGATGCATA TTGTACTATA ATGGAACCTA GTGAAATTGT    14820

TTTATCAAAA CTTAAAAGAT TGTCACTCTT GGAAGAAAAT AATCTATTAA AATGGATCAT    14880

TTTATCAAAG AAGAGGAATA ATGAATGGTT ACATCATGAA ATCAAAGAAG GAGAAAGAGA    14940

TTATGGAATC ATGAGACCAT ATCATATGGC ACTACAAATC TTTGGATTTC AAATCAATTT    15000

AAATCATCTG GCGAAAGAAT TTTTATCAAC CCCAGATCTG ACTAATATCA ACAATATAAT    15060

CCAAAGTTTT CAGCGAACAA TAAAGGATGT TTTATTTGAA TGGATTAATA TAACTCATGA    15120

TGATAAGAGA CATAAAATTA GCGGAAGATA TAACATATTC CCACTGAAAA ATAAGGGAAA    15180

GTTAAGACTG CTATCGAGAA GACTAGTATT AAGTTGGATT TCATTATCAT TATCGACTCG    15240

ATTACTTACA GGTCGCTTTC CTGATGAAAA ATTTGAACAT AGAGCACAGA CTGGATATGT    15300

ATCATTAGCT GATACTGATT TAGAATCATT AAAGTTATTG TCGAAAAACA TCATTAAGAA    15360

TTACAGAGAG TGTATAGGAT CAATATCATA TTGGTTTCTA ACCAAAGAAG TTAAAATACT    15420

TATGAAATTG ATCGGTGGTG CTAAATTATT AGGAATTCCC AGACAATATA AGAACCCGA     15480

AGACCAGTTA TTTAGAAAACT ACAATCAACA TGATGAATTT GATATCGATT AAAACATAAA    15540

TACAATGAAG ATATATCCTA ACCTTTATCT TTAAGCCTAG GAATAGACAA AAAGTAAGAA    15600

AAACATGTAA TATATATATA CCAAACAGAG TTCTTCTCTT GTTTGGTTAT AGTGAGTCGT    15660
```

-continued

ATTACAATC                                                          15669

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

AATACGACTC ACTATAACCA AACAAGAGAA C                                  31

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCAAGTACTA TGAGATGCTT CATT                                          24

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CCCTATAATT TCAACATGTT GAGCCTATTT G                                  31

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GATTAAAATG TTGGTCGACT TAGTTGCTTC C                                  31

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CCATAGAGAG TCCATGGAAA GCGACGCTAA AAACTATC                            38

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CGGTGTCGTT TCTTTGTCGA CTCATTGGCA ATTGTTG                  37

(2) INFORMATION FOR SEQ ID NO:8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCAAAGCGTG CCCGGGCCAT GGACACTGAA TCTAACAATG GC              42

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GAAATTCCTT AATCGATTCT CTAGATTC                              28

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCCATCAACT GTAACATACG TAAGAAAGAC                          30

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GGTTAGGATA TGTCGACATT GTATTTATG                            29

(2) INFORMATION FOR SEQ ID NO:12:

(i) SEQUENCE CHARACTERISTICS:
        (A) LENGTH: 43 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGGGTTATGC TACTGCAGGC TTTTTTTCTC CCTTAGCCAT CCG        43

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CTCCATTCTA GANTTATAAA AATTATAGAG TTCCC        35

(2) INFORMATION FOR SEQ ID NO:14:

(i) SEQUENCE CHARACTERISTICS:
        (A) LENGTH: 15660 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TAATACGACT CACTATAACC AAACAAGAGA AGAAACTTGT CTGGGAATAT AAATTTAACT        60

TTAAATTAAC TTAGGATTAA AGACATTGAC TAGAAGGTCA AGAAAAGGGA ACTCTATAAT       120

TTCAAAAATG TTGAGCCTAT TTGATACATT TAATGCACGT AGGCAAGAAA ACATAACAAA       180

ATCAGCCGGT GGAGCTATCA TTCCTGGACA GAAAAATACT GTCTCTATAT TCGCCCTTGG       240

ACCGACAATA ACTGATGATA ATGAGAAAAT GACATTAGCT CTTCTATTTC TATCTCATTC       300

ACTAGATAAT GAGAAACAAC ATGCACAAAG GCAGGGTTC TTGGTGTCTT TATTGTCAAT        360

GGCTTATGCC AATCCAGAGC TCTACCTAAC AACAAATGGA AGTAATGCAG ATGTCAAGTA       420

TGTCATATAC ATGATTGAGA AAGATCTAAA ACGGCAAAAG TATGGAGGAT TTGTGGTTAA       480

GACGAGAGAG ATGATATATG AAAAGACAAC TGATTGGATA TTTGGAAGTG ACCTGGATTA       540

TGATCAGGAA ACTATGTTGC AGAACGGCAG GAACAATTCA ACAATTGAAG ACCTTGTCCA       600

CACATTTGGG TATCCATCAT GTTTAGGAGC TCTTATAATA CAGATCTGGA TAGTTCTGGT       660

CAAAGCTATC ACTAGTATCT CAGGGTTAAG AAAAGGCTTT TTCACCCGAT GGAAGCTTTT       720

CAGACAAGAT GGAACAGTGC AGGCAGGGCT GGTATTGAGC GGTGACACAG TGGATCAGAT       780

TGGGTCAATC ATGCGGTCTC AACAGAGCTT GGTAACTCTT ATGGTTGAAA CATTAATAAC       840

AATGAATACC AGCAGAAATG ACCTCACAAC CATAGAAAAG AATATACAAA TTGTTGGCAA       900

CTACATAAGA GATGCAGGTC TCGCTTCATT CTTCAATACA ATCAGATATG GAATTGAGAC       960

CAGAATGGCA GCTTTGACTC TATCCACTCT CAGACCAGAT ATCAATAGAT TAAAAGCTTT      1020

GATGGAACTG TATTTATCAA AGGGACCACG CGCTCCTTTC ATCTGTATCC TCAGAGATCC      1080

TATACATGGT GAGTTCGCAC CAGGCAACTA TCCTGCCATA TGGAGCTATG CAATGGGGGT      1140

GGCAGTTGTA CAAAATAGAG CCATGCAACA GTATGTGACG GGAAGATCAT ATCTAGACAT      1200

TGATATGTTC CAGCTAGGAC AAGCAGTAGC ACGTGATGCC GAAGCTCAAA TGAGCTCAAC      1260

```
ACTGGAAGAT GAACTTGGAG TGACACACGA ATCTAAAGAA AGCTTGAAGA GACATATAAG    1320

GAACATAAAC AGTTCAGAGA CATCTTTCCA CAAACCGACA GGTGGATCAG CCATAGAGAT    1380

GGCAATAGAT GAAGAGCCAG AACAATTCGA ACATAGAGCA GATCAAGAAC AAAATGGAGA    1440

ACCTCAATCA TCCATAATTC AATATGCCTG GGCAGAAGGA AATAGAAGCG ATGATCAGAC    1500

TGAGCAAGCT ACAGAATCTG ACAATATCAA GACCGAACAA CAAACATCA GAGACAGACT    1560

AAACAAGAGA CTCAACGACA AGAAGAAACA AAGCAGTCAA CCACCCACTA ATCCCACAAA    1620

CAGAACAAAC CAGGACGAAA TAGATGATCT GTTTAACGCA TTTGGAAGCA ACTAATCGAA    1680

TCAACATTTT AATCTAAATC AATAATAAAT AAGAAAAACT TAGGATTAAA GAATCCTATC    1740

ATACCGGAAT ATAGGGTGGT AAATTTAGAG TCTGCTTGAA ACTCAATCAA TAGAGAGTTG    1800

ATGGAAAGCG ATGCTAAAAA CTATCAAATC ATGGATTCTT GGGAAGAGGA ATCAAGAGAT    1860

AAATCAACTA ATATCTCCTC GGCCCTCAAC ATCATTGAAT TCATACTCAG CACCGACCCC    1920

CAAGAAGACT TATCGGAAAA CGACACAATC AACACAAGAA CCCAGCAACT CAGTGCCACC    1980

ATCTGTCAAC CAGAAATCAA ACCAACAGAA ACAAGTGAGA AAGATAGTGG ATCAACTGAC    2040

AAAAATAGAC AGTCTGGGTC ATCACACGAA TGTACAACAG AAGCAAAAGA TAGAAATATT    2100

GATCAGGAAA CTGTACAGAG AGGACCTGGG AGAAGAAGCA GCTCAGATAG TAGAGCTGAG    2160

ACTGTGGTCT CTGGAGGAAT CCCCAGAAGC ATCACAGATT CTAAAAATGG AACCCAAAAC    2220

ACGGAGGATA TTGATCTCAA TGAAATTAGA AAGATGGATA AGGACTCTAT TGAGGGGAAA    2280

ATGCGACAAT CTGCAAATGT TCCAAGCGAG ATATCAGGAA GTGATGACAT ATTTACAACA    2340

GAACAAAGTA GAAACAGTGA TCATGGAAGA AGCCTGGAAT CTATCAGTAC ACCTGATACA    2400

AGATCAATAA GTGTTGTTAC TGCTGCAACA CCAGATGATG AAGAAGAAAT ACTAATGAAA    2460

AATAGTAGGA CAAAGAAAAG TTCTTCAACA CATCAAGAAG ATGACAAAAG AATTAAAAAA    2520

GGGGGAAAAG GAAAGACTG GTTTAAGAAA TCAAAGATA CCGACAACCA GATACCAACA    2580

TCAGACTACA GATCCACATC AAAAGGGCAG AAGAAAATCT CAAAGACAAC AACCACCAAC    2640

ACCGACACAA AGGGGCAAAC AGAAATACAG ACAGAATCAT CAGAAACACA ATCCTCATCA    2700

TGGAATCTCA TCATCGACAA CAACACCGAC CGGAACGAAC AGACAAGCAC AACTCCTCCA    2760

ACAACAACTT CCAGATCAAC TTATACAAAA GAATCGATCC GAACAAACTC TGAATCCAAA    2820

CCCAAGACAC AAAAGACAAA TGGAAAGGAA AGGAAGGATA CAGAAGAGAG CAATCGATTT    2880

ACAGAGAGGG CAATTACTCT ATTGCAGAAT CTTGGTGTAA TTCAATCCAC ATCAAAACTA    2940

GATTTATATC AAGACAAACG AGTTGTATGT GTAGCAAATG TACTAAACAA TGTAGATACT    3000

GCATCAAAGA TAGATTTCCT GGCAGGATTA GTCATAGGGG TTTCAATGGA CAACGACACA    3060

AAATTAACAC AGATACAAAA TGAAATGCTA AACCTCAAAG CAGATCTAAA GAAAATGGAC    3120

GAATCACATA GAAGATTGAT AGAAAATCAA AGAGAACAAC TGTCATTGAT CACGTCACTA    3180

ATTTCAAATC TCAAAATTAT GACTGAGAGA GGAGGAAAGA AAGACCAAAA TGAATCCAAT    3240

GAGAGAGTAT CCATGATCAA AACAAAATTG AAAGAAGAAA AGATCAAGAA GACCAGGTTT    3300

GACCCACTTA TGGAGGCACA AGGCATTGAC AAGAATATAC CCGATCTATA TCGACATGCA    3360

GGAGATACAC TAGAGAACGA TGTACAAGTT AAATCAGAGA TATTAAGTTC ATACAATGAG    3420

TCAAATGCAA CAAGACTAAT ACCCAAAAAA GTGAGCAGTA CAATGAGATC ACTAGTTGCA    3480

GTCATCAACA ACAGCAATCT CTCACAAAGC ACAAACAAT CATACATAAA CGAACTCAAA    3540

CGTTGCAAAA ATGATGAAGA AGTATCTGAA TTAATGGACA TGTTCAATGA AGATGTCAAC    3600
```

```
AATTGCCAAT GATCCAACAA AGAAACGACA CCGAACAAAC AGACAAGAAA CAACAGTAGA    3660

TCAAAACCTG TCAACACACA CAAAATCAAG CAGAATGAAA CAACAGATAT CAATCAATAT    3720

ACAAATAAGA AAAACTTAGG ATTAAAGAAT AAATTAATCC TTGTCCAAAA TGAGTATAAC    3780

TAACTCTGCA ATATACACAT TCCCAGAATC ATCATTCTCT GAAAATGGTC ATATAGAACC    3840

ATTACCACTC AAAGTCAATG AACAGAGGAA AGCAGTACCC CACATTAGAG TTGCCAAGAT    3900

CGGAAATCCA CCAAAACACG GATCCCGGTA TTTAGATGTC TTCTTACTCG GCTTCTTCGA    3960

GATGGAACGA ATCAAAGACA ATACGGGAG TGTGAATGAT CTCGACAGTG ACCCGAGTTA    4020

CAAAGTTTGT GGCTCTGGAT CATTACCAAT CGGATTGGCT AAGTACACTG GAATGACCA    4080

GGAATTGTTA CAAGCCGCAA CCAAACTGGA TATAGAAGTG AGAAGAACAG TCAAAGCGAA    4140

AGAGATGGTT GTTTACACGG TACAAAATAT AAAACCAGAA CTGTACCCAT GGTCCAATAG    4200

ACTAAGAAAA GGAATGCTGT TCGATGCCAA CAAAGTTGCT CTTGCTCCTC AATGTCTTCC    4260

ACTAGATAGG AGCATAAAAT TTAGAGTAAT CTTCGTGAAT TGTACGGCAA TTGGATCAAT    4320

AACCTTGTTC AAAATTCCTA AGTCAATGGC ATCACTATCT CTACCCAACA CAATATCAAT    4380

CAATCTGCAG GTACACATAA AAACAGGGGT TCAGACTGAT TCTAAAGGGA TAGTTCAAAT    4440

TTTGGATGAG AAAGGCGAAA AATCACTGAA TTTCATGGTC CATCTCGGAT TGATCAAAAG    4500

AAAAGTAGGC AGAATGTACT CTGTTGAATA CTGTAAACAG AAAATCGAGA AAATGAGATT    4560

GATATTTTCT TTAGGACTAG TTGGAGGAAT CAGTCTTCAT GTCAATGCAA CTGGGTCCAT    4620

ATCAAAAACA CTAGCAAGTC AGCTGGTATT CAAAAGAGAG ATTTGTTATC CTTTAATGGA    4680

TCTAAATCCG CATCTCAATC TAGTTATCTG GCTTCATCA GTAGAGATTA CAAGAGTGGA    4740

TGCAATTTTC CAACCTTCTT TACCTGGCGA GTTCAGATAC TATCCTAATA TTATTGCAAA    4800

AGGAGTTGGG AAAATCAAAC AATGGAACTA GTAATCTCTA TTTTAGTCCG GACGTATCTA    4860

TTAAGCCGAA GCAAATAAAG GATAATCAAA AACTTAGGAC AAAAGAGGTC AATACCAACA    4920

ACTATTAGCA GTCACACTCG CAAGAATAAG AGAGAAGGGA CCAAAAAAGT CAAATAGGAG    4980

AAATCAAAAC AAAAGGTACA GAACACCAGA ACAACAAAAT CAAAACATCC AACTCACTCA    5040

AAACAAAAAT TCCAAAAGAG ACCGGCAACA CAACAAGCAC TGAACACAAT GCCAACTTCA    5100

ATACTGCTAA TTATTACAAC CATGATCATG GCATCTTTCT GCCAAATAGA ATCACAAAA    5160

CTACAGCACG TAGGTGTATT GGTCAACAGT CCCAAAGGGA TGAAGATATC ACAAAACTTT    5220

GAAACAAGAT ATCTAATTTT GAGCCTCATA CCAAAAATAG AAGACTCTAA CTCTTGTGGT    5280

GACCAACAGA TCAAGCAATA CAAGAAGTTA TTGGATAGAC TGATCATCCC TTTATATGAT    5340

GGATTAAGAT TACAGAAAGA TGTGATAGTA ACCAATCAAG AATCCAATGA AAACACTGAT    5400

CCCAGAACAA AACGATTCTT TGGAGGGGTA ATTGGAACCA TTGCTCTGGG AGTAGCAACC    5460

TCAGCACAAA TTACAGCGGC AGTTGCTCTG GTTGAAGCCA AGCAGGCAAG ATCAGACATC    5520

GAAAAACTCA AGAAGCAAT TAGGGACACA AACAAAGCAG TGCAGTCAGT TCAGAGCTCC    5580

ATAGGAAATT TAATAGTAGC AATTAAATCA GTCCAGGATT ATGTTAACAA AGAAATCGTG    5640

CCATCGATTG CGAGGCTAGG TTGTGAAGCA GCAGGACTTC AATTAGGAAT TGCATTAACA    5700

CAGCATTACT CAGAATTAAC AAACATATTT GGTGATAACA TAGGATCGTT ACAAGAAAAA    5760

GGAATAAAAT TACAAGGTAT AGCATCATTA TACCGCACAA ATATCACAGA ATATTCACA    5820

ACATCAACAG TTGATAAATA TGATATCTAT GATCTGTTAT TTACAGAATC AATAAAGGTG    5880

AGAGTTATAG ATGTTGACTT GAATGATTAC TCAATCACCC TCCAAGTCAG ACTCCCTTTA    5940

TTAACTAGGC TGCTGAACAC TCAGATCTAC AAAGTAGATT CCATATCATA TAACATCCAA    6000
```

```
AACAGAGAAT GGTATATCCC TCTTCCCAGC CATATCATGA CGAAAGGGGC ATTTCTAGGT    6060

GGAGCAGACG TCAAAGAATG TATAGAAGCA TTCAGCAGCT ATATATGCCC TTCTGATCCA    6120

GGATTTGTAT TAAACCATGA AATAGAGAGC TGCTTATCAG GAAACATATC CCAATGTCCA    6180

AGAACAACGG TCACATCAGA CATTGTTCCA AGATATGCAT TTGTCAATGG AGGAGTGGTT    6240

GCAAACTGTA TAACAACCAC CTGTACATGC AACGGAATTG GTAATAGAAT CAATCAACCA    6300

CCTGATCAAG GAGTAAAAAT TATAACACAT AAAGAATGTA GTACAATAGG TATCAACGGA    6360

ATGCTGTTCA ATACAAATAA AGAAGGAACT CTTGCATTCT ATACACCAAA TGATATAACA    6420

CTAAACAATT CTGTTGCACT TGATCCAATT GACATATCAA TCGAGCTCAA CAAGGCCAAA    6480

TCAGATCTAG AAGAATCAAA AGAATGGATA AGAAGGTCAA ATCAAAAACT AGATTCTATT    6540

GGAAATTGGC ATCAATCTAG CACTACAATC ATAATTATTT TGATAATGAT CATTATATTG    6600

TTTATAATTA ATATAACGAT AATTACAATT GCAATTAAGT ATTACAGAAT TCAAAAGAGA    6660

AATCGAGTGG ATCAAAATGA CAAGCCATAT GTACTAACAA ACAAATAACA TATCTACAGA    6720

TCATTAGATA TTAAAATTAT AAAAAACTTA GGAGTAAAGT TACGCAATCC AACTCTACTC    6780

ATATAATTGA GGAAGGACCC AATAGACAAA TCCAAATTCG AGATGGAATA CTGGAAGCAT    6840

ACCAATCACG GAAAGGATGC TGGTAATGAG CTGGAGACGT CTATGGCTAC TCATGGCAAC    6900

AAGCTCACTA ATAAGATAAT ATACATATTA TGGACAATAA TCCTGGTGTT ATTATCAATA    6960

GTCTTCATCA TAGTGCTAAT TAATTCCATC AAAAGTGAAA AGGCCCACGA ATCATTGCTG    7020

CAAGACATAA ATAATGAGTT TATGGAAATT ACAGAAAAGA TCCAAATGGC ATCGGATAAT    7080

ACCAATGATC TAATACAGTC AGGAGTGAAT ACAAGGCTTC TTACAATTCA GAGTCATGTC    7140

CAGAATTACA TACCAATATC ATTGACACAA CAGATGTCAG ATCTTAGGAA ATTCATTAGT    7200

GAAATTACAA TTAGAAATGA TAATCAAGAA GTGCTGCCAC AAAGAATAAC ACATGATGTA    7260

GGTATAAAAC CTTTAAATCC AGATGATTTT TGGAGATGCA CGTCTGGTCT TCCATCTTTA    7320

ATGAAAACTC CAAAAATAAG GTTAATGCCA GGGCCGGGAT TATTAGCTAT GCCAACGACT    7380

GTTGATGGCT GTGTTAGAAC TCCGTCTTTA GTTATAAATG ATCTGATTTA TGCTTATACC    7440

TCAAATCTAA TTACTCGAGG TTGTCAGGAT ATAGGAAAAT CATATCAAGT CTTACAGATA    7500

GGGATAATAA CTGTAAACTC AGACTTGGTA CCTGACTTAA ATCCTAGGAT CTCTCATACC    7560

TTTAACATAA ATGACAATAG GAAGTCATGT TCTCTAGCAC TCCTAAATAT AGATGTATAT    7620

CAACTGTGTT CAACTCCCAA AGTTGATGAA AGATCAGATT ATGCATCATC AGGCATAGAA    7680

GATATTGTAC TTGATATTGT CAATTATGAT GGTTCAATCT CAACAACAAG ATTTAAGAAT    7740

AATAACAAA GCTTTGATCA ACCATATGCT GCACTATACC CATCTGTTGG ACCAGGGATA    7800

TACTACAAAG GCAAAATAAT ATTTCTCGGG TATGGAGGTC TTGAACATCC AATAAATGAG    7860

AATGTAATCT GCAACACAAC TGGGTGCCCC GGGAAAACAC AGAGAGACTG TAATCAAGCA    7920

TCTCATAGTA CTTGGTTTTC AGATAGGAGG ATGGTCAACT CCATCATTGT TGTTGACAAA    7980

GGCTTAAACT CAATTCCAAA ATTGAAAGTA TGGACGATAT CTATGCGACA AAATTACTGG    8040

GGGTCAGAAG GAAGGTTACT TCTACTAGGT AACAAGATCT ATATATATAC AAGATCTACA    8100

AGTTGGCATA GCAAGTTACA ATTAGGAATA ATTGATATTA CTGATTACAG TGATATAAGG    8160

ATAAAATGGA CATGGCATAA TGTGCTATCA AGACCAGGAA ACAATGAATG TCCATGGGGA    8220

CATTCATGTC CAGATGGATG TATAACAGGA GTATATACTG ATGCATATCC ACTCAATCCC    8280

ACAGGGAGCA TTGTGTCATC TGTCATATTA GACTCACAAA AATCGAGAGT GAACCCAGTC    8340
```

```
ATAACTTACT CAACAGCAAC CGAAAGAGTA AACGAGCTGG CCATCCTAAA CAGAACACTC    8400

TCAGCTGGAT ATACAACAAC AAGCTGCATT ACACACTATA ACAAAGGATA TTGTTTTCAT    8460

ATAGTAGAAA TAAATCATAA AAGCTTAAAC ACATTTCAAC CCATGTTGTT CAAAACAGAG    8520

ATTCCAAAAA GCTGCAGTTA ATCATAATTA ACCATAATAT GCATCAATCT ATCTATAATA    8580

CAAGTATATG ATAAGTAATC AGCAATCAGA CAATAGACAA AAGGGAAATA TAAAAAACTT    8640

AGGAGCAAAG CGTGCTCGGG AAATGGACAC TGAATCTAAC AATGGCACTG TATCTGACAT    8700

ACTCTATCCT GAGTGTCACC TTAACTCTCC TATCGTTAAA GGTAAAATAG CACAATTACA    8760

CACTATTATG AGTCTACCTC AGCCTTATGA TATGGATGAC GACTCAATAC TAGTTATCAC    8820

TAGACAGAAA ATAAAACTTA ATAAATTGGA TAAAAGACAA CGATCTATTA GAAGATTAAA    8880

ATTAATATTA ACTGAAAAAG TGAATGACTT AGGAAAATAC ACATTTATCA GATATCCAGA    8940

AATGTCAAAA GAAATGTTCA AATTATATAT ACCTGGTATT AACAGTAAAG TGACTGAATT    9000

ATTACTTAAA GCAGATAGAA CATATAGTCA AATGACTGAT GGATTAAGAG ATCTATGGAT    9060

TAATGTGCTA TCAAAATTAG CCTCAAAAAA TGATGGAAGC AATTATGATC TTAATGAAGA    9120

AATTAATAAT ATATCGAAAG TTCACACAAC CTATAAATCA GATAAATGGT ATAATCCATT    9180

CAAAACATGG TTTACTATCA AGTATGATAT GAGAAGATTA CAAAAAGCTC GAAATGAGAT    9240

CACTTTTAAT GTTGGGAAGG ATTATAACTT GTTAGAAGAC CAGAAGAATT TCTTATTGAT    9300

ACATCCAGAA TTGGTTTTGA TATTAGATAA ACAAAACTAT AATGGTTATC TAATTACTCC    9360

TGAATTAGTA TTGATGTATT GTGACGTAGT CGAAGGCCGA TGGAATATAA GTGCATGTGC    9420

TAAGTTAGAT CCAAAATTAC AATCTATGTA TCAGAAAGGT AATAACCTGT GGGAAGTGAT    9480

AGATAAAATTG TTTCCAATTA TGGGAGAAAA GACATTTGAT GTGATATCGT TATTAGAACC    9540

ACTTGCATTA TCCTTAATTC AAACTCATGA TCCTGTTAAA CAACTAAGAG GAGCTTTTTT    9600

AAATCATGTG TTATCCGAGA TGGAATTAAT ATTTGAATCT AGAGAATCGA TTAAGGAATT    9660

TCTGAGTGTA GATTACATTG ATAAAATTTT AGATATATTT AATAAGTCTA CAATAGATGA    9720

AATAGCAGAG ATTTTCTCTT TTTTTAGAAC ATTTGGGCAT CCTCCATTAG AAGCTAGTAT    9780

TGCAGCAGAA AAGGTTAGAA AATATATGTA TATTGGAAAA CAATTAAAAT TTGACACTAT    9840

TAATAAATGT CATGCTATCT TCTGTACAAT AATAATTAAC GGATATAGAG AGAGGCATGG    9900

TGGACAGTGG CCTCCTGTGA CATTACCTGA TCATGCACAC GAATTCATCA TAAATGCTTA    9960

CGGTTCAAAC TCTGCGATAT CATATGAAAA TGCTGTTGAT TATTACCAGA GCTTTATAGG    10020

AATAAAATTC AATAAATTCA TAGAGCCTCA GTTAGATGAG GATTTGACAA TTTATATGAA    10080

AGATAAAGCA TTATCTCCAA AAAAATCAAA TTGGGACACA GTTTATCCTG CATCTAATTT    10140

ACTGTACCGT ACTAACGCAT CCAACGAATC ACGAAGATTA GTTGAAGTAT TTATAGCAGA    10200

TAGTAAATTT GATCCTCATC AGATATTGGA TTATGTAGAA TCTGGGGACT GGTTAGATGA    10260

TCCAGAATTT AATATTTCTT ATAGTCTTAA AGAAAAAGAG ATCAAACAGG AAGGTAGACT    10320

CTTTGCAAAA ATGACATACA AAATGAGAGC TACACAAGTT TTATCAGAGA CCCTACTTGC    10380

AAATAACATA GGAAAATTCT TTCAAGAAAA TGGGATGGTG AAGGGAGAGA TTGAATTACT    10440

TAAGAGATTA ACAACCATAT CAATATCAGG AGTTCCACGG TATAATGAAG TGTACAATAA    10500

TTCTAAAAGC CATACAGATG ACCTTAAAAC CTACAATAAA ATAAGTAATC TTAATTTGTC    10560

TTCTAATCAG AAATCAAAGA AATTTGAATT CAAGTCAACG GATATCTACA ATGATGGATA    10620

CGAGACTGTG AGCTGTTTCC TAACAACAGA TCTCAAAAAA TACTGTCTTA ATTGGAGATA    10680

TGAATCAACA GCTCTATTTG GAGAAACTTG CAACCAAATA TTTGGATTAA ATAAATTGTT    10740
```

```
TAATTGGTTA CACCCTCGTC TTGAAGGAAG TACAATCTAT GTAGGTGATC CTTACTGTCC    10800

TCCATCAGAT AAAGAACATA TATCATTAGA GGATCACCCT GATTCTGGTT TTTACGTTCA    10860

TAACCCAAGA GGGGGTATAG AAGGATTTTG TCAAAAATTA TGGACACTCA TATCTATAAG    10920

TGCAATACAT CTAGCAGCTG TTAGAATAGG CGTGAGGGTG ACTGCAATGG TTCAAGGAGA    10980

CAATCAAGCT ATAGCTGTAA CCACAAGAGT ACCCAACAAT TATGACTACA GAGTTAAGAA    11040

GGAGATAGTT TATAAAGATG TAGTGAGATT TTTTGATTCA TTAAGAGAAG TGATGGATGA    11100

TCTAGGTCAT GAACTTAAAT TAAATGAAAC GATTATAAGT AGCAAGATGT TCATATATAG    11160

CAAAAGAATC TATTATGATG GGAGAATTCT TCCTCAAGCT CTAAAAGCAT TATCTAGATG    11220

TGTCTTCTGG TCAGAGACAG TAATAGACGA AACAAGATCA GCATCTTCAA ATTTGGCAAC    11280

ATCATTTGCA AAAGCAATTG AGAATGGTTA TTCACCTGTT CTAGGATATG CATGCTCAAT    11340

TTTTAAGAAT ATTCAACAAC TATATATTGC CCTTGGGATG AATATCAATC CAACTATAAC    11400

ACAGAATATC AGAGATCAGT ATTTTAGGAA TCCAAATTGG ATGCAATATG CCTCTTTAAT    11460

ACCTGCTAGT GTTGGGGGAT TCAATTACAT GGCCATGTCA AGATGTTTTG TAAGGAATAT    11520

TGGTGATCCA TCAGTTGCCG CATTGGCTGA TATTAAAAGA TTTATTAAGG CGAATCTATT    11580

AGACCGAAGT GTTCTTTATA GGATTATGAA TCAAGAACCA GGTGAGTCAT CTTTTTTGGA    11640

CTGGGCTTCA GATCCATATT CATGCAATTT ACCACAATCT CAAAATATAA CCACCATGAT    11700

AAAAAATATA ACAGCAAGGA ATGTATTACA AGATTCACCA AATCCATTAT TATCTGGATT    11760

ATTCACAAAT ACAATGATAG AAGAAGATGA AGAATTAGCT GAGTTCCTGA TGGACAGGAA    11820

GGTAATTCTC CCTAGAGTTG CACATGATAT TCTAGATAAT TCTCTCACAG GAATTAGAAA    11880

TGCCATAGCT GGAATGTTAG ATACGACAAA ATCACTAATT CGGGTTGGCA TAAATAGAGG    11940

AGGACTGACA TATAGTTTGT TGAGGAAAAT CAGTAATTAC GATCTAGTAC AATATGAAAC    12000

ACTAAGTAGG ACTTTGCGAC TAATTGTAAG TGATAAAATC AAGTATGAAG ATATGTGTTC    12060

GGTAGACCTT GCCATAGCAT TGCGACAAAA GATGTGGATT CATTTATCAG GAGGAAGGAT    12120

GATAAGTGGA CTTGAAACGC CTGACCCATT AGAATTACTA TCTGGGGTAG TAATAACAGG    12180

ATCAGAACAT TGTAAAATAT GTTATTCTTC AGATGGCACA AACCCATATA CTTGGATGTA    12240

TTTACCCGGT AATATCAAAA TAGGATCAGC AGAAACAGGT ATATCGTCAT TAAGAGTTCC    12300

TTATTTTGGA TCAGTCACTG ATGAAAGATC TGAAGCACAA TTAGGATATA TCAAGAATCT    12360

TAGTAAACCT GCAAAAGCCG CAATAAGAAT AGCAATGATA TATACATGGG CATTTGGTAA    12420

TGATGAGATA TCTTGGATGG AAGCCTCACA GATAGCACAA ACACGTGCAA ATTTTACACT    12480

AGATAGTCTC AAAATTTTAA CACCGGTAGC TACATCAACA AATTTATCAC ACAGATTAAA    12540

GGATACTGCA ACTCAGATGA AATTCTCCAG TACATCATTG ATCAGAGTCA GCAGATTCAT    12600

AACAATGTCC AATGATAACA TGTCTATCAA AGAAGCTAAT GAAACCAAAG ATACTAATCT    12660

TATTTATCAA CAAATAATGT TAACAGGATT AAGTGTTTTC GAATATTTAT TTAGATTAAA    12720

AGAAACCACA GGACACAACC CTATAGTTAT GCATCTGCAC ATAGAAGATG AGTGTTGTAT    12780

TAAAGAAAGT TTTAATGATG AACATATTAA TCCAGAGTCT ACATTAGAAT TAATTCGATA    12840

TCCTGAAAGT AATGAATTTA TTTATGATAA AGACCCACTC AAAGATGTGG ACTTATCAAA    12900

ACTTATGGTT ATTAAAGACC ATTCTTACAC AATTGATATG AATTATTGGG ATGATACTGA    12960

CATCATACAT GCAATTTCAA TATGTACTGC AATTACAATA GCAGATACTA TGTCACAATT    13020

AGATCGAGAT AATTTAAAAG AGATAATAGT TATTGCAAAT GATGATGATA TTAATAGCTT    13080
```

-continued

| | | | | | |
|---|---|---|---|---|---|
|AATCACTGAA|TTTTTGACTC|TTGACATACT|TGTATTTCTC|AAGACATTTG|GTGGATTATT|13140|
|AGTAAATCAA|TTTGCATACA|CTCTTTATAG|TCTAAAAATA|GAAGGTAGGG|ATCTCATTTG|13200|
|GGATTATATA|ATGAGAACAC|TGAGAGATAC|TTCCCATTCA|ATATTAAAAG|TATTATCTAA|13260|
|TGCATTATCT|CATCCTAAAG|TATTCAAGAG|GTTCTGGGAT|TGTGGAGTTT|TAAACCCTAT|13320|
|TTATGGTCCT|AATACTGCTA|GTCAAGACCA|GATAAAACTT|GCCCTATCTA|TATGTGAATA|13380|
|TTCACTAGAT|CTATTTATGA|GAGAATGGTT|GAATGGTGTA|TCACTTGAAA|TATACATTTG|13440|
|TGACAGCGAT|ATGGAAGTTG|CAAATGATAG|GAAACAAGCC|TTTATTTCTA|GACACCTTTC|13500|
|ATTTGTTTGT|TGTTTAGCAG|AAATTGCATC|TTTCGGACCT|AACCTGTTAA|ACTTAACATA|13560|
|CTTGGAGAGA|CTTGATCTAT|TGAAACAATA|TCTTGAATTA|ATATTAAAG|AAGACCCTAC|13620|
|TCTTAAATAT|GTACAAATAT|CTGGATTATT|AATTAAATCG|TTCCCATCAA|CTGTAACATA|13680|
|CGTAAGAAAG|ACTGCAATCA|AATATCTAAG|GATTCGCGGT|ATTAGTCCAC|CTGAGGTAAT|13740|
|TGATGATTGG|GATCCGGTAG|AAGATGAAAA|TATGCTGGAT|AACATTGTCA|AAACTATAAA|13800|
|TGATAACTGT|AATAAAGATA|ATAAAGGGAA|TAAAATTAAC|AATTTCTGGG|GACTAGCACT|13860|
|TAAGAACTAT|CAAGTCCTTA|AAATCAGATC|TATAACAAGT|GATTCTGATG|ATAATGATAG|13920|
|ACTAGATGCT|AATACAAGTG|GTTTGACACT|TCCTCAAGGA|GGGAATTATC|TATCGCATCA|13980|
|ATTGAGATTA|TTCGGAATCA|ACAGCACTAG|TTGTCTGAAA|GCTCTTGAGT|TATCACAAAT|14040|
|TTTAATGAAG|GAAGTCAATA|AAGACAAGGA|CAGGCTCTTC|CTGGGAGAAG|GAGCAGGAGC|14100|
|TATGCTAGCA|TGTTATGATG|CCACATTAGG|ACCTGCAGTT|AATTATTATA|ATTCAGGTTT|14160|
|GAATATAACA|GATGTAATTG|GTCAACGAGA|ATTGAAAATA|TTTCCTTCAG|AGGTATCATT|14220|
|AGTAGGTAAA|AAATTAGGAA|ATGTGACACA|GATTCTTAAC|AGGGTAAAAG|TACTGTTCAA|14280|
|TGGGAATCCT|AATTCAACAT|GGATAGGAAA|TATGGAATGT|GAGAGCTTAA|TATGGAGTGA|14340|
|ATTAAATGAT|AAGTCCATTG|GATTAGTACA|TTGTGTATATG|GAAGGAGCTA|TCGGTAAATC|14400|
|AGAAGAAACT|GTTCTACATG|AACATTATAG|TGTTATAAGA|ATTACATACT|TGATTGGGGA|14460|
|TGATGATGTT|GTTTTAGTTT|CCAAAATTAT|ACCTACAATC|ACTCCGAATT|GGTCTAGAAT|14520|
|ACTTTATCTA|TATAAATTAT|ATTGGAAAGA|TGTAAGTATA|ATATCACTCA|AAACTTCTAA|14580|
|TCCTGCATCA|ACAGAATTAT|ATCTAATTTC|GAAAGATGCA|TATTGTACTA|TAATGGAACC|14640|
|TAGTGAAATT|GTTTTATCAA|AACTTAAAAG|ATTGTCACTC|TTGGAAGAAA|ATAATCTATT|14700|
|AAAATGGATC|ATTTTATCAA|AGAAGAGGAA|TAATGAATGG|TTACATCATG|AAATCAAAGA|14760|
|AGGAGAAAGA|GATTATGGAA|TCATGAGACC|ATATCATATG|GCACTACAAA|TCTTTGGATT|14820|
|TCAAATCAAT|TTAAATCATC|TGGCGAAAGA|ATTTTTATCA|ACCCCAGATC|TGACTAATAT|14880|
|CAACAATATA|ATCCAAAGTT|TTCAGCGAAC|AATAAAGGAT|GTTTTATTTG|AATGGATTAA|14940|
|TATAACTCAT|GATGATAAGA|GACATAAATT|AGGCGGAAGA|TATAACATAT|TCCCACTGAA|15000|
|AAATAAGGGA|AAGTTAAGAC|TGCTATCGAG|AAGACTAGTA|TTAAGTTGGA|TTTCATTATC|15060|
|ATTATCGACT|CGATTACTTA|CAGGTCGCTT|TCCTGATGAA|AAATTTGAAC|ATAGAGCACA|15120|
|GACTGGATAT|GTATCATTAG|CTGATACTGA|TTTAGAATCA|TTAAAGTTAT|TGTCGAAAAA|15180|
|CATCATTAAG|AATTACAGAG|AGTGTATAGG|ATCAATATCA|TATTGGTTTC|TAACCAAAGA|15240|
|AGTTAAAATA|CTTATGAAAT|TGATCGGTGG|TGCTAAATTA|TTAGGAATTC|CCAGACAATA|15300|
|TAAAGAACCC|GAAGACCAGT|TATTAGAAAA|CTACAATCAA|CATGATGAAT|TGATATCGA|15360|
|TTAAAACATA|AATACAATGA|AGATATATCC|TAACCTTTAT|CTTTAAGCCT|AGGAATAGAC|15420|
|AAAAAGTAAG|AAAAACATGT|AATATATATA|TACCAAACAG|AGTTCTTCTC|TTGTTTGGTG|15480|

```
GGTCGGCATG GCATCTCCAC CTCCTCGCGG TCCGGACCTG GCATCCGAA  GGAGGACGCA    15540

CGTCCACTCG GATGGCTAAG GGAGAGCCTG CAGTAGCATA ACCCCTTGGG GCCTCTAAAC    15600

GGGTCTTGAG GGGTTTTTTG CTGAAAGGAG GAACTATATA CGCGTCGACG GGCCCCGCGC    15660

(2) INFORMATION FOR SEQ ID NO:15:

(i) SEQUENCE CHARACTERISTICS:
        (A) LENGTH: 15666 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TAATACGACT CACTATAGGA CCAAACAAGA GAAGAAACTT GTCTGGGAAT ATAAATTTAA      60

CTTTAAATTA ACTTAGGATT AAAGACATTG ACTAGAAGGT CAAGAAAAGG GAACTCTATA     120

ATTTCAAAAA TGTTGAGCCT ATTTGATACA TTTAATGCAC GTAGGCAAGA AAACATAACA     180

AAATCAGCCG GTGGAGCTAT CATTCCTGGA CAGAAAATA  CTGTCTCTAT ATTCGCCCTT     240

GGACCGACAA TAACTGATGA TAATGAGAAA ATGACATTAG CTCTTCTATT TCTATCTCAT     300

TCACTAGATA ATGAGAAACA ACATGCACAA AGGGCAGGGT TCTTGGTGTC TTTATTGTCA     360

ATGGCTTATG CCAATCCAGA GCTCTACCTA ACAACAAATG GAAGTAATGC AGATGTCAAG     420

TATGTCATAT ACATGATTGA GAAAGATCTA AAACGGCAAA AGTATGGAGG ATTTGTGGTT     480

AAGACGAGAG AGATGATATA TGAAAAGACA ACTGATTGGA TATTTGGAAG TGACCTGGAT     540

TATGATCAGG AAACTATGTT GCAGAACGGC AGGAACAATT CAACAATTGA AGACCTTGTC     600

CACACATTTG GGTATCCATC ATGTTTAGGA GCTCTTATAA TACAGATCTG GATAGTTCTG     660

GTCAAAGCTA TCACTAGTAT CTCAGGGTTA AGAAAAGGCT TTTTCACCCG ATTGGAAGCT     720

TTCAGACAAG ATGGAACAGT GCAGGCAGGG CTGGTATTGA GCGGTGACAC AGTGGATCAG     780

ATTGGGTCAA TCATGCGGTC TCAACAGAGC TTGGTAACTC TTATGGTTGA ACATTAATA     840

ACAATGAATA CCAGCAGAAA TGACCTCACA ACCATAGAAA AGAATATACA AATTGTTGGC     900

AACTACATAA GAGATGCAGG TCTCGCTTCA TTCTTCAATA CAATCAGATA TGGAATTGAG     960

ACCAGAATGG CAGCTTTGAC TCTATCCACT CTCAGACCAG ATATCAATAG ATTAAAAGCT    1020

TTGATGGAAC TGTATTTATC AAAGGGACCA CGCGCTCCTT TCATCTGTAT CCTCAGAGAT    1080

CCTATACATG GTGAGTTCGC ACCAGGCAAC TATCCTGCCA TATGGAGCTA TGCAATGGGG    1140

GTGGCAGTTG TACAAAATAG AGCCATGCAA CAGTATGTGA CGGGAAGATC ATATCTAGAC    1200

ATTGATATGT TCCAGCTAGG ACAAGCAGTA GCACGTGATG CCGAAGCTCA AATGAGCTCA    1260

ACACTGGAAG ATGAACTTGG AGTGACACAC GAATCTAAAG AAAGCTTGAA GAGACATATA    1320

AGGAACATAA ACAGTTCAGA GACATCTTTC CACAAACCGA CAGGTGGATC AGCCATAGAG    1380

ATGGCAATAG ATGAAGAGCC AGAACAATTC GAACATAGAG CAGATCAAGA ACAAAATGGA    1440

GAACCTCAAT CATCCATAAT TCAATATGCC TGGGCAGAAG GAAATAGAAG CGATGATCAG    1500

ACTGAGCAAG CTACAGAATC TGACAATATC AAGACCGAAC AACAAAACAT CAGAGACAGA    1560

CTAAACAAGA GACTCAACGA CAAGAAGAAA CAAAGCAGTC AACCACCCAC TAATCCCACA    1620

AACAGAACAA ACCAGGACGA AATAGATGAT CTGTTTAACG CATTTGGAAG CAACTAATCG    1680

AATCAACATT TTAATCTAAA TCAATAATAA ATAAGAAAAA CTTAGGATTA AGAATCCTA     1740

TCATACCGGA ATATAGGGTG GTAAATTTAG AGTCTGCTTG AAACTCAATC AATAGAGAGT    1800
```

```
TGATGGAAAG CGATGCTAAA AACTATCAAA TCATGGATTC TTGGGAAGAG GAATCAAGAG    1860

ATAAATCAAC TAATATCTCC TCGGCCCTCA ACATCATTGA ATTCATACTC AGCACCGACC    1920

CCCAAGAAGA CTTATCGGAA AACGACACAA TCAACACAAG AACCCAGCAA CTCAGTGCCA    1980

CCATCTGTCA ACCAGAAATC AAACCAACAG AAACAAGTGA GAAAGATAGT GGATCAACTG    2040

ACAAAAATAG ACAGTCTGGG TCATCACACG AATGTACAAC AGAAGCAAAA GATAGAAATA    2100

TTGATCAGGA AACTGTACAG AGAGGACCTG GGAGAAGAAG CAGCTCAGAT AGTAGAGCTG    2160

AGACTGTGGT CTCTGGAGGA ATCCCCAGAA GCATCACAGA TTCTAAAAAT GGAACCCAAA    2220

ACACGGAGGA TATTGATCTC AATGAAATTA GAAAGATGGA TAAGGACTCT ATTGAGGGGA    2280

AAATGCGACA ATCTGCAAAT GTTCCAAGCG AGATATCAGG AAGTGATGAC ATATTTACAA    2340

CAGAACAAAG TAGAAACAGT GATCATGGAA GAAGCCTGGA ATCTATCAGT ACACCTGATA    2400

CAAGATCAAT AAGTGTTGTT ACTGCTGCAA CACCAGATGA TGAAGAAGAA ATACTAATGA    2460

AAAATAGTAG GACAAAGAAA AGTTCTTCAA CACATCAAGA AGATGACAAA AGAATTAAAA    2520

AAGGGGGAAA AGGGAAAGAC TGGTTTAAGA AATCAAAAGA TACCGACAAC CAGATACCAA    2580

CATCAGACTA CAGATCCACA TCAAAAGGGC AGAAGAAAAT CTCAAAGACA CAACCACCA    2640

ACACCGACAC AAAGGGGCAA ACAGAAATAC AGACAGAATC ATCAGAAACA CAATCCTCAT    2700

CATGGAATCT CATCATCGAC AACAACACCG ACCGGAACGA ACAGACAAGC ACAACTCCTC    2760

CAACAACAAC TTCCAGATCA ACTTATACAA AAGAATCGAT CCGAACAAAC TCTGAATCCA    2820

AACCCAAGAC ACAAAAGACA AATGGAAAGG AAAGGAAGGA TACAGAAGAG AGCAATCGAT    2880

TTACAGAGAG GGCAATTACT CTATTGCAGA ATCTTGGTGT AATTCAATCC ACATCAAAAC    2940

TAGATTTATA TCAAGACAAA CGAGTTGTAT GTGTAGCAAA TGTACTAAAC AATGTAGATA    3000

CTGCATCAAA GATAGATTTC CTGGCAGGAT TAGTCATAGG GGTTTCAATG GACAACGACA    3060

CAAAATTAAC ACAGATACAA AATGAAATGC TAAACCTCAA AGCAGATCTA AGAAAATGG    3120

ACGAATCACA TAGAAGATTG ATAGAAAATC AAAGAGAACA ACTGTCATTG ATCACGTCAC    3180

TAATTTCAAA TCTCAAAATT ATGACTGAGA GAGGAGGAAA GAAAGACCAA AATGAATCCA    3240

ATGAGAGAGT ATCCATGATC AAAACAAAAT TGAAAGAAGA AAAGATCAAG AAGACCAGGT    3300

TTGACCCACT TATGGAGGCA CAAGGCATTG ACAAGAATAT ACCCGATCTA TATCGACATG    3360

CAGGAGATAC ACTAGAGAAC GATGTACAAG TTAAATCAGA GATATTAAGT TCATACAATG    3420

AGTCAAATGC AACAAGACTA ATACCCAAAA AAGTGAGCAG TACAATGAGA TCACTAGTTG    3480

CAGTCATCAA CAACAGCAAT CTCTCACAAA GCACAAAACA ATCATACATA AACGAACTCA    3540

AACGTTGCAA AAATGATGAA GAAGTATCTG AATTAATGGA CATGTTCAAT GAAGATGTCA    3600

ACAATTGCCA ATGATCCAAC AAAGAAACGA CACCGAACAA ACAGACAAGA AACAACAGTA    3660

GATCAAAACC TGTCAACACA CACAAAATCA AGCAGAATGA AACAACAGAT ATCAATCAAT    3720

ATACAAATAA GAAAAACTTA GGATTAAAGA ATAAATTAAT CCTTGTCCAA AATGAGTATA    3780

ACTAACTCTG CAATATACAC ATTCCCAGAA TCATCATTCT CTGAAAATGG TCATATAGAA    3840

CCATTACCAC TCAAAGTCAA TGAACAGAGG AAAGCAGTAC CCCACATTAG AGTTGCCAAG    3900

ATCGGAAATC CACCAAAACA CGGATCCCGG TATTTAGATG TCTTCTTACT CGGCTTCTTC    3960

GAGATGGAAC GAATCAAAGA CAAATACGGG AGTGTGAATG ATCTCGACAG TGACCCGAGT    4020

TACAAAGTTT GTGGCTCTGG ATCATTACCA ATCGGATTGG CTAAGTACAC TGGGAATGAC    4080

CAGGAATTGT TACAAGCCGC AACCAAACTG GATATAGAAG TGAGAAGAAC AGTCAAAGCG    4140
```

-continued

| | |
|---|---|
| AAAGAGATGG TTGTTTACAC GGTACAAAAT ATAAAACCAG AACTGTACCC ATGGTCCAAT | 4200 |
| AGACTAAGAA AAGGAATGCT GTTCGATGCC AACAAAGTTG CTCTTGCTCC TCAATGTCTT | 4260 |
| CCACTAGATA GGAGCATAAA ATTTAGAGTA ATCTTCGTGA ATTGTACGGC AATTGGATCA | 4320 |
| ATAACCTTGT TCAAAATTCC TAAGTCAATG GCATCACTAT CTCTACCCAA CACAATATCA | 4380 |
| ATCAATCTGC AGGTACACAT AAAAACAGGG GTTCAGACTG ATTCTAAAGG GATAGTTCAA | 4440 |
| ATTTTGGATG AGAAAGGCGA AAAATCACTG AATTTCATGG TCCATCTCGG ATTGATCAAA | 4500 |
| AGAAAAGTAG GCAGAATGTA CTCTGTTGAA TACTGTAAAC AGAAAATCGA GAAAATGAGA | 4560 |
| TTGATATTTT CTTTAGGACT AGTTGGAGGA ATCAGTCTTC ATGTCAATGC AACTGGGTCC | 4620 |
| ATATCAAAAA CACTAGCAAG TCAGCTGGTA TTCAAAAGAG AGATTTGTTA TCCTTTAATG | 4680 |
| GATCTAAATC CGCATCTCAA TCTAGTTATC TGGGCTTCAT CAGTAGAGAT TACAAGAGTG | 4740 |
| GATGCAATTT TCCAACCTTC TTTACCTGGC GAGTTCAGAT ACTATCCTAA TATTATTGCA | 4800 |
| AAAGGAGTTG GGAAAATCAA ACAATGGAAC TAGTAATCTC TATTTTAGTC CGGACGTATC | 4860 |
| TATTAAGCCG AAGCAAATAA AGGATAATCA AAAACTTAGG ACAAAAGAGG TCAATACCAA | 4920 |
| CAACTATTAG CAGTCACACT CGCAAGAATA AGAGAGAAGG GACCAAAAAA GTCAAATAGG | 4980 |
| AGAAATCAAA ACAAAAGGTA CAGAACACCA GAACAACAAA ATCAAAACAT CCAACTCACT | 5040 |
| CAAAACAAAA ATTCCAAAAG AGACCGGCAA CACAACAAGC ACTGAACACA ATGCCAACTT | 5100 |
| CAATACTGCT AATTATTACA ACCATGATCA TGGCATCTTT CTGCCAAATA GATATCACAA | 5160 |
| AACTACAGCA CGTAGGTGTA TTGGTCAACA GTCCCAAAGG GATGAAGATA TCACAAAACT | 5220 |
| TTGAAACAAG ATATCTAATT TTGAGCCTCA TACCAAAAAT AGAAGACTCT AACTCTTGTG | 5280 |
| GTGACCAACA GATCAAGCAA TACAAGAAGT TATTGGATAG ACTGATCATC CCTTTATATG | 5340 |
| ATGGATTAAG ATTACAGAAA GATGTGATAG TAACCAATCA AGAATCCAAT GAAAACACTG | 5400 |
| ATCCCAGAAC AAAACGATTC TTTGGAGGGG TAATTGGAAC CATTGCTCTG GGAGTAGCAA | 5460 |
| CCTCAGCACA AATTACAGCG GCAGTTGCTC TGGTTGAAGC CAAGCAGGCA AGATCAGACA | 5520 |
| TCGAAAAACT CAAAGAAGCA ATTAGGGACA CAAACAAAGC AGTGCAGTCA GTTCAGAGCT | 5580 |
| CCATAGGAAA TTTAATAGTA GCAATTAAAT CAGTCCAGGA TTATGTTAAC AAAGAAATCG | 5640 |
| TGCCATCGAT TGCGAGGCTA GGTTGTGAAG CAGCAGGACT TCAATTAGGA ATTGCATTAA | 5700 |
| CACAGCATTA CTCAGAATTA ACAAACATAT TTGGTGATAA CATAGGATCG TTACAAGAAA | 5760 |
| AAGGAATAAA ATTACAAGGT ATAGCATCAT TATACCGCAC AAATATCACA GAAATATTCA | 5820 |
| CAACATCAAC AGTTGATAAA TATGATATCT ATGATCTGTT ATTTACAGAA TCAATAAAGG | 5880 |
| TGAGAGTTAT AGATGTTGAC TTGAATGATT ACTCAATCAC CCTCCAAGTC AGACTCCCTT | 5940 |
| TATTAACTAG GCTGCTGAAC ACTCAGATCT ACAAAGTAGA TTCCATATCA TATAACATCC | 6000 |
| AAAACAGAGA ATGGTATATC CCTCTTCCCA GCCATATCAT GACGAAAGGG GCATTTCTAG | 6060 |
| GTGGAGCAGA CGTCAAAGAA TGTATAGAAG CATTCAGCAG CTATATATGC CCTTCTGATC | 6120 |
| CAGGATTTGT ATTAAACCAT GAAATAGAGA GCTGCTTATC AGGAAACATA TCCCAATGTC | 6180 |
| CAAGAACAAC GGTCACATCA GACATTGTTC CAAGATATGC ATTTGTCAAT GGAGGAGTGG | 6240 |
| TTGCAAACTG TATAACAACC ACCTGTACAT GCAACGGAAT TGGTAATAGA ATCAATCAAC | 6300 |
| CACCTGATCA AGGAGTAAAA ATTATAACAC ATAAAGAATG TAGTACAATA GGTATCAACG | 6360 |
| GAATGCTGTT CAATACAAAT AAAGAAGGAA CTCTTGCATT CTATACACCA AATGATATAA | 6420 |
| CACTAAACAA TTCTGTTGCA CTTGATCCAA TTGACATATA AATCGAGCTC AACAAGGCCA | 6480 |
| AATCAGATCT AGAAGAATCA AAAGAATGGA TAAGAAGGTC AAATCAAAAA CTAGATTCTA | 6540 |

```
TTGGAAATTG GCATCAATCT AGCACTACAA TCATAATTAT TTTGATAATG ATCATTATAT    6600

TGTTTATAAT TAATATAACG ATAATTACAA TTGCAATTAA GTATTACAGA ATTCAAAAGA    6660

GAAATCGAGT GGATCAAAAT GACAAGCCAT ATGTACTAAC AAACAAATAA CATATCTACA    6720

GATCATTAGA TATTAAAATT ATAAAAAACT TAGGAGTAAA GTTACGCAAT CCAACTCTAC    6780

TCATATAATT GAGGAAGGAC CCAATAGACA AATCCAAATT CGAGATGGAA TACTGGAAGC    6840

ATACCAATCA CGGAAAGGAT GCTGGTAATG AGCTGGAGAC GTCTATGGCT ACTCATGGCA    6900

ACAAGCTCAC TAATAAGATA ATATACATAT TATGGACAAT AATCCTGGTG TTATTATCAA    6960

TAGTCTTCAT CATAGTGCTA ATTAATTCCA TCAAAAGTGA AAAGGCCCAC GAATCATTGC    7020

TGCAAGACAT AAATAATGAG TTTATGGAAA TTACAGAAAA GATCCAAATG GCATCGGATA    7080

ATACCAATGA TCTAATACAG TCAGGAGTGA ATACAAGGCT TCTTACAATT CAGAGTCATG    7140

TCCAGAATTA CATACCAATA TCATTGACAC AACAGATGTC AGATCTTAGG AAATTCATTA    7200

GTGAAATTAC AATTAGAAAT GATAATCAAG AAGTGCTGCC ACAAAGAATA ACACATGATG    7260

TAGGTATAAA ACCTTTAAAT CCAGATGATT TTTGGAGATG CACGTCTGGT CTTCCATCTT    7320

TAATGAAAAC TCCAAAAATA AGGTTAATGC CAGGGCCGGG ATTATTAGCT ATGCCAACGA    7380

CTGTTGATGG CTGTGTTAGA ACTCCGTCTT TAGTTATAAA TGATCTGATT TATGCTTATA    7440

CCTCAAATCT AATTACTCGA GGTTGTCAGG ATATAGGAAA ATCATATCAA GTCTTACAGA    7500

TAGGGATAAT AACTGTAAAC TCAGACTTGG TACCTGACTT AAATCCTAGG ATCTCTCATA    7560

CCTTTAACAT AAATGACAAT AGGAAGTCAT GTTCTCTAGC ACTCCTAAAT ATAGATGTAT    7620

ATCAACTGTG TTCAACTCCC AAAGTTGATG AAAGATCAGA TTATGCATCA TCAGGCATAG    7680

AAGATATTGT ACTTGATATT GTCAATTATG ATGGTTCAAT CTCAACAACA AGATTTAAGA    7740

ATAATAACAT AAGCTTTGAT CAACCATATG CTGCACTATA CCCATCTGTT GGACCAGGGA    7800

TATACTACAA AGGCAAAATA ATATTTCTCG GGTATGGAGG TCTTGAACAT CCAATAAATG    7860

AGAATGTAAT CTGCAACACA ACTGGGTGCC CCGGGAAAAC ACAGAGAGAC TGTAATCAAG    7920

CATCTCATAG TACTTGGTTT TCAGATAGGA GGATGGTCAA CTCCATCATT GTTGTTGACA    7980

AAGGCTTAAA CTCAATTCCA AAATTGAAAG TATGGACGAT ATCTATGCGA CAAAATTACT    8040

GGGGGTCAGA AGGAAGGTTA CTTCTACTAG GTAACAAGAT CTATATATAT ACAAGATCTA    8100

CAAGTTGGCA TAGCAAGTTA CAATTAGGAA TAATTGATAT TACTGATTAC AGTGATATAA    8160

GGATAAAATG GACATGGCAT AATGTGCTAT CAAGACCAGG AAACAATGAA TGTCCATGGG    8220

GACATTCATG TCCAGATGGA TGTATAACAG GAGTATATAC TGATGCATAT CCACTCAATC    8280

CCACAGGGAG CATTGTGTCA TCTGTCATAT TAGACTCACA AAAATCGAGA GTGAACCCAG    8340

TCATAACTTA CTCAACAGCA ACCGAAAGAG TAAACGAGCT GGCCATCCTA AACAGAACAC    8400

TCTCAGCTGG ATATACAACA ACAAGCTGCA TTACACACTA TAACAAAGGA TATTGTTTTC    8460

ATATAGTAGA AATAAATCAT AAAAGCTTAA ACACATTTCA ACCCATGTTG TTCAAAACAG    8520

AGATTCCAAA AAGCTGCAGT TAATCATAAT TAACCATAAT ATGCATCAAT CTATCTATAA    8580

TACAAGTATA TGATAAGTAA TCAGCAATCA GACAATAGAC AAAAGGGAAA TATAAAAAAC    8640

TTAGGAGCAA AGCGTGCTCG GGAAATGGAC ACTGAATCTA ACAATGGCAC TGTATCTGAC    8700

ATACTCTATC CTGAGTGTCA CCTTAACTCT CCTATCGTTA AAGGTAAAAT AGCACAATTA    8760

CACACTATTA TGAGTCTACC TCAGCCTTAT GATATGGATG ACGACTCAAT ACTAGTTATC    8820

ACTAGACAGA AAATAAAACT TAATAAATTG GATAAAAGAC AACGATCTAT TAGAAGATTA    8880
```

```
AAATTAATAT TAACTGAAAA AGTGAATGAC TTAGGAAAAT ACACATTTAT CAGATATCCA      8940

GAAATGTCAA AAGAAATGTT CAAATTATAT ATACCTGGTA TTAACAGTAA AGTGACTGAA      9000

TTATTACTTA AAGCAGATAG AACATATAGT CAAATGACTG ATGGATTAAG AGATCTATGG      9060

ATTAATGTGC TATCAAAATT AGCCTCAAAA AATGATGGAA GCAATTATGA TCTTAATGAA      9120

GAAATTAATA ATATATCGAA AGTTCACACA ACCTATAAAT CAGATAAATG GTATAATCCA      9180

TTCAAAACAT GGTTTACTAT CAAGTATGAT ATGAGAAGAT TACAAAAAGC TCGAAATGAG      9240

ATCACTTTTA ATGTTGGGAA GGATTATAAC TTGTTAGAAG ACCAGAAGAA TTTCTTATTG      9300

ATACATCCAG AATTGGTTTT GATATTAGAT AAACAAAACT ATAATGGTTA TCTAATTACT      9360

CCTGAATTAG TATTGATGTA TTGTGACGTA GTCGAAGGCC GATGGAATAT AAGTGCATGT      9420

GCTAAGTTAG ATCCAAAATT ACAATCTATG TATCAGAAAG GTAATAACCT GTGGGAAGTG      9480

ATAGATAAAT TGTTTCCAAT TATGGGAGAA AAGACATTTG ATGTGATATC GTTATTAGAA      9540

CCACTTGCAT TATCCTTAAT TCAAACTCAT GATCCTGTTA ACAACTAAG AGGAGCTTTT       9600

TTAAATCATG TGTTATCCGA GATGGAATTA ATATTTGAAT CTAGAGAATC GATTAAGGAA      9660

TTTCTGAGTG TAGATTACAT TGATAAAATT TTAGATATAT TTAATAAGTC TACAATAGAT      9720

GAAATAGCAG AGATTTTCTC TTTTTTTAGA ACATTTGGGC ATCCTCCATT AGAAGCTAGT      9780

ATTGCAGCAG AAAAGGTTAG AAAATATATG TATATTGGAA AACAATTAAA ATTTGACACT      9840

ATTAATAAAT GTCATGCTAT CTTCTGTACA ATAATAATTA ACGGATATAG AGAGAGGCAT      9900

GGTGGACAGT GGCCTCCTGT GACATTACCT GATCATGCAC ACGAATTCAT CATAAATGCT      9960

TACGGTTCAA ACTCTGCGAT ATCATATGAA AATGCTGTTG ATTATTACCA GAGCTTTATA     10020

GGAATAAAAT TCAATAAATT CATAGAGCCT CAGTTAGATG AGGATTTGAC AATTTATATG     10080

AAAGATAAAG CATTATCTCC AAAAAAATCA AATTGGGACA CAGTTTATCC TGCATCTAAT     10140

TTACTGTACC GTACTAACGC ATCCAACGAA TCACGAAGAT TAGTTGAAGT ATTTATAGCA     10200

GATAGTAAAT TTGATCCTCA TCAGATATTG GATTATGTAG AATCTGGGGA CTGGTTAGAT     10260

GATCCAGAAT TTAATATTTC TTATAGTCTT AAAGAAAAAG AGATCAAACA GGAAGGTAGA     10320

CTCTTTGCAA AAATGACATA CAAAATGAGA GCTACACAAG TTTTATCAGA GACCCTACTT     10380

GCAAATAACA TAGGAAAATT CTTTCAAGAA AATGGGATGG TGAAGGGAGA GATTGAATTA     10440

CTTAAGAGAT TAACAACCAT ATCAATATCA GGAGTTCCAC GGTATAATGA AGTGTACAAT     10500

AATTCTAAAA GCCATACAGA TGACCTTAAA ACCTACAATA AAATAAGTAA TCTTAATTTG     10560

TCTTCTAATC AGAAATCAAA GAAATTTGAA TTCAAGTCAA CGGATATCTA CAATGATGGA     10620

TACGAGACTG TGAGCTGTTT CCTAACAACA GATCTCAAAA AATACTGTCT TAATTGGAGA     10680

TATGAATCAA CAGCTCTATT TGGAGAAACT TGCAACCAAA TATTTGGATT AAATAAATTG     10740

TTTAATTGGT TACACCCTCG TCTTGAAGGA AGTACAATCT ATGTAGGTGA TCCTTACTGT     10800

CCTCCATCAG ATAAAGAACA TATATCATTA GAGGATCACC CTGATTCTGG TTTTTACGTT     10860

CATAACCCAA GAGGGGGTAT AGAAGGATTT TGTCAAAAAT TATGGACACT CATATCTATA     10920

AGTGCAATAC ATCTAGCAGC TGTTAGAATA GGCGTGAGGG TGACTGCAAT GGTTCAAGGA     10980

GACAATCAAG CTATAGCTGT AACCACAAGA GTACCCAACA ATTATGACTA CAGAGTTAAG     11040

AAGGAGATAG TTTATAAAGA TGTAGTGAGA TTTTTTGATT CATTAAGAGA AGTGATGGAT     11100

GATCTAGGTC ATGAACTTAA ATTAAATGAA ACGATTATAA GTAGCAAGAT GTTCATATAT     11160

AGCAAAAGAA TCTATTATGA TGGGAGAATT CTTCCTCAAG CTCTAAAAGC ATTATCTAGA     11220

TGTGTCTTCT GGTCAGAGAC AGTAATAGAC GAAACAAGAT CAGCATCTTC AAATTTGGCA     11280
```

```
ACATCATTTG CAAAAGCAAT TGAGAATGGT TATTCACCTG TTCTAGGATA TGCATGCTCA    11340

ATTTTTAAGA ATATTCAACA ACTATATATT GCCCTTGGGA TGAATATCAA TCCAACTATA    11400

ACACAGAATA TCAGAGATCA GTATTTTAGG AATCCAAATT GGATGCAATA TGCCTCTTTA    11460

ATACCTGCTA GTGTTGGGGG ATTCAATTAC ATGGCCATGT CAAGATGTTT TGTAAGGAAT    11520

ATTGGTGATC CATCAGTTGC CGCATTGGCT GATATTAAAA GATTTATTAA GGCGAATCTA    11580

TTAGACCGAA GTGTTCTTTA TAGGATTATG AATCAAGAAC CAGGTGAGTC ATCTTTTTTG    11640

GACTGGGCTT CAGATCCATA TTCATGCAAT TTACCACAAT CTCAAAATAT AACCACCATG    11700

ATAAAAAATA TAACAGCAAG GAATGTATTA CAAGATTCAC CAAATCCATT ATTATCTGGA    11760

TTATTCACAA ATACAATGAT AGAAGAAGAT GAAGAATTAG CTGAGTTCCT GATGGACAGG    11820

AAGGTAATTC TCCCTAGAGT TGCACATGAT ATTCTAGATA ATTCTCTCAC AGGAATTAGA    11880

AATGCCATAG CTGGAATGTT AGATACGACA AAATCACTAA TTCGGGTTGG CATAAATAGA    11940

GGAGGACTGA CATATAGTTT GTTGAGGAAA ATCAGTAATT ACGATCTAGT ACAATATGAA    12000

ACACTAAGTA GGACTTTGCG ACTAATTGTA AGTGATAAAA TCAAGTATGA AGATATGTGT    12060

TCGGTAGACC TTGCCATAGC ATTGCGACAA AAGATGTGGA TTCATTTATC AGGAGGAAGG    12120

ATGATAAGTG GACTTGAAAC GCCTGACCCA TTAGAATTAC TATCTGGGGT AGTAATAACA    12180

GGATCAGAAC ATTGTAAAAT ATGTTATTCT TCAGATGGCA CAAACCCATA TACTTGGATG    12240

TATTTACCCG GTAATATCAA AATAGGATCA GCAGAAACAG GTATATCGTC ATTAAGAGTT    12300

CCTTATTTTG GATCAGTCAC TGATGAAAGA TCTGAAGCAC AATTAGGATA TATCAAGAAT    12360

CTTAGTAAAC CTGCAAAAGC CGCAATAAGA ATAGCAATGA TATATACATG GCATTTGGT    12420

AATGATGAGA TATCTTGGAT GGAAGCCTCA CAGATAGCAC AAACACGTGC AAATTTTACA    12480

CTAGATAGTC TCAAAATTTT AACACCGGTA GCTACATCAA CAAATTTATC ACACAGATTA    12540

AAGGATACTG CAACTCAGAT GAAATTCTCC AGTACATCAT TGATCAGAGT CAGCAGATTC    12600

ATAACAATGT CCAATGATAA CATGTCTATC AAAGAAGCTA ATGAAACCAA AGATACTAAT    12660

CTTATTTATC AACAAATAAT GTTAACAGGA TTAAGTGTTT TCGAATATTT ATTTAGATTA    12720

AAAGAAACCA CAGGACACAA CCCTATAGTT ATGCATCTGC ACATAGAAGA TGAGTGTTGT    12780

ATTAAAGAAA GTTTTAATGA TGAACATATT AATCCAGAGT CTACATTAGA ATTAATTCGA    12840

TATCCTGAAA GTAATGAATT TATTTATGAT AAAGACCCAC TCAAAGATGT GGACTTATCA    12900

AAACTTATGG TTATTAAAGA CCATTCTTAC ACAATTGATA TGAATTATTG GGATGATACT    12960

GACATCATAC ATGCAATTTC AATATGTACT GCAATTACAA TAGCAGATAC TATGTCACAA    13020

TTAGATCAG ATAATTTAAA AGAGATAATA GTTATTGCAA ATGATGATGA TATTAATAGC    13080

TTAATCACTG AATTTTTGAC TCTTGACATA CTTGTATTTC TCAAGACATT TGGTGGATTA    13140

TTAGTAAATC AATTTGCATA CACTCTTTAT AGTCTAAAAA TAGAAGGTAG GGATCTCATT    13200

TGGGATTATA TAATGAGAAC ACTGAGAGAT ACTTCCCATT CAATATTAAA AGTATTATCT    13260

AATGCATTAT CTCATCCTAA AGTATTCAAG AGGTTCTGGG ATTGTGGAGT TTTAAACCCT    13320

ATTTATGGTC CTAATACTGC TAGTCAAGAC CAGATAAAAC TTGCCCTATC TATATGTGAA    13380

TATTCACTAG ATCTATTTAT GAGAGAATGG TTGAATGGTG TATCACTTGA AATATACATT    13440

TGTGACAGCG ATATGGAAGT TGCAAATGAT AGGAAACAAG CCTTTATTTC TAGACACCTT    13500

TCATTTGTTT GTTGTTTAGC AGAAATTGCA TCTTTCGGAC CTAACCTGTT AAACTTAACA    13560

TACTTGGAGA GACTTGATCT ATTGAAACAA TATCTTGAAT TAAATATTAA AGAAGACCCT    13620
```

-continued

```
ACTCTTAAAT ATGTACAAAT ATCTGGATTA TTAATTAAAT CGTTCCCATC AACTGTAACA    13680

TACGTAAGAA AGACTGCAAT CAAATATCTA AGGATTCGCG GTATTAGTCC ACCTGAGGTA    13740

ATTGATGATT GGGATCCGGT AGAAGATGAA AAATATGCTGG ATAACATTGT CAAAACTATA   13800

AATGATAACT GTAATAAAGA TAATAAAGGG AATAAAATTA ACAATTTCTG GGGACTAGCA   13860

CTTAAGAACT ATCAAGTCCT TAAAATCAGA TCTATAACAA GTGATTCTGA TGATAATGAT    13920

AGACTAGATG CTAATACAAG TGGTTTGACA CTTCCTCAAG GAGGGAATTA TCTATCGCAT    13980

CAATTGAGAT TATTCGGAAT CAACAGCACT AGTTGTCTGA AAGCTCTTGA GTTATCACAA    14040

ATTTTAATGA AGGAAGTCAA TAAAGACAAG GACAGGCTCT TCCTGGGAGA AGGAGCAGGA    14100

GCTATGCTAG CATGTTATGA TGCCACATTA GGACCTGCAG TTAATTATTA TAATTCAGGT    14160

TTGAATATAA CAGATGTAAT TGGTCAACGA GAATTGAAAA TATTTCCTTC AGAGGTATCA    14220

TTAGTAGGTA AAAAATTAGG AAATGTGACA CAGATTCTTA ACAGGGTAAA AGTACTGTTC    14280

AATGGGAATC CTAATTCAAC ATGGATAGGA AATATGGAAT GTGAGAGCTT AATATGGAGT    14340

GAATTAAATG ATAAGTCCAT TGGATTAGTA CATTGTGATA TGGAAGGAGC TATCGGTAAA    14400

TCAGAAGAAA CTGTTCTACA TGAACATTAT AGTGTTATAA GAATTACATA CTTGATTGGG    14460

GATGATGATG TTGTTTTAGT TTCCAAAATT ATACCTACAA TCACTCCGAA TTGGTCTAGA    14520

ATACTTTATC TATATAAATT ATATTGGAAA GATGTAAGTA TAATATCACT CAAAACTTCT    14580

AATCCTGCAT CAACAGAATT ATATCTAATT TCGAAAGATG CATATTGTAC TATAATGGAA    14640

CCTAGTGAAA TTGTTTTATC AAAACTTAAA AGATTGTCAC TCTTGGAAGA AAATAATCTA    14700

TTAAAATGGA TCATTTTATC AAAGAAGAGG AATAATGAAT GGTTACATCA TGAAATCAAA    14760

GAAGGAGAAA GAGATTATGG AATCATGAGA CCATATCATA TGGCACTACA AATCTTTGGA    14820

TTTCAAATCA ATTTAAATCA TCTGGCGAAA GAATTTTTAT CAACCCCAGA TCTGACTAAT    14880

ATCAACAATA TAATCCAAAG TTTTCAGCGA ACAATAAAGG ATGTTTTATT TGAATGGATT    14940

AATATAACTC ATGATGATAA GAGACATAAA TTAGGCGGAA GATATAACAT ATTCCCACTG    15000

AAAAATAAGG GAAAGTTAAG ACTGCTATCG AGAAGACTAG TATTAAGTTG GATTTCATTA    15060

TCATTATCGA CTCGATTACT TACAGGTCGC TTTCCTGATG AAAAATTTGA ACATAGAGCA    15120

CAGACTGGAT ATGTATCATT AGCTGATACT GATTTAGAAT CATTAAAGTT ATTGTCGAAA    15180

AACATCATTA AGAATTACAG AGAGTGTATA GGATCAATAT CATATTGGTT TCTAACCAAA    15240

GAAGTTAAAA TACTTATGAA ATTGATCGGT GGTGCTAAAT TATTAGGAAT TCCCAGACAA    15300

TATAAAGAAC CCGAAGACCA GTTATTAGAA AACTACAATC AACATGATGA ATTTGATATC    15360

GATTAAAACA TAAATACAAT GAAGATATAT CCTAACCTTT ATCTTTAAGC CTAGGAATAG    15420

ACAAAAAGTA AGAAAAACAT GTAATATATA TATACCAAAC AGAGTTCTTC TCTTGTTTGG    15480

TGGGTCGGCA TGGCATCTCC ACCTCCTCGC GGTCCGGACC TGGGCATCCG AAGGAGGACG    15540

CACGTCCACT CGGATGGCTA AGGGAGAGCC TGCAGTAGCA TAACCCCTTG GGGCCTCTAA    15600

ACGGGTCTTG AGGGGTTTTT TGCTGAAAGG AGGAACTATA TACGCGTCGA CGGGCCCCGC    15660

GCTCAC                                                              15666
```

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGATTTGCGC GCAATTTAAA TCATCTGG                                              28

(2) INFORMATION FOR SEQ ID NO:17:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CCCAGGTCGG ACCGCGAGGA GGTGGAGATG CCATGCCAGC CCACCAAAAC AAGAGAAGAA           60

CTCTGTTTGG                                                                  70

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GGCCCGTCGA CGCGTAATAC GACTCACTAT AGGACCAAAC AAGAG                           45

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CGGCATCACG TGCTAC                                                           16

(2) INFORMATION FOR SEQ ID NO:20:

(i) SEQUENCE CHARACTERISTICS:
        (A) LENGTH: 6843 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ATGTTGAGCC TATTTGATAC ATTTAATGCA CGTAGGCAAG AAAACATAAC AAAATCAGCC           60

GGTGGAGCTA TCATTCCTGG ACAGAAAAAT ACTGTCTCTA TATTCGCCCT TGGACCGACA          120

ATAACTGATG ATAATGAGAA AATGACATTA GCTCTTCTAT TTCTATCTCA TTCACTAGAT          180

AATGAGAAAC AACATGCACA AAGGGCAGGG TTCTTGGTGT CTTTATTGTC AATGGCTTAT          240

GCCAATCCAG AGCTCTACCT AACAACAAAT GGAAGTAATG CAGATGTCAA GTATGTCATA          300

TACATGATTG AGAAAGATCT AAAACGGCAA AAGTATGGAG GATTTGTGGT TAAGACGAGA          360

GAGATGATAT ATGAAAAGAC AACTGATTGG ATATTTGGAA GTGACCTGGA TTATGATCAG          420

```
GAAACTATGT TGCAGAACGG CAGGAACAAT TCAACAATTG AAGACCTTGT CCACACATTT    480

GGGTATCCAT CATGTTTAGG AGCTCTTATA ATACAGATCT GGATAGTTCT GGTCAAAGCT    540

ATCACTAGTA TCTCAGGGTT AAGAAAAGGC TTTTTCACCC GATTGGAAGC TTTCAGACAA    600

GATGGAACAG TGCAGGCAGG GCTGGTATTG AGCGGTGACA CAGTGGATCA GATTGGGTCA    660

ATCATGCGGT CTCAACAGAG CTTGGTAACT CTTATGGTTG AAACATTAAT AACAATGAAT    720

ACCAGCAGAA ATGACCTCAC AACCATAGAA AAGAATATAC AAATTGTTGG CAACTACATA    780

AGAGATGCAG GTCTCGCTTC ATTCTTCAAT ACAATCAGAT ATGGAATTGA GACCAGAATG    840

GCAGCTTTGA CTCTATCCAC TCTCAGACCA GATATCAATA GATTAAAAGC TTTGATGGAA    900

CTGTATTTAT CAAAGGGACC ACGCGCTCCT TTCATCTGTA TCCTCAGAGA TCCTATACAT    960

GGTGAGTTCG CACCAGGCAA CTATCCTGCC ATATGGAGCT ATGCAATGGG GGTGGCAGTT   1020

GTACAAAATA GAGCCATGCA ACAGTATGTG ACGGGAAGAT CATATCTAGA CATTGATATG   1080

TTCCAGCTAG GACAAGCAGT AGCACGTGAT GCCGAAGCTC AAATGAGCTC AACACTGGAA   1140

GATGAACTTG GAGTGACACA CGAATCTAAA GAAAGCTTGA AGAGACATAT AAGGAACATA   1200

AACAGTTCAG AGACATCTTT CCACAAACCG ACAGGTGGAT CAGCCATAGA GATGGCAATA   1260

GATGAAGAGC CAGAACAATT CGAACATAGA GCAGATCAAG AACAAAATGG AGAACCTCAA   1320

TCATCCATAA TTCAATATGC CTGGGCAGAA GGAAATAGAA GCGATGATCA GACTGAGCAA   1380

GCTACAGAAT CTGACAATAT CAAGACCGAA CAACAAAACA TCAGAGACAG ACTAAACAAG   1440

AGACTCAACG ACAAGAAGAA ACAAAGCAGT CAACCACCCA CTAATCCCAC AAACAGAACA   1500

AACCAGGACG AAATAGATGA TCTGTTTAAC GCATTTGGAA GCAACTAAGT CGACGATCCG   1560

GCTGCTAACA AAGCCCGAAA GGAAGCTGAG TTGGCTGCTG CCACCGCTGA GCAATAACTA   1620

GCATAACCCC TTGGGGCCTC TAAACGGGTC TTGAGGGGTT TTTTGCTGAA AGGAGGAACT   1680

ATATCCGGAT CGAGATCAAT TCTGTGAGCG TATGGCAAAC GAAGGAAAAA TAGTTATAGT   1740

AGCCGCACTC GATGGGACAT TTCAACGTAA ACCGTTTAAT AATATTTTGA ATCTTATTCC   1800

ATTATCTGAA ATGGTGGTAA AACTAACTGC TGTGTGTATG AAATGCTTTA AGGAGGCTTC   1860

CTTTTCTAAA CGATTGGGTG AGGAAACCGA GATAGAAATA ATAGGAGGTA ATGATATGTA   1920

TCAATCGGTG TGTAGAAAGT GTTACATCGA CTCATAATAT TATATTTTTT ATCTAAAAAA   1980

CTAAAAATAA ACATTGATTA AATTTTAATA TAATACTTAA AAATGGATGT TGTGTCGTTA   2040

GATAAACCGT TTATGTATTT TGAGGAAATT GATAATGAGT TAGATTACGA ACCAGAAAGT   2100

GCAAATGAGG TCGCAAAAAA ACTGCCGTAT CAAGGACAGT TAAAACTATT ACTAGGAGAA   2160

TTATTTTTTC TTAGTAAGTT ACAGCGACAC GGTATATTAG ATGGTGCCAC CGTAGTGTAT   2220

ATAGGATCTG CTCCCGGTAC ACATATACGT TATTTGAGAG ATCATTTCTA TAATTTAGGA   2280

GTGATCATCA AATGGATGCT AATTGACGGC CGCCATCATG ATCCTATTTT AAATGGATTG   2340

CGTGATGTGA CTCTAGTGAC TCGGTTCGTT GATGAGGAAT ATCTACGATC CATCAAAAAA   2400

CAACTGCATC CTTCTAAGAT TATTTTAATT TCTGATGTGA GATCCAAACG AGGAGGAAAT   2460

GAACCTAGTA CGGCGGATTT ACTAAGTAAT TACGCTCTAC AAAATGTCAT GATTAGTATT   2520

TTAAACCCCG TGGCGTCTAG TCTTAAATGG AGATGCCCGT TCCAGATCA ATGGATCAAG   2580

GACTTTTATA TCCCACACGG TAATAAAATG TTACAACCTT TGCTCCTTC ATATTCAGGG   2640

CCGTCGTTTT ACAACGTCGT GACTGGGAAA ACCCTGGCGT TACCCAACTT AATCGCCTTG   2700

CAGCACATCC CCCTTTCGCC AGCTGGCGTA ATAGCGAAGA GGCCCGCACC GATCGCCCTT   2760
```

-continued

| | | | | | |
|---|---|---|---|---|---|
| CCCAACAGTT | GCGCAGCCTG | AATGGCGAAT | GGCGCGACGC | GCCCTGTAGC | GGCGCATTAA | 2820 |
| GCGCGGCGGG | TGTGGTGGTT | ACGCGCAGCG | TGACCGCTAC | ACTTGCCAGC | GCCCTAGCGC | 2880 |
| CCGCTCCTTT | CGCTTTCTTC | CCTTCCTTTC | TCGCCACGTT | CGCCGGCTTT | CCCCGTCAAG | 2940 |
| CTCTAAATCG | GGGGCTCCCT | TTAGGGTTCC | GATTTAGTGC | TTTACGGCAC | CTCGACCCCA | 3000 |
| AAAAACTTGA | TTAGGGTGAT | GGTTCACGTA | GTGGGCCATC | GCCCTGATAG | ACGGTTTTTC | 3060 |
| GCCCTTTGAC | GTTGGAGTCC | ACGTTCTTTA | ATAGTGGACT | CTTGTTCCAA | ACTGGAACAA | 3120 |
| CACTCAACCC | TATCTCGGTC | TATTCTTTTG | ATTTATAAGG | GATTTTGCCG | ATTTCGGCCT | 3180 |
| ATTGGTTAAA | AAATGAGCTG | ATTTAACAAA | AATTTAACGC | GAATTTTAAC | AAAATATTAA | 3240 |
| CGTTTACAAT | TTCCCAGGTG | GCACTTTTCG | GGGAAATGTG | CGCGGAACCC | CTATTTGTTT | 3300 |
| ATTTTTCTAA | ATACATTCAA | ATATGTATCC | GCTCATGAGA | CAATAACCCT | GATAAATGCT | 3360 |
| TCAATAATAT | TGAAAAAGGA | AGAGTATGAG | TATTCAACAT | TTCCGTGTCG | CCCTTATTCC | 3420 |
| CTTTTTTGCG | GCATTTTGCC | TTCCTGTTTT | TGCTCACCCA | GAAACGCTGG | TGAAAGTAAA | 3480 |
| AGATGCTGAA | GATCAGTTGG | GTGCACGAGT | GGGTTACATC | GAACTGGATC | TCAACAGCGG | 3540 |
| TAAGATCCTT | GAGAGTTTTC | GCCCCGAAGA | ACGTTTTCCA | ATGATGAGCA | CTTTTAAAGT | 3600 |
| TCTGCTATGT | GGCGCGGTAT | TATCCCGTAT | TGACGCCGGG | CAAGAGCAAC | TCGGTCGCCG | 3660 |
| CATACACTAT | TCTCAGAATG | ACTTGGTTGA | GTACTCACCA | GTCACAGAAA | AGCATCTTAC | 3720 |
| GGATGGCATG | ACAGTAAGAG | AATTATGCAG | TGCTGCCATA | ACCATGAGTG | ATAACACTGC | 3780 |
| GGCCAACTTA | CTTCTGACAA | CGATCGGAGG | ACCGAAGGAG | CTAACCGCTT | TTTTGCACAA | 3840 |
| CATGGGGGAT | CATGTAACTC | GCCTTGATCG | TTGGGAACCG | GAGCTGAATG | AAGCCATACC | 3900 |
| AAACGACGAG | CGTGACACCA | CGATGCCTGT | AGCAATGGCA | ACAACGTTGC | GCAAACTATT | 3960 |
| AACTGGCGAA | CTACTTACTC | TAGCTTCCCG | GCAACAATTA | ATAGACTGGA | TGGAGGCGGA | 4020 |
| TAAAGTTGCA | GGACCACTTC | TGCGCTCGGC | CCTTCCGGCT | GGCTGGTTTA | TTGCTGATAA | 4080 |
| ATCTGGAGCC | GGTGAGCGTG | GGTCTCGCGG | TATCATTGCA | GCACTGGGGC | CAGATGGTAA | 4140 |
| GCCCTCCCGT | ATCGTAGTTA | TCTACACGAC | GGGGAGTCAG | GCAACTATGG | ATGAACGAAA | 4200 |
| TAGACAGATC | GCTGAGATAG | GTGCCTCACT | GATTAAGCAT | TGGTAACTGT | CAGACCAAGT | 4260 |
| TTACTCATAT | ATACTTTAGA | TTGATTTAAA | ACTTCATTTT | TAATTTAAAA | GGATCTAGGT | 4320 |
| GAAGATCCTT | TTTGATAATC | TCATGACCAA | AATCCCTTAA | CGTGAGTTTT | CGTTCCACTG | 4380 |
| AGCGTCAGAC | CCCGTAGAAA | AGATCAAAGG | ATCTTCTTGA | GATCCTTTTT | TTCTGCGCGT | 4440 |
| AATCTGCTGC | TTGCAAACAA | AAAAACCACC | GCTACCAGCG | GTGGTTTGTT | TGCCGGATCA | 4500 |
| AGAGCTACCA | ACTCTTTTTC | CGAAGGTAAC | TGGCTTCAGC | AGAGCGCAGA | TACCAAATAC | 4560 |
| TGTCCTTCTA | GTGTAGCCGT | AGTTAGGCCA | CCACTTCAAG | AACTCTGTAG | CACCGCCTAC | 4620 |
| ATACCTCGCT | CTGCTAATCC | TGTTACCAGT | GGCTGCTGCC | AGTGGCGATA | AGTCGTGTCT | 4680 |
| TACCGGGTTG | GACTCAAGAC | GATAGTTACC | GGATAAGGCG | CAGCGGTCGG | GCTGAACGGG | 4740 |
| GGGTTCGTGC | ACACAGCCCA | GCTTGGAGCG | AACGACCTAC | ACCGAACTGA | GATACCTACA | 4800 |
| GCGTGAGCTA | TGAGAAAGCG | CCACGCTTCC | CGAAGGGAGA | AAGGCGGACA | GGTATCCGGT | 4860 |
| AAGCGGCAGG | GTCGGAACAG | GAGAGCGCAC | GAGGGAGCTT | CCAGGGGGAA | ACGCCTGGTA | 4920 |
| TCTTTATAGT | CCTGTCGGGT | TTCGCCACCT | CTGACTTGAG | CGTCGATTTT | TGTGATGCTC | 4980 |
| GTCAGGGGGG | CGGAGCCTAT | GGAAAAACGC | CAGCAACGCG | GCCTTTTTAC | GGTTCCTGGC | 5040 |
| CTTTTGCTGG | CCTTTTGCTC | ACATGTTCTT | TCCTGCGTTA | TCCCCTGATT | CTGTGGATAA | 5100 |
| CCGTATTACC | GCCTTTGAGT | GAGCTGATAC | CGCTCGCCGC | AGCCGAACGA | CCGAGCGCAG | 5160 |

```
CGAGTCAGTG AGCGAGGAAG CGGAAGAGCG CCCAATACGC AAACCGCCTC TCCCCGCGCG      5220

TTGGCCGATT CATTAATGCA GCTGGCACGA CAGGTTTCCC GACTGGAAAG CGGGCAGTGA      5280

GCGCAACGCA ATTAATGTGA GTTAGCTCAC TCATTAGGCA CCCCAGGCTT TACACTTTAT      5340

GCTTCCGGCT CGTATGTTGT GTGGAATTGT GAGCGGATAA CAATTTCACA CAGGAAACAG      5400

CTATGACCAT GATTACGCCA AGCTTTTGCG ATCAATAAAT GGATCACAAC CAGTATCTCT      5460

TAACGATGTT CTTCGCAGAT GATGATTCAT TTTTTAAGTA TTTGGCTAGT CAAGATGATG      5520

AATCTTCATT ATCTGATATA TTGCAAATCA CTCAATATCT AGACTTTCTG TTATTATTAT      5580

TGATCCAATC AAAAAATAAA TTAGAAGCCG TGGGTCATTG TTATGAATCT CTTTCAGAGG      5640

AATACAGACA ATTGACAAAA TTCACAGACT TTCAAGATTT TAAAAAACTG TTTAACAAGG      5700

TCCCTATTGT TACAGATGGA AGGGTCAAAC TTAATAAAGG ATATTTGTTC GACTTTGTGA      5760

TTAGTTTGAT GCGATTCAAA AAAGAATCCT CTCTAGCTAC CACCGCAATA GATCCTGTTA      5820

GATACATAGA TCCTCGTCGC AATATCGCAT TTTCTAACGT GATGGATATA TTAAAGTCGA      5880

ATAAAGTGAA CAATAATTAA TTCTTTATTG TCATCATGAA CGGCGGACAT ATTCAGTTGA      5940

TAATCGGCCC CATGTTTTCA GGTAAAAGTA CAGAATTAAT TAGACGAGTT AGACGTTATC      6000

AAATAGCTCA ATATAAATGC GTGACTATAA AATATTCTAA CGATAATAGA TACGAACGG       6060

GACTATGGAC GCATGATAAG AATAATTTTG AAGCATTGGA AGCAACTAAA CTATGTGATG      6120

TCTTGGAATC AATTACAGAT TTCTCCGTGA TAGGTATCGA TGAAGGACAG TTCTTTCCAG      6180

ACATTGTTGA ATTGATCTCG ATCCCGCGAA ATTAATACGA CTCACTATAG GGAGACCACA      6240

ACGGTTTCCC TCTAGCGGGA TCAATTCCGC CCCTCTCCCT CCCCCCCCCC TAACGTTACT      6300

GGCCGAAGCC GCTTGGAATA AGGCCGGTGT GCGTTTGTCT ATATGTTATT TTCCACCATA      6360

TTGCCGTCTT TTGGCAATGT GAGGGCCCGG AAACCTGGCC CTGTCTTCTT GACGAGCATT      6420

CCTAGGGGTC TTTCCCCTCT CGCCAAAGGA ATGCAAGGTC TGTTGAATGT CGTGAAGGAA      6480

GCAGTTCCTC TGGAAGCTTC TTGAAGACAA ACAACGTCTG TAGCGACCCT TTGCAGGCAG      6540

CGGAACCCCC CACCTGGCGA CAGGTGCCTC TGCGGCCAAA AGCACGTGT ATAAGATACA       6600

CCTGCAAAGG CGGCACAACC CCAGTGCCAC GTTGTGAGTT GGATAGTTGT GGAAAGAGTC      6660

AAATGGCTCT CCTCAAGCGT ATTCAACAAG GGGCTGAAGG ATGCCCAGAA GGTACCCCAT      6720

TGTATGGGAT CTGATCTGGG GCCTCGGTGC ACATGCTTTA CATGTGTTTA GTCGAGGTTA      6780

AAAAACGTCT AGGCCCCCCG AACCACGGGG ACGTGGTTTT CCTTTGAAAA ACACGATAAT      6840

ACC                                                                   6843

(2) INFORMATION FOR SEQ ID NO:21:

(i) SEQUENCE CHARACTERISTICS:
        (A) LENGTH: 7107 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

ATGGAAAGCG ACGCTAAAAA CTATCAAATC ATGGATTCTT GGGAAGAGGA ATCAAGAGAT        60

AAATCAACTA ATATCTCCTC GGCCCTCAAC ATCATTGAAT TCATACTCAG CACCGACCCC       120

CAAGAAGACT TATCGGAAAA CGACACAATC AACACAAGAA CCCAGCAACT CAGTGCCACC       180

ATCTGTCAAC CAGAAATCAA ACCAACAGAA ACAAGTGAGA AAGATAGTGG ATCAACTGAC       240
```

```
AAAAATAGAC AGTCCGGGTC ATCACACGAA TGTACAACAG AAGCAAAAGA TAGAAATATT      300

GATCAGGAAA CTGTACAGAG AGGACCTGGG AGAAGAAGCA GCTCAGATAG TAGAGCTGAG      360

ACTGTGGTCT CTGGAGGAAT CCCCAGAAGC ATCACAGATT CTAAAAATGG AACCCAAAAC      420

ACGGAGGATA TTGATCTCAA TGAAATTAGA AGATGGATA AGGACTCTAT TGAGGGAAA        480

ATGCGACAAT CTGCAAATGT TCCAAGCGAG ATATCAGGAA GTGATGACAT ATTTACAACA      540

GAACAAAGTA GAAACAGTGA TCATGGAAGA AGCCTGGAAT CTATCAGTAC ACCTGATACA      600

AGATCAATAA GTGTTGTTAC TGCTGCAACA CCAGATGATG AAGAAGAAAT ACTAATGAAA      660

AATAGTAGGA CAAAGAAAAG TTCTTCAACA CATCAAGAAG ATGACAAAAG AATTAAAAAA      720

GGGGGAAAAG GGAAAGACTG GTTTAAGAAA TCAAAAGATA CCGACAACCA GATACCAACA      780

TCAGACTACA GATCCACATC AAAAGGGCAG AAGAAAATCT CAAAGACAAC AACCACCAAC      840

ACCGACACAA AGGGGCAAAC AGAAATACAG ACAGAATCAT CAGAAACACA ATCCTCATCA      900

TGGAATCTCA TCATCGACAA CAACACCGAC CGGAACGAAC AGACAAGCAC AACTCCTCCA      960

ACAACAACTT CCAGATCAAC TTATACAAAA GAATCGATCC GAACAAACTC TGAATCCAAA     1020

CCCAAGACAC AAAAGACAAA TGGAAAGGAA AGGAAGGATA CAGAAGAGAG CAATCGATTT     1080

ACAGAGAGGG CAATTACTCT ATTGCAGAAT CTTGGTGTAA TTCAATCCAC ATCAAAACTA     1140

GATTTATATC AAGACAAACG AGTTGTATGT GTAGCAAATG TACTAAACAA TGTAGATACT     1200

GCATCAAAGA TAGATTTCCT GGCAGGATTA GTCATAGGGG TTTCAATGGA CAACGACACA     1260

AAATTAACAC AGATACAAAA TGAAATGCTA AACCTCAAAG CAGATCTAAA GAAAATGGAC     1320

GAATCACATA GAAGATTGAT AGAAAATCAA AGAGAACAAC TGTCATTGAT CACGTCACTA     1380

ATTTCAAATC TCAAAATTAT GACTGAGAGA GGAGGAAAGA AAGACCAAAA TGAATCCAAT     1440

GAGAGAGTAT CCATGATCAA AACAAAATTG AAGAAGAAA AGATCAAGAA GACCAGGTTT      1500

GACCCACTTA TGGAGGCACA AGGCATTGAC AAGAATATAC CCGATCTATA TCGACATGCA     1560

GGAGATACAC TAGAGAACGA TGTACAAGTT AAATCAGAGA TATTAAGTTC ATACAATGAG     1620

TCAAATGCAA CAAGACTAAT ACCCAAAAAA GTGAGCAGTA CAATGAGATC ACTAGTTGCA     1680

GTCATCAACA ACAGCAATCT CTCACAAAGC ACAAAACAAT CATACATAAA CGAACTCAAA     1740

CGTTGCAAAA ATGATGAAGA AGTATCTGAA TTAATGGACA TGTTCAATGA AGATGTCAAC     1800

AATTGCCAAT GAGTCGACGA TCCGGCTGCT AACAAAGCCC GAAAGGAAGC TGAGTTGGCT     1860

GCTGCCACCG CTGAGCAATA ACTAGCATAA CCCCTTGGGG CCTCTAAACG GGTCTTGAGG     1920

GGTTTTTTGC TGAAAGGAGG AACTATATCC GGATCGAGAT CAATTCTGTG AGCGTATGGC     1980

AAACGAAGGA AAAATAGTTA TAGTAGCCGC ACTCGATGGG ACATTTCAAC GTAAACCGTT     2040

TAATAATATT TTGAATCTTA TTCCATTATC TGAAATGGTG GTAAAACTAA CTGCTGTGTG     2100

TATGAAATGC TTTAAGGAGG CTTCCTTTTC TAAACGATTG GGTGAGGAAA CCGAGATAGA     2160

AATAATAGGA GGTAATGATA TGTATCAATC GGTGTGTAGA AAGTGTTACA TCGACTCATA     2220

ATATTATATT TTTTATCTAA AAAACTAAAA ATAAACATTG ATTAAATTTT AATATAATAC     2280

TTAAAAATGG ATGTTGTGTC GTTAGATAAA CCGTTTATGT ATTTTGAGGA AATTGATAAT     2340

GAGTTAGATT ACGAACCAGA AAGTGCAAAT GAGGTCGCAA AAAACTGCC GTATCAAGGA      2400

CAGTTAAAAC TATTACTAGG AGAATTATTT TTTCTTAGTA AGTTACAGCG ACACGGTATA     2460

TTAGATGGTG CCACCGTAGT GTATATAGGA CTGCTCCCG GTACACATAT ACGTTATTTG      2520

AGAGATCATT TCTATAATTT AGGAGTGATC ATCAAATGGA TGCTAATTGA CGGCCGCCAT     2580
```

```
CATGATCCTA TTTTAAATGG ATTGCGTGAT GTGACTCTAG TGACTCGGTT CGTTGATGAG    2640

GAATATCTAC GATCCATCAA AAAACAACTG CATCCTTCTA AGATTATTTT AATTTCTGAT    2700

GTGAGATCCA AACGAGGAGG AAATGAACCT AGTACGGCGG ATTTACTAAG TAATTACGCT    2760

CTACAAAATG TCATGATTAG TATTTTAAAC CCCGTGGCGT CTAGTCTTAA ATGGAGATGC    2820

CCGTTTCCAG ATCAATGGAT CAAGGACTTT TATATCCCAC ACGGTAATAA AATGTTACAA    2880

CCTTTTGCTC CTTCATATTC AGGGCCGTCG TTTTACAACG TCGTGACTGG GAAAACCCTG    2940

GCGTTACCCA ACTTAATCGC CTTGCAGCAC ATCCCCCTTT CGCCAGCTGG CGTAATAGCG    3000

AAGAGGCCCG CACCGATCGC CCTTCCCAAC AGTTGCGCAG CCTGAATGGC GAATGGCGCG    3060

ACGCGCCCTG TAGCGGCGCA TTAAGCGCGG CGGGTGTGGT GGTTACGCGC AGCGTGACCG    3120

CTACACTTGC CAGCGCCCTA GCGCCCGCTC CTTTCGCTTT CTTCCCTTCC TTTCTCGCCA    3180

CGTTCGCCGG CTTTCCCCGT CAAGCTCTAA ATCGGGGGCT CCCTTTAGGG TTCCGATTTA    3240

GTGCTTTACG GCACCTCGAC CCCAAAAAAC TTGATTAGGG TGATGGTTCA CGTAGTGGGC    3300

CATCGCCCTG ATAGACGGTT TTTCGCCCTT TGACGTTGGA GTCCACGTTC TTTAATAGTG    3360

GACTCTTGTT CCAAACTGGA ACAACACTCA ACCCTATCTC GGTCTATTCT TTTGATTTAT    3420

AAGGGATTTT GCCGATTTCG GCCTATTGGT TAAAAAATGA GCTGATTTAA CAAAAATTTA    3480

ACGCGAATTT TAACAAAATA TTAACGTTTA CAATTTCCCA GGTGGCACTT TTCGGGGAAA    3540

TGTGCGCGGA ACCCCTATTT GTTTATTTTT CTAAATACAT TCAAATATGT ATCCGCTCAT    3600

GAGACAATAA CCCTGATAAA TGCTTCAATA ATATTGAAAA AGGAAGAGTA TGAGTATTCA    3660

ACATTTCCGT GTCGCCCTTA TTCCCTTTTT TGCGGCATTT TGCCTTCCTG TTTTTGCTCA    3720

CCCAGAAACG CTGGTGAAAG TAAAAGATGC TGAAGATCAG TTGGGTGCAC GAGTGGGTTA    3780

CATCGAACTG GATCTCAACA GCGGTAAGAT CCTTGAGAGT TTTCGCCCCG AAGAACGTTT    3840

TCCAATGATG AGCACTTTTA AAGTTCTGCT ATGTGGCGCG GTATTATCCC GTATTGACGC    3900

CGGGCAAGAG CAACTCGGTC GCCGCATACA CTATTCTCAG AATGACTTGG TTGAGTACTC    3960

ACCAGTCACA GAAAAGCATC TTACGGATGG CATGACAGTA AGAGAATTAT GCAGTGCTGC    4020

CATAACCATG AGTGATAACA CTGCGGCCAA CTTACTTCTG ACAACGATCG GAGGACCGAA    4080

GGAGCTAACC GCTTTTTTGC ACAACATGGG GGATCATGTA ACTCGCCTTG ATCGTTGGGA    4140

ACCGGAGCTG AATGAAGCCA TACCAAACGA CGAGCGTGAC ACCACGATGC CTGTAGCAAT    4200

GGCAACAACG TTGCGCAAAC TATTAACTGG CGAACTACTT ACTCTAGCTT CCCGGCAACA    4260

ATTAATAGAC TGGATGGAGG CGGATAAAGT TGCAGGACCA CTTCTGCGCT CGGCCCTTCC    4320

GGCTGGCTGG TTTATTGCTG ATAAATCTGG AGCCGGTGAG CGTGGGTCTC GCGGTATCAT    4380

TGCAGCACTG GGGCCAGATG GTAAGCCCTC CCGTATCGTA GTTATCTACA CGACGGGGAG    4440

TCAGGCAACT ATGGATGAAC GAAATAGACA GATCGCTGAG ATAGGTGCCT CACTGATTAA    4500

GCATTGGTAA CTGTCAGACC AAGTTTACTC ATATATACTT TAGATTGATT TAAAACTTCA    4560

TTTTTAATTT AAAAGGATCT AGGTGAAGAT CCTTTTTGAT AATCTCATGA CCAAAATCCC    4620

TTAACGTGAG TTTTCGTTCC ACTGAGCGTC AGACCCCGTA GAAAAGATCA AAGGATCTTC    4680

TTGAGATCCT TTTTTTCTGC GCGTAATCTG CTGCTTGCAA ACAAAAAAAC CACCGCTACC    4740

AGCGGTGGTT TGTTTGCCGG ATCAAGAGCT ACCAACTCTT TTTCCGAAGG TAACTGGCTT    4800

CAGCAGAGCG CAGATACCAA ATACTGTCCT TCTAGTGTAG CCGTAGTTAG GCCACCACTT    4860

CAAGAACTCT GTAGCACCGC CTACATACCT CGCTCTGCTA ATCCTGTTAC CAGTGGCTGC    4920

TGCCAGTGGC GATAAGTCGT GTCTTACCGG GTTGGACTCA AGACGATAGT TACCGGATAA    4980
```

```
GGCGCAGCGG TCGGGCTGAA CGGGGGGTTC GTGCACACAG CCCAGCTTGG AGCGAACGAC    5040

CTACACCGAA CTGAGATACC TACAGCGTGA GCTATGAGAA AGCGCCACGC TTCCCGAAGG    5100

GAGAAAGGCG GACAGGTATC CGGTAAGCGG CAGGGTCGGA ACAGGAGAGC GCACGAGGGA    5160

GCTTCCAGGG GGAAACGCCT GGTATCTTTA TAGTCCTGTC GGGTTTCGCC ACCTCTGACT    5220

TGAGCGTCGA TTTTTGTGAT GCTCGTCAGG GGGCGGAGC CTATGGAAAA ACGCCAGCAA     5280

CGCGGCCTTT TTACGGTTCC TGGCCTTTTG CTGGCCTTTT GCTCACATGT TCTTTCCTGC    5340

GTTATCCCCT GATTCTGTGG ATAACCGTAT TACCGCCTTT GAGTGAGCTG ATACCGCTCG    5400

CCGCAGCCGA ACGACCGAGC GCAGCGAGTC AGTGAGCGAG GAAGCGGAAG AGCGCCCAAT    5460

ACGCAAACCG CCTCTCCCCG CGCGTTGGCC GATTCATTAA TGCAGCTGGC ACGACAGGTT    5520

TCCCGACTGG AAAGCGGGCA GTGAGCGCAA CGCAATTAAT GTGAGTTAGC TCACTCATTA    5580

GGCACCCCAG GCTTTACACT TTATGCTTCC GGCTCGTATG TTGTGTGGAA TTGTGAGCGG    5640

ATAACAATTT CACACAGGAA ACAGCTATGA CCATGATTAC GCCAAGCTTT TGCGATCAAT    5700

AAATGGATCA CAACCAGTAT CTCTTAACGA TGTTCTTCGC AGATGATGAT TCATTTTTTA    5760

AGTATTTGGC TAGTCAAGAT GATGAATCTT CATTATCTGA TATATTGCAA ATCACTCAAT    5820

ATCTAGACTT TCTGTTATTA TTATTGATCC AATCAAAAAA TAAATTAGAA GCCGTGGGTC    5880

ATTGTTATGA ATCTCTTTCA GAGGAATACA GACAATTGAC AAAATTCACA GACTTTCAAG    5940

ATTTTAAAAA ACTGTTTAAC AAGGTCCCTA TTGTTACAGA TGGAAGGGTC AAACTTAATA    6000

AAGGATATTT GTTCGACTTT GTGATTAGTT TGATGCGATT CAAAAAAGAA TCCTCTCTAG    6060

CTACCACCGC AATAGATCCT GTTAGATACA TAGATCCTCG TCGCAATATC GCATTTTCTA    6120

ACGTGATGGA TATATTAAAG TCGAATAAAG TGAACAATAA TTAATTCTTT ATTGTCATCA    6180

TGAACGGCGG ACATATTCAG TTGATAATCG GCCCCATGTT TTCAGGTAAA AGTACAGAAT    6240

TAATTAGACG AGTTAGACGT TATCAAATAG CTCAATATAA ATGCGTGACT ATAAAATATT    6300

CTAACGATAA TAGATACGGA ACGGGACTAT GGACGCATGA TAAGAATAAT TTTGAAGCAT    6360

TGGAAGCAAC TAAACTATGT GATGTCTTGG AATCAATTAC AGATTCTCC GTGATAGGTA     6420

TCGATGAAGG ACAGTTCTTT CCAGACATTG TTGAATTGAT CTCGATCCCG CGAAATTAAT    6480

ACGACTCACT ATAGGGAGAC CACAACGGTT TCCCTCTAGC GGGATCAATT CCGCCCCTCT    6540

CCCTCCCCCC CCCCTAACGT TACTGGCCGA AGCCGCTTGG AATAAGGCCG GTGTGCGTTT    6600

GTCTATATGT TATTTTCCAC CATATTGCCG TCTTTTGGCA ATGTGAGGGC CCGGAAACCT    6660

GGCCCTGTCT TCTTGACGAG CATTCCTAGG GGTCTTTCCC CTCTCGCCAA AGGAATGCAA    6720

GGTCTGTTGA ATGTCGTGAA GGAAGCAGTT CCTCTGGAAG CTTCTTGAAG ACAAACAACG    6780

TCTGTAGCGA CCCTTTGCAG GCAGCGGAAC CCCCCACCTG GCGACAGGTG CCTCTGCGGC    6840

CAAAAGCCAC GTGTATAAGA TACACCTGCA AAGGCGGCAC AACCCCAGTG CCACGTTGTG    6900

AGTTGGATAG TTGTGGAAAG AGTCAAATGG CTCTCCTCAA GCGTATTCAA CAAGGGGCTG    6960

AAGGATGCCC AGAAGGTACC CCATTGTATG GGATCTGATC TGGGGCCTCG GTGCACATGC    7020

TTTACATGTG TTTAGTCGAG GTTAAAAAAC GTCTAGGCCC CCCGAACCAC GGGGACGTGG    7080

TTTTCCTTTG AAAACACGA TAATACC                                         7107
```

(2) INFORMATION FOR SEQ ID NO:22:

(i) SEQUENCE CHARACTERISTICS:
        (A) LENGTH: 12011 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:22:

```
ATGGACACTG AATCTAACAA TGGCACTGTA TCTGACATAC TCTATCCTGA GTGTCACCTT          60

AACTCTCCTA TCGTTAAAGG TAAAATAGCA CAATTACACA CTATTATGAG TCTACCTCAG         120

CCTTATGATA TGGATGACGA CTCAATACTA GTTATCACTA GACAGAAAAT AAAACTTAAT         180

AAATTGGATA AAAGACAACG ATCTATTAGA AGATTAAAAT TAATATTAAC TGAAAAAGTG         240

AATGACTTAG GAAAATACAC ATTTATCAGA TATCCAGAAA TGTCAAAAGA AATGTTCAAA         300

TTATATATAC CTGGTATTAA CAGTAAAGTG ACTGAATTAT TACTTAAAGC AGATAGAACA         360

TATAGTCAAA TGACTGATGG ATTAAGAGAT CTATGGATTA ATGTGCTATC AAAATTAGCC         420

TCAAAAAATG ATGGAAGCAA TTATGATCTT AATGAAGAAA TTAATAATAT ATCGAAAGTT         480

CACACAACCT ATAAATCAGA TAAATGGTAT AATCCATTCA AACATGGTT  TACTATCAAG         540

TATGATATGA GAAGATTACA AAAAGCTCGA AATGAGATCA CTTTTAATGT TGGGAAGGAT         600

TATAACTTGT TAGAAGACCA GAAGAATTTC TTATTGATAC ATCCAGAATT GGTTTTGATA         660

TTAGATAAAC AAAACTATAA TGGTTATCTA ATTACTCCTG AATTAGTATT GATGTATTGT         720

GACGTAGTCG AAGGCCGATG GAATATAAGT GCATGTGCTA AGTTAGATCC AAAATTACAA         780

TCTATGTATC AGAAAGGTAA TAACCTGTGG GAAGTGATAG ATAAATTGTT TCCAATTATG         840

GGAGAAAAGA CATTTGATGT GATATCGTTA TTAGAACCAC TTGCATTATC CTTAATTCAA         900

ACTCATGATC CTGTTAAACA ACTAAGAGGA GCTTTTTTAA ATCATGTGTT ATCCGAGATG         960

GAATTAATAT TTGAATCTAG AGAATCGATT AAGGAATTTC TGAGTGTAGA TTACATTGAT        1020

AAAATTTTAG ATATATTTAA TAAGTCTACA ATAGATGAAA TAGCAGAGAT TTTCTCTTTT        1080

TTTAGAACAT TTGGGCATCC TCCATTAGAA GCTAGTATTG CAGCAGAAAA GGTTAGAAAA        1140

TATATGTATA TTGGAAAACA ATTAAAATTT GACACTATTA ATAAATGTCA TGCTATCTTC        1200

TGTACAATAA TAATTAACGG ATATAGAGAG AGGCATGGTG GACAGTGGCC TCCTGTGACA        1260

TTACCTGATC ATGCACACGA ATTCATCATA AATGCTTACG GTTCAAACTC TGCGATATCA        1320

TATGAAAATG CTGTTGATTA TTACCAGAGC TTTATAGGAA TAAAATTCAA TAAATTCATA        1380

GAGCCTCAGT TAGATGAGGA TTTGACAATT TATATGAAAG ATAAAGCATT ATCTCCAAAA        1440

AAATCAAATT GGGACACAGT TTATCCTGCA TCTAATTTAC TGTACCGTAC TAACGCATCC        1500

AACGAATCAC GAAGATTAGT TGAAGTATTT ATAGCAGATA GTAAATTTGA TCCTCATCAG        1560

ATATTGGATT ATGTAGAATC TGGGGACTGG TTAGATGATC CAGAATTTAA TATTTCTTAT        1620

AGTCTTAAAG AAAAAGAGAT CAAACAGGAA GGTAGACTCT TTGCAAAAAT GACATACAAA        1680

ATGAGAGCTA CACAAGTTTT ATCAGAGACA CTACTTGCAA ATAACATAGG AAAATTCTTT        1740

CAAGAAAATG GGATGGTGAA GGGAGAGATT GAATTACTTA AGAGATTAAC AACCATATCA        1800

ATATCAGGAG TTCCACGGTA TAATGAAGTG TACAATAATT CTAAAAGCCA TACAGATGAC        1860

CTTAAAACCT ACAATAAAAT AAGTAATCTT AATTTGTCTT CTAATCAGAA ATCAAAGAAA        1920

TTTGAATTCA AGTCAACGGA TATCTACAAT GATGGATACG AGACTGTGAG CTGTTTCCTA        1980

ACAACAGATC TCAAAAAATA CTGTCTTAAT TGGAGATATG AATCAACAGC TCTATTTGGA        2040

GAAACTTGCA ACCAAATATT TGGATTAAAT AAATTGTTTA ATTGGTTACA CCCTCGTCTT        2100

GAAGGAAGTA CAATCTATGT AGGTGATCCT TACTGTCCTC CATCAGATAA AGAACATATA        2160
```

```
TCATTAGAGG ATCACCCTGA TTCTGGTTTT TACGTTCATA ACCCAAGAGG GGGTATAGAA    2220

GGATTTTGTC AAAAATTATG GACACTCATA TCTATAAGTG CAATACATCT AGCAGCTGTT    2280

AGAATAGGCG TGAGGGTGAC TGCAATGGTT CAAGGAGACA ATCAAGCTAT AGCTGTAACC    2340

ACAAGAGTAC CCAACAATTA TGACTACAGA GTTAAGAAGG AGATAGTTTA TAAAGATGTA    2400

GTGAGATTTT TTGATTCATT AAGAGAAGTG ATGGATGATC TAGGTCATGA ACTTAAATTA    2460

AATGAAACGA TTATAAGTAG CAAGATGTTC ATATATAGCA AAAGAATCTA TTATGATGGG    2520

AGAATTCTTC CTCAAGCTCT AAAAGCATTA TCTAGATGTG TCTTCTGGTC AGAGACAGTA    2580

ATAGACGAAA CAAGATCAGC ATCTTCAAAT TTGGCAACAT CATTTGCAAA AGCAATTGAG    2640

AATGGTTATT CACCTGTTCT AGGATATGCA TGCTCAATTT TTAAGAACAT TCAACAACTA    2700

TATATTGCCC TTGGGATGAA TATCAATCCA ACTATAACAC AGAATATCAG AGATCAGTAT    2760

TTTAGGAATC CAAATTGGAT GCAATATGCC TCTTTAATAC CTGCTAGTGT TGGGGGATTC    2820

AATTACATGG CCATGTCAAG ATGTTTTGTA AGGAATATTG TGATCCATC AGTTGCCGCA    2880

TTGGCTGATA TTAAAAGATT TATTAAGGCG AATCTATTAG ACCGAAGTGT TCTTTATAGG    2940

ATTATGAATC AAGAACCAGG TGAGTCATCT TTTTTGGACT GGGCTTCAGA TCCATATTCA    3000

TGCAATTTAC CACAATCTCA AAATATAACC ACCATGATAA AAAATATAAC AGCAAGGAAT    3060

GTATTACAAG ATTCACCAAA TCCATTATTA TCTGGATTAT TCACAAATAC AATGATAGAA    3120

GAAGATGAAG AATTAGCTGA GTTCCTGATG GACAGGAAGG TAATTCTCCC TAGAGTTGCA    3180

CATGATATTC TAGATAATTC TCTCACAGGA ATTAGAAATG CCATAGCTGG AATGTTAGAT    3240

ACGACAAAAT CACTAATTCG GGTTGGCATA AATAGAGGAG GACTGACATA TAGTTTGTTG    3300

AGGAAAATCA GTAATTACGA TCTAGTACAA TATGAAACAC TAAGTAGGAC TTTGCGACTA    3360

ATTGTAAGTG ATAAAATCAA GTATGAAGAT ATGTGTTCGG TAGACCTTGC CATAGCATTG    3420

CGACAAAAGA TGTGGATTCA TTTATCAGGA GGAAGGATGA TAAGTGGACT TGAAACGCCT    3480

GACCCATTAG AATTACTATC TGGGGTAGTA ATAACAGGAT CAGAACATTG TAAAATATGT    3540

TATTCTTCAG ATGGCACAAA CCCATATACT TGGATGTATT TACCCGGTAA TATCAAAATA    3600

GGATCAGCAG AAACAGGTAT ATCGTCATTA AGAGTTCCTT ATTTTGGATC AGTCACTGAT    3660

GAAAGATCTG AAGCACAATT AGGATATATC AAGAATCTTA GTAAACCTGC AAAAGCCGCA    3720

ATAAGAATAG CAATGATATA TACATGGGCA TTTGGTAATG ATGAGATATC TTGGATGGAA    3780

GCCTCACAGA TAGCACAAAC ACGTGCAAAT TTTACACTAG ATAGTCTCAA AATTTTAACA    3840

CCGGTAGCTA CATCAACAAA TTTATCACAC AGATTAAAGG ATACTGCAAC TCAGATGAAA    3900

TTCTCCAGTA CATCATTGAT CAGAGTCAGC AGATTCATAA CAATGTCCAA TGATAACATG    3960

TCTATCAAAG AAGCTAATGA AACCAAAGAT ACTAATCTTA TTTATCAACA AATAATGTTA    4020

ACAGGATTAA GTGTTTTCGA ATATTTATTT AGATTAAAAG AAACCACAGG ACACAACCCT    4080

ATAGTTATGC ATCTGCACAT AGAAGATGAG TGTTGTATTA AGAAAGTTT TAATGATGAA    4140

CATATTAATC CAGAGTCTAC ATTAGAATTA ATTCGATATC CTGAAAGTAA TGAATTTATT    4200

TATGATAAAG ACCCACTCAA AGATGTGGAC TTATCAAAAC TTATGGTTAT TAAAGACCAT    4260

TCTTACACAA TTGATATGAA TTATTGGGAT GATACTGACA TCATACATGC AATTTCAATA    4320

TGTACTGCAA TTCAAATAGC AGATACTATG TCACAATTAG ATCGAGATAA TTTAAAAGAG    4380

ATAAATAGTTA TTGCAAATGA TGATGATATT AATAGCTTAA TCACTGAATT TTTGACTCTT    4440

GACATACTTG TATTTCTCAA GACATTTGGT GGATTATTAG TAAATCAATT TGCATACACT    4500

CTTTATAGTC TAAAAATAGA AGGTAGGGAT CTCATTTGGG ATTATATAAT GAGAACACTG    4560
```

```
AGAGATACTT CCCATTCAAT ATTAAAAGTA TTATCTAATG CATTATCTCA TCCTAAAGTA    4620

TTCAAGAGGT TCTGGGATTG TGGAGTTTTA AACCCTATTT ATGGTCCTAA TACTGCTAGT    4680

CAAGACCAGA TAAAACTTGC CCTATCTATA TGTGAATATT CACTAGATCT ATTTATGAGA    4740

GAATGGTTGA ATGGTGTATC ACTTGAAATA TACATTGTG ACAGCGATAT GGAAGTTGCA    4800

AATGATAGGA AACAAGCCTT TATTTCTAGA CACCTTTCAT TTGTTTGTTG TTTAGCAGAA    4860

ATTGCATCTT TCGGACCTAA CCTGTTAAAC TTAACATACT TGGAGAGACT TGATCTATTG    4920

AAACAATATC TTGAATTAAA TATTAAAGAA GACCCTACTC TTAAATATGT ACAAATATCT    4980

GGATTATTAA TTAAATCGTT CCCATCAACT GTAACATACG TAAGAAAGAC TGCAATCAAA    5040

TATCTAAGGA TTCGCGGTAT TAGTCCACCT GAGGTAATTG ATGATTGGGA TCCGGTAGAA    5100

GATGAAAATA TGCTGGATAA CATTGTCAAA ACTATAAATG ATAACTGTAA TAAAGATAAT    5160

AAAGGGAATA AAATTAACAA TTTCTGGGGA CTAGCACTTA AGAACTATCA AGTCCTTAAA    5220

ATCAGATCTA TAACAAGTGA TTCTGATGAT AATGATAGAC TAGATGCTAA TACAAGTGGT    5280

TTGACACTTC CTCAAGGAGG GAATTATCTA TCGCATCAAT TGAGATTATT CGGAATCAAC    5340

AGCACTAGTT GTCTGAAAGC TCTTGAGTTA TCACAAATTT TAATGAAGGA AGTCAATAAA    5400

GACAAGGACA GGCTCTTCCT GGGAGAAGGA GCAGGAGCTA TGCTAGCATG TTATGATGCC    5460

ACATTAGGAC CTGCAGTTAA TTATTATAAT TCAGGTTTGA ATATAACAGA TGTAATTGGT    5520

CAACGAGAAT TGAAAATATT TCCTTCAGAG GTATCATTAG TAGGTAAAAA ATTAGGAAAT    5580

GTGACACAGA TTCTTAACAG GGTAAAAGTA CTGTTCAATG GGAATCCTAA TTCAACATGG    5640

ATAGGAAATA TGGAATGTGA GAGCTTAATA TGGAGTGAAT TAAATGATAA GTCCATTGGA    5700

TTAGTACATT GTGATATGGA AGGAGCTATC GGTAAATCAG AAGAAACTGT TCTACATGAA    5760

CATTATAGTG TTATAAGAAT TACATACTTG ATTGGGGATG ATGATGTTGT TTTAGTTTCC    5820

AAAATTATAC CTACAATCAC TCCGAATTGG TCTAGAAATAC TTTATCTATA TAAATTATAT    5880

TGGAAAGATG TAAGTATAAT ATCACTCAAA ACTTCTAATC CTGCATCAAC AGAATTATAT    5940

CTAATTTCGA AAGATGCATA TTGTACTATA ATGGAACCTA GTGAAATTGT TTTATCAAAA    6000

CTTAAAAGAT TGTCACTCTT GGAAGAAAAT AATCTATTAA AATGGATCAT TTTATCAAAG    6060

AAGAGGAATA ATGAATGGTT ACATCATGAA ATCAAAGAAG GAGAAAGAGA TTATGGAATC    6120

ATGAGACCAT ATCATATGGC ACTACAAATC TTTGGATTTC AAATCAATTT AAATCATCTG    6180

GCGAAAGAAT TTTATCAAC CCCAGATCTG ACTAATATCA ACAATATAAT CCAAAGTTTT    6240

CAGCGAACAA TAAAGGATGT TTTATTTGAA TGGATTAATA TAACTCATGA TGATAAGAGA    6300

CATAAATTAG GCGGAAGATA TAACATATTC CCACTGAAAA ATAAGGGAAA GTTAAGACTG    6360

CTATCGAGAA GACTAGTATT AAGTTGGATT TCATTATCAT TATCGACTCG ATTACTTACA    6420

GGTCGCTTTC CTGATGAAAA ATTTGAACAT AGAGCACAGA CTGGATATGT ATCATTAGCT    6480

GATACTGATT TAGAATCATT AAAGTTATTG TCGAAAAACA TCATTAAGAA TTACAGAGAG    6540

TGTATAGGAT CAATATCATA TTGGTTTCTA ACCAAAGAAG TTAAAATACT TATGAAATTG    6600

ATTGGTGGTG CTAAATTATT AGGAATTCCC AGACAATATA AGAACCCGA AGACCAGTTA    6660

TTAGAAAACT ACAATCAACA TGATGAATTT GATATCGATT AAAACATAAA TACAATGTCG    6720

ACGATCCGGC TGCTAACAAA GCCCGAAAGG AAGCTGAGTT GGCTGCTGCC ACCGCTGAGC    6780

AATAACTAGC ATAACCCCTT GGGGCCTCTA AACGGGTCTT GAGGGGTTTT TTGCTGAAAG    6840

GAGGAACTAT ATCCGGATCG AGATCAATTC TGTGAGCGTA TGGCAAACGA AGGAAAAATA    6900
```

| | |
|---|---|
| GTTATAGTAG CCGCACTCGA TGGGACATTT CAACGTAAAC CGTTTAATAA TATTTTGAAT | 6960 |
| CTTATTCCAT TATCTGAAAT GGTGGTAAAA CTAACTGCTG TGTGTATGAA ATGCTTTAAG | 7020 |
| GAGGCTTCCT TTTCTAAACG ATTGGGTGAG GAAACCGAGA TAGAAATAAT AGGAGGTAAT | 7080 |
| GATATGTATC AATCGGTGTG TAGAAAGTGT TACATCGACT CATAATATTA TATTTTTAT | 7140 |
| CTAAAAAACT AAAAATAAAC ATTGATTAAA TTTTAATATA ATACTTAAAA ATGGATGTTG | 7200 |
| TGTCGTTAGA TAAACCGTTT ATGTATTTTG AGGAAATTGA TAATGAGTTA GATTACGAAC | 7260 |
| CAGAAAGTGC AAATGAGGTC GCAAAAAAAC TGCCGTATCA AGGACAGTTA AAACTATTAC | 7320 |
| TAGGAGAATT ATTTTTTCTT AGTAAGTTAC AGCGACACGG TATATTAGAT GGTGCCACCG | 7380 |
| TAGTGTATAT AGGATCTGCT CCCGGTACAC ATATACGTTA TTTGAGAGAT CATTTCTATA | 7440 |
| ATTTAGGAGT GATCATCAAA TGGATGCTAA TTGACGGCCG CCATCATGAT CCTATTTTAA | 7500 |
| ATGGATTGCG TGATGTGACT CTAGTGACTC GGTTCGTTGA TGAGGAATAT CTACGATCCA | 7560 |
| TCAAAAAACA ACTGCATCCT TCTAAGATTA TTTTAATTTC TGATGTGAGA TCCAAACGAG | 7620 |
| GAGGAAATGA ACCTAGTACG GCGGATTTAC TAAGTAATTA CGCTCTACAA AATGTCATGA | 7680 |
| TTAGTATTTT AAACCCCGTG GCGTCTAGTC TTAAATGGAG ATGCCCGTTT CCAGATCAAT | 7740 |
| GGATCAAGGA CTTTTATATC CCACACGGTA ATAAAATGTT ACAACCTTTT GCTCCTTCAT | 7800 |
| ATTCAGGGCC GTCGTTTTAC AACGTCGTGA CTGGGAAAAC CCTGGCGTTA CCCAACTTAA | 7860 |
| TCGCCTTGCA GCACATCCCC CTTTCGCCAG CTGGCGTAAT AGCGAAGAGG CCCGCACCGA | 7920 |
| TCGCCCTTCC CAACAGTTGC GCAGCCTGAA TGGCGAATGG CGCGACGCGC CCTGTAGCGG | 7980 |
| CGCATTAAGC GCGGCGGGTG TGGTGGTTAC GCGCAGCGTG ACCGCTACAC TTGCCAGCGC | 8040 |
| CCTAGCGCCC GCTCCTTTCG CTTTCTTCCC TTCCTTTCTC GCCACGTTCG CCGGCTTTCC | 8100 |
| CCGTCAAGCT CTAAATCGGG GGCTCCCTTT AGGGTTCCGA TTTAGTGCTT TACGGCACCT | 8160 |
| CGACCCCAAA AAACTTGATT AGGGTGATGG TTCACGTAGT GGGCCATCGC CCTGATAGAC | 8220 |
| GGTTTTTCGC CCTTTGACGT TGGAGTCCAC GTTCTTTAAT AGTGGACTCT TGTTCCAAAC | 8280 |
| TGGAACAACA CTCAACCCTA TCTCGGTCTA TTCTTTTGAT TTATAAGGGA TTTTGCCGAT | 8340 |
| TTCGGCCTAT TGGTTAAAAA ATGAGCTGAT TTAACAAAAA TTTAACGCGA ATTTTAACAA | 8400 |
| AATATTAACG TTTACAATTT CCCAGGTGGC ACTTTTCGGG GAAATGTGCG CGGAACCCCT | 8460 |
| ATTTGTTTAT TTTTCTAAAT ACATTCAAAT ATGTATCCGC TCATGAGACA ATAACCCTGA | 8520 |
| TAAATGCTTC AATAATATTG AAAAAGGAAG AGTATGAGTA TTCAACATTT CCGTGTCGCC | 8580 |
| CTTATTCCCT TTTTTGCGGC ATTTTGCCTT CCTGTTTTTG CTCACCCAGA AACGCTGGTG | 8640 |
| AAAGTAAAAG ATGCTGAAGA TCAGTTGGGT GCACGAGTGG GTTACATCGA ACTGGATCTC | 8700 |
| AACAGCGGTA AGATCCTTGA GAGTTTTCGC CCCGAAGAAC GTTTTCCAAT GATGAGCACT | 8760 |
| TTTAAAGTTC TGCTATGTGG CGCGGTATTA TCCCGTATTG ACGCCGGGCA AGAGCAACTC | 8820 |
| GGTCGCCGCA TACACTATTC TCAGAATGAC TTGGTTGAGT ACTCACCAGT CACAGAAAAG | 8880 |
| CATCTTACGG ATGGCATGAC AGTAAGAGAA TTATGCAGTG CTGCCATAAC CATGAGTGAT | 8940 |
| AACACTGCGG CCAACTTACT TCTGACAACG ATCGGAGGAC CGAAGGAGCT AACCGCTTTT | 9000 |
| TTGCACAACA TGGGGGATCA TGTAACTCGC CTTGATCGTT GGGAACCGGA GCTGAATGAA | 9060 |
| GCCATACCAA ACGACGAGCG TGACACCACG ATGCCTGTAG CAATGGCAAC AACGTTGCGC | 9120 |
| AAACTATTAA CTGGCGAACT ACTTACTCTA GCTTCCCGGC AACAATTAAT AGACTGGATG | 9180 |
| GAGGCGGATA AAGTTGCAGG ACCACTTCTG CGCTCGGCCC TTCCGGCTGG CTGGTTTATT | 9240 |
| GCTGATAAAT CTGGAGCCGG TGAGCGTGGG TCTCGCGGTA TCATTGCAGC ACTGGGGCCA | 9300 |

-continued

```
GATGGTAAGC CCTCCCGTAT CGTAGTTATC TACACGACGG GGAGTCAGGC AACTATGGAT    9360
GAACGAAATA GACAGATCGC TGAGATAGGT GCCTCACTGA TTAAGCATTG GTAACTGTCA    9420
GACCAAGTTT ACTCATATAT ACTTTAGATT GATTTAAAAC TTCATTTTTA ATTTAAAAGG    9480
ATCTAGGTGA AGATCCTTTT TGATAATCTC ATGACCAAAA TCCCTTAACG TGAGTTTTCG    9540
TTCCACTGAG CGTCAGACCC CGTAGAAAAG ATCAAAGGAT CTTCTTGAGA TCCTTTTTTT    9600
CTGCGCGTAA TCTGCTGCTT GCAAACAAAA AAACCACCGC TACCAGCGGT GGTTTGTTTG    9660
CCGGATCAAG AGCTACCAAC TCTTTTTCCG AAGGTAACTG GCTTCAGCAG AGCGCAGATA    9720
CCAAATACTG TCCTTCTAGT GTAGCCGTAG TTAGGCCACC ACTTCAAGAA CTCTGTAGCA    9780
CCGCCTACAT ACCTCGCTCT GCTAATCCTG TTACCAGTGG CTGCTGCCAG TGGCGATAAG    9840
TCGTGTCTTA CCGGGTTGGA CTCAAGACGA TAGTTACCGG ATAAGGCGCA GCGGTCGGGC    9900
TGAACGGGGG GTTCGTGCAC ACAGCCCAGC TTGGAGCGAA CGACCTACAC CGAACTGAGA    9960
TACCTACAGC GTGAGCTATG AGAAAGCGCC ACGCTTCCCG AAGGGAGAAA GGCGGACAGG   10020
TATCCGGTAA GCGGCAGGGT CGGAACAGGA GAGCGCACGA GGGAGCTTCC AGGGGGAAAC   10080
GCCTGGTATC TTTATAGTCC TGTCGGGTTT CGCCACCTCT GACTTGAGCG TCGATTTTTG   10140
TGATGCTCGT CAGGGGGGCG GAGCCTATGG AAAAACGCCA GCAACGCGGC CTTTTTACGG   10200
TTCCTGGCCT TTTGCTGGCC TTTTGCTCAC ATGTTCTTTC CTGCGTTATC CCCTGATTCT   10260
GTGGATAACC GTATTACCGC CTTTGAGTGA GCTGATACCG CTCGCCGCAG CCGAACGACC   10320
GAGCGCAGCG AGTCAGTGAG CGAGGAAGCG GAAGAGCGCC CAATACGCAA ACCGCCTCTC   10380
CCCGCGCGTT GGCCGATTCA TTAATGCAGC TGGCACGACA GGTTTCCCGA CTGGAAAGCG   10440
GGCAGTGAGC GCAACGCAAT TAATGTGAGT TAGCTCACTC ATTAGGCACC CCAGGCTTTA   10500
CACTTTATGC TTCCGGCTCG TATGTTGTGT GGAATTGTGA GCGGATAACA ATTTCACACA   10560
GGAAACAGCT ATGACCATGA TTACGCCAAG CTTTTGCGAT CAATAAATGG ATCACAACCA   10620
GTATCTCTTA ACGATGTTCT TCGCAGATGA TGATTCATTT TTTAAGTATT TGGCTAGTCA   10680
AGATGATGAA TCTTCATTAT CTGATATATT GCAAATCACT CAATATCTAG ACTTTCTGTT   10740
ATTATTATTG ATCCAATCAA AAAATAAATT AGAAGCCGTG GGTCATTGTT ATGAATCTCT   10800
TTCAGAGGAA TACAGACAAT TGACAAAATT CACAGACTTT CAAGATTTTA AAAAACTGTT   10860
TAACAAGGTC CCTATTGTTA CAGATGGAAG GGTCAAACTT AATAAAGGAT ATTTGTTCGA   10920
CTTTGTGATT AGTTTGATGC GATTCAAAAA AGAATCCTCT CTAGCTACCA CCGCAATAGA   10980
TCCTGTTAGA TACATAGATC CTCGTCGCAA TATCGCATTT TCTAACGTGA TGGATATATT   11040
AAAGTCGAAT AAAGTGAACA ATAATTAATT CTTTATTGTC ATCATGAACG GCGGACATAT   11100
TCAGTTGATA ATCGGCCCCA TGTTTTCAGG TAAAAGTACA GAATTAATTA GACGAGTTAG   11160
ACGTTATCAA ATAGCTCAAT ATAAATGCGT GACTATAAAA TATTCTAACG ATAATAGATA   11220
CGGAACGGGA CTATGGACGC ATGATAAGAA TAATTTTGAA GCATTGGAAG CAACTAAACT   11280
ATGTGATGTC TTGGAATCAA TTACAGATTT CTCCGTGATA GGTATCGATG AAGGACAGTT   11340
CTTTCCAGAC ATTGTTGAAT TGATCTCGAT CCCGCGAAAT TAATACGACT CACTATAGGG   11400
AGACCACAAC GGTTTCCCTC TAGCGGGATC AATTCCGCCC CTCTCCCTCC CCCCCCCTA    11460
ACGTTACTGG CCGAAGCCGC TTGGAATAAG GCCGGTGTGC GTTTGTCTAT ATGTTATTTT   11520
CCACCATATT GCCGTCTTTT GGCAATGTGA GGGCCCGGAA ACCTGGCCCT GTCTTCTTGA   11580
CGAGCATTCC TAGGGGTCTT TCCCCTCTCG CCAAAGGAAT GCAAGGTCTG TTGAATGTCG   11640
```

```
TGAAGGAAGC AGTTCCTCTG GAAGCTTCTT GAAGACAAAC AACGTCTGTA GCGACCCTTT    11700

GCAGGCAGCG GAACCCCCCA CCTGGCGACA GGTGCCTCTG CGGCCAAAAG CCACGTGTAT    11760

AAGATACACC TGCAAAGGCG GCACAACCCC AGTGCCACGT TGTGAGTTGG ATAGTTGTGG    11820

AAAGAGTCAA ATGGCTCTCC TCAAGCGTAT TCAACAAGGG GCTGAAGGAT GCCCAGAAGG    11880

TACCCCATTG TATGGGATCT GATCTGGGGC CTCGGTGCAC ATGCTTTACA TGTGTTTAGT    11940

CGAGGTTAAA AAACGTCTAG GCCCCCCGAA CCACGGGGAC GTGGTTTTCC TTTGAAAAAC    12000

ACGATAATAC C                                                        12011
```

(2) INFORMATION FOR SEQ ID NO:23:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:23:

```
GATCGATGCT AGCCC                                                    15
```

(2) INFORMATION FOR SEQ ID NO:24:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:24:

```
GATCGGGCTA GCATC                                                    15
```

(2) INFORMATION FOR SEQ ID NO:25:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:25:

```
TTACATGGCC AT                                                       12
```

(2) INFORMATION FOR SEQ ID NO:26:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:26:

```
TCACATGGCG AT                                                       12
```

(2) INFORMATION FOR SEQ ID NO:27:

(i) SEQUENCE CHARACTERISTICS:
    (A) LENGTH: 12 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TTTGGACTGG GC                                                    12

(2) INFORMATION FOR SEQ ID NO:28:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TTTTGATTGG GC                                                    12

(2) INFORMATION FOR SEQ ID NO:29:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TGGTCCTAAT ACTG                                                  14

(2) INFORMATION FOR SEQ ID NO:30:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TGGGCCTAAT ATCG                                                  14

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GCATTATCTA GATGTGTCTT CTGGTCAGAG                                  30

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:32:

CCTGAATTAT AATAATTAAC TGCAGGTCCT                                              30

(2) INFORMATION FOR SEQ ID NO:33:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:33:

GGGAAAGAAT CCAGAGACAA GAACGG                                                  26

(2) INFORMATION FOR SEQ ID NO:34:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:34:

GGTGAAGTTG TGGATCCATT TGATTG                                                  26

(2) INFORMATION FOR SEQ ID NO:35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:35:

CAACCTGTAA GGTACCAGCA TCCG                                                    24

(2) INFORMATION FOR SEQ ID NO:36:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:36:

GATATGGTGT TAGGCCTTGA TCTGTTC                                                 27

(2) INFORMATION FOR SEQ ID NO:37:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:37:

CGCCATGGAA AAATCAGAGA TCCTCTTCT        29

(2) INFORMATION FOR SEQ ID NO:38:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CTGGATCCTA ATTGGAGTTG TTACCCATGT A        31

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

AACCATGGCT GAAAAAGGGA AAA        23

(2) INFORMATION FOR SEQ ID NO:40:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GGTGAAGCTT AAGATGTGAT TTTACATATT TTA        33

(2) INFORMATION FOR SEQ ID NO:41:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

AAATAGGATC CCTACAGATC ATTAGATATT AAAAT        35

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

CGCCATGGTG TTCAGTGCTT GTTG        24

(2) INFORMATION FOR SEQ ID NO:43:

```
    (i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:43:

CCACAAGCTT AATTAACCAT AATATGCATC A                                31

(2) INFORMATION FOR SEQ ID NO:44:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:44:

TTCCATGGAT TTGGATTTGT CTATTGGGT                                   29

(2) INFORMATION FOR SEQ ID NO:45:

(i) SEQUENCE CHARACTERISTICS:
         (A) LENGTH: 15462 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:45:

ACCAAACAAG AGAAGAAACT TGCTTGGTAA TATAAATTTA ACTTAAAATT AACTTAGGAT    60

TTAAGACATT GACTAGAAGG TCAAGAAAAG GGAACTCTAT AATTTCAAAA ATGTTGAGCC   120

TATTTGATAC ATTTAATGCA CGTAGGCAAG AAAACATAAC AAAATCAGCC GGTGGAGCTA   180

TCATTCCTGG ACAGAAAAAT ACTGTCTCTA TATTCGCCCT TGGACCGACA ATAACTGATG   240

ATAATGAGAA AATGACATTA GCTCTTCTAT TTCTATCTCA TTCACTAGAT AATGAGAAAC   300

AACATGCACA AAGGGCAGGG TTCTTGGTGT CTTTATTGTC AATGGCTTAT GCCAATCCAG   360

AGCTCTACCT AACAACAAAT GGAAGTAATG CAGATGCCAA GTATGTCATA TACATGATTG   420

AGAAAGATCT AAAACGGCAA AAGTATGGAG GATTTGTGGT TAAGACGAGA GAGATGATAT   480

ATGAAAAGAC AACTGATTGG ATATTTGGAA GTGACCTGGA TTATGATCAG GAAACTATGT   540

TGCAGAACGG CAGGAACAAT TCAACAATTG AAGACCTTGT CCACACATTT GGGTATCCAT   600

CATGTTTAGG AGCTCTTATA ATACAGATCT GGATAGTTCT GGTCAAAGCT ATCACTAGTA   660

TCTCAGGGTT AAGAAAAGGC TTTTTCACCC GATTGGAAGC TTTCAGACAA GATGGAACAG   720

TGCAGGCAGG GCTGGTATTG AGCGGTGACA CAGTGGATCA GATTGGGTCA ATCATGCGGT   780

CTCAACAGAG CTTGGTAACT CTTATGGTTG AAACATTAAT AACAATGAAT ACCAGCAGAA   840

ATGACCTCAC AACCATAGAA AAGAATATAC AAATTGTTGG CAACTACATA AGAGATGCAG   900

GTCTCGCTTC ATTCTTCAAT ACAATCGAT ATGGAATTGA GACCAGAATG GCAGCTTTGA    960

CTCTATCCAC TCTCAGACCA GATATCAATA GATTAAAAGC TTTGATGGAA CTGTATTTAT  1020

CAAAGGGACC ACGCGCTCCT TTCATCTGTA TCCTCAGAGA TCCTATACAT GGTGAGTTCG  1080

CACCAGGCAA CTATCCTGCC ATATGGAGCT ATGCAATGGG GGTGGCAGTT GTACAAAATA  1140
```

-continued

| | |
|---|---|
| GAGCCATGCA ACAGTATGTG ACGGGAAGAT CATATCTAGA CATTGATATG TTCCAGCTAG | 1200 |
| GACAAGCAGT AGCACGTGAT GCCGAAGCTC AAATGAGCTC AACACTGGAA GATGAACTTG | 1260 |
| GAGTGACACA CGAAGCTAAA GAAAGCTTGA AGAGACATAT AAGGAACATA AACAGTTCAG | 1320 |
| AGACATCTTT CCACAAACCG ACAGGTGGAT CAGCCATAGA GATGGCAATA GATGAAGAGC | 1380 |
| CAGAACAATT CGAACATAGA GCAGATCAAG AACAAAATGG AGAACCTCAA TCATCCATAA | 1440 |
| TTCAATATGC CTGGGCAGAA GGAAATAGAA GCGATGATCA GACTGAGCAA GCTACAGAAT | 1500 |
| CTGACAATAT CAAGACCGAA CAACAAAACA TCAGAGACAG ACTAAACAAG AGACTCAACG | 1560 |
| ACAAGAAGAA ACAAAGCAGT CAACCACCCA CTAATCCCAC AAACAGAACA AACCAGGACG | 1620 |
| AAATAGATGA TCTGTTTAAC GCATTTGGAA GCAACTAATC GAATCAACAT TTTAATCTAA | 1680 |
| ATCAATAATA AATAAGAAAA ACTTAGGATT AAAGAATCCT ATCATACCGG AATATAGGGT | 1740 |
| GGTAAATTTA GAGTCTGCTT GAAACTCAAT CAATAGAGAG TTGATGGAAA GCGATGCTAA | 1800 |
| AAACTATCAA ATCATGGATT CTTGGGAAGA GGAATCAAGA GATAAATCAA CTAATATCTC | 1860 |
| CTCGGCCCTC AACATCATTG AATTCATACT CAGCACCGAC CCCCAAGAAG ACTTATCGGA | 1920 |
| AAACGACACA ATCAACACAA GAACCCAGCA ACTCAGTGCC ACCATCTGTC AACCAGAAAT | 1980 |
| CAAACCAACA GAAACAAGTG AGAAAGATAG TGGATCAACT GACAAAAATA GACAGTCTGG | 2040 |
| GTCATCACAC GAATGTACAA CAGAAGCAAA AGATAGAAAC ATTGATCAGG AAACTGTACA | 2100 |
| GAGAGGACCT GGGAGAAGAA GCAGCTCAGA TAGTAGAGCT GAGACTGTGG TCTCTGGAGG | 2160 |
| AATCCCCAGA AGCATCACAG ATTCTAAAAA TGGAACCCAA AACACGGAGG ATATTGATCT | 2220 |
| CAATGAAATT AGAAAGATGG ATAAGGACTC TATTGAGGGG AAAATGCGAC AATCTGCAAA | 2280 |
| TGTTCCAAGC GAGATATCAG GAAGTGATGA CATATTTACA ACAGAACAAA GTAGAAACAG | 2340 |
| TGATCATGGA AGAAGCCTGG AATCTATCAG TACACCTGAT ACAAGATCAA TAAGTGTTGT | 2400 |
| TACTGCTGCA ACACCAGATG ATGAAGAAGA AATACTAATG AAAAATAGTA GGACAAAGAA | 2460 |
| AAGTTCTTCA ACACATCAAG AAGATGACAA AAGAATTAAA AAAGGGGGAA AAGGGAAAGA | 2520 |
| CTGGTTTAAG AAATCAAAAG ATACCGACAA CCAGATACCA ACATCAGACT ACAGATCCAC | 2580 |
| ATCAAAAGGG CAGAAGAAAA TCTCAAAGAC AACAACCACC AACACCGACA CAAAGGGGCA | 2640 |
| AACAGAAATA CAGACAGAAT CATCAGAAAC ACAATCCTCA TCATGGAATC TCATCATCGA | 2700 |
| CAACAACACC GACCGGAACG AACAGACAAG CACAACTCCT CCAACAACAA CTTCCAGATC | 2760 |
| AACTTATACA AAAGAATCGA TCCGAACAAA CTCTGAATCC AAACCCAAGA CACAAAAGAC | 2820 |
| AAATGGAAAG GAAAGGAAGG ATACAGAAGA GAGCAATCGA TTTACAGAGA GGGCAATTAC | 2880 |
| TCTATTGCAG AATCTTGGTG TAATTCAATC CACATCAAAA CTAGATTTAT ATCAAGACAA | 2940 |
| ACGAGTTGTA TGTGTAGCAA ATGTACTAAA CAATGTAGAT ACTGCATCAA AGATAGATTT | 3000 |
| CCTGGCAGGA TTAGTCATAG GGGTTTCAAT GGACAACGAC ACAAAATTAA CACAGATACA | 3060 |
| AAATGAAATG CTAAACCTCA AAGCAGATCT AAAGAAAATG GACGAATCAC ATAGAAGATT | 3120 |
| GATAGAAAAT CAAAGAGAAC AACTGTCATT GATCACGTCA CTAATTTCAA ATCTCAAAAT | 3180 |
| TATGACTGAG AGAGGAGGAA AGAAAGACCA AAATGAATCC AATGAGAGAG TATCCATGAT | 3240 |
| CAAAACAAAA TTGAAAGAAG AAAAGATCAA GAAGACCAGG TTTGACCCAC TTATGGAGGC | 3300 |
| ACAAGGCATT GACAAGAATA TACCCGATCT ATATCGACAT GCAGGAGATA CACTAGAAAA | 3360 |
| CGATGTACAA GTTAAATCAG AGATATTAAG TTCATACAAT GAGTCAAATG CAACAAGACT | 3420 |
| AATACCCAAA AAAGTGAGCA GTACAATGAG ATCACTAGTT GCAGTCATCA ACAACAGCAA | 3480 |
| TCTCTCACAA AGCACAAAAC AATCATACAT AAACGAACTC AAACGTTGCA AAAATGATGA | 3540 |

```
AGAAGTATCT GAATTAATGG ACATGTTCAA TGAAGATGTC AACAATTGCC AATGATCCAA    3600

CAAAGAAACG ACACCGAACA AACAGACAAG AAACAACAGT AGATCAAAAC CTGTCAACAC    3660

ACACAAAATC AAGCAGAATG AAACAACAGA TATCAATCAA TATACAAATA AGAAAAACTT    3720

AGGATTAAAG AATAAATTAA TCCTTGTCCA AAATGAGTAT AACTAACTCT GCAATATACA    3780

CATTCCCAGA ATCATCATTC TCTGAAAATG GTCATATAGA ACCATTACCA CTCAAAGTCA    3840

ATGAACAGAG GAAAGCAGTA CCCCACATTA GAGTTGCCAA GATCGGAAAT CCACCAAAAC    3900

ACGGATCCCG GTATTTAGAT GTCTTCTTAC TCGGCTTCTT CGAGATGGAA CGAATCAAAG    3960

ACAAATACGG GAGTGTGAAT GATCTCGACA GTGACCCGAG TTACAAAGTT TGTGGCTCTG    4020

GATCATTACC AATCGGATTG GCTAAGTACA CTGGGAATGA CCAGGAATTG TTACAAGCCG    4080

CAACCAAACT GGATATAGAA GTGAGAAGAA CAGTCAAAGC GAAAGAGATG GTTGTTTACA    4140

CGGTACAAAA TATAAAACCA GAACTGTACC CATGGTCCAA TAGACTAAGA AAAGGAATGC    4200

TGTTCGATGC CAACAAAGTT GCTCTTGCTC CTCAATGTCT TCCACTAGAT AGGAGCATAA    4260

AATTTAGAGT AATCTTCGTG AATTGTACGG CAATTGGATC AATAACCTTG TTCAAAATTC    4320

CTAAGTCAAT GGCATCACTA TCGTTAACCA ACACAATATC AATCAATCTG CAGGTACACA    4380

TAAAAACAGG GGTTCAGACT GATTCTAAAG GGATAGTTCA AATTTTGGAT GAGAAAGGCG    4440

AAAAATCACT GAATTTCATG GTCCATCTCG GATTGATCAA AGAAAAGTA GGCAGAATGT     4500

ACTCTGTTGA ATACTGTAAA CAGAAAATCG AGAAATGAG ATTGATATTT TCTTTAGGAC     4560

TAGTTGGAGG AATCAGTCTT CATGTCAATG CAACTGGGTC CATATCAAAA ACACTAGCAA    4620

GTCAGCTGGT ATTCAAAAGA GAGATTTGTT ATCCTTTAAT GGATCTAAAT CCGCATCTCA    4680

ATCTAGTTAT CTGGGCTTCA TCAGTAGAGA TTACAAGAGT GGATGCAATT TTCCAACCTT    4740

CTTTACCTGG CGAGTTCAGA TACTATCCTA ATATTATTGC AAAAGGAGTT GGGAAAATCA    4800

AACAATGGAA CTAGTAATCT CTATTTTAGT CCGGACGTAT CTATTAAGCC GAAGCAAATA    4860

AAGGATAATC AAAAACTTAG GACAAAAGAG GTCAATACCA ACAACTATTA GCAGTCACAC    4920

TCGCAAGAAT AAGAGAGAAG GGACCAAAAA AGTCAAATAG GAGAAATCAA AACAAAAGGT    4980

ACAGAACACC AGAACAACAA AATCAAAACA TCCAACTCAC TCAAAACAAA AATTCCAAAA    5040

GAGACCGGCA ACACAACAAG CACTGAACAC AATGCCAACT TCAATACTGC TAATTATTAC    5100

AACCATGATC ATGGCATCTT TCTGCCAAAT AGATATCACA AAACTACAGC ACGTAGGTGT    5160

ATTGGTCAAC AGTCCCAAAG GGATGAAGAT ATCACAAAAC TTTGAAACAA GATATCTAAT    5220

TTTGAGCCTC ATACCAAAAA TAGAAGACTC TAACTCTTGT GGTGACCAAC AGATCAAGCA    5280

ATACAAGAAG TTATTGGATA GACTGATCAT CCCTTTATAT GATGGATTAA GATTACAAA     5340

AGATGTGATA GTAACCAATC AAGAATCCAA TGAAAACACT GATCCCAGAA CAAAACGATT    5400

CTTTGGAGGG GTAATTGGAA CCATTGCTCT GGGAGTAGCA ACCTCAGCAC AAATTACAGC    5460

GGCAGTTGCT CTGGTTGAAG CCAAGCAGGC AAGATCAGAC ATCGAAAAAC TCAAAGAAGC    5520

AATTAGGGAC ACAAACAAAG CAGTGCAGTC AGTTCAGAGC TCCATAGGAA ATTTAATAGT    5580

AGCAATTAAA TCAGTCCAGG ATTATGTTAA CAAAGAAATC GTGCCATCGA TTGCGAGGCT    5640

AGGTTGTGAA GCAGCAGGAC TTCAATTAGG AATTGCATTA ACACAGCATT ACTCAGAATT    5700

AACAAACATA TTTGGTGATA ACATAGGATC GTTACAAGAA AAAGGAATAA AATTACAAGG    5760

TATAGCATCA TTTATACCGCA CAAATATCAC AGAAATATTC ACAACATCAA CAGTTGATAA    5820

ATATGATATC TATGATCTGT TATTTACAGA ATCAATAAAG GTGAGAGTTA TAGATGTTGA    5880
```

```
CTTGAATGAT TACTCAATCA CCCTCCAAGT CAGACTCCCT TTATTAACTA GGCTGCTGAA    5940

CACTCAGATC TACAAAGTAG ATTCCATATC ATATAACATC CAAAACAGAG AATGGTATAT    6000

CCCTCTTCCC AGCCATATCA TGACGAAAGG GGCATTTCTA GGTGGAGCAG ACGTCAAAGA    6060

ATGTATAGAA GCATTCAGCA GCTATATATG CCCTTCTGAT CCAGGATTTG TATTAAACCA    6120

TGAAATAGAG AGCTGCTTAT CAGGAAACAT ATCCCAATGT CCAAGAACAA CGGTCACATC    6180

AGACATTGTT CCAAGATATG CATTTGTCAA TGGAGGAGTG GTTGCAAACT GTATAACAAC    6240

CACCTGTACA TGCAACGGAA TTGGTAATAG AATCAATCAA CCACCTGATC AAGGAGTAAA    6300

AATTATAACA CATAAAGAAT GTAGTACTGT GGGTATCAAC GGAATGCTGT TCAATACAAA    6360

TAAAGAAGGA ACTCTTGCAT TCTATACACC AAATGATATA ACACTAAACA ATTCTGTTAC    6420

ACTGGATCCA ATTGACATAT CAATCGAGCT CAACAAGGCC AAATCAGATC TAGAAGAATC    6480

AAAAGAATGG ATAAGAAGGT CAAATCAAAA ACTAGATTCT ATTGGAAATT GGCATCAATC    6540

TAGCACTACA ATCATAATTA TTTTGATAAT GATCATTATA TTGTTTATAA TTAATATAAC    6600

GATAATTACA ATTGCAATTA AGTATTACAG AATTCAAAAG AGAAATCGAG TGGATCAAAA    6660

TGACAAGCCA TATGTACTAA CAAACAAATA ACATATCTAC AGATCATTAG ATATTAAAAT    6720

TATAAAAAAC TTAGGAGTAA AGTTACGCAA TCCAACTCTA CTCATATAAT TGAGGAAGGA    6780

CCCAATAGAC AAATCCAAAT TCGAGATGGA ATACTGGAAG CATACCAATC ACGGAAAGGA    6840

TGCTGGTAAT GAGCTGGAGA CGTCTATGGC TACTCATGGC AACAAGCTCA CTAATAAGAT    6900

AATATACATA TTATGGACAA TAATCCTGGT GTTATTATCA ATAGTCTTCA TCATAGTGCT    6960

AATTAATTCC ATCAAAAGTG AAAAGGCCCA CGAATCATTG CTGCAAGACA TAAATAATGA    7020

GTTTATGGAA ATTACAGAAA AGATCCAAAT GGCATCGGAT AATACCAATG ATCTAATACA    7080

GTCAGGAGTG AATACAAGGC TTCTTACAAT TCAGAGTCAT GTCCAGAATT ACATACCAAT    7140

ATCATTGACA CAACAGATGT CAGATCTTAG GAAATTCATT AGTGAAATTA CAATTAGAAA    7200

TGATAATCAA GAAGTGCTGC CACAAAGAAT AACACATGAT GTAGGTATAA AACCTTTAAA    7260

TCCAGATGAT TTTTGGAGAT GCACGTCTGG TCTTCCATCT TTAATGAAAA CTCCAAAAAT    7320

AAGGTTAATG CCAGGGCCGG GATTATTAGC TATGCCAACG ACTGTTGATG GCTGTGTTAG    7380

AACTCCGTCT TTAGTTATAA ATGATCTGAT TTATGCTTAT ACCTCAAATC TAATTACTCG    7440

AGGTTGTCAG GATATAGGAA AATCATATCA AGTCTTACAG ATAGGGATAA TAACTGTAAA    7500

CTCAGACTTG GTACCTGACT TAAATCCTAG GATCTCTCAT ACCTTTAACA TAAATGACAA    7560

TAGGAAGTCA TGTTCTCTAG CACTCCTAAA TATAGATGTA TATCAACTGT GTTCAACTCC    7620

CAAAGTTGAT GAAAGATCAG ATTATGCATC ATCAGGCATA GAAGATATTG TACTTGATAT    7680

TGTCAATTAT GATGGTTCAA TCTCAACAAC AAGATTTAAG AATAATAACA TAAGCTTTGA    7740

TCAACCATAT GCTGCACTAT ACCCATCTGT TGGACCAGGG ATATACTACA AAGGCAAAAT    7800

AATATTTCTC GGGTATGGAG GTCTTGAACA TCCAATAAAT GAGAATGTAA TCTGCAACAC    7860

AACTGGGTGC CCCGGGAAAA CACAGAGAGA CTGTAATCAA GCATCTCATA GTACTTGGTT    7920

TTCAGATAGG AGGATGGTCA ACTCCATCAT TGTGGCTGAC AAAGGCTTAA ACTCAATTCC    7980

AAAATTGAAA GTATGGACGA TATCTATGCG ACAAAATTAC TGGGGGTCAG AAGGAAGGTT    8040

ACTTCTACTA GGTAACAAGA TCTATATATA TACAAGATCT ACAAGTTGGC ATAGCAAGTT    8100

ACAATTAGGA ATAATTGATA TTACTGATTA CAGTGATATA AGGATAAAAT GGACATGGCA    8160

TAATGTGCTA TCAAGACCAG GAAACAATGA ATGTCCATGG GGACATTCAT GTCCAGATGG    8220

ATGTATAACA GGAGTATATA CTGATGCATA TCCACTCAAT CCCACAGGGA GCATTGTGTC    8280
```

| | |
|---|---|
| ATCTGTCATA TTAGACTCAC AAAAATCGAG AGTGAACCCA GTCATAACTT ACTCAACAGC | 8340 |
| AACCGAAAGA GTAAACGAGC TGGCCATCCT AAACAGAACA CTCTCAGCTG GATATACAAC | 8400 |
| AACAAGCTGC ATTACACACT ATAACAAAGG ATATTGTTTT CATATAGTAG AAATAAATCA | 8460 |
| TAAAAGCTTA AACACATTTC AACCCATGTT GTTCAAAACA GAGATTCCAA AAAGCTGCAG | 8520 |
| TTAATCATAA TTAACCATAA TATGCATCAA TCTATCTATA ATACAAGTAT ATGATAAGTA | 8580 |
| ATCAGCAATC AGACAATAGA CAAAAGGGAA ATATAAAAAA CTTAGGAGCA AAGCGTGCTC | 8640 |
| GGGAAATGGA CACTGAATCT AACAATGGCA CTGTATCTGA CATACTCTAT CCTGAGTGTC | 8700 |
| ACCTTAACTC TCCTATCGTT AAAGGTAAAA TAGCACAATT ACACACTATT ATGAGTCTAC | 8760 |
| CTCAGCCTTA TGATATGGAT GACGACTCAA TACTAGTTAT CACTAGACAG AAAATAAAAC | 8820 |
| TTAATAAATT GGATAAAAGA CAACGATCTA TTAGAAGATT AAAATTAATA TTAACTGAAA | 8880 |
| AAGTGAATGA CTTAGGAAAA TACACATTTA TCAGATATCC AGAAATGTCA AAAGAAATGT | 8940 |
| TCAAATTATA TATACCTGGT ATTAACAGTA AAGTGACTGA ATTATTACTT AAAGCAGATA | 9000 |
| GAACATATAG TCAAATGACT GATGGATTAA GAGATCTATG GATTAATGTG CTATCAAAAT | 9060 |
| TAGCCTCAAA AAATGATGGA AGCAATTATG ATCTTAATGA AGAAATTAAT AATATATCGA | 9120 |
| AAGTTCACAC AACCTATAAA TCAGATAAAT GGTATAATCC ATTCAAAACA TGGTTTACTA | 9180 |
| TCAAGTATGA TATGAGAAGA TTACAAAAAG CTCGAAATGA GATCACTTTT AATGTTGGGA | 9240 |
| AGGATTATAA CTTGTTAGAA GACCAGAAGA ATTTCTTATT GATACATCCA GAATTGGTTT | 9300 |
| TGATATTAGA TAAACAAAAC TATAATGGTT ATCTAATTAC TCCTGAATTA GTATTGATGT | 9360 |
| ATTGTGACGT AGTCGAAGGC CGATGGAATA TAAGTGCATG TGCTAAGTTA GATCCAAAAT | 9420 |
| TACAATCTAT GTATCAGAAA GGTAATAACC TGTGGGAAGT GATAGATAAA TTGTTTCCAA | 9480 |
| TTATGGGAGA AAAGACATTT GATGTGATAT CGTTATTAGA ACCACTTGCA TTATCCTTAA | 9540 |
| TTCAAACTCA TGATCCTGTT AAACAACTAA GAGGAGCTTT TTTAAATCAT GTGTTATCCG | 9600 |
| AGATGGAATT AATATTTGAA TCTAGAGAAT CGATTAAGGA ATTTCTGAGT GTAGATTACA | 9660 |
| TTGATAAAAT TTTAGATATA TTTAATAAGT CTACAATAGA TGAAATAGCA GAGATTTTCT | 9720 |
| CTTTTTTTAG AACATTTGGG CATCCTCCAT TAGAAGCTAG TATTGCAGCA GAAAAGGTTA | 9780 |
| GAAAATATAT GTATATTGGA AAACAATTAA AATTTGACAC TATTAATAAA TGTCATGCTA | 9840 |
| TCTTCTGTAC AATAATAATT AACGGATATA GAGAGAGGCA TGGTGGACAG TGGCCTCCTG | 9900 |
| TGACATTACC TGATCATGCA CACGAATTCA TCATAAATGC TTACGGTTCA AACTCTGCGA | 9960 |
| TATCATATGA AAATGCTGTT GATTATTACC AGAGCTTTAT AGGAATAAAA TTCAATAAAT | 10020 |
| TCATAGAGCC TCAGTTAGAT GAGGATTTGA CAATTTATAT GAAAGATAAA GCATTATCTC | 10080 |
| CAAAAAAATC AAATTGGGAC ACAGTTTATC CTGCATCTAA TTTACTGTAC CGTACTAACG | 10140 |
| CATCCAACGA ATCACGAAGA TTAGTTGAAG TATTTATAGC AGATAGTAAA TTTGATCCTC | 10200 |
| ATCAGATATT GGATTATGTA GAATCTGGGG ACTGGTTAGA TGATCCAGAA TTTAATATTT | 10260 |
| CTTATAGTCT TAAAGAAAAA GAGATCAAAC AGGAAGGTAG ACTCTTTGCA AAAATGACAT | 10320 |
| ACAAAATGAG AGCTACACAA GTTTTATCAG AGACCCTACT TGCAAATAAC ATAGGAAAAT | 10380 |
| TCTTTCAAGA AAATGGGATG GTGAAGGGAG AGATTGAATT ACTTAAGAGA TTAACAACCA | 10440 |
| TATCAATATC AGGAGTTCCA CGGTATAATG AAGTGTACAA TAATTCTAAA AGCCATACAG | 10500 |
| ATGACCTTAA AACCTACAAT AAAAATAAGTA ATCTTAATTT GTCTTCTAAT CAGAAATCAA | 10560 |
| AGAAATTTGA ATTCAAGTCA ACGGATATCT ACAATGATGG ATACGAGACT GTGAGCTGTT | 10620 |

```
TCCTAACAAC AGATCTCAAA AAATACTGTC TTAATTGGAG ATATGAATCA ACAGCTCTAT    10680

TTGGAGAAAC TTGCAACCAA ATATTTGGAT TAAATAAATT GTTTAATTGG TTACACCCTC    10740

GTCTTGAAGG AAGTACAATC TATGTAGGTG ATCCTTACTG TCCTCCATCA GATAAAGAAC    10800

ATATATCATT AGAGGATCAC CCTGATTCTG GTTTTTACGT TCATAACCCA AGAGGGGGTA    10860

TAGAAGGATT TTGTCAAAAA TTATGGACAC TCATATCTAT AAGTGCAATA CATCTAGCAG    10920

CTGTTAGAAT AGGCGTGAGG GTGACTGCAA TGGTTCAAGG AGACAATCAA GCTATAGCTG    10980

TAACCACAAG AGTACCCAAC AATTATGACT ACAGAGTTAA GAAGGAGATA GTTTATAAAG    11040

ATGTAGTGAG ATTTTTTGAT TCATTAAGAG AAGTGATGGA TGATCTAGGT CATGAACTTA    11100

AATTAAATGA AACGATTATA AGTAGCAAGA TGTTCATATA TAGCAAAAGA ATCTATTATG    11160

ATGGGAGAAT TCTTCCTCAA GCTCTAAAAG CATTATCTAG ATGTGTCTTC TGGTCAGAGA    11220

CAGTAATAGA CGAAACAAGA TCAGCATCTT CAAATTTGGC AACATCATTT GCAAAAGCAA    11280

TTGAGAATGG TTATTCACCT GTTCTAGGAT ATGCATGCTC AATTTTTAAG AATATTCAAC    11340

AACTATATAT TGCCCTTGGG ATGAATATCA ATCCAACTAT AACACAGAAT ATCAGAGATC    11400

AGTATTTTAG GAATCCAAAT TGGATGCAAT ATGCCTCTTT AATACCTGCT AGTGTTGGGG    11460

GATTCAATCA CATGGCGATG TCAAGATGTT TTGTAAGGAA TATTGGTGAT CCATCAGTTG    11520

CCGCATTGGC TGATATTAAA AGATTTATTA AGGCGAATCT ATTAGACCGA AGTGTTCTTT    11580

ATAGGATTAT GAATCAAGAA CCAGGTGAGT CATCTTTTTT TGATTGGGCT TCAGATCCAT    11640

ATTCATGCAA TTTACCACAA TCTCAAAATA TAACCACCAT GATAAAAAAT ATAACAGCAA    11700

GGAATGTATT ACAAGATTCA CCAAATCCAT TATTATCTGG ATTATTCACA AATACAATGA    11760

TAGAAGAAGA TGAAGAATTA GCTGAGTTCC TGATGGACAG GAAGGTAATT CTCCCTAGAG    11820

TTGCACATGA TATTCTAGAT AATTCTCTCA CAGGAATTAG AAATGCCATA GCTGGAATGT    11880

TAGATACGAC AAAATCACTA ATTCGGGTTG GCATAAATAG AGGAGGACTG ACATATAGTT    11940

TGTTGAGGAA AATCAGTAAT TACGATCTAG TACAATATGA AACACTAAGT AGGACTTTGC    12000

GACTAATTGT AAGTGATAAA ATCAAGTATG AAGATATGTG TTCGGTAGAC CTTGCCATAG    12060

CATTGCGACA AAAGATGTGG ATTCATTTAT CAGGAGGAAG GATGATAAGT GGACTTGAAA    12120

CGCCTGACCC ATTAGAATTA CTATCTGGGG TAGTAATAAC AGGATCAGAA CATTGTAAAA    12180

TATGTTATTC TTCAGATGGC ACAAACCCAT ATACTTGGAT GTATTTACCC GGTAATATCA    12240

AAATAGGATC AGCAGAAACA GGTATATCGT CATTAAGAGT TCCTTATTTT GGATCAGTCA    12300

CTGATGAAAG ATCTGAAGCA CAATTAGGAT ATATCAAGAA TCTTAGTAAA CCTGCAAAAG    12360

CCGCAATAAG AATAGCAATG ATATATACAT GGGCATTTGG TAATGATGAG ATATCTTGGA    12420

TGGAAGCCTC ACAGATAGCA CAAACACGTG CAAATTTTAC ACTAGATAGT CTCAAAATTT    12480

TAACACCGGT AGCTACATCA ACAAATTTAT CACACAGATT AAAGGATACT GCAACTCAGA    12540

TGAAATTCTC CAGTACATCA TTGATCAGAG TCAGCAGATT CATAACAATG TCCAATGATA    12600

ACATGTCTAT CAAAGAAGCT AATGAAACCA AGATACTAA TCTTATTTAT CAACAAATAA    12660

TGTTAACAGG ATTAAGTGTT TTCGAATATT TATTTAGATT AAAAGAAACC ACAGGACACA    12720

ACCCTATAGT TATGCATCTG CACATAGAAG ATGAGTGTTG TATTAAAGAA GTTTTAATG    12780

ATGAACATAT TAATCCAGAG TCTACATTAG AATTAATTCG ATATCCTGAA AGTAATGAAT    12840

TTATTTATGA TAAAGACCCA CTCAAAGATG TGGACTTATC AAAACTTATG GTTATTAAAG    12900

ACCATTCTTA CACAATTGAT ATGAATTATT GGGATGATAC TGACATCATA CATGCAATTT    12960

CAATATGTAC TGCAATTACA ATAGCAGATA CTATGTCACA ATTAGATCGA GATAATTTAA    13020
```

```
AAGAGATAAT AGTTATTGCA AATGATGATG ATATTAATAG CTTAATCACT GAATTTTTGA    13080

CTCTTGACAT ACTTGTATTT CTCAAGACAT TTGGTGGATT ATTAGTAAAT CAATTTGCAT    13140

ACACTCTTTA TAGTCTAAAA ATAGAAGGTA GGGATCTCAT TTGGGATTAT ATAATGAGAA    13200

CACTGAGAGA TACTTCCCAT TCAATATTAA AAGTATTATC TAATGCATTA TCTCATCCTA    13260

AAGTATTCAA GAGGTTCTGG GATTGTGGAG TTTTAAACCC TATTTATGGG CCTAATATCG    13320

CTAGTCAAGA CCAGATAAAA CTTGCCCTAT CTATATGTGA ATATTCACTA GATCTATTTA    13380

TGAGAGAATG GTTGAATGGT GTATCACTTG AAATATACAT TTGTGACAGC GATATGGAAG    13440

TTGCAAATGA TAGGAAACAA GCCTTTATTT CTAGACACCT TTCATTTGTT TGTTGTTTAG    13500

CAGAAATTGC ATCTTTCGGA CCTAACCTGT TAAACTTAAC ATACTTGGAG AGACTTGATC    13560

TATTGAAACA ATATCTTGAA TTAAATATTA AGAAGACCC TACTCTTAAA TATGTACAAA     13620

TATCTGGATT ATTAATTAAA TCGTTCCCAT CAACTGTAAC ATACGTAAGA AAGACTGCAA    13680

TCAAATATCT AAGGATTCGC GGTATTAGTC CACCTGAGGT AATTGATGAT TGGGATCCGG    13740

TAGAAGATGA AAATATGCTG GATAACATTG TCAAAACTAT AAATGATAAC TGTAATAAAG    13800

ATAATAAAGG GAATAAAATT AACAATTTCT GGGGACTAGC ACTTAAGAAC TATCAAGTCC    13860

TTAAAATCAG ATCTATAACA AGTGATTCTG ATGATAATGA TAGACTAGAT GCTAATACAA    13920

GTGGTTTGAC ACTTCCTCAA GGAGGGAATT ATCTATCGCA TCAATTGAGA TTATTCGGAA    13980

TCAACAGCAC TAGTTGTCTG AAAGCTCTTG AGTTATCACA AATTTTAATG AAGGAAGTCA    14040

ATAAAGACAA GGACAGGCTC TTCCTGGGAG AAGGAGCAGG AGCTATGCTA GCATGTTATG    14100

ATGCCACATT AGGACCTGCA GTTAATTATT ATAATTCAGG TTTGAATATA ACAGATGTAA    14160

TTGGTCAACG AGAATTGAAA ATATTTCCTT CAGAGGTATC ATTAGTAGGT AAAAAATTAG    14220

GAAATGTGAC ACAGATTCTT AACAGGGTAA AAGTACTGTT CAATGGGAAT CCTAATTCAA    14280

CATGGATAGG AAATATGGAA TGTGAGAGCT TAATATGGAG TGAATTAAAT GATAAGTCCA    14340

TTGGATTAGT ACATTGTGAT ATGGAAGGAG CTATCGGTAA ATCAGAAGAA ACTGTTCTAC    14400

ATGAACATTA TAGTGTTATA AGAATTACAT ACTTGATTGG GGATGATGAT GTTGTTTTAG    14460

TTTCCAAAAT TATACCTACA ATCACTCCGA ATTGGTCTAG AATACTTTAT CTATATAAAT    14520

TATATTGGAA AGATGTAAGT ATAATATCAC TCAAAACTTC TAATCCTGCA TCAACAGAAT    14580

TATATCTAAT TTCGAAAGAT GCATATTGTA CTATAATGGA ACCTAGTGAA ATTGTTTTAT    14640

CAAAACTTAA AAGATTGTCA CTCTTGGAAG AAAATAATCT ATTAAAATGG ATCATTTTAT    14700

CAAAGAAGAG GAATAATGAA TGGTTACATC ATGAAATCAA AGAAGGAGAA AGAGATTATG    14760

GAATCATGAG ACCATATCAT ATGGCACTAC AAATCTTTGG ATTTCAAATC AATTTAAATC    14820

ATCTGGCGAA AGAATTTTTA TCAACCCCAG ATCTGACTAA TATCAACAAT ATAATCCAAA    14880

GTTTTCAGCG AACAATAAAG GATGTTTTAT TTGAATGGAT TAATATAACT CATGATGATA    14940

AGAGACATAA ATTAGGCGGA AGATATAACA TATTCCCACT GAAAAATAAG GGAAAGTTAA    15000

GACTGCTATC GAGAAGACTA GTATTAAGTT GGATTTCATT ATCATTATCG ACTCGATTAC    15060

TTACAGGTCG CTTTCCTGAT GAAAAATTTG AACATAGAGC ACAGACTGGA TATGTATCAT    15120

TAGCTGATAC TGATTTAGAA TCATTAAAGT TATTGTCGAA AACATCATT AAGAATTACA     15180

GAGAGTGTAT AGGATCAATA TCATATTGGT TTCTAACCAA AGAAGTTAAA ATACTTATGA    15240

AATTGATCGG TGGTGCTAAA TTATTAGGAA TTCCCAGACA ATATAAAGAA CCCGAAGACC    15300

AGTTATTAGA AAACTACAAT CAACATGATG AATTTGATAT CGATTAAAAC ATAAATACAA    15360
```

```
TGAAGATATA TCCTAACCTT TATCTTTAAG CCTAGGAATA GACAAAAAGT AAGAAAAACA    15420

TGTAATATAT ATATACCAAA CAGAGTTCTT CTCTTGTTTG GT                      15462
```

(2) INFORMATION FOR SEQ ID NO:46:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

```
TTGTCTGGGA AT                                                       12
```

(2) INFORMATION FOR SEQ ID NO:47:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

```
TTGCCTGGGA AT                                                       12
```

(2) INFORMATION FOR SEQ ID NO:48:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

```
TTGTTTGGGA AT                                                       12
```

(2) INFORMATION FOR SEQ ID NO:49:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

```
TTGTCTGGTA AT                                                       12
```

(2) INFORMATION FOR SEQ ID NO:50:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

```
AACTTTAAAT TA                                                       12
```

(2) INFORMATION FOR SEQ ID NO:51:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

AACTTAAAAT TA                                               12

(2) INFORMATION FOR SEQ ID NO:52:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

TTAAAGACAT TG                                               12

(2) INFORMATION FOR SEQ ID NO:53:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

TTTAAGACAT TG                                               12

(2) INFORMATION FOR SEQ ID NO:54:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

GCAGATGTCA AG                                               12

(2) INFORMATION FOR SEQ ID NO:55:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

GCAGATGCCA AG                                               12

(2) INFORMATION FOR SEQ ID NO:56:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

CGAATCTAAA GA                                                          12

(2) INFORMATION FOR SEQ ID NO:57:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CGAAGCTAAA GA                                                          12

(2) INFORMATION FOR SEQ ID NO:58:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

GAAATATTGA TC                                                          12

(2) INFORMATION FOR SEQ ID NO:59:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

GAAACATTGA TC                                                          12

(2) INFORMATION FOR SEQ ID NO:60:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

TCTCTACCCA AC                                                          12

(2) INFORMATION FOR SEQ ID NO:61:

(i) SEQUENCE CHARACTERISTICS:
        (A) LENGTH: 12 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:61:

TCGTTAACCA AC                      12

(2) INFORMATION FOR SEQ ID NO:62:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:62:

AGTACAATAG GT                      12

(2) INFORMATION FOR SEQ ID NO:63:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:63:

AGTACTGTGG GT                      12

(2) INFORMATION FOR SEQ ID NO:64:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:64:

GCACTTGATC CA                      12

(2) INFORMATION FOR SEQ ID NO:65:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:65:

ACACTGGATC CA                      12

(2) INFORMATION FOR SEQ ID NO:66:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:66:

-continued

CCATCATTGT TGTTGACAA                                                19

(2) INFORMATION FOR SEQ ID NO:67:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

CCATCATTGT GGCTGACAA                                                19

(2) INFORMATION FOR SEQ ID NO:68:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

TTACATGGCC A                                                        11

(2) INFORMATION FOR SEQ ID NO:69:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

TCACATGGCG A                                                        11

(2) INFORMATION FOR SEQ ID NO:70:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

TTTGGACTGG GC                                                       12

(2) INFORMATION FOR SEQ ID NO:71:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

TTTTGATTGG GC                                                       12

```
(2) INFORMATION FOR SEQ ID NO:72:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:72:

GGTCCTAATA CT                                                                  12

(2) INFORMATION FOR SEQ ID NO:73:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:73:

GGGCCTAATA TC                                                                  12

(2) INFORMATION FOR SEQ ID NO:74:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:74:

CCATAGAGAG TCCATGGAAA GCGACGCTAA AAACTATC                                      38
```

PRODUCTION OF ATTENUATED PARAINFLUENZA VIRUS VACCINES FROM CLONED NUCLEOTIDE SEQUENCES

RELATED APPLICATIONS

The present application claims the benefit under Title 35 of U.S. C. 119(e) of Provisional Application No. 60/047,575, filed May 23, 1997, and U.S. Provisional Application No. 60/059,385, filed Sep. 19, 1997, each of which is incorporated herein by reference.

BACKGROUND OF THE INVENTION

Human parainfluenza viruses (HPIV), HPIV1, HPIV2, and HPIV3 are significant causes of bronchiolitis, croup and pneumonia in infants and children. Karron et al., *J. Infect. Dis.* 172: 1445–50 (1995); Collins et al. "Parainfluenza Viruses", p. 1205–1243. In B. N. Fields et al., eds., *Fields Virology*, 3rd ed, vol. 1. Lippincott-Raven Publ., Philadelphia (1996); Murphy et al., *Virus Res.* 11:1–15 (1988). Infections by these viruses result in substantial morbidity in children less than 3 years of age, and are responsible for approximately 20% of hospitalizations among young infants and children for respiratory tract infections.

Despite considerable efforts to develop effective vaccine therapies against HPIV, no approved vaccine agents have yet been achieved for any HPIV strain, nor for ameliorating HPIV related illnesses. To date, only two live attenuated PIV vaccine candidates have received particular attention. One of these candidates is a bovine PIV (BPIV) strain that is antigenically related to HPIV3, and which has been shown to protect animals against HPIV3. BPIV3 is attenuated, genetically stable and immunogenic in human infants and children (Karron et al., *J. Inf. Dis.* 171:1107–14 (1995a); Karron et al., *J. Inf. Dis.* 172:1445–1450, (1995b)). A second PIV3 vaccine candidate, JS cp45 is a cold-adapted mutant of the JS wildtype (wt) strain of HPIV3 (Karron et al., (1995b), supra; Belshe et al., *J. Med. Virol.* 10:235–42 (1982)). This live, attenuated, cold-passaged (cp) PIV3 vaccine candidate exhibits temperature-sensitive (ts), cold-adaptation (ca), and attenuation (att) phenotypes which are stable after viral replication in vivo. The cp45 virus is protective against human PIV3 challenge in experimental animals and is attenuated, genetically stable, and immunogenic in seronegative human infants and children (Hall et al., *Virus Res.* 22:173–184 (1992); Karron et al., (1995b), supra.

HPIV3 is a member of the *Paramyxovirus* genus of the Paramyxovirus family, order Mononegavirales. Its genome is a single strand of negative-sense RNA 15462 nucleotides (nt) in length (Galinski et al., *Virology* 165: 499–510, (1988); Stokes et al., *Virus Res.* 25:91–103 (1992)) and encodes at least eight proteins (Collins et al., supra, (1996); Galinski, supra, (1991); Spriggs and Collins, *J. Gen. Virol.* 67: 2705–2719, (1986)). Three of these proteins are associated with the RNA genome to form the nucleocapsid; namely the nucleocapsid protein N, phosphoprotein P, and large polymerase subunit L. Three additional proteins are associated with the envelope, namely the matrix protein M, taught to mediate viral attachment and release, the hemagglutinin-neuraminidase protein HN, and the fusion protein F. Two other proteins, HN and F, represent the neutralizing and protective antigens of PIVs (Collins et al. In *Fields Virology*, 3rd ed., 1:1205–43 (1996)). Significant sequence divergence in these two protective antigens among different PIVs is the basis for the type specificity of protective immunity against these pathogens (id.).

Another protein of PIV, the C protein, is encoded by an overlapping open reading frame (ORF) of the P protein mRNA (Spriggs and Collins, 1986), and the D protein is generated by RNA editing of the P cistron (Galinski et al. *Virology* 186:543–50 (1992)). The P mRNA also contains an internal ORF which has the potential to encode a cystein-rich domain called V. The V ORF is also found in other paramyxoviruses and typically is accessed by RNA editing, but this is not the case with PIV. Presently, it is not known whether the PIV V ORF is expressed.

The viral genome of PIV also contains extragenic leader and trailer regions, possessing promoters required for viral replication and transcription. Thus, the PIV genetic map is represented as 3' leader-N-P/C/D-M-F-HN-L-trailer. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination.

Identification of attenuating mutations in cp45 and other PIV3 vaccine candidates is of interest for a variety of reasons. In particular, it will be useful to understand the genetic basis of attenuation and to characterize the molecular virology and pathogenesis of attenuated HPIV3 strains to provide clinically acceptable vaccines for use against these and other paramyxoviruses, especially HPIV1 and HPIV2 which together account for an additional 7% of pediatric hospital admissions. To achieve these and related goals, a method for producing virus with a wt phenotype from cDNA is needed to determine which mutation(s) in the cp45 virus specify the ts, ca and att phenotypes and which gene(s) of the BPIV3 specify the attenuation phenotype.

The complete nucleotide sequences of the prototype PIV3 strain, and of the JS wt HPIV3 and cp45 strains have been determined (Stokes et al., supra., (1992); Stokes et al., *Virus Res.* 30: 43–52 (1993)). From these studies, the cp45 strain was shown to possess at least seventeen nucleotide substitutions compared to the parental JS wt HPIV3 strain, eight of which are correlated with changes to viral proteins. However, it has not been previously shown which of these identified mutations specify desired, e.g., ts, ca, and att, phenotypes. Recently, growth of cp45 at nonpermissive temperatures was reported to be complemented by coexpression of a cDNA clone of the L gene of the 47885 wt PIV3 strain (Ray et al., *J. Virol.* 70:580–584 (1996)), suggesting that the L gene may contain one or more mutations which contribute to the ts phenotype of cp45. However, the results of this study are complicated by the fact that the 47885 strain is not isogenic with the JS parent of cp45 (for example, the two viruses are 4% different at the nucleotide level, and the L proteins differ at 41 amino acid positions (Stokes et al., supra, (1992); published erratum appears in *Virus Res.* 27:96 (1993); *Virus Res.* 25:91–103. Also, this method of complementation does not provide a clear measurement of the relative contribution of the L gene mutation(s) to the overall ts phenotype of cp45.

Rescue and analysis of attenuating mutations in PIV3 and other RNA viruses require effective methods to manipulate cDNAs for the particular viruses of interest. Despite previous advancements identifying cDNAs for PIV, manipulation of the genomic RNA of this and other negative-sense RNA viruses has proven difficult. One major obstacle in this regard is that the naked genomic RNA of these viruses is noninfectious.

Successful methods for direct genetic manipulation of non-segmented negative strand RNA viruses have only recently begun to be developed (for reviews, see Conzelmann, *J. Gen. Virol.* 77:381–89 (1996); Palese et al., *Proc. Natl. Acad. Sci. U.S.A.* 93:11354–58, (1996)). Functional nucleocapsids have been successfully generated from the intracellular coexpression of separately transfected plasmids bearing the T7 RNA polymerase promoter and encoding either genomic or antigenomic RNA and the N, P, and L proteins. The intracellular cDNA expression is driven by T7 RNA polymerase which is produced by co-infecting with a vaccinia recombinant virus. This approach was first used to determine the transcription and replication requirements of cDNA-encoded minireplicons. Some success has been achieved in the application of these general methods to rescue infectious rabies virus, vesicular stomatitis virus (VSV), measles virus, and Sendai virus from cDNA-encoded antigenomic RNA in the presence of the nucleocapsid N, phosphoprotein P, and large polymerase subunit L (Garcin et al., *EMBO J.* 14:6087–6094 (1995); Lawson et al., *Proc. Natl. Acad. Sci. U.S.A.* 92:4477–81 (1995); Radecke et al., *EMBO J.* 14:5773–5784 (1995); Schnell et al., *EMBO J.* 13:4195–203 (1994); Whelan et al., *Proc. Natl. Acad. Sci. U.S.A.* 92:8388–92 (1995)). Respiratory synctial virus (RSV) has also been recovered from cDNA encoded antigenome but this required the transfection of an additional plasmid encoding the M2 ORF 1 transcription elongation factor (Collins et al., 1995).

Rescue of infectious PIV virus and other Mononegavirales members is complicated by virtue of their non-segmented negative-strand RNA genome. The genomic ribonucleoprotein complexes (RNPs) of segmented genome viruses, such as influenza, are generally small in size and loosely structured, and can be assembled in vitro from RNA and required viral proteins. However, PIV and other Mononegavirales members feature much larger and more tightly structured RNPs, which tend to be refractory to functional association in vitro. Furthermore, the coding potential of HPIV3 P mRNA is complicated by cotranscriptional "RNA editing" (Galinski et al., *Virology* 186: 543–50 (1992)). The resultant shifts in reading frame can access internal ORFs which are expressed as chimeras fused to the N-terminal part of P. In addition, HPIV3 appears to differ from most other paramyxoviruses which express a chimeric V protein, as noted above. The corresponding set of proteins from HPIV3 editing has not yet been identified, and the internal V ORF of HPIV3 is separated from the editing site by numerous translational stop codons (Galinski et al. (1992, supra). Yet another complicating factor is that editing by BPIV3 and HPIV3 produces a novel chimeric protein D, in which the upstream half of P is fused to a domain encoded by a second internal ORF (Pelet et al., *EMBO J.* 10: 443–448 (1991); Galinski et al., supra, (1992)). The D protein does not have a counterpart in other paramyxoviruses.

In view of the foregoing, an urgent need exists in the art for tools and methods to engineer safe and effective vaccines to alleviate the serious health problems attributable to PIV, particularly illnesses among infants and children attributable to HPIV3. Quite surprisingly, the present invention satisfies these and other related needs.

SUMMARY OF THE INVENTION

The present invention provides novel tools and methods for introducing defined, predetermined structural and phenotypic changes into infectious PIV. In one embodiment of the invention, an isolated polynucleotide molecule is provided which comprises an operably linked transcriptional promoter, a polynucleotide sequence encoding a PIV genome or antigenome, and a transcriptional terminator.

The PIV genome or antigenome can be a human or nonhuman PIV sequence, or a recombinantly modified version thereof. In one embodiment, the polynucleotide sequence encodes a chimeric genome or antigenome comprising a human PIV sequence recombinantly joined with a nonhuman PIV sequence, such as a gene or gene segment from bovine PIV (BPIV). In additional examples, the polynucleotide encodes a chimera of sequences from a nonhuman PIV and at least one other PIV of human or nonhuman origin.

In other embodiments, the invention provides an isolated infectious PIV particle comprising a recombinant PIV (rPIV) genome or antigenome. The isolated infectious PIV particle can be a viral or subviral particle. As used herein, subviral particle refers to any infectious PIV particle which lacks a structural element, eg., a gene segment, gene, protein, or protein functional domain, which is present in a complete virus (eg., an assembled virion including a complete genome or antigenome, nucleocapsid and envelope). Thus, one example of a subviral particle of the invention is an infectious nucleocapsid containing a genome or antigenome, and the products of N, P, and L genes. Other subviral particles are produced by partial or complete deletions or substitutions of non-essential genes and/or their products (eg., F, HN, M, or C), among other non-essential structural elements.

The isolated infectious PIV particle is preferably a human PIV, more preferably human PIV3 (HPIV3). The invention also provides isolated, infectious particles from bovine or murine PIV (BPIV or MPIV), as well as particles comprising chimeric sequences from two or more different PIV genomes, for example particles incorporating polynucleotide sequences from HPIV3 and HPIV1, from HPIV3 and HPIV2 sequences, or comprised of HPIV3 and BPIV sequences.

In related aspects of the invention, isolated, infectious PIV particles are provided which incorporate nucleotide sequences from HPIV3 joined to at least one sequence from a heterologous PIV, such as HPIV1, HPIV2, BPIV or MPIV. For example, entire genes of HPIV3 may be replaced by counterpart genes from other forms of PIV, such as the HN and/or F glycoprotein genes of PIV1 or PIV2. Alternatively, a selected gene segment, for example a cytoplasmic tail, transmembrane domain or ectodomain of HN or F of HPIV1 or HPIV2, can be substituted for a corresponding gene segment in a counterpart HPIV3 gene to yield constructs encoding chimeric proteins, e.g. fusion proteins having a cytoplasmic tail and/or transmembrane domain of PIV3 fused to an ectodomain of PIV1 or PIV2. Alternatively, genes or gene segments from one PIV can be added (i.e., without substitution) within a heterologous PIV background to create novel immunogenic properties within the resultant clone.

Other modifications can be produced by introducing into a PIV genome or antigenome a nucleotide insertion, rearrangement, deletion or substitution selected to encode a desired phenotypic alteration, such as one that results in attenuation, temperature-sensitivity, cold-adaptation, small plaque size, host range restriction, improved growth in vitro or a change in an immunogenic epitope of PIV. In one aspect of the invention, mutations occurring in biologically derived, attenuated PIV are identified and introduced individually or in combination into a full-length PIV clone. Typically these mutations are single amino acid changes displayed by biologically derived mutant viruses over a wild-type PIV, for example changes exhibited by PIV mutants having ts, ca or att phenotypes. These changes from biologically derived mutant PIV are incorporated into a recombinant PIV clone to specify desired characteristics in the resultant virus. Exemplary mutations include amino acid changes which specify an attenuated phenotype in the HPIV3 strain JS cp45. Among these exemplary mutations are mutations occurring within the PIV polymerase gene L specifying ts, ca or att phenotypes, for example amino acid substitutions occurring at $Tyr_{942}$, $Leu_{992}$, and/or $Thr_{1558}$ of the JS wild type PIV strain. In more detailed aspects, attenuated PIV recombinants are described wherein $Tyr_{942}$ is replaced by His, $Leu_{992}$ is replaced by Phe, and/or $Thr_{1558}$ is replaced by Ile.

Also provided within the invention are recombinant PIV having multiple, phenotype-specifying mutations introduced in selected combinations into the genome or antigenome of an infectious clone to yield desired characteristics including attenuation, temperature sensitivity, cold-adaptation, small plaque size, host range restriction, etc. For example, PIV clones are provided which incorporate at least two separate mutations adopted from a biologically derived PIV mutant, e.g., two ts mutations from HPIV3 JS cp45. Multiply attenuated viruses are thus obtained by selecting mutations from a "menu" of identified lesions and introducing these mutations in various combinations to calibrate a vaccine virus to selected levels of attenuation, immunogenicity and stability.

In additional embodiments, the invention provides for supplementation of one or more mutations adopted from biologically derived PIV, e.g., ts, ca or att mutations, with additional types of mutations involving the same or different genes. Target genes for mutation in this context include the nucleocapsid protein N, phosphoprotein P, large polymerase subunit L, matrix protein M, hemagglutinin-neuraminidase protein HN, fusion protein F and the C, D and V ORF products. In preferred aspects, attenuating mutations adopted from biologically derived PIV are incorporated within a chimeric PIV recombinant, e.g., a PIV recombinant having nucleotide sequences from both HPIV3 and HPIV1, or from both HPIV and BPIV viruses.

In other embodiments, the invention provides methods for producing an infectious PIV particle, e.g, a viral or subviral particle, from one or more isolated polynucleotide molecules encoding a PIV genome or antigenome (see also copending U.S. provisional patent application No. 60/047, 575, filed May 23, 1997, incorporated herein by reference in its entirety). To produce an infectious PIV particle according to these methods, an expression vector comprising an isolated polynucleotide molecule encoding a PIV genome or antigenome is coexpressed in a cell or cell-free system with an expression vector comprising one or more isolated polynucleotide molecules encoding N, P, and L proteins of a PIV, whereby an infectious PIV particle is produced.

The PIV genome or antigenome and the N, P, and L proteins may be coexpressed by a single expression vector, or by separate expression vectors. In alternate embodiments, the N, P, and L proteins are each encoded on separate expression vectors.

Within the aforementioned methods, the polynucleotide molecule encoding the PIV genome or antigenome may correspond to a genomic or antigenomic sequence of human, bovine or murine PIV. Alternatively, the PIV encoding polynucleotide may be a chimera of a human PIV genomic or antigenomic sequence and at least one non-human PIV genomic or antigenomic sequence. In additional methods for producing infectious PIV, the polynucleotide encoding the PIV genome or antigenome is a chimera of two or more human PIV genomes, for example a polynucleotide containing sequences from HPIV3 joined to sequences from one or more related forms of human PIV, such as human PIV1 or human PIV2. Individual genes of human PIV3 may be substituted by counterpart genes from heterologous PIV, for example the HN and F glycoprotein genes of PIV1 or PIV2, to yield a modified genome or antigenome encoding a chimeric PIV. Alternatively, a selected, heterologous gene segment, such as a cytoplasmic tail, transmembrane domain or ectodomain of HN or F of HPIV1 or HPIV2, can be substituted for a counterpart gene segment in a different PIV type or different gene, e.g., HN or F of HPIV3, to yield constructs encoding chimeric proteins, e.g. fusion proteins having a cytoplasmic tail and/or transmembrane domain of PIV3 fused to an ectodomain of PIV1 or PIV2.

In yet additional methods for producing infectious PIV, the PIV genome or antigenome is modified to yield a chimera of a human PIV genomic or antigenomic sequence and at least one non-human PIV sequence, for example a polynucleotide containing sequences from both human and bovine PIV.

In other methods for producing infectious PIV, the PIV genome or antigenome is modified by a nucleotide insertion, rearrangement, deletion or substitution selected to encode a desirable phenotypic alteration, such as one that results in attenuation, temperature-sensitivity, cold-adaptation, small plaque size, host range restriction, or a change in an immunogenic epitope of PIV. Alternatively, the polynucleotide molecule encoding the PIV genome or antigenome can be modified to encode non-PIV molecules, e.g., a cytokine, a T-helper epitope, a restriction site marker, or a protein of a different microbial pathogen (e.g., virus, bacterium or fungus) capable of eliciting a protective immune response in the intended host. In one embodiment, the PIV genome or antigenome is modified to encode protein from a human RSV or from measles virus.

In other embodiments of the invention a cell or cell-free expression system (e.g., a cell-free lysate) is provided which incorporates an expression vector comprising an isolated polynucleotide molecule encoding a PIV genome or antigenome, and an expression vector comprising one or more isolated polynucleotide molecules encoding N, P, and L proteins of a PIV. Upon expression, the genome or antigenome and N, P, and L proteins combine to produce an infectious PIV particle, such as a viral or subviral particle. The isolated polynucleotide molecules encoding the PIV genome or antigenome and the one or more isolated polynucleotide molecules encoding N, P, and L proteins of PIV can be expressed by a single vector, or the genome and one or more of the N, P, and L proteins can be incorporated into two or more separate vectors.

BRIEF DESCRIPTION OF THE DRAWINGS

FIG. 2 depicts sequence markers in cDNA encoded genomic RNA of the HN (1) and L(2) genes of HPIV3. Sequences are negative sense, mutations are boxed.

1) A non-coding nt substitution at 7903 removes a Hga I site from JS wt. Nucleotide substitutions in JS cDNA at 7913 and 7915 create a Sca I site and change amino acid 370 from proline to threonine, ablating the antibody epitope recognized by mAb 170/7 and 423/6. Also, the HN gene was found to contain an additional point mutation at nt 7593 which had not been recognized previously. This results in a threonine to isoleucine change at amino acid position 263 in the HN protein.

2) The three incidental non-coding mutations in the L gene of JS cDNA that occurred during plasmid construction or assembly are boxed.

FIG. 3 includes a diagram (not to scale) of the PIV3-CAT cDNA (top, drawn as a circular plasmid) and the encoded minigenome RNA (bottom, drawn as a single strand of negative-sense RNA, 3' to 5').

Plasmid: The T7 promoter is shown as a black arrow pointing in the direction of transcription. Positions are shown for the delta ribozyme, the T7 transcriptional terminator, the inserted vaccinia virus transcriptional terminators ($T_7$CT and $T_5$AT), restriction enzyme sites, and the coding sequence for the various domains of the encoded minigenome.

Minigenome RNA: The 5' (right hand) end of the minigenome is defined by the promoter for T7 RNA polymerase, which contributes an extension of two nonviral G residues. These are not included in length calculations. The 3' end is defined by the ribozyme and is free of any heterologous nucleotides. PIV3-specific regions are shown as open boxes. The CAT ORF is shaded and the negative-sense complements of the translational initiation (UAC) and termination (AUU) codons are shown. Nucleotide positions are indicated according to the shortest, 898-nucleotide minigenome. Nucleotide lengths of specific regions are given in parentheses. The sequence of positions 90 to 124 (3' to 5', negative-sense) is shown at the bottom; PIV3-specific sequence is underlined, the complement of a vaccinia virus transcriptional terminator is overlined, the complement of the XbaI site is italicized, and the complement of the translational start codon for the CAT ORF is in bold. The site where 0 to 6 G residues were inserted, resulting in PIV3-CAT 0 to +6, is indicated. Abbreviations: GS, transcriptional gene-start motif; GE, transcriptional gene-end termination/polyadenylation motif; NT, nontranslated gene sequence.

FIG. 4 depicts expression of CAT enzyme by minigenomes PIV3-CAT 0 to +6. Cells were transfected with plasmids encoding the indicated PIV3-CAT minigenome and the N, P and L proteins, and were infected simultaneously with vaccinia virus recombinant vTF7-3 expressing T7 RNA polymerase. Lysates were prepared 48 h post-infection, and samples representing 3000 cells were analyzed for CAT activity. Activities are expressed relative to the +2 minigenome, which is a multiple of six, as 100. Samples in which the L plasmid was omitted did not have CAT activity detectable under these conditions.

FIGS. 5A and 5B depict synthesis of mini-antigenomic RNA by PIV3-CAT minigenomes 0 to +6. Cells were transfected and infected as described for FIG. 4, except for controls in which N plasmid (lane 1) or L plasmid (lane 2) was omitted. The PIV3-CAT minigenome plasmid which was transfected in each case is indicated. Cell lysates were prepared at 48 h post-transfection: one aliquot was treated with micrococcal nuclease (treated) and the second was mock-treated (untreated), followed by processing for RNA purification. The RNAs were analyzed by Northern blot hybridization with a negative-sense CAT riboprobe. As a marker and control for nuclease treatment, the RSV-CAT C2 minigenome (Grosfeld et al., *J. Virol.* 69:5677–5686 (1995), incorporated herein by reference in its entirety) was complemented by the RSV N, P and L proteins and was processed in parallel (Lane 10). Autoradiograms of the hybridized blots are shown in FIG. 5A. FIG. 5B shows phosphorimager analysis in which the amount of hybridization relative to the +2 minigenome was calculated separately for the treated and untreated samples.

FIGS. 6A and 6B depict synthesis of polyadenylated mRNA by PIV3-CAT minigenomes 0 to +6. Using aliquots of cells from the same experiment as shown in FIGS. 5A and 5B, total intracellular RNA was harvested at 48 h post-transfection and fractionated by oligo(dT) chromatography into bound and unbound fractions, which were analyzed by Northern blot hybridization with a negative-sense CAT riboprobe. FIG. 6A shows autoradiograms of the hybridized blots. FIG. 6B shows the phosphorimager analysis in which the amount of hybridization was normalized relative to the bound RNA fraction of the +2 minigenome, this was calculated separately for the bound and unbound fractions.

FIGS. 7A and 7B depict accumulation of intracellular minigenome in response to plasmid encoding PIV3-CAT minigenomes 0 to +6. This is a continuation of the experiment shown in FIGS. 5A and 5B. Thus, cells which had been transfected with plasmids encoding a minigenome and the N, P and L proteins and infected with vTF7-3 were harvested 48 h post-transfection and cell lysates were prepared. One aliquot of lysate was treated with micrococcal nuclease (treated) and the other was mock-treated (untreated), followed by processing for RNA purification. The RNAs were analyzed by Northern blot hybridization with a positive-sense CAT riboprobe, whereas in FIG. 5A the riboprobe was negative-sense. FIG. 7A shows autoradiograms of the hybridized blots. FIG. 7B shows phosphorimager analysis in which the amount of hybridization relative to the +2 minigenome was calculated separately for the treated and untreated samples.

FIGS. 8–10 illustrate construction of p3/7(131)2G. p3/7(131)2G encodes a complete positive-sense HPIV3 antigenome and contains two G residues between the T7 promoter and nucleotide 1 of the antigenome. The construction involved modification separately of the left and right halves of cDNA 218(131) encoding the negative-sense genome. Using the same strategy, a second cDNA, p3/7(131) was constructed which is identical to p3/7(131)2G except that the two G residues were omitted.

FIG. 8 depicts construction of p(Left+2G), performed by replacing the ribozyme and T7 transcription terminator of p218(A*A'CC'D*E) with a T7 promoter including two G residues. p218 (A*A'CC'D*E) was used as the template in a PCR that amplified the left-hand 1224 nucleotides of the HPIV3 genome (black rectangle labeled "PIV3seq.") using a left hand PCR primer that introduced the T7 promoter. This PCR fragment was cloned into the MluI-PmlI window of p218(A*A'CC'D*E), resulting in p(Left+2G).

FIG. 9 depicts construction of p(Right+), performed by replacing the T7 promoter of p(E*FF'GHIHKL*) with a ribozyme and T7 terminator placed adjacent to PIV3 nucleotide 15642 in the positive-sense (antigenome) strand.

p(E*FF'GHIHKL*) was used as a template in a PCR that amplified the right-hand 649 nucleotides of the HPIV3 genome (black rectangle labeled "PIV3 seq.") using a mutagenic oligonucleotide that added part of the delta ribozyme (including a naturally-occurring RsrII site). This PCR product was cloned into the RsrII-BssHII window of p3/7 to yield pPIV3-3/7, thus reconstructing a complete ribozyme flanked by the T7 terminator. The SwaI-NgoMI fragment of pPIV3-3/7 was cloned into the SwaI-NgoMI windows of p(E*FF'GHIHKL*), resulting in p(Right+). The locations of the seven sequence markers are indicated with asterisks.

Figure 10:
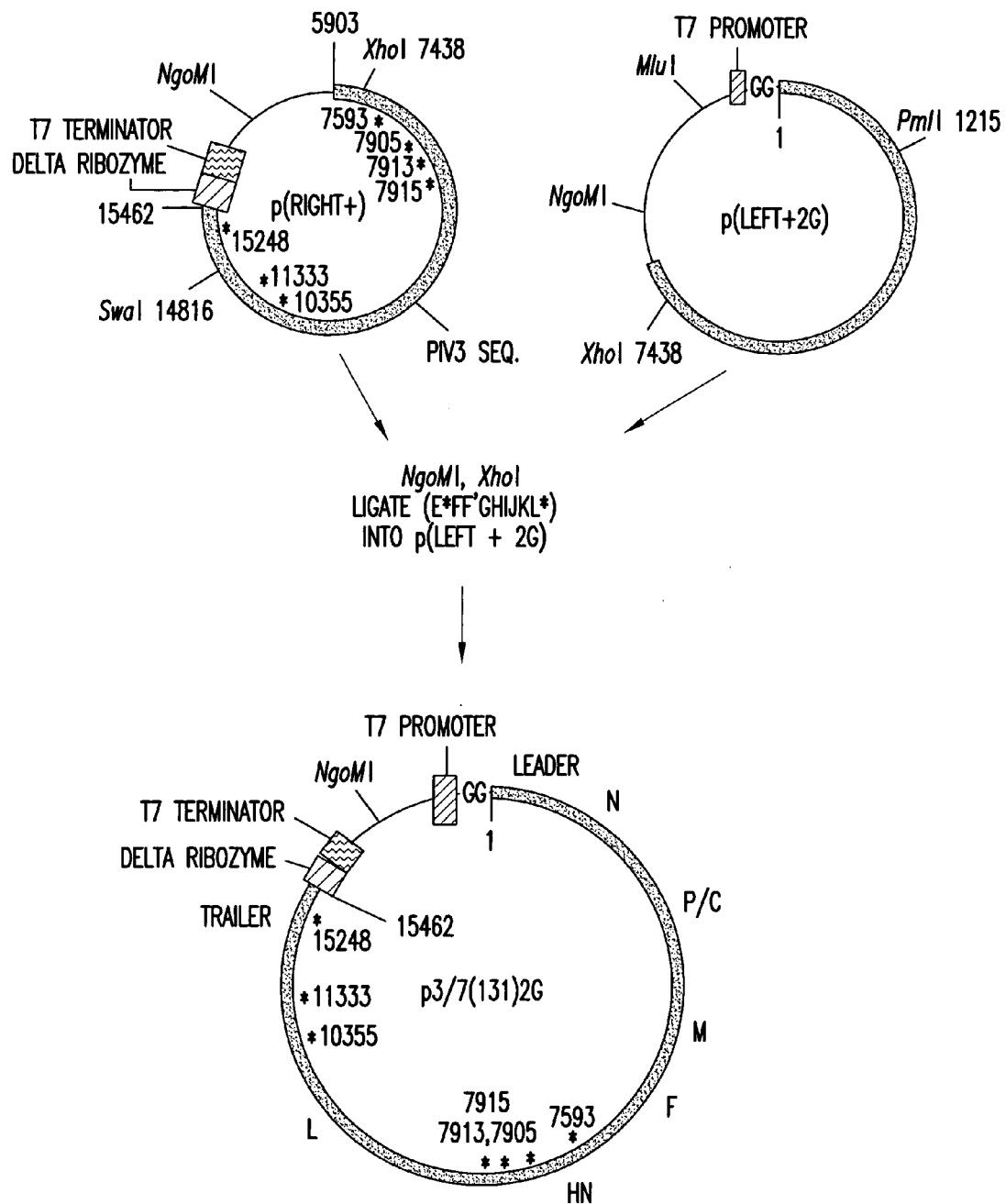

FIG. 10 depicts construction of p3/7(131)2G. The NgoMI-XhoI fragment of p(Right+) was cloned into the NgoMI-XhoI window of p(Left+2G), resulting in p3/7(131) 2G. The positions of HPIV3 genes are indicated (not to scale). The locations of sequence markers are indicated with asterisks.

Figure 11:
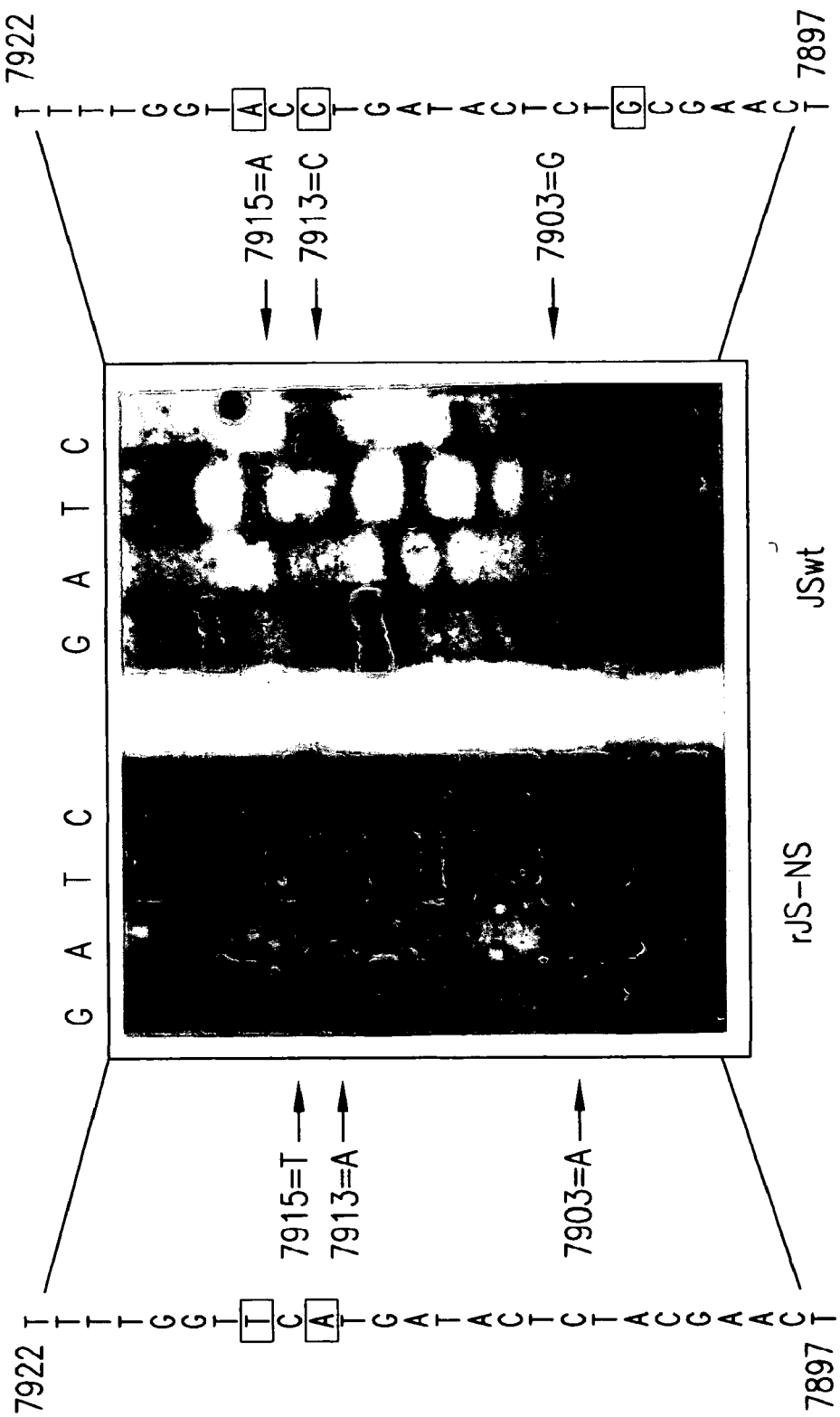

FIG. 11 shows sequence confirmation of a negative sense recombinant PIV3. A 1379 bp fragment (nucleotides 7334–8713) spanning the mutations at 7903, 7913, and 7915 was generated by RT-PCR of RNA from infected cells and then analyzed by cycle-sequencing. The mutations differentiating recombinant PIV from JS wt are indicated by arrows. The complete sequence from nt 7897 to 7922 is shown in the margin next to each gel, with the three nucleotide differences indicated in bold.

Figure 12:
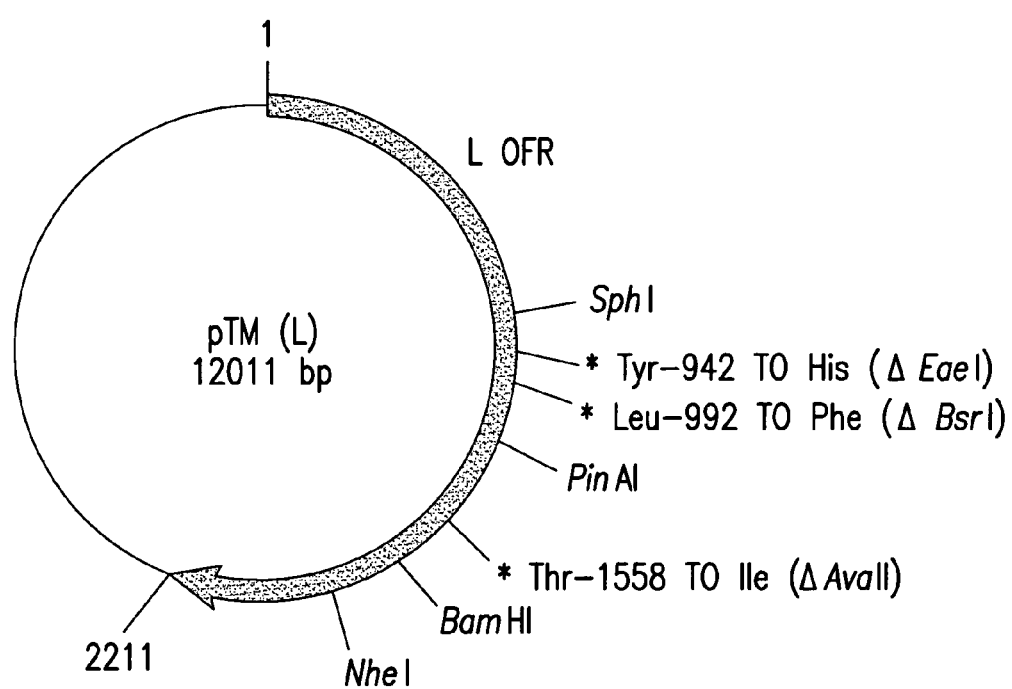

FIG. 12 provides a map of plasmid pTM(L)942/992/1558, which contains the PIV3 L cDNA with amino acid substitutions at positions 942, 992, and 1558 in the L protein sequence. The relative position of each of coding change is indicated, together with the aa difference and the naturally-occurring restriction site which was deliberately ablated as a marker. Restriction sites used for cloning (SphI, PinAI, BamHI and NheI) are indicated. The arrow shows the direction of the L protein coding sequence and is numbered according to amino acid position.

Figure 13:
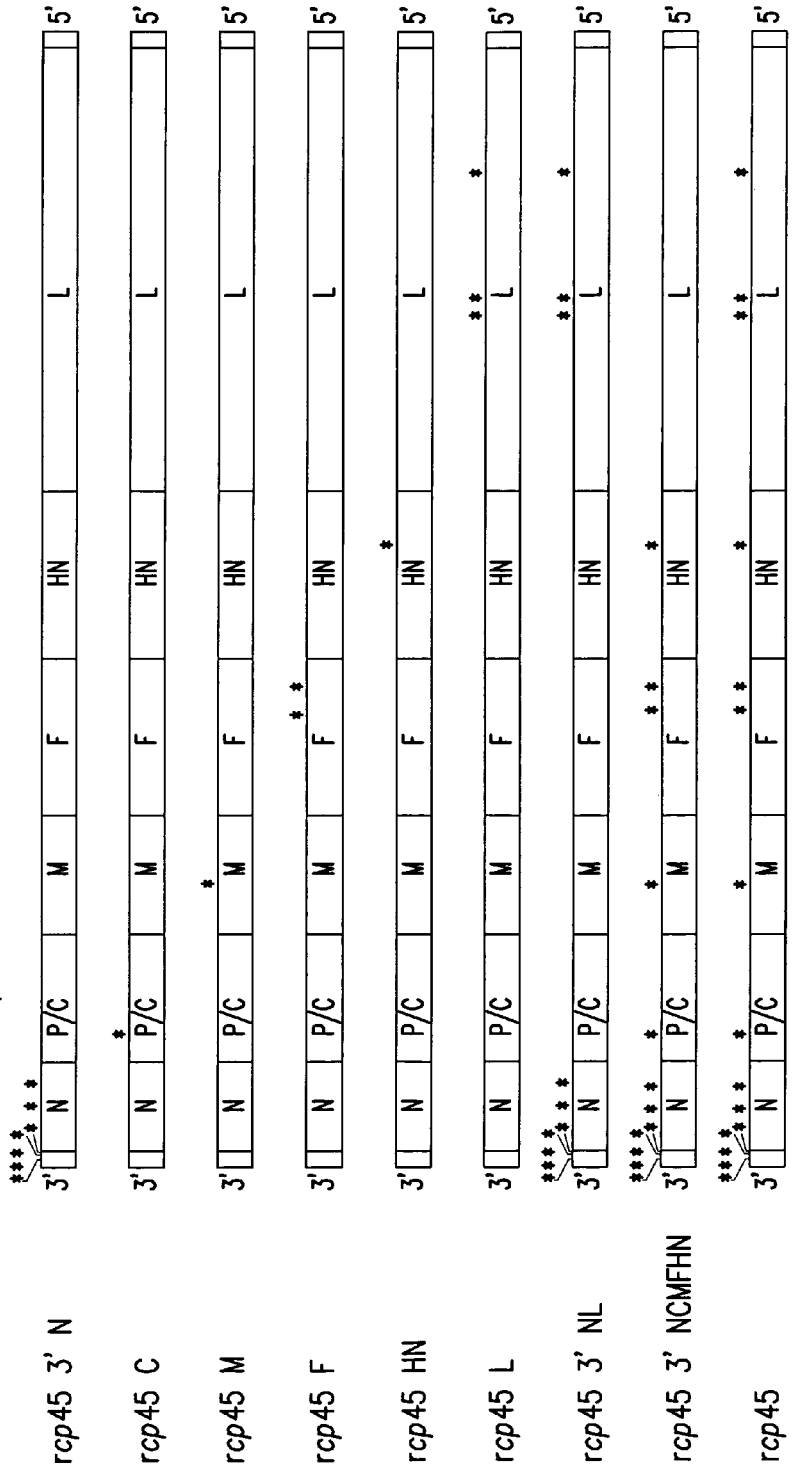

FIG. 13 is a schematic representation of recombinant PIV3 viruses bearing representative mutations within the invention.

Figure 14:
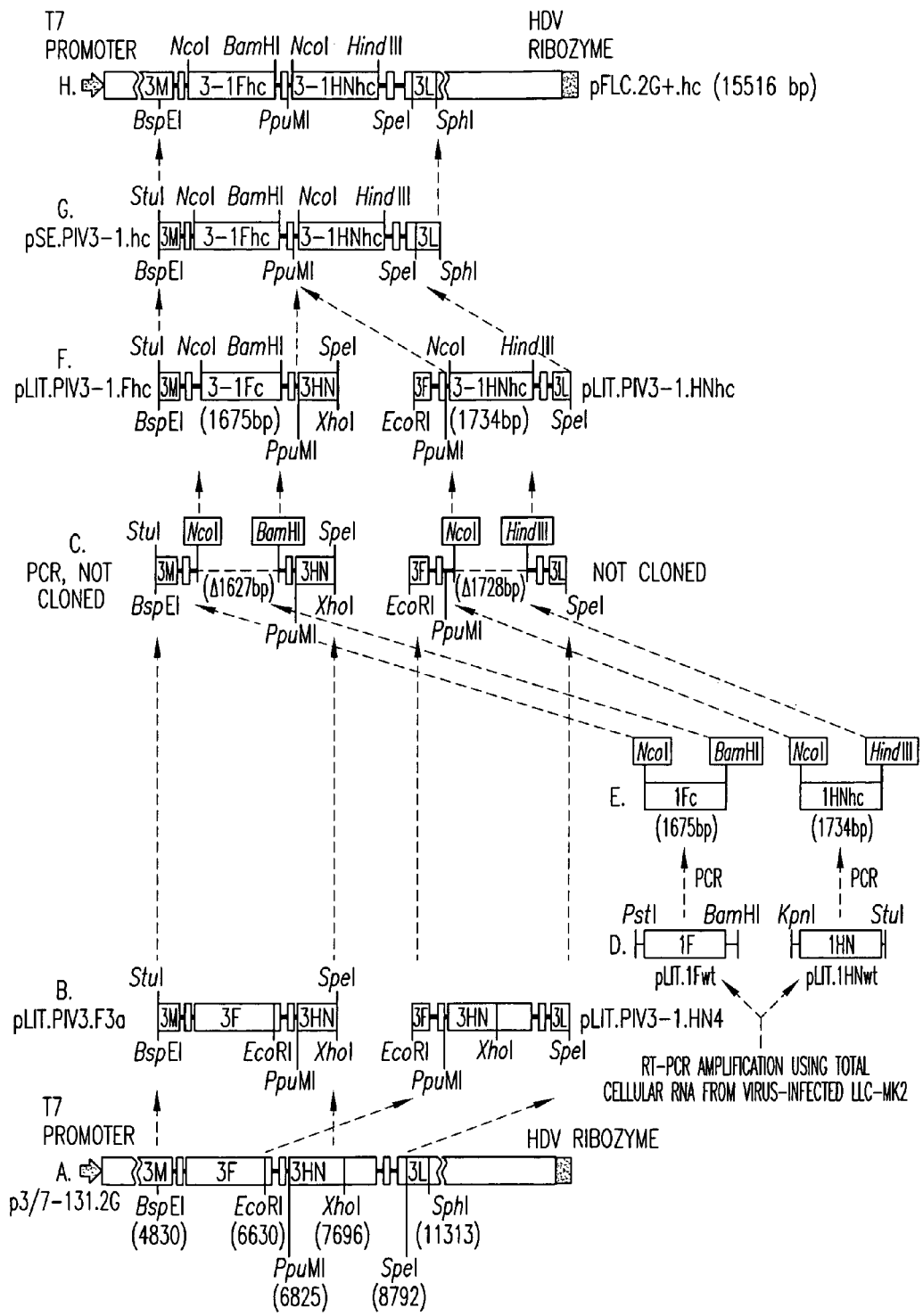

FIG. 14 illustrates construction of cDNA encoding the chimeric PIV3-PIV1 antigenome in which the PIV3 HN and F ORFs were replaced by those of PIV1. First (starting from the bottom left) the PIV3 F and HN genes were subcloned (as BspE-I I-Xho I and EcoR I-Spe I fragments) from the full-length PIV3 cDNA clone p3/7(131)2G (Panel A) to generate pLit.PIV3.F3a and pLit.PIV3.HN4 (Panel B), respectively. PCR mutagenesis (Panel C) was performed to delete the complete coding regions of the PIV3 F and HN genes and to introduce new restriction sites (boxed). PIV1 F and HN cDNAs were prepared from infected-cell RNA by RT-PCR and cloned into pLITMUS28 (Panel D). These clones, pLit.1Fwt and pLit.1HNwt, were used as templates for modification of the PIV1 F and HN genes at their start and stop codons to introduce new restriction sites compatible with those introduced in the PIV3 deletions (Panel E). Chimeric F and HN genes were constructed by importing the PIV1 coding regions into the PIV3 deletions to generate pLit.PIV3-1.Fhc and pLit.PIV3-1.HNhc (Panel F). The chimeric F and HN were assembled together to generate pSE.PIV3-1.hc (Panel G). The F and HN chimeric segment was introduced into full-length PIV3 clone p3/7(131)2G by replacing its BspE I-Sph I fragment to generate pFLC.2G+ .hc (Panel H). The small boxes between genes represent the gene end, intergenic, and gene start regions, and the lines represent the non-coding regions. Shaded portions are from PIV1, open boxes are from PIV3. The black arrows depict the T7 promoter, while black boxes depict the hepatitis delta virus (HDV) ribozyme.

Figure 15A:
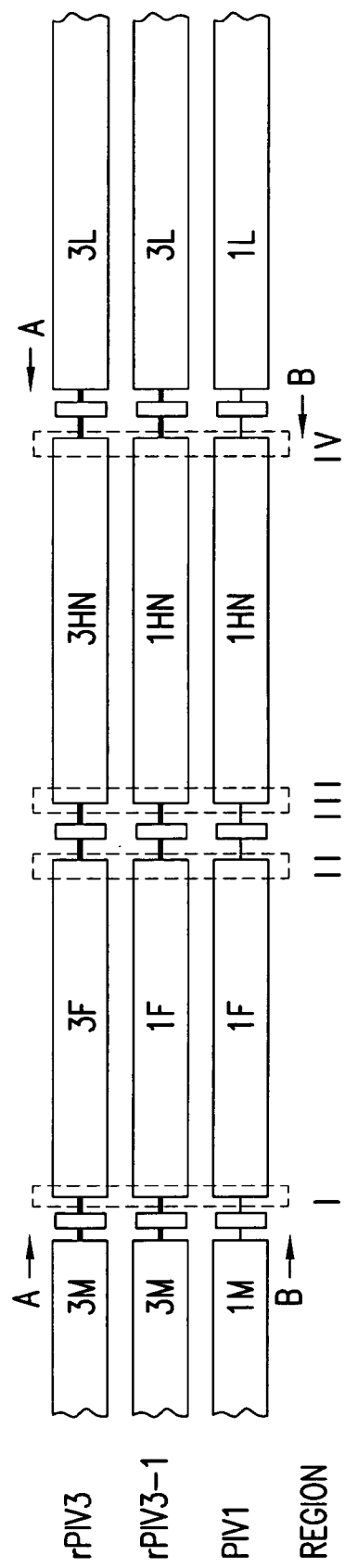

FIG. 15A is a diagram of the chimeric HN and F genes of the chimeric rPIV3-1 (middle) in parallel with that of rPIV3/JS (top; alternatively referred to herein as rJS and JS wt rPIV3) and PIV1/Wash64 (bottom). The four junction regions containing the sequence transitions from PIV3 to PIV1 are boxed and numbered I to IV. Each small box between genes represents the gene end, intergenic, and gene start region, and the lines represent the non-coding regions. RT-PCR primers, specific to PIV3 M and L genes (primer pair A at top) or specific to PIV1 M and HN genes (primer pair B at bottom) used in FIG. 14B, are depicted as arrows.

Figure 15B:
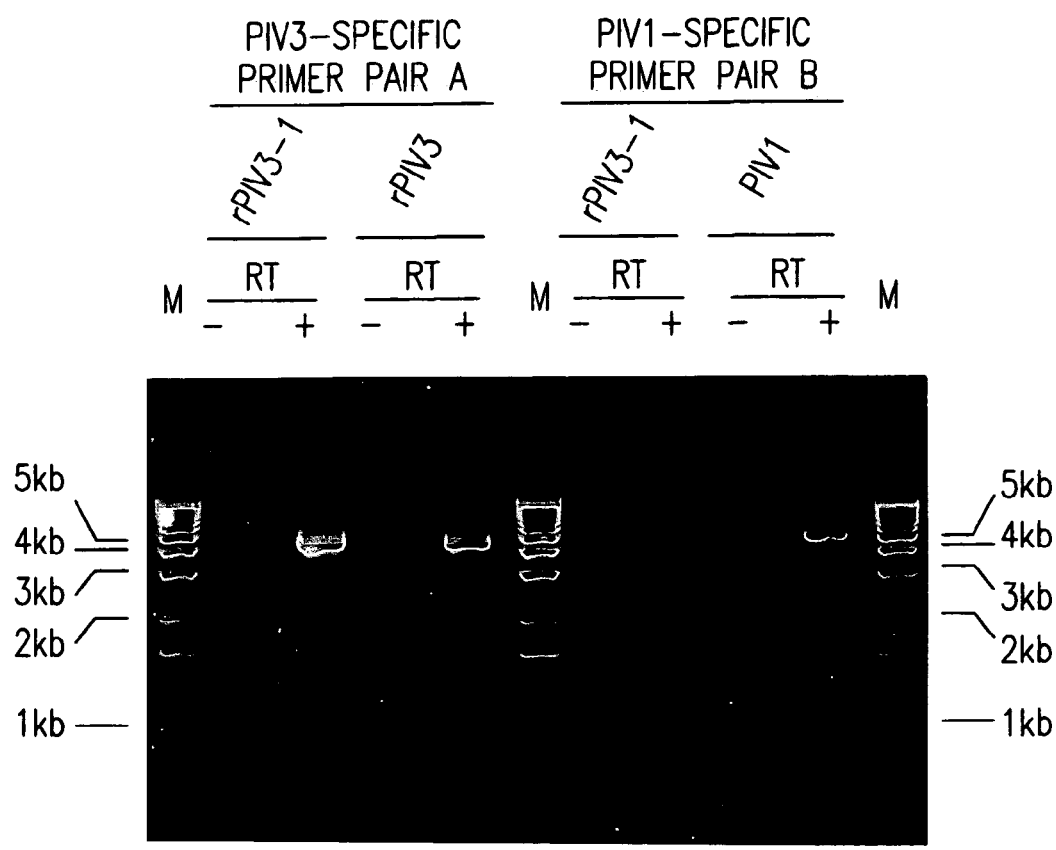

FIG. 15B shows an evaluation of RT-PCR products generated using virion RNA (vRNA) as template and the PIV3- or PIV1-specific primer pairs described in FIG. 14A. The reverse transcription step was omitted in a duplicate of each template, as indicated, to confirm that the PCR product was derived from RNA. For rPIV3-1, the PIV3-specific primer pair A gave rise to the expected 4.6 kb product, whereas primer pair B, specific to PIV-1 sequences not present in rPIV3-1, did not yield product. Positive controls using rPIV3/JS (labeled as rPIV3) or PIV1/Wash64 (labeled as PIV1) vRNA are shown in parallel.

Figure 16:
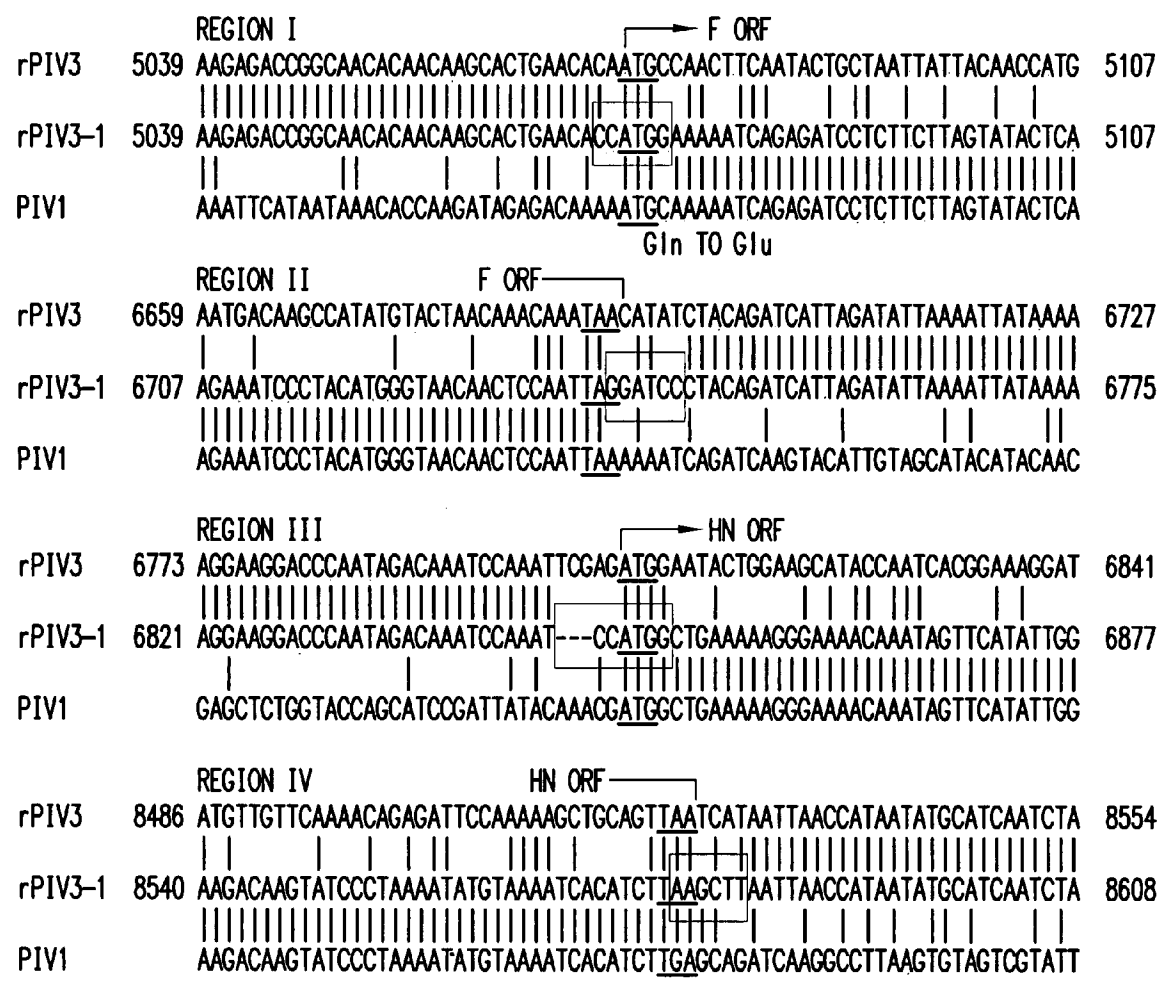

FIG. 16 represents sequences of PIV3-PIV1 junctions in the RT-PCR products of rPIV3-1 shown in FIG. 14B were determined. The sequence for each of the four junction regions (Regions I–IV) is presented and aligned with the corresponding regions of rPIV3/JS (top line) and PIV1/Wash64 (bottom line), which were sequenced in parallel from RT-PCR products. Vertical bars indicate sequence identity, and the boxed regions indicate introduced mutations and restriction sites. The Gln to Glu codon change in the chimeric F gene is indicated by shaded box. Start and stop codons are underlined.

Figure 17:
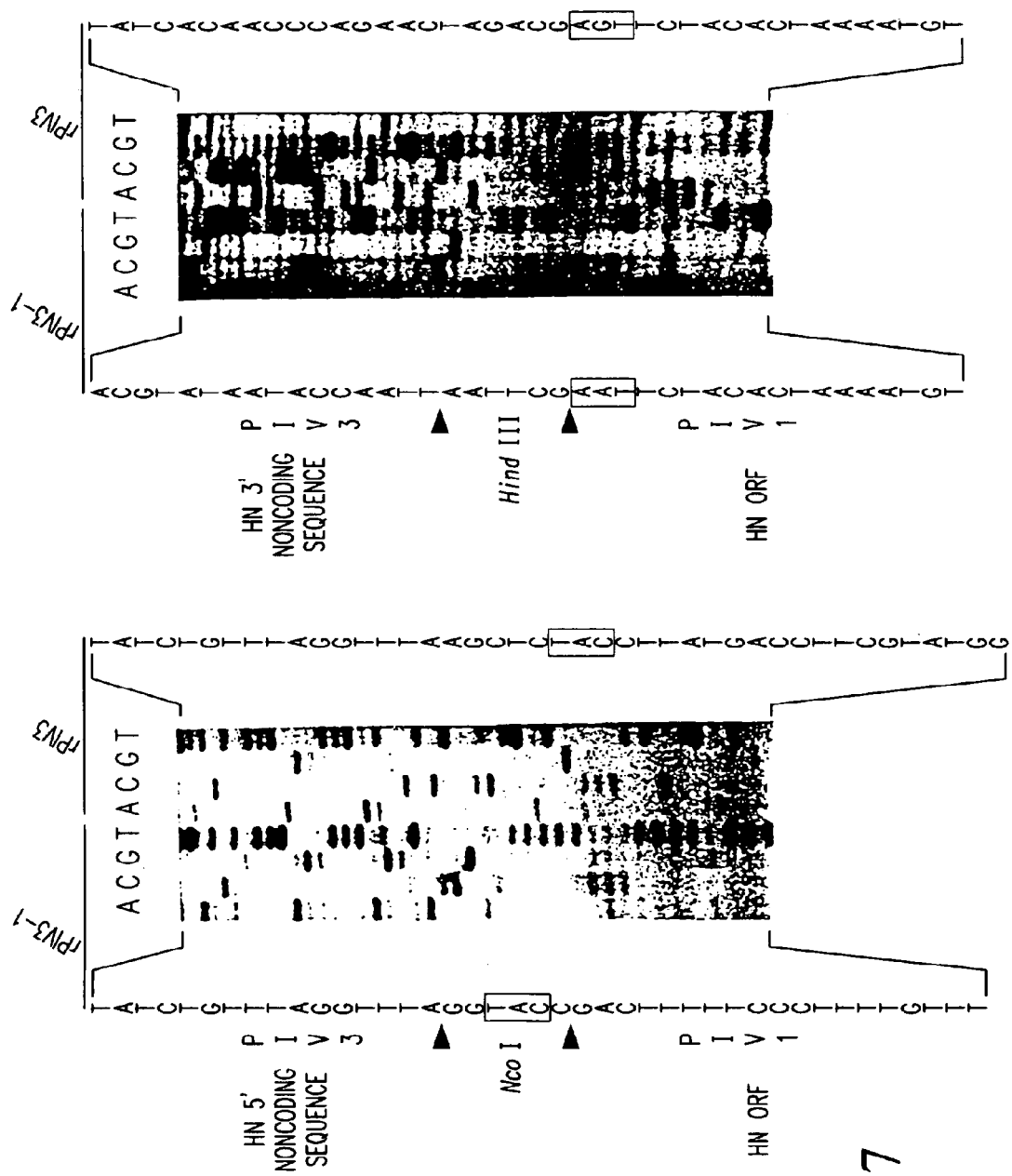

FIG. 17 shows sequencing gels for region III (left) and IV (right) of RT-PCR products of rPIV3-1 compared with rPIV3 (left) or PIV1 (right). Start and stop codons are marked by a box, restriction sites are marked by arrows.

Figure 18:
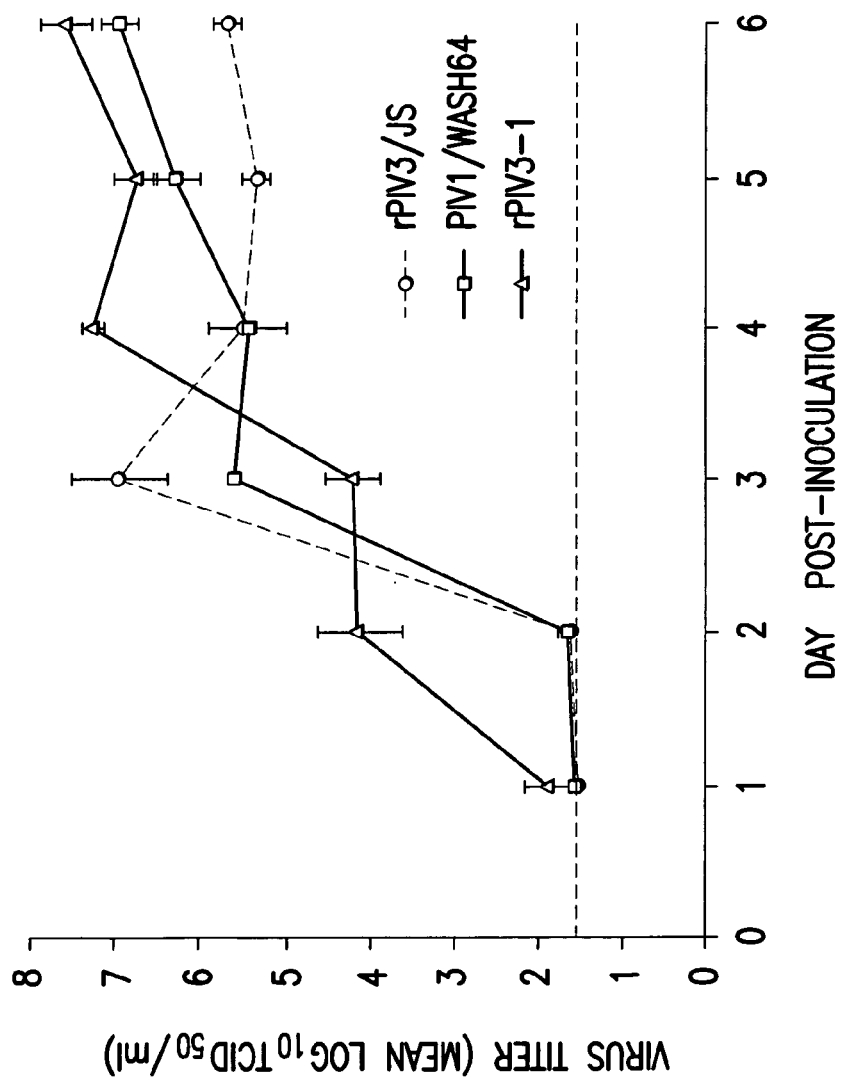

FIG. 18 depicts multicycle growth of parental and chimeric PIVs in tissue culture. LLC-MK2 cell monolayers were inoculated with virus at an MOI of 0.01, and virus-infected cells were incubated at 32° C. in the presence of trypsin. Tissue culture supernatants were harvested at 24 hour intervals, frozen, and analyzed in the same $TCID_{50}$ assay using hemadsorption to identify virus-infected cultures. Each point represents the mean titer of three separate cultures, with S.E. Indicated. The dotted horizontal line indicates the lower limit of viral detection.

Figure 19:
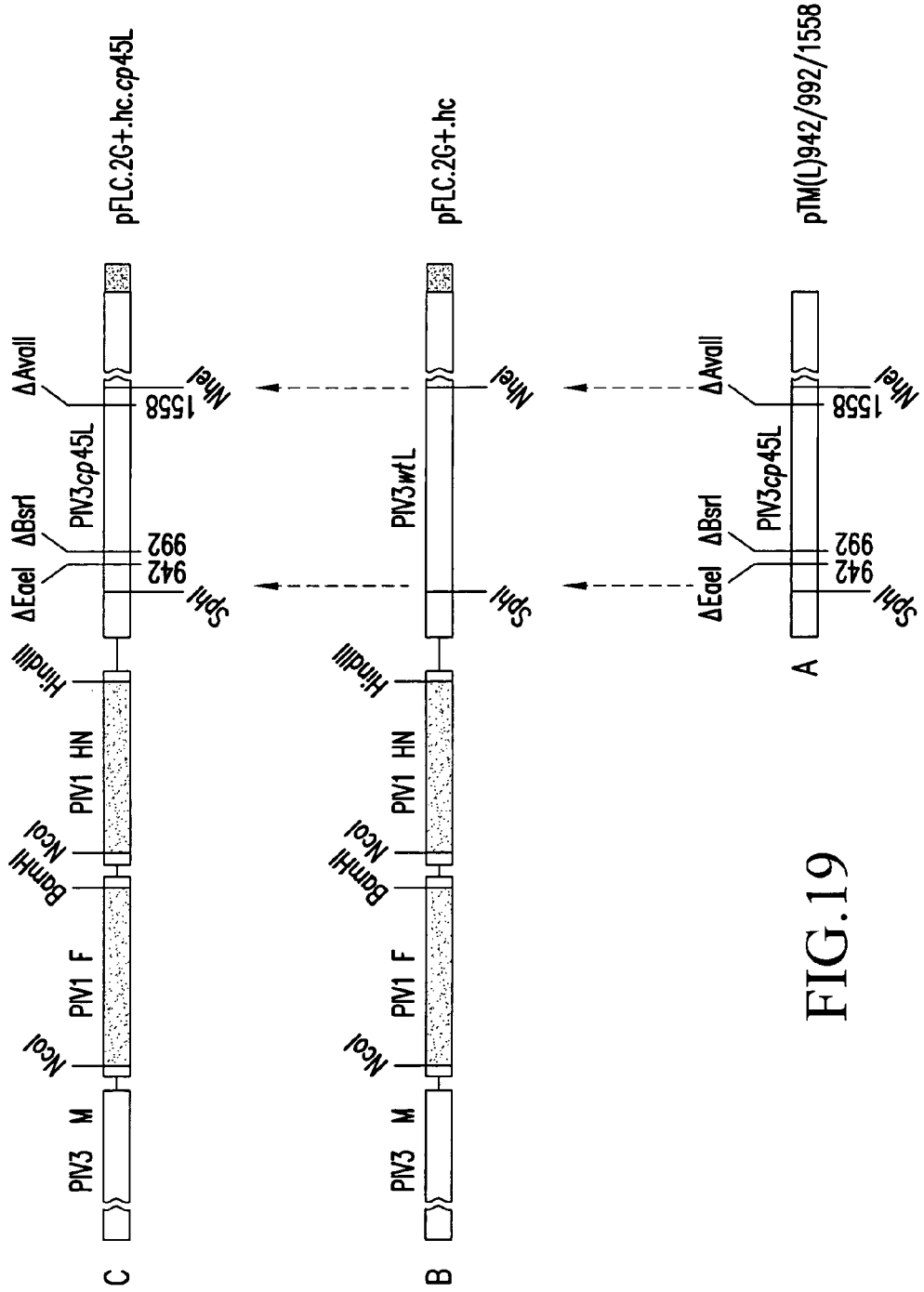

FIG. 19 illustrates introduction of the three L gene mutations of cp45 into pFLC.2G+.hc, the antigenomic cDNA clone of the chimeric virus rPIV3-1. pTM(L)942/992/1558 (A) is a plasmid clone of the L gene that carries the three mutations found in cp45. The mutation at amino acid position 942 in the PIV3 L protein is a tyr (wt) to his (cp45) substitution and a nearby Eae I site was ablated to mark this site. Similarly, the 992 mutation is a leu to phe change with a Bsr I site ablated and the 1558 mutation is a thr to ile change with an Ava II site ablated. The 2.9 kb SphI-NheI fragment present in pTM(L)942/992/1558 was introduced into pFLC.2G+hc (B), the plasmid carrying the full length cDNA clone of rPIV3-1, to give pFLC+hc.cp45L (C). For the constructs in (B) and (C), the black boxes indicate the location of the hepatitis D virus ribozyme and the T7 terminator, the shaded regions are the PIV1 HN and F ORFs, and the open boxes represent sequences derived from PIV3.

pFLC.2G+.hc.cp45L was used in the transfection to yield the attenuated chimeric recombinant virus designated rPIV3-1.cp45L.

DESCRIPTION OF THE SPECIFIC EMBODIMENTS

The present invention provides compositions and methods for producing and modifying infectious PIV from isolated polynucleotide molecules, preferably cDNA. Infectious PIV particles are produced by a recombinant coexpression system that permits introduction of defined changes into infectious PIV. These modifications are useful in a wide variety of applications, including the development of live attenuated vaccine strains bearing predetermined, defined attenuating mutations.

Infectious PIV of the invention are produced by intracellular or cell-free coexpression of one or more isolated polynucleotide molecules that encode a PIV genome or antigenome RNA, together with one or more polynucleotides encoding viral proteins necessary to generate a transcribing, replicating nucleocapsid. Among the viral proteins useful for coexpression to yield infectious PIV are the major nucleocapsid protein (N) protein, nucleocapsid phosphoprotein (P), large (L) polymerase protein, fusion protein (F), hemagglutinin-neuraminidase glycoprotein (HN), and matrix (M) protein. Also useful in this context are products of the C, D and V ORFs of PIV.

cDNAs encoding a PIV genome or antigenome are constructed for intracellular or in vitro coexpression with the necessary viral proteins to form infectious PIV. By "PIV antigenome" is meant an isolated positive-sense polynucleotide molecule which serves as a template for synthesis of progeny PIV genome. Preferably a cDNA is constructed which is a positive-sense version of the PIV genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant PIV (rPIV) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant PIV" is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from a cDNA-expressed PIV genome or antigenome, the genome or antigenome is coexpressed with those PIV N, P and L proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins.

In certain embodiments of the invention, complementing sequences encoding proteins necessary to generate a transcribing, replicating PIV nucleocapsid are provided by one or more helper viruses. Such helper viruses can be wild type or mutant. Preferably, the helper virus can be distinguished phenotypically from the virus encoded by the PIV cDNA. For example, it is desirable to provide monoclonal antibodies which react immunologically with the helper virus but not the virus encoded by the PIV cDNA. Such antibodies can be neutralizing antibodies. In some embodiments, the antibodies can be used in affinity chromatography to separate the helper virus from the recombinant virus. To aid the procurement of such antibodies, mutations can be introduced into the PIV cDNA to provide antigenic diversity from the helper virus, such as in the HN or F glycoprotein genes.

In alternate embodiments of the invention, the N, P, L and other desired PIV proteins are encoded by one or more non-viral expression vectors, which can be the same or separate from that which encodes the genome or antigenome. Additional proteins may be included as desired, each encoded by its own vector or by a vector encoding one or more of the N, P, L and other desired PIV proteins, or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology*, 210: 202–205 (1995), incorporated herein by reference in its entirety). The viral proteins, and/or T7 RNA polymerase, can also be provided by transformed mammalian cells or by transfection of preformed mRNA or protein.

A PIV antigenome may be constructed for use in the present invention by, e.g., assembling cloned cDNA segments, representing in aggregate the complete antigenome, by polymerase chain reaction or the like (PCR; described in, e.g., U.S. Pat. Nos. 4,683,195 and 4,683,202, and *PCR Protocols: A Guide to Methods and Applications*, Innis et al., eds., Academic Press, San Diego (1990), each incorporated herein by reference in its entirety) of reverse-transcribed copies of PIV mRNA or genome RNA. For example, a first construct is generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type (e.g., Grosfeld et al., (1995), supra), which would yield a 3' end containing a single nonviral nucleotide, or can be any of the other suitable ribozymes such as that of hepatitis delta virus (Perrotta et al., *Nature* 350:434–436 (1991), incorporated herein by reference in its entirety) which would yield a 3' end free of non-PIV nucleotides. The left- and righthand ends are then joined via a common restriction site.

A variety of nucleotide insertions, deletions and rearrangements can be made in the PIV genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Alternative means to construct cDNA encoding the genome or antigenome include reverse transcription-PCR using improved PCR conditions (e.g., as described in Cheng et al., *Proc. Natl. Acad. Sci. USA* 91:5695–5699 (1994)), incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the larger size genome or antigenome.

Isolated polynucleotides (e.g., cDNA) encoding the genome or antigenome may be inserted into appropriate host cells by transfection, electroporation, mechanical insertion, transduction or the like, into cells which are capable of supporting a productive PIV infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., *Cell* 14: 725 (1978); Corsaro and Pearson, *Somatic Cell Genetics* 7: 603 (1981); Graham and Van der Eb, *Virology* 52: 456 (1973)), electroporation (Neumann et al., *EMBO J.* 1: 841–845 (1982)), DEAE-dextran mediated transfection (Ausubel et al., (ed.) *Current Protocols in Molecular Biology*, John Wiley and Sons, Inc., NY (1987), cationic lipid-mediated transfection (Hawley-Nelson et al., *Focus* 15: 73–79 (1993)) or a commercially available transfection regent, e.g., LipofectACE® (Life Technologies, Gaithersburg, Md.) or the like (each of the foregoing references are incorporated herein by reference in its entirety).

As noted above, in some embodiments of the invention the N, P, L and other desired PIV proteins are encoded by one or more helper viruses which is phenotypically distinguishable from that which encodes the genome or antigenome. The N, P, L and other desired PIV proteins can also be encoded by one or more expression vectors which can be the same or separate from that which encodes the genome or antigenome, and various combinations thereof. Additional proteins may be included as desired, encoded by its own vector or by a vector encoding one or more of the N, P, L and other desired PIV proteins, or the complete genome or antigenome.

The compositions and methods of the invention permit analysis and manipulation of PIV molecular biology and pathogenic mechanisms using, e.g., defined mutations to alter the function or expression of selected PIV proteins. Using these methods and compositions, one can readily distinguish mutations responsible for desired phenotypic changes from silent incidental mutations, and select phenotype-specific mutations for incorporation into a recombinant PIV genome or antigenome for vaccine production.

Modifications of PIV provided within the invention are directed toward the production of improved vaccine viruses, e.g., to enhance viral attenuation and vaccine immunogenicity, to ablate epitopes associated with undesirable immunopathology, to accommodate antigenic drift, etc. To achieve these and other objectives, the compositions and methods of the invention allow for a wide variety of modifications to be introduced into a PIV genome or antigenome for incorporation into infectious, recombinant PIV. For example, foreign genes or gene segments encoding protective antigens or epitopes may be added within a PIV clone to generate PIV virus strains capable of inducing immunity to both PIV and another virus or agent from which the protective antigen was derived. Alternatively, foreign genes may be inserted, in whole or in part, encoding modulators of the immune system, such as cytokines, to enhance immunogenicity of a vaccine virus.

Other mutations which may be included within PIV clones of the invention include, for example, substitution of heterologous genes or gene segments (e.g., a gene segment encoding a cytoplasmic tail of a glycoprotein gene) with a counterpart gene or gene segment in a PIV clone. Alternatively, the relative order of genes within a PIV clone can be changed, the PIV genome promoter can be replaced with its antigenome counterpart, or selected gene(s) rendered non-functional (e.g., by functional ablation involving introduction of a stop codon to prevent expression of the gene). Other modifications in a PIV clone can be made to facilitate manipulations, such as the insertion of unique restriction sites in various non-coding or coding regions or elsewhere. In addition, nontranslated gene sequences can be removed to increase capacity for inserting foreign sequences.

Thus, by providing infectious clones of PIV the invention permits a wide range of alterations to be recombinantly produced within the PIV genome (or antigenome), yielding defined mutations which specify desired phenotypic changes. By "infectious clone" is meant cDNA or its product, synthetic or otherwise, RNA capable of being directly incorporated into infectious virions which can be transcribed into genomic or antigenomic RNA capable of serving as a template to produce the genome of infectious viral or subviral particles. As noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA subjects provide for better ease of manipulation than large cDNA subjects, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen® kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding an PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15–35 nucleotides in the case of genome segments encoding small functional domains of proteins, e.g., epitopic sites, to about 50, 75, 100, 200–500, and 500–1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. In one such exemplary modification, a sequence at the cleavage site of the F protein can be modified and the effects of this modification on growth in tissue culture and infection and pathogenesis of the resultant PIV can be routinely determined in experimental animals.

Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock, et al., *J. Virol.* 67: 2772–8 (1993), incorporated herein by reference in its entirety), whose rescue-dependent status is useful in characterizing those mutants that may be too inhibitory to be recovered in replication-independent infectious virus.

The present invention further provides tools and methods to readily distinguish between silent incidental mutations and mutations responsible for phenotype differences, for example by introducing suspect mutations, separately and in various combinations, into the genome or antigenome of infectious wild-type (i.e., for one or more phenotypic character such as temperature sensitivity, replication in a selected host, etc.) PIV. This process permits identification of mutations responsible for desired vaccine phenotypes such as attenuation, temperature sensitivity, cold-adaptation, small plaque size, host range restriction, etc. Mutations identified by these methods can then be introduced in various combinations to modify a vaccine virus to an appropriate level of attenuation, etc., as desired. Moreover, the present invention provides the ability to combine mutations from different strains of virus into a single vaccine strain.

As noted above, mutations incorporated within recombinantly altered PIV clones may be selected based on their ability to alter expression and/or function of a selected PIV protein, yielding a desired phenotypic change, or for a variety of other purposes. Desired phenotypic changes include, e.g., changes in viral growth in culture, temperature sensitivity, plaque size, attenuation, and immunogenicity. For example, a polynucleotide sequence encoding the genome or antigenome can be modified by a nucleotide insertion, rearrangement, deletion or substitution to specify attenuation, temperature-sensitivity, cold-adaptation, small plaque size, host range restriction, alteration in gene expression, or a change in an immunogenic epitope.

In one aspect of the invention, mutations occurring in biologically derived, attenuated PIV are identified and introduced individually or in combination into a full-length PIV clone, and the phenotypes of rescued recombinant viruses containing the introduced mutations are determined. In exemplary embodiments, amino acid changes displayed by biologically derived mutant viruses over a wild-type PIV, for example changes exhibited by PIV mutants having ts, ca or att phenotypes, are incorporated within recombinant PIV clones. These changes from biologically derived mutant PIV specify desired characteristics in the resultant clones, e.g., an attenuation phenotype specified by a mutation adopted from the HPIV3 mutant JS cp45 deposited in accordance with the terms of the Budapest Treaty with the American Type Culture Collection (ATCC) of 10801 University Blvd. Manassas, Va. 20110-2209, U.S.A., and granted the designation PTA-2419. These changes are preferably introduced into recombinant virus using two or three nucleotide changes compared to a corresponding wild type or biologically derived mutant sequence, which has the effect of stabilizing the mutation against genetic reversion.

The present invention also provides recombinant PIV having multiple, phenotype-specifying mutations introduced in selected combinations into the genome or antigenome of an infectious clone. This process, coupled with evaluation of phenotype, provides mutant recombinant PIV having such desired characteristics as attenuation, temperature sensitivity, cold-adaptation, small plaque size, host range restriction, etc. Thus, exemplary PIV clones are disclosed herein which incorporate one or more, and preferably at least two attenuating mutations, e.g., ts, ca or att mutations adopted from a biologically derived PIV mutant, such as JS cp45. Target genes for adopting biologically derived mutations in a recombinant PIV in this context include the nucleocapsid protein N, phosphoprotein P, large polymerase subunit L, matrix protein M, hemagglutinin-neuraminidase protein HN, fusion protein F and the C, D and V ORF products. Also targeted are extragenic sequences, eg., sequences in the 3' leader or trailer regions of a PIV genome, and in cis-acting elements such as gene start and gene end sequences, eg., the N gene start signal. Exemplary mutations incorporated in recombinant PIV herein include one or more nucleotide substitutions specifying amino acid change(s) in the polymerase L gene, e.g., at $Tyr_{942}$, $Leu_{992}$, and/or $Thr_{1558}$. For example, PIV recombinants are disclosed wherein $Tyr_{942}$ is replaced by His, $Leu_{992}$ is replaced by Phe, and/or $Thr_{1558}$ is replaced by Ile. These mutations have been successfully incorporated in various exemplary PIV recombinants herein, including r942, r992, r1558, r942/992, r992/1558, r942/1558, or r942/992/1558 recombinants described in the Examples below. Other exemplary mutations adopted from a biologically derived PIV mutant include one or more mutations in the N protein, including specific mutations at a position corresponding to residues $Val_{96}$ or $Ser_{389}$ of JS cp45. In more detailed aspects, these mutations are represented as $Val_{96}$ to Ala or $Ser_{389}$ to Ala. Also disclosed in the Examples below are recombinant PIV which encode an amino acid substitution in the C protein, eg., a mutation at a position corresponding to $Ile_{96}$ of JS cp45, preferably represented by a substitution of $Ile_{96}$ to Thr. Further exemplary mutations adopted from biologically derived PIV mutants include one or more mutations in the F protein, including mutations adopted from JS cp45 at a position corresponding to residues $Ile_{420}$ or $Ala_{450}$ of JS cp45, preferably represented by acid substitutions $Ile_{420}$ to Val or $Ala_{450}$ to Thr. Other PIV recombinants within the invention adopt one or more amino acid substitutions in the HN protein, as exemplified hereinbelow by a recombinant PIV adopting a mutation at a position corresponding to residue $Val_{384}$ of JS cp45, preferably represented by the substitution $Val_{384}$ to Ala. Yet additional examples within this aspect of the invention include recombinant PIV which incorporate one or more mutations in an extragenic sequence, eg., a 3' leader sequence of recombinant PIV genome or antigenome. Exemplary mutations in this context include mutations in the 3' leader occurs at one or more positions corresponding to nucleotide 23, 24, and/or 28 of JS cp45, for example a T to C change at nucleotide 23, a C to T change at nucleotide 24, or a G to T change at nucleotide 28. Yet additional extragenic mutations include one or more mutations in a N gene start sequence, as exemplified hereinbelow by a mutation in the N gene start sequence at a position corresponding to nucleotide 62 of JS cp45, preferably represented by a A to T change. The above exemplary mutations adopted from biologically derived mutant PIV are evaluated and combined into recombinant PIV in the Examples below to result, individually and/or in combination, in novel, attenuated candidate vaccine strains, as exemplified by the recombinants designated herein as rcp45, rcp45 3'NCMFHN, rcp45 3'NL, rcp45 3'N, and rcp45 F. Other PIV recombinants within the invention will incorporate a plurality and up to a full complement of the mutations present in one or more of these exemplary recombinants, as well as mutations identified in other biologically derived mutant PIV strains identified and adopted in a recombinant PIV according to the teachings herein.

Mutations identified according to the methods disclosed herein are compiled into a "menu" and introduced in various combinations to calibrate a vaccine virus to a selected level of attenuation, immunogenicity and stability. In preferred embodiments, the invention provides for supplementation of one or more mutations adopted from biologically derived PIV, e.g., ts, ca or att mutations, with additional types of mutations involving the same or different genes. Target genes for mutation in this context also include the nucleocapsid protein N, phosphoprotein P, large polymerase subunit L, matrix protein M, hemagglutinin-neuraminidase protein HN, fusion protein F and the C, D and V ORF products. In one aspect, recombinant PIVs are provided wherein at least one attenuating mutation occurs in the PIV polymerase gene L and involves a nucleotide substitution specifying a ts or att phenotype adopted from a biologically derived mutant PIV strain, for example JS cp45. Exemplary HPIV3 recombinants disclosed herein include the r942, r992, r1558, r942/992, r992/1558, r942/1558, or r942/992/1558 recombinants described in the Examples below. These exemplary PIV clones incorporate one or more nucleotide substitutions resulting in an amino acid change in the polymerase gene, e.g., at $Tyr_{942}$, $Leu_{992}$, and/or $Thr_{1558}$. For example, PIV recombinants are disclosed wherein $Tyr_{942}$ is replaced by His, $Leu_{992}$ is replaced by Phe, and/or $Thr_{1558}$ is replaced by Ile. Preferably, two or three mutations are incorporated in a codon specifying an attenuating mutation adding increased stability against phenotypic reversion.

In additional aspects, a variety of other genetic alterations can be produced in a recombinant PIV genome or antigenome for incorporation into infectious recombinant PIV, alone or together with one or more attenuating mutations adopted from a biologically derived mutant PIV. Heterologous genes (e.g. from different PIV strains or non-PIV sources such as another virus, e.g., RSV or measles virus) may be inserted or substituted, in whole or in part, the order of genes changed, gene overlap removed, the PIV genome promoter replaced with its antigenome counterpart, and even entire, non-essential genes deleted. In one aspect, a selected PIV gene, for example the C, D, or V ORF, is functionally deleted to yield a recombinant PIV having novel phenotypic characteristics, for example enhanced growth in vitro and/or attenuation in vivo. An infectious PIV clone of the invention can also be engineered to enhance its immunogenicity and induce a level of protection greater than that provided by natural infection, or to ablate epitopes associated with undesirable immunopathologic reactions. Enhanced immunogenicity of the vaccines produced by the present invention addresses one of the greatest obstacles to controlling PIV, namely the incomplete nature of immunity induced by natural infection. In this context, additional gene(s) or gene segment(s) may be inserted into or proximate to the PIV genome or antigenome which may be placed under the control of a common or independent set of transcription signals. Genes of interest include those encoding cytokines (e.g., IL-2 through IL-15, especially IL-2, IL-6 and IL-12, etc.) and proteins rich in T helper cell epitopes. The additional protein can be expressed either as a separate protein or as a chimera engineered from a second copy of one of the PIV proteins, such as HN. This provides the ability to modify and improve the immune response against PIV both quantitatively and qualitatively.

Other mutations useful within the invention involve replacement of the 3' end of genome with its counterpart from antigenome, which is associated with changes in RNA replication and transcription. In addition, intergenic regions can be shortened or lengthened or changed in sequence content. In yet additional aspects, PIV useful in a vaccine formulation can be conveniently modified to accommodate antigenic drift in circulating virus. Typically the modification will be in the HN and/or F proteins. For example, a selected antigenic form of an entire HN or F gene, or the segment(s) encoding particular immunogenic regions thereof, is incorporated into a PIV genome or antigenome cDNA by replacement of a counterpart region in the infectious clone, or by adding one or more copies of the gene such that several antigenic forms are represented in the resultant clone. Progeny virus produced from the modified PIV cDNA are then used in vaccination protocols against emerging strains.

Other mutations for use in infectious PIV of the invention include mutations in cis-acting signals identified during mutational analysis of PIV minigenomes. For example, insertional and deletional analysis of leader and trailer and flanking sequences identify viral promoters and transcription signals and provide a series of mutations associated with varying degrees of reduction of RNA replication or transcription. Saturation mutagenesis (whereby each position in turn is modified to each of the nucleotide alternatives) of these cis-acting signals also identifies mutations which reduce or increase RNA replication or transcription. Any of these mutations can be inserted into the complete antigenome or genome as described herein.

Additional modifications in PIV clones can be made to facilitate manipulations, such as the insertion of unique restriction sites in various intergenic regions or elsewhere. Nontranslated gene sequences can also be removed to increase capacity for inserting foreign sequences.

Certain substitutions, insertions, deletions or rearrangements of genes or gene segments within recombinant PIV of the invention (e.g., substitutions of a gene segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or gene segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, gene segments, proteins or protein regions, are typically from heterologous sources (e.g., from different PIV genes, or representing the same (i.e., homologous or allelic) gene or gene segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding gene segments embrace an assemblage of species having a range of size and sequence variations defined by a common biological activity among the domain or gene segment variants. For example, two selected protein domains encoded by counterpart gene segments within the invention share substantially the same qualitative activity, such as providing a membrane spanning function, a specific binding activity, an immunological recognition site, etc. More typically, a specific biological activity shared between counterparts, e.g., between selected protein segments or proteins, will be substantially similar quantitatively, i.e., they will not vary in respective quantitative activity levels by more than 30%, preferably by no more than 20%, more preferably by no more than 5–10%.

Counterpart genes and gene segments, as well as other polynucleotides disclosed herein for producing recombinant PIV within the invention, preferably share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant PIV of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis (2nd ed., E. S. Golub & D. R. Gren, eds., Sinauer Associates, Sunderland, Mass., 1991), incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Moreover, amino acids may be modified by glycosylation, phosphorylation and the like.

The infectious PIV produced from cDNA-expressed genome or antigenome can be any of the PIV or PIV-like strains, e.g., human, bovine, murine, etc. To engender a protective immune response, the PIV strain may be one which is endogenous to the subject being immunized, such as human PIV being used to immunize humans. The genome or antigenome can be modified, however, to express heterologous PIV genes or gene segments, or genes or gene segments from other heterologous sources, e.g., RSV or measles virus. Thus, infectious PIV intended for administration to humans may be human PIV that has been modified to contain genes or gene segments from a bovine or murine PIV type such as for the purpose of attenuation. BPIV3 possesses host range mutations that restrict its replication in rhesus monkeys and humans (Karron et al., supra, 1995a; van Wyke Coelingh et al., 1988), each incorporated herein by reference in its entirety). Gene(s), mutations and cis-acting regulatory sequences of BPIV3 that specify desired phenotypes, e.g., host range restriction, will be identified by their substitution for corresponding sequences in rPIV of the invention, and incorporated within further modified rPIV to develop yet additional useful vaccine agents. Similarly, mutations of JS cp45 which are known to impart non-ts host-range attenuating mutations for the rhesus monkey (Hall et al., supra, (1992)) will likewise be identified and incorporated into modified rPIV vaccine agents of the invention. Alternatively, a bovine PIV may be modified to contain genes that encode, e.g., proteins or immunogenic epitopes that elicit protection against human PIV infection. For example, human PIV glycoprotein genes can be substituted for counterpart bovine glycoprotein genes, such that the bovine PIV elicits a protective immune response in humans against human PIV strains.

In exemplary embodiments, individual genes, gene segments, or single or multiple nucleotides of one PIV are substituted by counterpart sequence(s) from a heterologous PIV or other source. For example, heterologous gene segments, such as one encoding a cytoplasmic tail, transmembrane domain or ectodomain, an epitopic site or region, a binding site or region, an active site or region containing an active site, etc., of a selected protein from one PIV is substituted for a counterpart gene segment in another PIV to yield novel recombinants, for example recombinants expressing a chimeric protein having a cytoplasmic tail and/or transmembrane domain of one PIV fused to an ectodomain of another PIV. Preferred genome segments in this regard range from about 15–35 nucleotides in the case of gene segments encoding small functional domains of proteins, e.g., epitopic sites, to about 50, 75, 100, 200–500, or 500–1,500 or more nucleotides for gene segments encoding larger domains or protein regions.

In one aspect of the invention, selected domains of HN and/or F proteins of one PIV strain are substituted into a heterologous PIV clone to produce a recombinant virus capable of stimulating a cross-protective immune response against both PIV strains in an immunized host. In other aspects, modified PIV clones are provided which comprise a chimera of a human PIV genomic or antigenomic sequence and at least one non-human PIV sequence, for example a polynucleotide containing sequences from both human and bovine PIV. The replacement of a human PIV coding sequence or non-coding sequence (e.g., a promoter, gene-end, gene-start, intergenic or other cis-acting element) with a counterpart bovine or murine PIV sequence yields recombinants having a variety of possible attenuating effects. For example, a host range effect will often arise from a heterologous PIV gene not functioning efficiently in a human cell, from incompatibility of the heterologous sequence or protein with a biologically interactive human PIV sequence or protein (e.g., a sequence or protein that ordinarily cooperates with the substituted sequence or protein for viral transcription, translation, assembly, etc.), among other useful attenuating effects. In yet another aspect of the invention, insertion of foreign genes or gene segments, and in some cases of noncoding nucleotide sequences, into the PIV genome results in a desired increase in genome length causing yet additional, desired phenotypic effects. Increased genome length is expected to result in attenuation of the resultant PIV clone, dependent in part upon the length of the insert. In addition, the expression of certain proteins from a gene inserted into recombinant PIV will result in attenuation of the virus due to the action of the protein. This has been described for IL-2 expressed in vaccinia virus (see, e.g., Flexner et al., *Nature* 33:-259–62 (1987)) and also would be expected for gamma interferon.

Deletions, insertions, substitutions and other mutations involving changes of whole viral genes or gene segments in recombinant PIV of the invention yield highly stable vaccine candidates, which are particularly important in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., *EMBO. J.* 16:578–87 (1997), incorporated herein by reference). Ablation of such genes in vaccine viruses is expected to reduce virulence and pathogenesis and/or improve immunogenicity.

In preferred aspects of the invention, the modified PIV clones represent a chimera of two or more human PIV genomes, for example a clone containing polynucleotide sequences from HPIV3 joined to sequences from one or more heterologous human PIV, such as HPIV1 and HPIV2. Thus, individual genes or gene segments of human PIV3 may be replaced or supplemented with counterpart genes or gene segments from HPIV 1 or HPIV2, or visa versa. In one example described hereinbelow, the invention provides a PIV clone, rPIV3-1, into which both the HN and F glycoprotein genes of HPIV1 are substituted for their counterpart genes in an HPIV3 background, yielding a chimeric virus having immunological characteristics representative of both parental strains.

In additional aspects of the invention, chimeric PIV or PIV clones having other alterations of genes or gene segments, as described above, are further modified by introducing one or more attenuating mutations adopted from a biologically derived mutant PIV, e.g., HPIV3 JS cp45 to achieve an attenuated, or further attenuated, chimeric mutant derivative. For example, one or more human PIV coding or non-coding polynucleotides may be substituted with a counterpart sequence from a heterologous human PIV, bovine PIV or murine PIV as described above, and this alteration may be combined with one or more mutations specifying, e.g., a ts, ca or att phenotype adopted from a biologically derived attenuated PIV mutant, to yield an attenuated or further attenuated (i.e., compared to either the chimeric clone or biologically derived parent virus) vaccine virus. Alternatively, functional deletion of a non-essential gene or gene segment, such as the C, D or V ORF, may be combined in a recombinant PIV with one or more mutations specifying a ts, ca or att phenotype from biologically derived PIV mutants to yield an attenuated vaccine strain. These combinatorial modifications yield recombinant PIV having desired phenotypic characteristics, e.g., increased yield of virus, enhanced attenuation, and/or genetic resistance to reversion from an attenuated phenotype, due to the combined effects of the different selected mutations.

In one combinatorial mutation design, a modified PIV is provided which comprises a chimera of a human PIV genomic or antigenomic sequence and at least one non-human PIV sequence, for example a polynucleotide containing sequences from both human and bovine PIV, and which also incorporates one or more mutations adopted from biologically derived PIV, e.g., one or more naturally occurring ts, ca or att mutations. Alternatively, the modified PIV can be a chimera of two or more human PIV genomes, for example a polynucleotide containing sequences from HPIV3 joined to sequences from one or more heterologous human PIVs, such as HPIV1 and HPIV2, which further incorporates one or more ts, ca att or other selected mutations from biologically derived PIV (e.g., a nucleotide substitution specifying a ts, ca or att phenotype adopted from a biologically derived mutant PIV strain such as JS cp45). In more detailed aspects, individual genes or gene segments of human PIV3 are replaced or supplemented with counterpart genes or gene segments from HPIV1 or HPIV2, or visa versa, in a clone that is attenuated or further attenuated by, e.g., a nucleotide change encoding an amino acid substitution conferring a ts mutation in the large polymerase L gene. For example, the invention provides PIV clones having the HN and/or F glycoprotein genes of HPIV1 substituted for their counterpart genes in an HPIV3 background, wherein the phenotype of the resultant chimeric clone is further modified by ts, ca or att mutation(s) encoded within one or more of the N, P, L, M, HN, F, C, D and V genes. Various combinations from a menu of possible mutations disclosed herein can be made to calibrate a vaccine virus to a selected level of attenuation, immunogenicity and stability, e.g., to achieve a satisfactorily attenuated and immunogenic, chimeric virus having immunological characteristics representative of multiple PIV strains. In one aspect, recombinant PIVs are provided wherein at least one attenuating mutation occurs in the PIV polymerase gene L (as exemplified by the recombinants r942, r992, r1558, r942/992, r942/1558, r992/1558, or r942/992/1558 described in the Examples below) incorporated in a chimeric PIV background. For example, useful chimeric PIV recombinants within this aspect of the invention will have one or more genes or gene segments of the HN and/or F glycoprotein genes from, e.g., HPIV1 substituted for their counterpart gene(s) in a heterologous background, e.g., in an HPIV3 clone, and will further incorporate one or more attenuating mutations, eg., nucleotide substitutions resulting in an amino acid change in the polymerase gene (such as change from Tyr to His at position 942, a change from Leu to Phe at position 992, and/or a change from Thr to Ile at position 1558) from a biologically derived PIV mutant. One such chimeric, attenuated recombinant exemplified hereinbelow is rPIV3-1.cp45L, a derivative of rPIV3-1 which incorporates all three L gene mutations specified above from JS cp45.

Yet additional mutations which can be incorporated in a chimeric PIV background for developing vaccine strains will be selected from biologically derived mutations in other genes, or will be created de novo in a recombinant genome by standard site directed mutagenesis or other purely recombinant mutagenic methods. Target genes for adopting biologically derived mutations or creating novel mutations in a recombinant PIV in this context include the nucleocapsid protein N, phosphoprotein P, large polymerase subunit L, matrix protein M, hemagglutinin-neuraminidase protein HN, fusion protein F and the C, D and V ORF products. Also targeted are extragenic sequences, eg., sequences in the 3' leader or trailer regions of a PIV genome. Exemplary mutations identified and incorporated in non-chimeric, recombinant PIV, described above will thus be readily incorporated within a chimeric PIV background, eg., as exemplified by rPIV3-1. These exemplary mutations include one or more mutations in the N protein, including specific mutations at a position corresponding to residues $Val_{96}$ or $Ser_{389}$ of JS cp45. In more detailed aspects, these mutations are represented as $Val_{96}$ to Ala or $Ser_{389}$ to Ala. Also desired for incorporation in chimeric PIV recombinants are mutations in the C protein, eg., a mutation at a position corresponding to $Ile_{96}$ of JS cp45, preferably represented by a substitution of $Ile_{96}$ to Thr, as described above. Further exemplary mutations for incorporation in a chimeric PIV background include one or more mutations in the F protein, for example adopted from JS cp45 at a position corresponding to residues $Ile_{420}$ or $Ala_{450}$, eg., substitutions $Ile_{420}$ to Val or $Ala_{450}$ to Thr. Yet additional chimeric PIV recombinants within the invention will adopt one or more amino acid substitutions in the HN protein, for example a mutation at a position corresponding to residue $Val_{384}$ of JS cp45, such as $Val_{384}$ to Ala. Yet additional chimeric recombinants will incorporate one or more mutations in an extragenic sequence, eg., a 3' leader sequence of the recombinant genome or antigenome. Exemplary mutations in this context include mutations in the 3' leader occurs at one or more positions corresponding to nucleotide 23, 24, 28, and/or 45 of JS cp45, for example a T to C change at nucleotide 23, a C to T change at nucleotide 24, a G to T change at nucleotide 28, or a T to A change at nucleotide 45. Yet additional extragenic mutations for incorporation within a chimeric PIV background include one or more mutations in a N gene start sequence, as exemplified herein by a mutation in the N gene start sequence at a position corresponding to nucleotide 62 of JS cp45, such as a A to T change. These exemplary mutations evaluated and combined into recombinant PIV in the Examples below will be readily incorporated within a chimeric PIV recombinant using the methods and tools provided herein, and will specify, individually and/or in combination, desired phenotypic changes to yield yet additional attenuated chimeric vaccine strains within the invention.

In additional combinatorial mutation designs, modified PIVs are provided which incorporate one or more of the foregoing ts, ca or att mutations adopted from biologically derived PIV or generated recombinantly in a PIV clone of the invention, in combination with another, distinct mutation disclosed herein (e.g., a deletion, addition, or rearrangement of a PIV N, P, L, M, HN, F, C, D or V gene or gene segment, or a gene or gene segment from another source such as RSV or measles virus). Also in this case, various combinations from a menu of mutations disclosed herein can be made to calibrate the vaccine virus to a selected level of attenuation, immunogenicity and stability. Thus, recombinant PIVs are provided which exhibit at least one attenuating mutation from a biologically derived PIV mutant, e.g., a mutation in the PIV polymerase gene L as found in JS cp45, or a recombinantly generated mutation, and which further incorporates one or more additional changes selected from, e.g., substitution or introduction of a heterologous gene or gene segment from a non-PIV source (e.g., an immunogenic RSV or measles gene or epitope, or a gene encoding a cytokine), a change in the order of viral genes to alter expression levels, removal of gene overlap, substitution of a PIV genome promoter with its antigenome counterpart, shortening, lengthening or removal of intergenic regions, e.g., to increase capacity for inserting foreign sequences, mutations in cis-acting signals to reduce or increase RNA replication or transcription, insertion of unique restriction sites, or deletion of even entire, non-essential genes, among other changes.

For vaccine use, virus produced according to the present invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, Mg$^{++}$ and HEPES, with or without adjuvant, as further described below.

PIV vaccines of the invention contain as an active ingredient an immunogenically effective amount of PIV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a PIV composition as described herein, via aerosol, droplet, oral, topical or other route, the immune system of the host responds to the vaccine by producing antibodies specific for PIV virus proteins, e.g., F and HN glycoproteins. As a result of the vaccination with an immunogenically effective amount of PIV produced as described herein, the host becomes at least partially or completely immune to PIV infection, or resistant to developing moderate or severe PIV infection, particularly of the lower respiratory tract.

The host to which the vaccines are administered can be any mammal which is susceptible to infection by PIV or a closely related virus and which host is capable of generating a protective immune response to the antigens of the vaccinizing strain. Accordingly, the invention provides methods for creating vaccines for a variety of human and veterinary uses.

The vaccine compositions containing the PIV of the invention are administered to a host susceptible to or otherwise at risk for PIV infection to enhance the host's own immune response capabilities. Such an amount is defined to be a "immunogenically effective dose." In this use, the precise amount of PIV to be administered within an effective dose will depend on the host's state of health and weight, the mode of administration, the nature of the formulation, etc., but will generally range from about $10^3$ to about $10^6$ plaque forming units (PFU) or more of virus per host, more commonly from about $10^4$ to $10^5$ PFU virus per host. In any event, the vaccine formulations should provide a quantity of modified PIV of the invention sufficient to effectively protect the host patient against serious or life-threatening PIV infection.

The PIV produced in accordance with the present invention can be combined with viruses of other PIV serotypes or strains to achieve protection against multiple PIV serotypes or strains. Alternatively, protection against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may protect against different strains of the same or different serotype.

In some instances it may be desirable to combine the PIV vaccines of the invention with vaccines which induce protective responses to other agents, particularly other childhood viruses. In another aspect of the invention the PIV can be employed as a vector for protective antigens of other pathogens, such as respiratory syncytial virus (RSV) or measles virus, by incorporating the sequences encoding those protective antigens into the PIV genome or antigenome which is used to produce infectious PIV, as described herein. The cloning of RSV cDNA and other disclosure relevant to the invention is described in copending U.S. patent application Ser. Nos. 08/534,768, 60/021,773, 08/720,132, 60/046,141, 60/047,634, and 08/892,403, and PCT patent application PCT/US97/12269, each incorporated herein by reference.

Single or multiple administrations of the vaccine compositions of the invention can be carried out. In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) PIV and/or other subject viral infections. Similarly, adults who are particularly susceptible to repeated or serious PIV infection, for example health care workers, day care workers, family members of young children, the elderly, and individuals with compromised cardiopulmonary function, may require multiple immunizations to establish and/or maintain protective immune responses.

Levels of induced immunity provided by the vaccines of the invention can be monitored by measuring amounts of neutralizing secretory and serum antibodies. Based on these measurements, vaccine dosages can be adjusted or vaccinations repeated as necessary to maintain desired levels of protection. Further, different vaccine viruses may be advantageous for different recipient groups. For example, an engineered PIV strain expressing an additional protein rich in T cell epitopes may be particularly advantageous for adults rather than for infants.

In yet another aspect of the invention the PIV is employed as a vector for transient gene therapy of the respiratory tract. According to this embodiment the recombinant PIV genome or antigenome incorporates a sequence which is capable of encoding a gene product of interest. The gene product of interest is under control of the same or a different promoter from that which controls PIV expression. The infectious PIV produced by coexpressing the recombinant PIV genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant PIV is administered in an amount sufficient to result in the expression of therapeutic or prophylactic levels of the desired gene product. Representative gene products which may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

EXAMPLE I

Construction of Plasmid p218(131) Encoding Negative Sense PIV Genomic RNA

Figure 1:
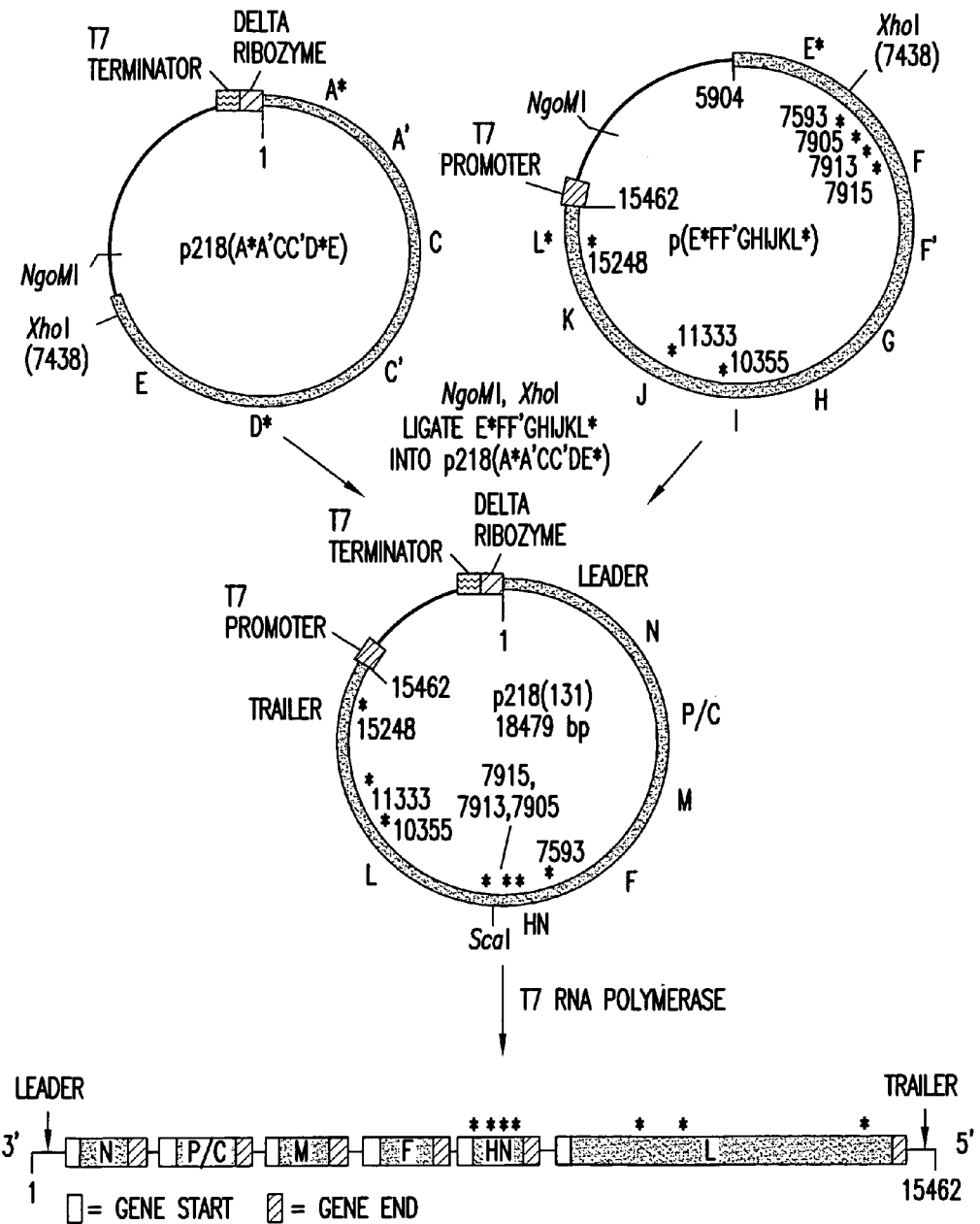
FIG. 1 illustrates construction of the plasmid p218(131), encoding a complete copy of HPIV3 genomic RNA. The diagram of p218(A*A'CC'D*E) (top left) illustrates the location of the T7 terminator and delta ribozyme adjacent to nucleotide 1 of the HPIV3 genome. The top right diagram of p(E*FF'GHIJKL*) illustrates the locations of the 7 sequencing markers (asterisk), see FIG. 2 below, and the T7 promoter adjacent to nucleotide 15462 of HPIV3. The 15 overlapping clones used to construct the full length genomic cDNA are indicated by letters on the outside of the two plasmids. The unique restriction sites NgoMI and XhoI were used to clone p218(131) which encodes the complete negative-sense genomic RNA of HPIV3 illustrated at the bottom. The location of each sequencing marker in p218(131) differentiating recombinant JS from JS wt is indicated by an asterisk.
Figure 3:
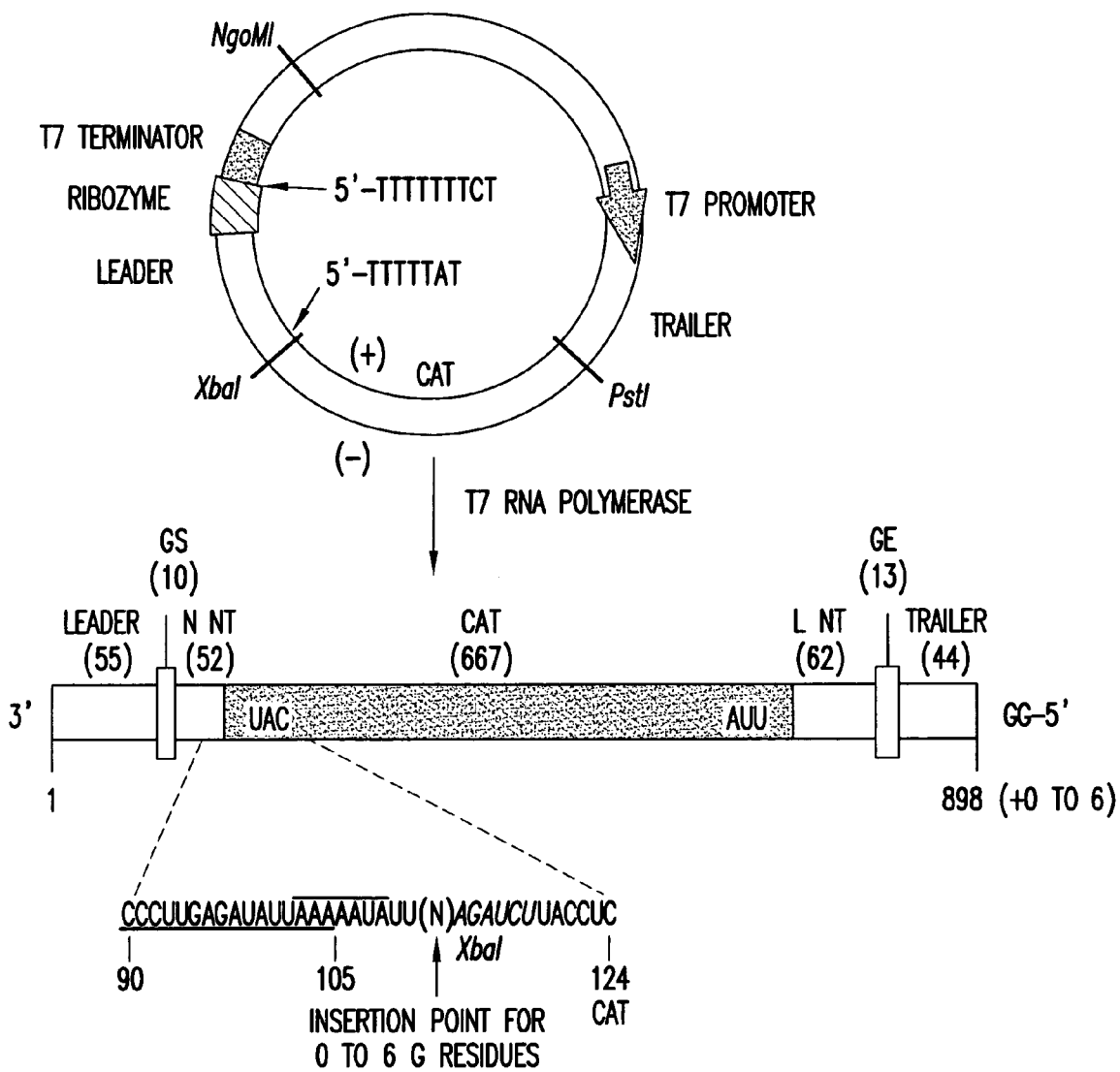
Figure 4:
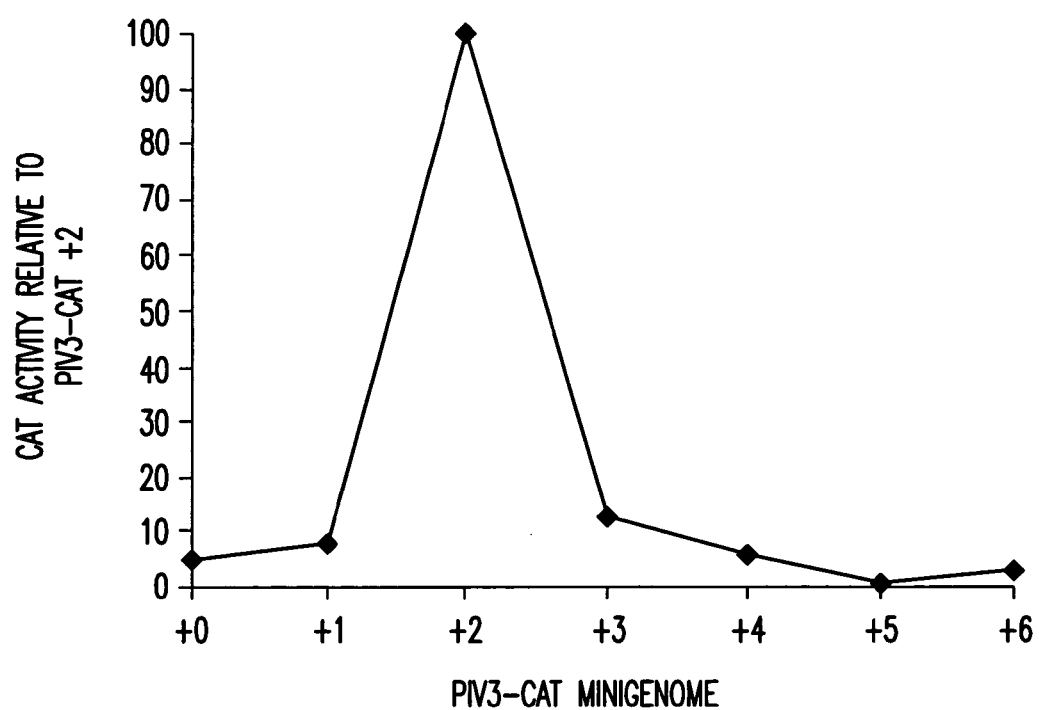

A full cDNA clone designated p218(131) (FIG. 1; SEQ ID NO: 1) (deposited under the terms of the Budapest Treaty with the American Type Culture Collection (ATCC) of 12301 Parklawn Drive, Rockville, Md. 20852, U.S.A., and granted the designation 97991) was constructed to encode the complete 15462 nt genomic sequence of HPIV3 JS strain. A hepatitis delta ribozyme was placed abutting the 3' end of the genomic sequence such that self-cleavage would yield the 3' end of HPIV3 (Perrotta and Been, Nature 350: 434–436, (1991), incorporated herein by reference in its entirety). A T7 transcription terminator was placed following the delta ribozyme. The T7 promoter was placed adjacent to the 5' end of the genomic sequence such that the 5' terminal nucleotide of the HPIV3 genome was the first nucleotide synthesized. In this configuration, the cDNA encodes a complete negative-sense copy of PIV3 genomic RNA containing the correct genomic termini without any additional heterologous nucleotides.

The HPIV3 cDNA was assembled from 14 overlapping subclones (termed A*-L, which letters in parentheses designate individual plasmids and do not refer to specific viral genes) constructed by reverse transcription (RT) and polymerase chain reaction (PCR) of RNA isolated from virions purified by sucrose gradient centrifugation (Stokes et al., supra, 1992; Stokes et al., supra, 1993, each incorporated herein by reference in its entirety). The subclones spanned the following nucleotides of genomic RNA (numbered with the 3'end designated as position 1): 1–2058 (A*), 1874–3111 (A'), 3086–5140 (C), 4348–5276 (C'), 5072–6695 (D*), 5904–8532 (E), 7806–9898 (F), 9632–10740 (F'), 9760–10955 (G), 10862–11925 (H), 11835–12868 (I), 12426–13677 (J), 13630–14496 (K), and 14467–15462 (L). Each fragment was cloned into pBluescript KSII (Stratagene, La Jolla, Calif.) using conventional cloning techniques and was sequenced completely.

Plasmid p(L) was then subjected to site-directed mutagenesis to introduce the T7 promoter via a single-stranded DNA intermediate according to the MUTA-GENE procedure (BioRad, Hercules, Calif.). The T7 promoter was positioned so that transcription initiates at the precise 5' end of the HPIV3 genome using the negative-sense mutagenic primer: 5'-AATACGACTCACTATA*ACCAAACAAGAGAAG-3 (SEQ ID NO: 2; T7 sequences are italicized, HPIV3-specific sequences are underlined, and the 5'-end HPIV3 nucleotide, genome position 15462, is indicated by an asterisk). This modified p(L) was designated p(L*). Plasmid p(E) was modified to yield p(E*) by the same method using the negative-sense mutagenic oligonucleotide 5'-CCAAG TACTATGAGATGCTTGATT-3' (SEQ ID NO: 3) to insert three nucleotide substitutions (underlined) into the HN gene at HPIV3 position 7903, 7913, 7915 (FIG. 1). These substitutions removed an Hga I site, inserted a Sca I site, and modified amino acid 370 of the encoded HN protein such that the epitope recognized by monoclonal antibodies (mAb) 423/6 and 170/7 was ablated (van Wyke Coelingh et al., J. Virol. 61:1473–1477, (1987), incorporated herein by reference). The p(E*) to p(K) subclones were assembled in a step-wise fashion into the p(L*) plasmid to give p(E*FF'GHIJKL*) (FIG. 1A). This plasmid includes HPIV3 nucleotides 5904–15462 with the T7 promoter adjacent to nucleotide 15462 at the 5' end of the genome. Subclones p(A*) to p(E) were assembled into a second, overlapping subclone, p(A*A'CC'D*E) which contained HPIV3 nucleotides 1–8532.

Both subclones p(E*FF'GHIJKL*) and p(A*A'CC'D*E) were sequenced completely. In addition to the introduced point mutations described above, the cDNA differed from the authentic JS HPIV3 sequence (Stokes et al., supra, 1992) by a single nucleotide substitution at position 1615 which was within the N gene and caused a substitution at amino acid 506 in the encoded protein. Three other nucleotide substitutions were found at positions 10355, 11333, and 15248 in the L gene which did not change the encoded protein (FIG. 2). These three noncoding changes were retained as additional sequence markers to identify recombinant virus (designated rPIV) derived from cDNA, and the mutation in the N gene was corrected as described later.

Subclone p(A*A'CC'D*E) was then modified to insert the hepatitis delta virus ribozyme and T7 terminator adjacent to HPIV3 position 1. An HPIV3 minigenome in which the 3' end of the HPIV3 genome (GGT↓GGG) (underlined) was generated through self-cleavage of a flanking hepatitis delta virus antigenomic ribozyme (shown in part in bold-type) was previously constructed (Dimock and Collins, J. Virol. 67: 2772–2778, (1993); Perrotta and Been, supra, (1991), each incorporated herein by reference in its entirety). The ribozyme in turn was followed by a T7 transcription terminator. This minigenome cDNA was used as a template in a PCR reaction which modified the sequence adjacent to the ribozyme cleavage site to be a Sma I site (CCC↓GGG) and placed an ApaI site (GGGCC↓C) on the downstream side of the T7 terminator. The PCR product was cloned into pKSII which had been digested with BssHII and made blunt-ended by filling in, yielding p218.

p218 was designed such that any sequence could be introduced into the opened Sma I site by blunt-end ligation and its RNA transcript would be cleaved at the delta ribozyme cut site (NNN↓GGG). The p(A*A'CC'D*E) subclone was digested with Hga I and Sal I (8533), which released the HPIV3 cDNA, and was filled in with dNTPs and T4 DNA polymerase to give blunt termini. The Hga I site is 10 nucleotides upstream of HPIV3 position 1 and, when digested and filled in, leaves a blunt terminus beginning with HPIV3 position 1. The modified Hga I-Sal I fragment was gel purified and cloned into the Sma I site of p218. The mutation in the N gene (T at nt 1615) was corrected to the JS wt sequence (A at nt 1615) (see GenBank accession #Z11575, incorporated herein by reference) using Kunkel mutagenesis (Kunkel et al., Methods Enzymol. 154: 367–382, (1987), incorporated herein by reference in its entirety). This plasmid was designated p218(A*A'CC'D*E) (FIG. 1).

The Xho I-Ngo MI fragment of p(E*FF'GHIJKL*), which contained the T7 promoter and the HPIV3 cDNA from nucleotides 7438–15462, was cloned into the Xho I-Ngo MI window of p218(A*A'CC'D*E) (FIG. 1). This joined the two fragments of HPIV3 cDNA at HPIV3 nucleotide 7438, yielding a plasmid containing a full-length HPIV3 cDNA encoding a negative-sense genomic RNA with the above-mentioned three desired mutations in the HN gene and three incidental mutations in the L gene. The final construct, designated p218(131) (FIG. 1; SEQ ID NO: 1), was then sequenced in its entirety by automated sequencing at the NCI Frederick Cancer Research and Development Center (Frederick, Md.) using the Taq DYE Deoxy Terminator cycle sequencing kit (ABI, Foster City, Calif.). This identified an additional change in the HN gene, namely a change of C to T in the HN gene at position 7593 which changed HN amino acid 263 from threonine to isoleucine that is also indicated in FIG. 2.

EXAMPLE II

Transcription and RNA Replication System for HPIV3

The present example describes compositions and methods for producing a reconstituted transcription and RNA replication system for human parainfluenza virus type 3 (HPIV3). This exemplary system was developed using components expressed intracellularly from transfected plasmids driven by a T7 RNA polymerase supplied by a vaccinia virus recombinant. The system is based on a negative-sense analog of HPIV3 genomic RNA in which the viral genes were deleted and replaced with a polynucleotide encoding bacterial chloramphenicol acetyl transferase (CAT). The N, P and L proteins are expressed from cotransfected plasmids so as to direct efficient transcription and RNA replication. Transcription according to this example yields subgenomic polyadenylated mRNA, which can be readily isolated, e.g., by oligo(dT) chromatography. RNA replication according to this example yields mini-antigenome and progeny minigenome, which are shown to be encapsidated based on resistance to digestion with micrococcal nuclease.

A) Viruses and Cells

A vaccinia virus recombinant, vTF7-3, that expresses bacteriophage T7 RNA polymerase, was provided as described by Fuerst et al. (Proc. Natl. Acad. Sci. U.S.A. 83: 8122–8126, 1986, incorporated herein by reference in its entirety). HEp-2 monolayer cultures were maintained at 37° C. in 5% $CO_2$ with OptiMEM 1 (Life Technologies, Gaithersburg, Md.) supplemented with 20% fetal bovine serum (FBS), 50 µg/ml gentamicin sulfate and 2 mM glutamine.

B) cDNAs cDNAs corresponding to ORFs of the N, P, and L genes of the JS strain of HPIV3 (GenBank #Z11575; Stokes et al., 1992) were individually cloned into the Nco I-Sal I window of plasmid pTM-1, in which transcription is mediated by T7 RNA polymerase and translation by an internal ribosome entry site preceding the foreign ORF (Elroy-Stein et al., Proc. Natl. Acad. Sci. U.S.A. 86: 6126–6130 (1989), incorporated herein by reference in its entirety). Each gene was first modified by polymerase chain reaction (PCR) to place an Nco I or Nco I-compatible site at the translational start site and a Sal I site on the downstream end.

The plasmid p(131), which is similar to p218(131) except that it lacks the hepatitis delta virus ribozyme, was used as a template for each PCR. The primers used to amplify the N ORF were CCCTATAATTTCAACATGTTGAGC-CTATTTG (SEQ ID NO: 4; forward primer relative to positive-sense) and GATTAAAAATGTTGGTCGACTTAGT-TGCTTCC (SEQ ID NO: 5; italics represent restriction enzyme sites, and the translational start site is in bold). The PCR product, a 1578 bp fragment flanked by an Afl III and Sal I site, was cloned into the Nco I-Sal I window of pTM-1 to yield pTM(N).

The primers used to amplify the PIV3 phosphoprotein (P)ORF were 5'-CCATAGAGAGTCCATGGAAAGCGAT-GCTAAAAACTATC-3' (SEQ ID NO:6; forward primer) and 5'-CGGTGTCGTTTCTTTGTCGACTCATTG-GCAATTGTTG-3' (SEQ ID NO:7; reverse primer). A full-length cDNA of JS strain of genomic RNA (p131) was used as template for the PCR. The resultant PCR product was an 1851 bp fragment flanked by an Nco I and Sal I restriction site (in italics). The PCR product was then cloned into the Nco I-Sal I window of pTM-1 to yield pTM(P).

A second PCR was performed to amplify the PIV3 phosphoprotein P ORF without the C ORF. p131 was again used as template cDNA. A different forward primer and the same reverse primer were used to amplify the PIV3 P ORF without C; 5'-CCATAGAGAGTCCATGGAAAGCGA CGCTAAAAACTATC-3, (SEQ ID NO: 74; forward primer) and 5'-CGGTGTCGTTTCTTTGTCGACTCATTG-GCAATTGTTG-3' (SEQ ID NO:7; reverse primer). The resultant PCR product was an 1851 bp fragment flanked by an Nco I and Sal I restriction site (designated by italics). The underlined nucleotide in the forward primer represents a nucleotide substitution which is silent in the P ORF but changes the start codon of the C ORF to threonine. The next start codon for the C ORF is more than 400 nucleotides downstream. Thus, only the P protein would be produced. The PCR product was then cloned into the Nco I-Sal I window of pTM-1 to yield a second plasmid, pTM(P no C).

The L ORF of HPIV3 was cloned into pTM-1 in three parts: the ends were derived from PCR products and the main body was a restriction fragment from p218(131). The upstream end of the L ORF was amplified using the primers GCAAAGCGTGCCCGGGCCATGGACACT-GAATCTAACAATGGC (SEQ ID NO: 8) and GAAATTC-CTTAATCGATTCTCTAGATTC (SEQ ID NO: 9). This yielded the 1,020-bp PCR product L1 in which positions 8625–9645 of the full-length genome were flanked by Sma I and Nco I sites on the upstream end and a Cla I site on the downstream end (all three sites are italicized). The downstream end of the L ORF was amplified using the primers CCCATCAACTGTAACATACGTAAGAAAGAC (SEQ ID NO: 10) and GGTTAGGATATGTCGACATTGTATTTATG (SEQ ID NO: 11). This yielded the 1,733-bp PCR product L2 in which positions 13,645–15,378 of the full-length genome were flanked by a SnaB I and Sal I site (italicized). Plasmid p(131) was digested with Cla I and Pst I to yield the 4,487-bp fragment L middle containing positions 9,630–14,120 of the full-length genome. L1 and L middle were joined at the common Cla I site and cloned into the Sma I-Pst I window of pBluescript to yield p(L1+L middle). The L2 fragment was then cloned into the Pst I-Sal I window of p(L1+L middle) to yield the complete L ORF flanked by Nco I and Sal I. This was then cloned into the Nco I-Sal I window of pTM-1 to yield pTM(L). The sequences of PCR-generated regions of pTM(N) (SEQ ID NO: 20), pTM(P) (SEQ ID NO: 21), and pTM(L) (SEQ ID NO: 22) were confirmed by the dideoxynucleotide sequencing method.

To increase the efficiency of T7 transcription, certain modifications were made to a cDNA construct encoding a negative-sense PIV minigenome, called PIV3-CAT(-) (Dimock and Collins, *J. Virol.* 67: 2772–2778 (1993), incorporated herein by reference in its entirety). PIV3-CAT(-) includes the 3'-terminal 111 nucleotides and 5'-terminal 115 nucleotides of the HPIV3 genome fused to a negative-sense copy of the CAT ORF. This cDNA was designed to yield, upon linearization with HgaI and transcription with T7 RNA polymerase, a minigenome containing the exact correct ends of the HPIV3 genome. Two successive rounds of PCR, using mutagenic oligonucleotides which added successive extensions to the cDNA end, were used to replace the HgaI site with the hepatitis delta ribozyme (Perotta and Been, *Nature* 350: 434–436 (1991), incorporated herein by reference in its entirety), such that self-cleavage generates the correct 3' HPIV3 genomic end. A T7 transcriptional termination signal was inserted immediately after the ribozyme (FIG. 3) to yield PIV3-CAT-delta.

PIV3-CAT-delta cDNA was modified by PCR mutagenesis to insert one, two or three G residues between the T7 promoter and the 5' end of the minigenome, using restriction sites flanking the trailer and T7 promoter. This modification yielded increased efficiency of T7 transcription. In preliminary experiments, the minigenome containing two G residues, called PIV3-CAT-GG, was the most active in the expression of CAT in the reconstituted transcription and replication system described below, and was used for all subsequent derivatives.

The PIV3-CAT-GG cDNA was further modified by overlapping PCR mutagenesis to introduce modifications simultaneously at two sites, as follows. First, the sequence $T_7CT$, which contains tandem transcriptional termination motifs for the vaccinia virus early-stage RNA polymerase ($T_5NT$) (Yuen and Moss, *Proc. Natl. Acad. Sci. U.S.A.* 84: 6417–6421 (1987), incorporated herein by reference in its entirety), was inserted into the positive-sense strand cDNA strand between the delta ribozyme and T7 transcriptional terminator (FIG. 1). This motif, and a second motif described herein below, were added to prevent promiscuous transcription of the CAT gene by the vaccinia virus early RNA polymerase. Second, the minigenome cDNA insert was modified at the junction between the N nontranslated region and CAT gene to contain (i) the insertion of a second vaccinia virus termination motif ($T_5AT$) into the positive-sense cDNA strand at positions 103 to 109 relative to the encoded minigenome, and (ii) the insertion of 0 to 6 G residues (negative-sense) at minigenome position 112 (FIG. 3). The overlapping PCR mutagenesis involved three sets of reactions (PCR 1, 2 and 3) performed as follows. PCR 1 was a set of seven parallel reactions [PCR1 (0) to (+6)] which used the PIV3-CAT-GG cDNA as a template and the following two mutagenic oligonucleotides as primers: the forward primer was: $^{-111}$GGGGTTATGCTACTGCAGGCTTTTTTTCTCCCTTAGCCATCCG$^{-62}$ (SEQ ID NO: 12) and the reverse primer was: $^{124}$CTC<u>CAT</u>TCTAGA(N)TTATAAAAATTATAGAGTTCCC$^{90}$ (SEQ ID NO: 13). The bold sequence in the first oligonucleotide is the upstream tandem vaccinia terminator, and the bold sequence in the second oligonucleotide is the second terminator. This reaction amplified the ribozyme and adjacent leader region and inserted the mutations described above. PCR 2 was a single reaction that used the PIV3-CAT-GG cDNA as a template, and a forward primer that hybridized in plasmid sequence upstream of a unique NgoMI site (FIG. 3), and a reverse primer complementary to the forward primer of reaction one. Thus, the products of PCR 1 and 2 overlapped at this latter sequence. The products of PCR 1 (0) to (+6) and PCR 2 were gel purified. The products of PCR1 (0) to (+6) were each mixed separately with an aliquot of PCR 2 product and amplified in a third reaction (PCR3 (0) to (+6)) which also contained the forward primer of PCR 2 and the reverse primer of PCR 1. The products of PCR3 (0) to (+6) were digested with NgoMI, which cuts in plasmid-specific sequence, and XbaI, which cuts at the upstream end of the CAT gene (FIG. 3), and cloned into the NgoMI-XbaI window of PIV3-CAT-GG. This resulted in a panel of cDNAs encoding minigenomes which were named according to the number of inserted G residues: PIV3-CAT 0 to PIV3-CAT +6. The structures of all DNA regions derived from PCR were confirmed by dideoxynucleotide sequencing.

C) Transfection

HEp-2 cells were grown to 90% confluence in 6 well plates. Each well of a six-well plate ($1.5\times10^6$ cells) was transfected with 0.4 µg pTM(P), 0.4 µg pTM(N), 0.05 µg pTM(L), and 0.4 µg minigenome plasmid. The plasmids were added to 0.1 ml of OptiMEM (Life Technologies) and mixed with 0.1 ml of OptiMEM containing 12 µl of LipofectACE (Life Technologies). After an incubation period of approximately 15 minutes at room temperature, 0.8 ml of OptiMEM 1 containing 2% calf serum and $1.5\times10^7$pfu of vTF7-3 was added to each well. The plates were incubated at 37° C. for 12 hours after which the media was replaced with fresh OptiMEM 1 containing 2% fetal bovine serum. The cells were then incubated at 37° C. for a total of 48 hours and harvested for RNA analysis and CAT assay. Each minigenome was represented in triplicate (3 wells) which was scraped into the medium and pooled.

D) CAT Assay

An aliquot representing 3.33% ($1.5\times10^5$ cells) of each pooled sample of harvested cells described above was removed for CAT assay. The aliquot was centrifuged at 1,000 rpm for 5 minutes and the supernatant discarded. The cell suspension was washed with 1 ml of 40 mM Tris, pH 7.5, 1 mM EDTA, 150 mM NaCl and resuspended in 50 µl 0.25 M Tris, pH 7.5. Lysate was prepared by three cycles of freezing and thawing and clarified by centrifuging at 8,000 rpm for 5 minutes. 1 µl of lysate was assayed for the ability to acetylate D-threo-[dichloroacetyl 1-$^{14}$C]chloramphenicol (Amersham) using a conventional assay (Gorman et al., *Mol. Cell. Biol.* 2: 1044–1051 (1982), incorporated herein by reference in its entirety). Acetylation was visualized by thin-layer chromatography and quantified by phosphoimager analysis (Molecular Dynamics, Sunnyvale, Calif.).

E) RNA Analysis

The remaining cell harvest of each pooled sample was divided into three equal parts for isolation of encapsidated RNA, total RNA, and mRNA. The three aliquots were centrifuged at 1,000 rpm for five minutes and the supernatants discarded. Two aliquots of cell suspension were resuspended in 50 µl of RSB (10 mM NaCl, 10 mM Tris, pH 7.5, 1.5 mM $MgCl_2$) containing 1% Triton X-100, 0.5% DOC. 50 µl of 10 mM Tris 7.5, 1 mM $CaCl_{21}$ and 20 µg (1 mg/ml stock) of micrococcal nuclease was then added to one aliquot, and the other received the same mixture without micrococcal nuclease (Baker & Moyer, *J. Virol.* 62: 834–838 (1988), incorporated herein by reference in its entirety). The purpose of the micrococcal nuclease was to destroy nonencapsidated RNA, and the conditions used had been optimized in preliminary experiments. The mixtures were incubated at 30° C. for 30 min and the RNA was isolated with Trizol (Life Technologies) according to the procedure of the supplier. The third aliquot of cell suspension was processed for RNA purification with Trizol and the purified RNA was separated by oligo(dT) cellulose chromatography into polyadenylated and nonpolyadenylated fractions (Grosfeld et al., *J. Virol.* 69: 5677–5686 (1995), incorporated herein by reference in its entirety). RNA samples were run on 1.5% agarose gels containing 0.44 M formaldehyde, transferred to nitrocellulose (Chomczynski, *Anal. Biochem.* 201: 134–139 (1992), incorporated herein by reference in its entirety), hybridized with strand specific riboprobes, and quantified by phosphoimager analysis.

EXAMPLE III

Construction and Expression of Modified PIV3 Minigenomes

In the present example, a panel of cDNAs was constructed to encode PIV3 minigenomes which differed in length by single nucleotide increments. Transcription and RNA replication in this reconstituted system were the most efficient for the minigenome whose length was an even multiple of six. In this context, members of the *Paramyxovirus* and *Morbillivirus* genera typically abide by a "rule of six," i.e., genomes (or minigenomes) replicate efficiently only when their nucleotide length is a multiple of six (thought to be a requirement for precise spacing of nucleotide residues relative to encapsidating NP protein). However, the present findings illustrate that minigenomes whose lengths were one nucleotide greater than or less than an even multiple of six were surprisingly active, especially in RNA replication.

A panel of seven cDNAs was constructed to encode seven PIV3-CAT minigenomes, called PIV3-CAT 0 to +6, that differ in length by single-nucleotide increments (FIG. 3). Each minigenome is a short negative-sense analog of HPIV3 genomic RNA in which the viral genes had been deleted and replaced with a negative-sense copy of the CAT ORF. The CAT ORF is flanked by nontranslated segments of the N and L genes, the N GS and L GE transcription motifs, and the 3' leader and 5' trailer extragenic termini of genomic RNA. The 5' end of each PIV3-CAT minigenome is defined by the adjacent promoter for T7 RNA polymerase. This promoter was constructed to contribute an extension of two nonviral G residues to the 5' end of the encoded minigenome, as described above. The presence of additional G residues adjacent to the nontranscribed core of the T7 promoter improves its transcriptional efficiency, and preliminary work showed that presence of two G residues provided the highest levels of activity in the reconstituted system described below. These two G residues are not included in minigenome length calculations. The 3' minigenome end is created by self-cleavage by an abutting hepatitis delta virus ribozyme, which would generate the correct 3'-terminal nucleotide. The seven PIV3-CAT minigenomes differ by single-nucleotide increases in length due to the insertion of 0 to 6 G residues at the junction between the N nontranslated region and the CAT gene (FIG. 3), and range in length from 898 to 904 nucleotides. The PIV3-CAT +2 minigenome is the only one which is an even multiple of six (it should be noted that each minigenome contained two additional nonviral G residues at the 5' end contributed by the T7 promoter, but it is assumed that these would be lost during intracellular HPIV3-mediated RNA replication).

Each PIV3-CAT cDNA was transfected into HEp-2 cells that had been infected with vTF7-3, a vaccinia virus recombinant that expresses T7 RNA polymerase. Plasmids encoding the N, P and L proteins under the control of the T7 promoter were transfected in parallel. The P cDNA had been modified by site-directed mutagenesis to eliminate the translational start site of the C ORF, as described above. Cells were harvested at 48 h post-infection. An aliquot of the cell suspension was processed for CAT enzyme assay (FIG. 4). The remaining cells were divided into three equal aliquots and processed for RNA analysis as described below.

The minigenome cDNA was further modified to contain two tandem vaccinia virus early-gene transcription termination motifs ($T_7NT$) in the positive-sense plasmid strand upstream of the PIV3-CAT insert, and a third one ($T_5AT$) in the same strand immediately upstream of the CAT ORF (FIG. 3). These were designed to minimize promiscuous transcription of the CAT ORF by vaccinia virus polymerase (Grosfeld et al. (1995), supra). CAT expression was reproducibly detected when each of PIV3-CAT minigenomes was complemented by the N, P and L plasmids (FIG. 4), and detection of CAT was dependent on all three PIV3 proteins. However, expression was much higher for PIV3-CAT+2, which has a nucleotide length that is an even multiple of six. Preferred ratios and amounts of the minigenome and support plasmids were determined based on CAT enzyme expression.

EXAMPLE IV

Synthesis of Positive-Sense RNAs by PIV Minigenomes

Transcription and replication of PIV minigenomes was confirmed by detection of RNA products of both processes. As described in the foregoing Example, three equal aliquots of cell suspension were taken for RNA analysis. One aliquot was used for oligo(dT) analysis, as described below. The other two aliquots were lysed with detergent and incubated with micrococcal nuclease or mock-treated. RNA was then isolated, separated by electrophoresis on formaldehyde agarose gels, transferred to nitrocellulose, and analyzed by hybridization with negative-sense CAT riboprobe. RNA from micrococcal-treated and mock-treated lysates are shown in FIG. 5A upper and lower panels, respectively.

Analysis of RNA from mock-treated lysates showed that complementation of each minigenome with the N, P and L plasmids resulted in the synthesis of a band of RNA which was very similar in size to a marker consisting of RNA expressed by the 931-nucleotide RSV-CAT C2 minigenome (Grosfeld et al. (1995), supra). Phosphorimagery analysis is shown in FIG. 5B. Little or no RNA was detected when the N or L plasmids were omitted, confirming that these RNAs are products of the reconstituted PIV3 polymerase.

Each PIV3-CAT minigenome is expected to encode two positive-sense RNAs, namely the mini-antigenome and the subgenomic CAT mRNA. Each mini-antigenome is expected to be the exact complement of its minigenome, which was 898 to 904 nucleotides in length. The predicted subgenomic mRNA is defined by the GS and GE signals, and is expected to be 804 nucleotides in length and contain a polyA tail of 100 to 200 nucleotides.

Figure 5A:
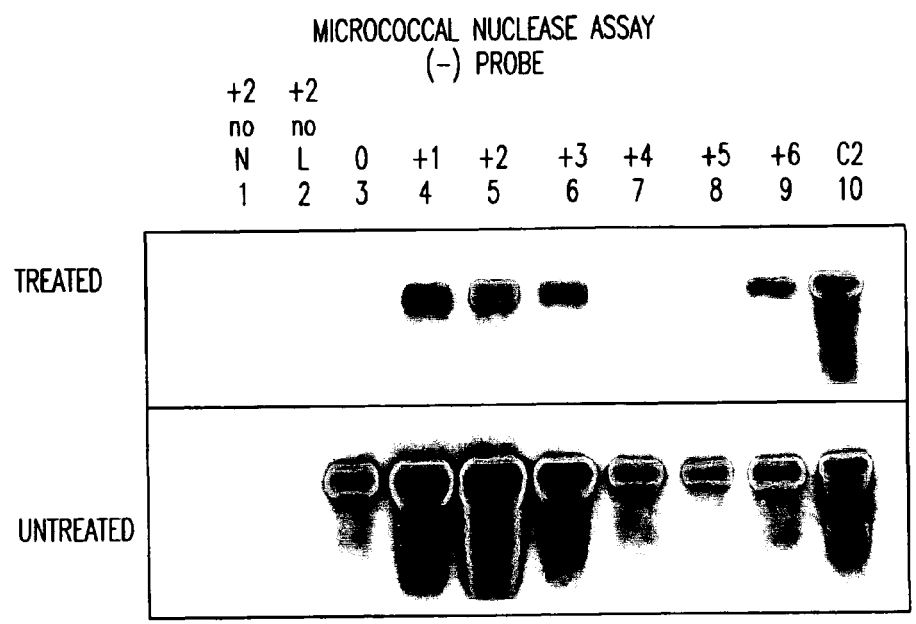

Detection of a single gel band of positive-sense RNA in FIG. 5A (lower panel) suggested that the antigenome and mRNA were not resolved by gel electrophoresis. Accordingly, treatment with micrococcal nuclease was used to identify antigenome RNA, since the antigenome (and genome) but not mRNA would be encapsidated and resistant to digestion. The use of micrococcal nuclease for this purpose is well established (Baker & Moyer (1988), supra), and the conditions selected were verified with RSV minireplicons and shown to completely degrade mRNA contained in the HEp-2 cell lysates. Residual RNA was purified and analyzed by Northern blot analysis with negative-sense riboprobe (FIG. 5A, upper panel) and quantitated by phosphorimagery (FIG. 5B; note that in this analysis the micrococcal-treated and untreated RNA amounts were normalized separately). These investigations revealed the presence of a population of protected RNA corresponding to the positive-sense encapsidated mini-antigenome. Among several experiments, this protected RNA accounted for approximately 3 to 15% of the positive-sense RNA.

Figure 5B:
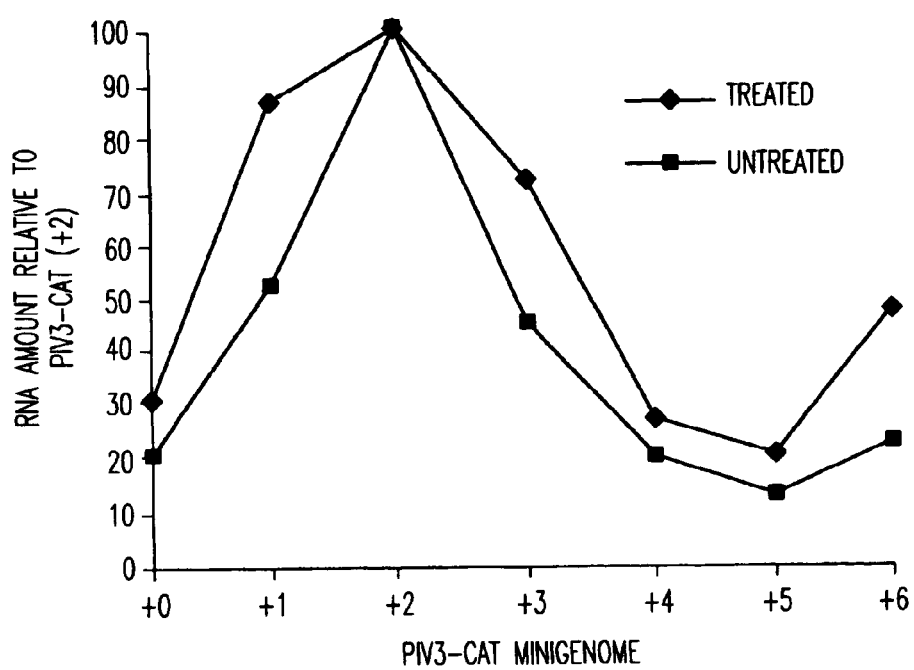

For both the total and the micrococcal-resistant RNA, accumulation was greatest in the case of the +2 minigenome, which is 900 nucleotides in length and thus a multiple of six. However, substantial amounts of RNA also accumulated in the case of the minigenomes which did not exhibit a length corresponding to a multiple of six nucleotides, in particular minigenomes +1 and +3 which were one nucleotide longer or shorter than the +2 minigenome. In fact, the amount of encapsidated antigenome produced by the +1 and +3 minigenomes was 85% and 72% that of the +2 minigenome (FIG. 5B). Even the least efficient minigenome, the +5 minigenome, was 20% as active as the +2 minigenome as determined by measurement of accumulated encapsidated RNA. In the case of measurements to detect total positive-sense RNA, the +1 and +3 minigenomes produced 52% and 45% as much total RNA as the +2 minigenome.

Figure 6A:
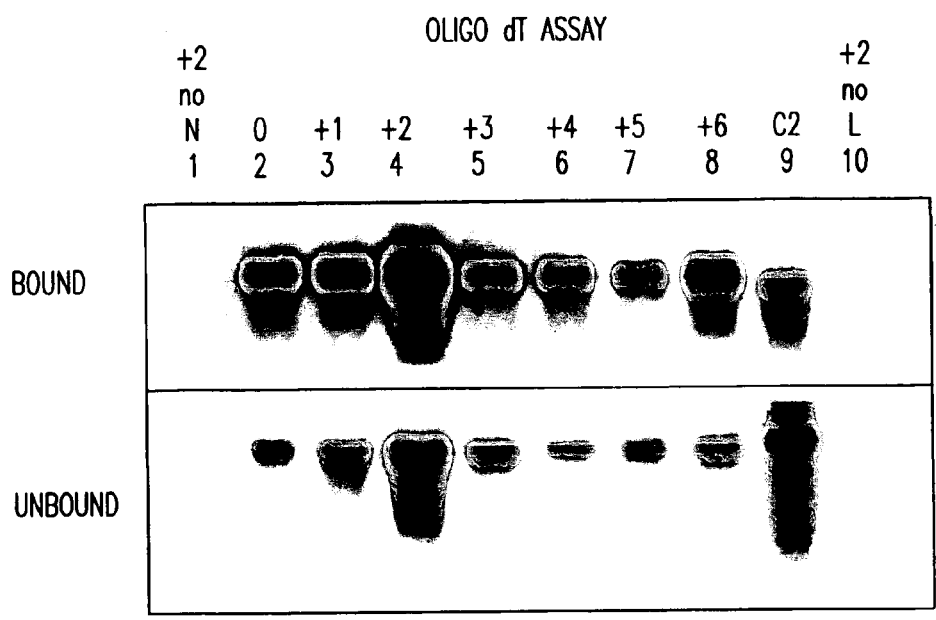
Figure 6B:
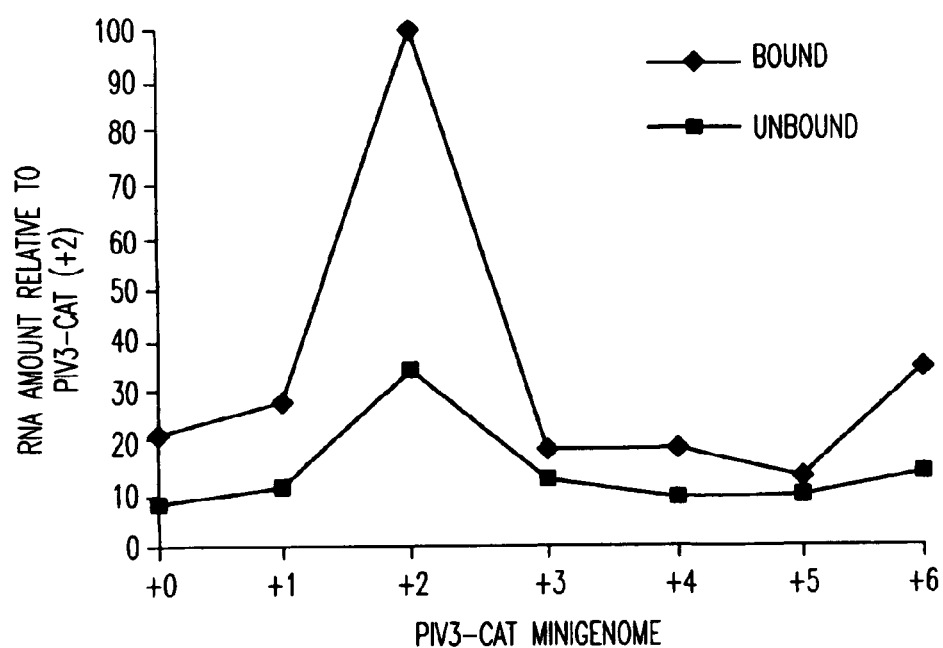

To confirm the presence of subgenomic mRNA, the final aliquot of harvested cell suspension was processed for RNA purification. The RNA was then subjected to oligo(dT) chromatography. RNAs which failed to bind, and those which bound and were eluted in low salt buffer, were analyzed by Northern blot hybridization (FIG. 6A) and phosphorimagery (FIG. 6B; note that in this case the bound and unbound are normalized together relative to the bound RNA of the +2 minigenome). These assays showed that approximately 64% of positive-sense RNA was polyadenylated, as expected for subgenomic mRNA. The accumulation of mRNA was greatest for the +2 minigenome. However, substantial amounts of mRNA also were observed for the other minigenomes. The amount of mRNA synthesized by the +1 and +3 minigenomes was 30% and 20% respectively compared to that synthesized by the +2 minigenome, and was approximately 13% for the least active minigenomes.

EXAMPLE V

Synthesis of Negative Sense RNA by PIV Minigenomes

Figure 7A:
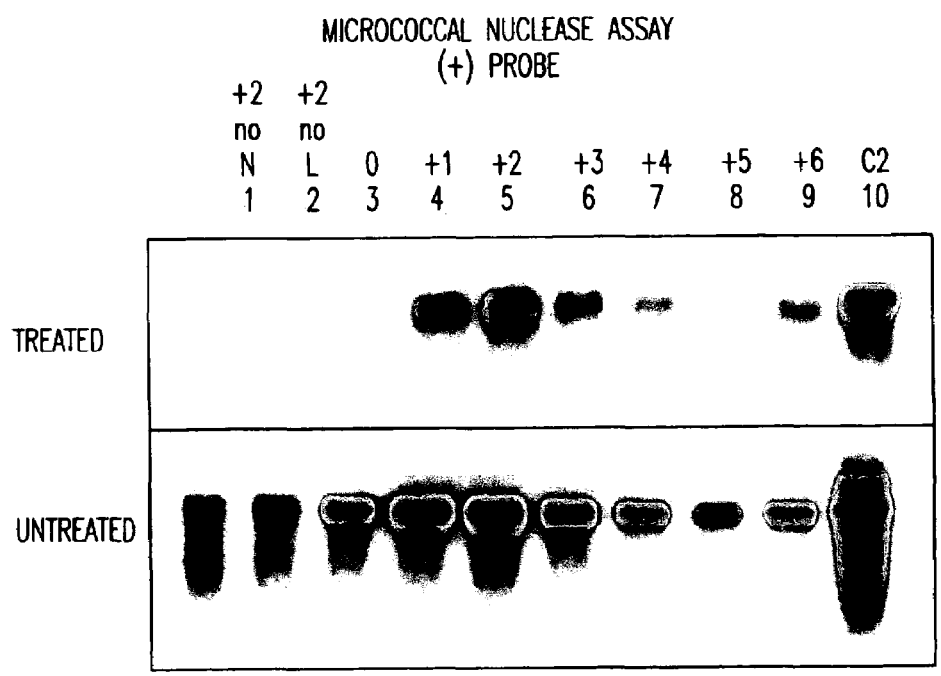
Figure 7B:
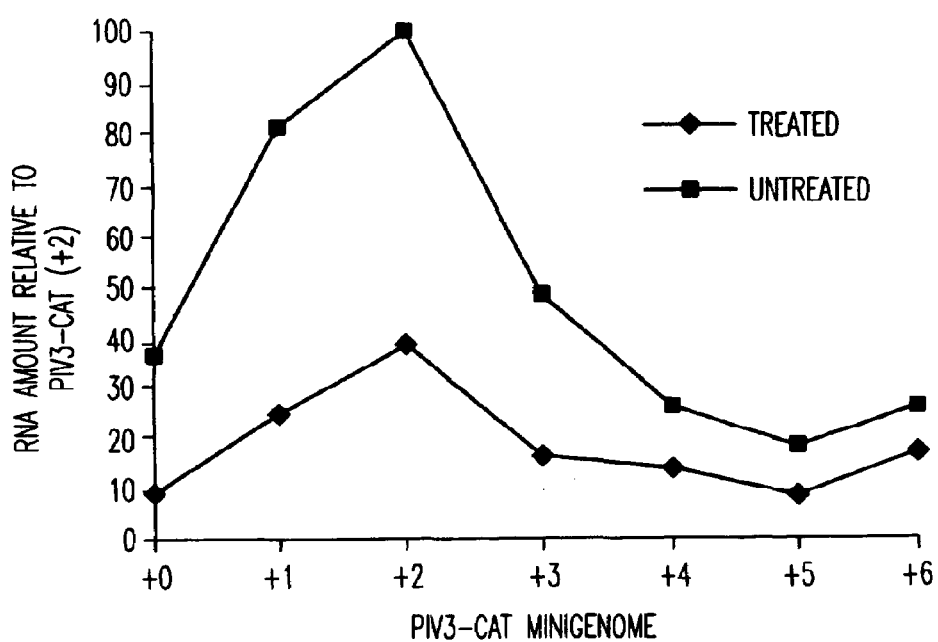
Figure 8:
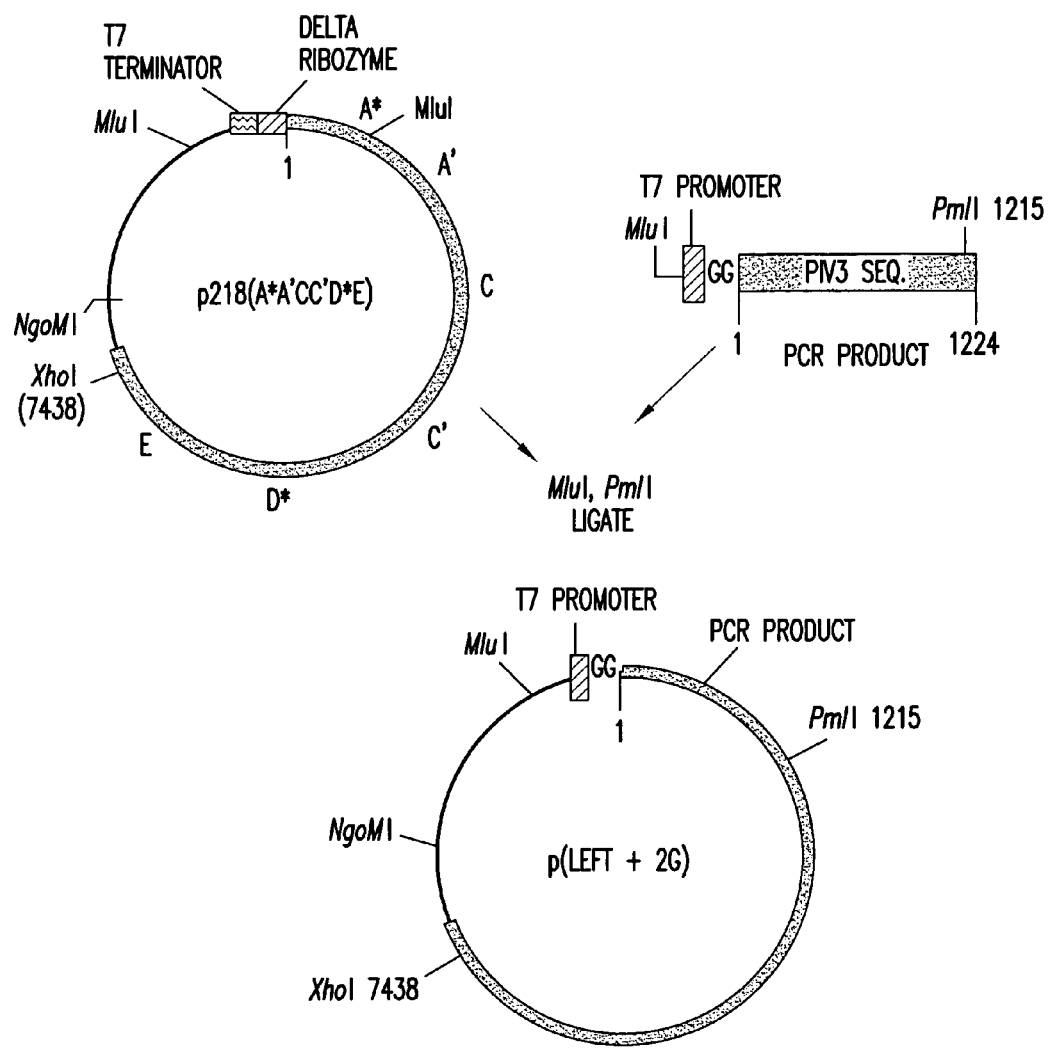
Figure 9:
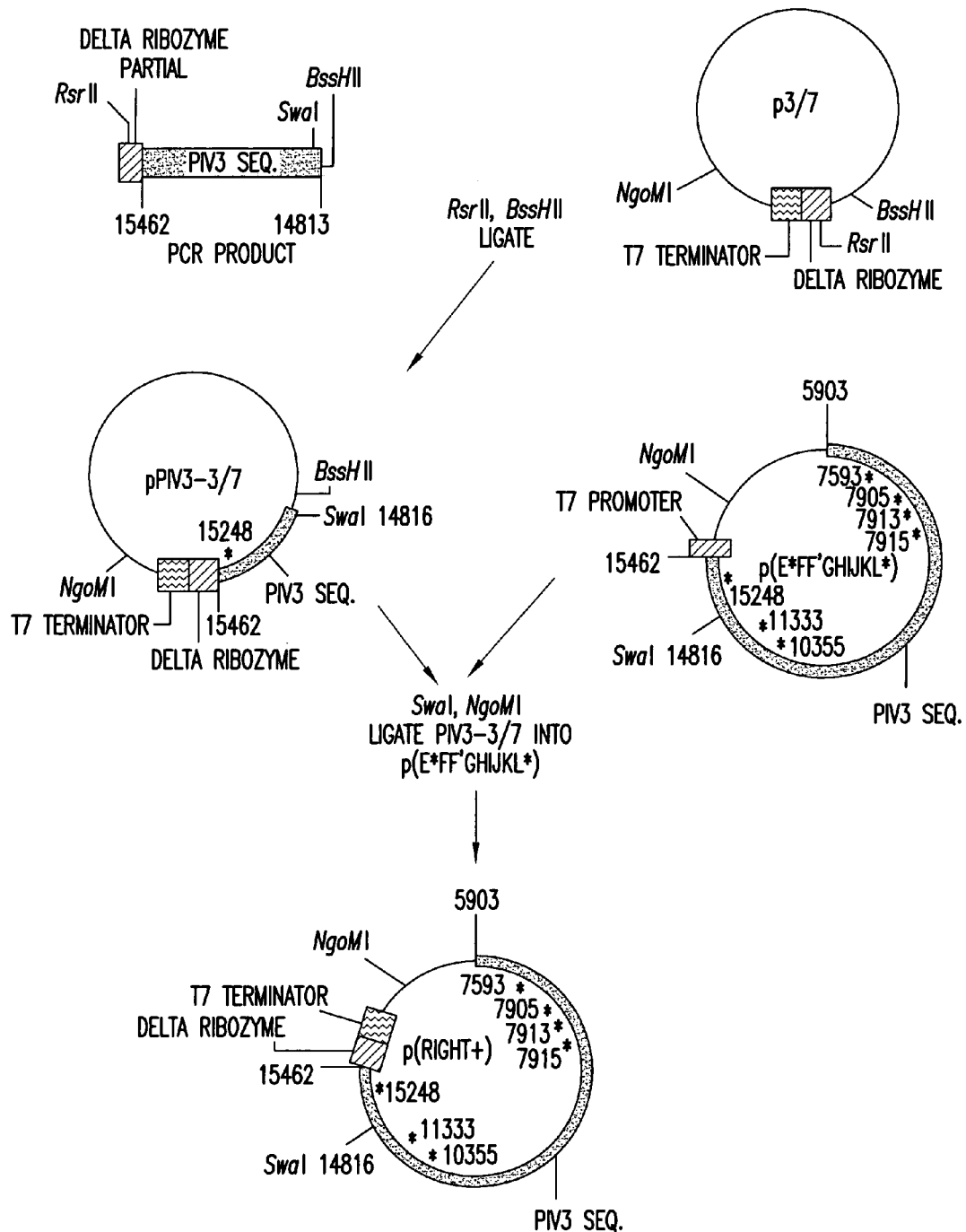

The various PIV3-CAT minigenomes described in the foregoing examples directed synthesis of mRNA and positive-sense encapsidated mini-antigenome, the latter representing the first step in RNA replication. The second step in RNA replication involves synthesis of encapsidated progeny minigenome from the mini-antigenome product. To evaluate this latter process, the samples of RNA from mock-treated and nuclease-treated lysates described in the preceding Example were analyzed by Northern blot hybridization with positive-sense CAT riboprobe (FIG. 7A) and quantitated by phosphorimagery (FIG. 7B).

Analysis of RNA from mock-treated lysates (FIG. 7A, lower panel) showed that considerable amounts of minigenome accumulated intracellularly in all samples, including negative controls in which the N or L support plasmid was omitted. The analyses described in FIGS. 5A–B and 6A–B showed that the synthesis of positive-sense RNA was insignificant under these conditions. Therefore, the minigenome observed in the absence of N or L could not be the product of RNA replication mediated by the reconstituted HPIV3 polymerase, and instead must be the product of T7 transcription of transfected plasmid.

Minigenome produced by the reconstituted HPIV3 polymerase is expected to be encapsidated, whereas much of the minigenome produced by T7 RNA polymerase is expected to be unencapsidated. Therefore, RNA from the same micrococcal nuclease-treated samples described for FIGS. 5A–B were used to prepare a second blot, which was hybridized with positive-sense CAT riboprobe (FIG. 7A, upper panel). This showed that all minigenome RNA accumulated in the absence of the N protein was degraded (FIG. 7A, upper panel, lane 1), as expected. Essentially all of the minigenome which accumulated in the absence of L was also sensitive to degradation (FIG. 7A, upper panel, lane 2). Plasmid-derived minigenome synthesized in the absence of L, and in the presence of N and P alone, did not appear to occur efficiently.

When the complete set of three support plasmids was present, significant amounts of micrococcal nuclease-resistant minigenome RNA accumulated for each of the minigenomes (FIG. 7A, upper panel). As was the case with the positive-sense RNAs, the greatest amount of progeny minigenome was observed with the +2 minigenome. The +1 and +3 minigenomes were next in abundance, with levels of genomic RNA that were 67% and 42% of that of the +2 minigenome.

The foregoing examples demonstrate that the HPIV3 N, P and L proteins were necessary and sufficient for efficient transcription and RNA replication. The very robust nature of transcription and RNA replication mediated by the reconstituted PIV3 polymerase confirmed the functionality of the encoded proteins. It is further expected that inclusion of additional viral proteins within the expression system will augment or modify these processes. Coexpression of PIV C, D and potentially V, within the compositions and methods of the invention will be useful, e.g., to augment and/or modify RNA replication. For this purpose, plasmids will be constructed and assayed according to the foregoing methods to achieve coexpression of one or more of these elements to determine their effects on PIV transcription and RNA replication, as well as on PIV phenotype in suitable infection models.

EXAMPLE VI

Construction of Infectious, Recombinant PIV from cDNA

The following examples describe production of infectious, recombinant PIV (rPIV) by intracellular co-expression of four plasmid-borne cDNAs. These cDNAs separately encode a complete HPIV3 genome and the HPIV3 nucleocapsid protein N, the phosphoprotein P, and the polymerase protein L.

A) Viruses and Cells

Modified vaccinia strain Ankara (MVA), the vaccinia virus recombinant that expresses bacteriophage T7 RNA polymerase, was provided according to Wyatt et al., *Virol.* 210:202–205, 1995, incorporated herein by reference in its entirety. HEp-2 monolayer cultures were maintained at 37° C. in 5% $CO_2$ with OptiMEM 1 (Life Technologies) supplemented with 2% FBS, 50 μg/ml gentamicin sulfate and 2 mM glutamine. The JS wt strain of HPIV3 and its attenuated ts derivative, JS cp45, were propagated in LLC-MK2 cells as described by Hall et al., *Virus Res.* 22: 173–184, (1992), incorporated herein by reference in its entirety.

B) cDNAs

The full cDNA clone designated p218(131) (FIG. 1, SEQ ID NO: 1) encoding a complete genomic sequence of HPIV3 was constructed as described above. A second cDNA clone designated p3/7(131) (SEQ ID NO: 14) (deposited under the terms of the Budapest Treaty with the ATCC, and granted the designation 97990) was constructed to encode a complete antigenomic sequence of HPIV3. p3/7(131) differs from p218(131) in that the positions of the T7 promoter and the ribozyme/T7 terminator relative to the HPIV3 cDNA insert have been interchanged. Thus, the first nucleotide synthesized in p3/7(131) is the 5' end of the antigenome, namely the positive-sense complement of genome position 1, and the 3' antigenome end defined by ribozyme cleavage is the complement of genome position 15462. A third clone designated p3/7(131)2G (SEQ ID NO: 15) (deposited under the terms of the Budapest Treaty with the ATCC, and granted the designation 97989) was also constructed identical to p3/7 (131), except that two G residues were inserted between the 5' end of the antigenome and the T7 promoter.

For construction of p/37(131)2G and p3/7(131), the two plasmids p(A*A'CC'D*E) and p(E*FF'GHIJKL*) were modified and joined to encode the complete positive-sense antigenome of HPIV3. First, the T7 terminator and delta ribozyme abutting the 3' end of HPIV3 in p(A*A'CC'D*E) were replaced by a T7 promoter using PCR (see FIG. 8). The positive-sense primer 5-GGCCCGTCGACGCGTAATACGACTCACTATAGG<u>ACCAAACAAGAG-</u>3' (SEQ ID NO: 18) placed the T7 promoter (bold) adjacent to the 3' leader of HPIV3 (HPIV3 sequence underlined) with 2 G residues inserted between these two elements to improve transcription. A unique Mlu I site (italicized) was placed upstream of the T7 promoter for cloning purposes (FIG. 8). The negative-sense primer 5'-$^{1224}$CGGCATCACGTGCTAC$^{1209}$-3 (SEQ ID NO: 19) spanned nt 1209-1224 of the HPIV3 N gene and included a unique Pml I site (italicized) present in the natural HPIV3 sequence. Both the PCR product and the parent template p218(A*A'CC'D*E) were digested with Mlu I and Pml I and the PCR product was then cloned into the Mlu I-Pml I window. A second PCR reaction was done using the same negative-sense primer and a positive-sense primer without 2G residues inserted between the T7 promoter and 3' end of HPIV3. These plasmids were designated p(Left +2G) and p(Left +). The construction of p(Left +2G) is illustrated in FIG. 8, the construction of p(Left +) followed the same strategy.

Plasmid p(E*FF'GHIJKL*) was modified by PCR to place the delta ribozyme and T7 terminator adjacent to the 5' end of HPIV3 (FIG. 9). The positive-sense primer: 5'-GGATTTGCGCGC$^{14813}$<u>AATTTAAATCATCTGG</u>$^{4828}$-3' (SEQ ID NO: 16) introduced a BssH II site (italicized) just upstream of a unique Swa I site (italicized, underlined) in the L gene of HPIV3 (HPIV3 specific sequence is underlined). The negative-sense primer: 5'-CCCAGGTCGGACCGCGAGGAGGTGGAGATGCCATGCCAGCCC$^{15462}$<u>ACCAAAACAAGAGAAGAACTCTGTTTGG</u>$^{15435}$-3' (SEQ ID NO: 17) placed a portion of the delta ribozyme (bold) which included a naturally-occurring unique Rsr II site (italicized) adjacent to the 5' end of the HPIV3 genome (negative-sense underlined). This PCR product was digested with BssH II and Rsr II and cloned into the BssH II-Rsr II window of plasmid p3/7 (FIG. 9). Plasmid p3/7 is identical to p218 except that the delta ribozyme and T7 terminator are in the reverse orientation. The p3/7 plasmid containing the above-mentioned insertion was designated pPIV3-3/7 and contained the complete delta ribozyme and T7 terminator adjacent to 5' terminal 651 nucleotides of HPIV3. The SwaI and NgoMI fragment of plasmid pPIV3-3/7 was then isolated and cloned into the SwaI-NgoM I window of p(E*FF'GHIJKL*). The resulting plasmid, designated p(Right +) placed the complete delta ribozyme and T7 terminator adjacent to the 5 end of HPIV3 (see FIG. 9). The Xho I-NgoM I fragment of p(Right +) was cloned into the Xho I-NgoM I window of p(Left +) and p(Left +2G) resulting in plasmids p3/7(131) (SEQ ID NO: 14) and p3/7(131 2G) (SEQ ID NO: 15), respectively (FIG. 10). These each encode the complete positive-sense analog of HPIV3 antigenomic RNA, with the latter cDNA containing two G residues adjacent to the T7 promoter for improved transcriptional efficiency.

C) Transfection

HEp-2 cells were grown to 90% confluence in six well plates. Each well of a six-well plate ($1.5\times10^6$ cells) was transfected with the three previously-described support plasmids, 0.4 μg pTM(P), 0.4 μg pTM(N), 0.05 μg pTM(L), together with 5 μg of full-length genomic or antigenomic HPIV3 cDNA. The plasmids were added to 0.2 ml of OptiMEM 1 (Life Technologies) containing 12 μl of LipofectACE (Life Technologies). After an incubation period of approximately 15 minutes at room temperature, 0.8 ml of OptiMEM 1 containing 2% fetal bovine serum and $1.5\times10^7$ pfu of MVA-T7 was added to each well. The cultures were incubated at 32° C. for 12 hours, after which the media was replaced with fresh OptiMEM 1 containing 2% fetal bovine serum. The cultures were incubated at 32° C. for three additional days then harvested and passaged (referred to as passage 1) onto fresh HEp-2 monolayers. These passage 1 cultures were incubated at 32° C. for five days, and virus present in the culture was harvested, passaged once in LLC-MK2 cultures, and characterized by hemagglutination-inhibition (HAI) as described (van Wyke Coelingh et al., *Virol.* 143: 569–582, (1985) (incorporated herein by reference in its entirety) to determine if it possessed the monoclonal antibody resistant mutation (MARM) that marked virus recovered from cDNA.

D) Sequencing of Recombinant Virus

The presence of nucleotide sequence markers in the HN and L genes of recombinant PIV was determined by RT-PCR of RNA isolated from recovered virions. 1 ml of rPIV ($1\times10^5$ pfu/ml, passage level 2) was precipitated with 200 μl 25% polyethylene glycol by incubation on ice for one hour and centrifuging at 12,000 g for 15 minutes. The RNA was purified with TRIzol reagent (Life Technologies) following the manufacturer's recommended procedure. RT-PCR was performed with the Superscript kit (Life Technologies) following the manufacturer's recommended protocol. Control reactions were identical except that reverse transcriptase was omitted from the reaction to confirm that the PCR products were derived solely from virus RNA and not from possible contaminating cDNA plasmids. Four primer pairs were used to generate PCR products from nt 7334–8715, 9364–10854, 10939–15392, and 13623–15392. The resultant PCR products were then sequenced using cycle dideoxynucleotide sequence analysis (New England Biolabs, Beverly, Mass.).

EXAMPLE VII

Recovery of Recombinant Virus from cDNA Encoding Negative-Sense Genomic RNA

Plasmid p218(131) and the three support plasmids pTM (N), pTM(P), and pTM(L) were transfected into HEp-2 cells with MVA expressing T7 RNA polymerase. A control group consisting of pTM(N), pTM(P), pTM(L), and MVA was cotransfected into HEp-2 cells without p218(131). On day four, the transfection was harvested, passaged onto fresh HEp-2 cell monolayers for five days, and passaged again for 5 days in LLC-MK2 cultures (passage 2). Virus present in the passage 2 harvest was further characterized by HAI. Cultures from the transfection group which received the three support plasmids without the full-length genomic clone p218(131) did not yield HPIV3. The rPIV recovered virus was confirmed to be HPIV3 since it reacted in the HAI assay with the mAbs 77/5, 101/1, and 454/11 which are specific for HPIV3 (Table 1). It was presumptively identified as being cDNA-derived because it failed to react with mAbs 170/7 and 423/6, consistent with the MARM mutation which had been introduced into the cDNA.

TABLE 1 rJS-NS Contains the MARM Mutation Introduced into the p218(131) Full-Length Negative Sense cDNA

| Virus | Hemagglutination-inhibiting Antibody Titer (Reciprocal) of Indicated mAb | | | | |
|---|---|---|---|---|---|
| | 77/5[1] | 101/1[1] | 454/11[1] | 170/1[2] | 423/6[2] |
| JS wt[3] | 800 | 6400 | 6400 | 25,600 | 25,600 |
| rJS-NS[4] | 3200 | 25,600 | 6400 | ≦25 | ≦25 |

[1]mAb 77/5 recognizes antibody epitope IIB, mAbs 101/1 and 454/11 recognize antibody epitope IIIA of HN glycoprotein, all of which were not altered in p218(131).
[2]Mabs 170/7 and 423/6 which both recognize antibody epitope I of JSwt, fail to recognize rJS due to the MARM mutation at this site.
[3]Biologically derived wild type HPIV3 JS.
[4]Recombinant JS virus derived from negative-sense genomic cDNA.

To confirm that rPIV was indeed recovered from cDNA, it was analyzed in parallel with wild-type JS strain HPIV3 by RT-PCR using four primer pairs flanking the seven inserted marker mutations. Each PCR product obtained was dependent upon the inclusion of RT, indicating that each was derived from RNA and not from contaminating cDNA. Cycle-sequencing of the four PCR products confirmed that the sequence of the rPIV contained each of the seven markers, sequencing data showing three of the markers is illustrated in FIG. 11. The sequence differences between rPIV and JS wt in the HN gene, including nt 7903, 7913, and 7915 are readily apparent. Similar sequence analyses were carried out for the other four markers at nt positions 7593, 10355, 11333, and 15248, and the rPIV possessed each mutation.

These results demonstrate successful recovery of infectious rPIV from cDNA encoding a negative-sense genomic RNA. This differs from most published reports for recovery of nonsegmented negative strand RNA viruses, in which the cDNA used for virus recovery had been designed to encode positive-sense antigenomic RNA (Baron and Barrett, supra, 1997; Collins et al., supra, 1995; Conzelmann, supra, 1996; Garcin et al., supra, 1995; Lawson et al., supra, 1995; Radecke et al., supra, 1995; Whelan et al., supra, 1995). The recovery of infectious virus from a cDNA encoding genomic RNA had previously been reported only in the case of Sendai virus, and the efficiency of recovery was much lower than for cDNA encoding antigenomic RNA (Kato et al., 1996). In most other studies, the recovery of virus was achieved with antigenomic cDNA but not with genomic cDNA (Lawson et al., 1995; Whelan et al., 1995). A number of potential problems have been noted which may explain these refractory results, including possible annealment of cDNA-encoded genomic RNA with mRNA produced by the support plasmids; resulting in inactive hybrids (Conzelmann, supra, 1996; Lawson et al., supra, 1995). It has also been noted that T7 RNA polymerase appears to terminate preferentially at the gene junctions of genomic RNA, perhaps because the oligo U tract of the GE signal resembles the natural signal for transcription termination by T7 RNA polymerase (Whelan et al., supra, 1995).

EXAMPLE VII

Recovery of Recombinant Virus from cDNA Encoding Positive-Sense Antigenomic RNA

As described in more detail above, p3/7(131) and p3/7 (131)2G were constructed to encode a positive-sense, antigenome that give rise to recombinant PIV. Plasmid p3/7(131)2G is identical to p3/7(131) but for the addition of two G residues between the T7 promoter and the first nucleotide of the antigenome. The addition of two G residues between the T7 promoter and the first HPIV3 nucleotide p3/7(131)2G is based on the preceding examples demonstrating that the presence of the two added G residues (as opposed to 0, 1 or 3 added G residues) yielded substantially increased levels of minireplicon replication.

The two antigenome cDNAs [p3/7(131) and p3/7(131) 2G] were transfected separately into cells together with the N, P and L support plasmids, and were infected simultaneously with the MVA-T7 recombinant virus using the same procedure described above for p218(131). Infectious virus from each antigenomic cDNA was recovered and was presumptively identified as being cDNA-derived by its inability to react with mAbs 423/6 and 170/7.

The efficiency of virus recovery was evaluated for each of the antigenome cDNAs versus the genome cDNA p218 (131). Twelve transfection reactions using the negative-sense genome cDNA p218(131) (SEQ ID NO: 1) were conducted in parallel with twelve transfections using the positive-sense antigenome cDNA p3/7(131)2G (SEQ ID NO: 15) to compare efficiency of virus recovery from the two cDNAs. One ml of the transfection harvest from each well was titered on LLC-MK2 cells and the remaining 2 mls were passaged (passage 1) onto fresh LLC-MK2 cells. At day five, passage 1 was harvested and titered as described above. Recombinant virus was recovered from 12/12 wells transfected with p3/7(131)2G but from only 4/12 wells transfected with p218(131). The mean titer of virus present in culture of the passaged virus from the positive-sense antigenome was $10^{5.0}$, nearly ten-fold higher than that from the negative-sense genome, which was $10^{4.1}$. However, with one additional amplification the titers became equivalent.

virus, it is clear that extra-viral G residues at the 5'-terminal end of the antigenome are not deleterious to recovery of recombinant virus, and, in fact, appear to be advantageous (Garcin et al., supra, 1995; Radecke et al., supra, 1995; Kato et al., 1996). The genomic and antigenomic plasmids without two 5'-terminal guanine residues appeared equally effi-

TABLE 2

Comparison of the Efficiency of Recovery of Recombinant Virus from cDNAs Encoding Genomic or Antigenomic RNA, the latter with or without 2G residues adds to the T7 promoter.

| Experiment # | Transfected cDNA | Sense of Encoded RNA | Rescue Efficiency[1] | Mean Titer ($\log_{10}$ pfu/ml) of Recovered Virus[2] |
|---|---|---|---|---|
| #1 | p3/7(131)2G[3] | Antigenomic | 12/12 (100%) | 5.0 ± 0.27 |
|    | p218(131)      | Genomic     | 4/12 (33%)   | 4.1 ± 0.27 |
| #2 | p3/7(131)2G[3] | Antigenomic | 6/6 (100%)   | 6.6 ± 0.18 |
|    | p3/7(131)      | Antigenomic | 12/12 (100%) | 5.3 ± 0.12 |
|    | p218(131)      | Genomic     | 5/5 (100%)   | 4.9 ± 0.19 |

[1] Number of transfection cultures yielding rJS/number tested.
[2] The mean Titer ± standard error was determined following one passage of transfection harvest for five days in LLC-MK2 cells.
[3] Contains 2G residues between the T7 promoter and the 5' end of the antigenome.

The efficiency of recovery of recombinant virus from the three full-length plasmids encoding the genomic or antigenomic HPIV3 RNAs was next studied, (i) to determine whether genomic or antigenomic cDNA is more efficient at generating recombinant virus and (ii) to determine the effect of two extra 5' terminal G residues on the yield of recombinant viruses (Table 2.) Unfortunately, it was not possible to directly titer the transfection harvest by plaque titration because resid negative-sense rPIV were comparable to the JS wt virus in their level of replication at elevated temperatures of 39° C. and 40° C. (Table 3). This is in contrast to the ts mutant JS cp45 which exhibits a 30-fold reduction in titer at 37° C. and fails to produce plaques at 39° C. or 40° C.

TABLE 3

The rJS Resembles its Biologically Derived Parent JS Wild-Type Virus in the Level of Replication at Restrictive Temperature (39° C.–40° C.)

| Virus | Virus Titer (log 10 pfu/ml) | | | |
|---|---|---|---|---|
| | 32° C. | 37° C. | 39° C. | 40° C. |
| rJS-PS[1] | 6.1 | 6.1 | 6.1 | 6.6 |
| rJS-NS[2] | 6.9 | 7.1 | 7.1 | 7.0 |
| JScp45[3] | 6.3 | 4.3 | <0.7 | <0.7 |
| JS wt | 6.5 | 6.8 | 6.6 | 6.7 |

[1]Recombinant virus derived from the antigenomic-sense clone p3/7(131)2G
[2]Recombinant virus derived from the genomic-sense clone p218(131)
[3]JScp45 is a temperature sensitive mutant derived from JS wt.

The sequence of JS cp45 has been fully determined (Stokes et al., supra, 1993) and mutations have been identified in the leader, N, P, M, F, HN, and L genes. However, it is unknown which mutation(s) are responsible for the ca, att, or ts phenotypes. Because exemplary rPIV of the invention demonstrate the ts+ phenotype like the JS wt parent, cp45 mutations among other mutations known or yet to be discovered for PIV can be introduced, alone or in combination, into the full-length cDNA to pinpoint the effects of individual mutations or combinations thereof, e.g., by evaluating replication of the recombinant virus incorporating the mutation(s) of interest at elevated temperatures. The mutation(s) thus identified can be incorporated into effective, attenuated vaccine agents as described in the Examples below. These and other mutations incorporated into recombinant PIV can be further optimized by, e.g., mutagenesis to create two or more nucleotide substitutions per codon to render a recombinant virus that is more genetically stable than a biologically derived mutant strain.

EXAMPLE VIII

Replication of rPIV in Hamsters

Thirty-six 16-week-old golden Syrian hamsters were divided into four groups of nine and inoculated intranasally with 0.1 ml containing $10^{5.5}$ pfu of either rPIV recovered from negative-sense cDNA, rPIV recovered from positive-sense cDNA, JS cp45, or JS wt virus. On day 4, the hamsters were sacrificed and the lungs and nasal turbinates harvested. The lungs were homogenized in a 20% w/v L-15 suspension containing 2.5 µg/ml amphotericin B (Quality Biologicals, Gaithersburg, Md.), 200 µg/ml pipericillin (Lederle Laboratories, Pearl River, N.Y.), and 50 µg/ml gentamicin (Quality Biologicals). The nasal turbinates similarly were homogenized in a 10% w/v L-15 suspension. After homogenization, the samples were aliquoted and rapidly frozen in a dry ice-ethanol bath. Virus present in the samples were titered at a later date in 96 well plates of LLC-MK2 cells at 32° C. scoring CPE at five and seven days after inoculation. The mean $\log_{10}$ TCID$_{50}$/gm was calculated for each group of nine hamsters.

Table 4 illustrates that rPIV recovered from negative-sense cDNA, rPIV recovered from positive-sense cDNA replicate to substantially the same level as the JS wt in the upper and lower respiratory tract of hamsters. This is in contrast to the JS cp45 virus, which is attenuated at each site.

TABLE 4

The rJS Resembles its Biologically Derived Parent JS wt Virus in the Level of Replication in the Upper and Lower Respiratory Tract of Hamsters.

| Virus | Mean Virus Titer ($\log_{10}$ TCID$_{50}$/g)[5] | |
|---|---|---|
| | Nasal Turbinates | Lungs |
| rJS-PS[1] | 6.6 ± 0.2 | 4.1+0.3 |
| rJS-NS[2] | 6.4 ± 0.1 | 4.2 ± 0.2 |
| JScp45[3] | 4.2 ± 0.2 | ≦1.4 ± 0.0 |
| JS wt[4] | 6.3 ± 0.2 | 4.6 ± 0.3 |

[1]Recombinant virus recovered using p3/7(131)2G encoding the positive-sense HPIV3 antigenome.
[2]Recombinant virus recovered using p218(131) encoding the negative-sense HPIV3 genome.
[3]Biologically derived ts mutant.
[4]Biologically derived parent virus.
[5]Mean titers ± standard errors for nine hamsters per group.

Thus, exemplary rPIVs of the invention can retain the replicative capacity in hamsters exhibited by the biologically derived JS wt parent strain, whereby mutations such as those present in the JS cp45 candidate vaccine that restrict replication in hamsters and other hosts, including non-human primates and humans, can be identified and incorporated within modified rPIV strains of the invention, as described in the Examples below.

EXAMPLE IX

Identification of Amino Acid Substitutions in HPIV3 Specifying Attenuated Phenotypes, and Incorporation of Attenuating Mutations into Infections, Attenuated PIV Clones The ability to generate infectious PIV from cDNA facilitates development of live-attenuated parainfluenza virus vaccines. More specifically, by using the methods and tools disclosed herein the genetic basis of attenuation of PIV candidate vaccines can be readily determined, and infectious PIV vaccines produced from cDNA can be designed to achieve a finely calibrated level of attenuation and immunogenicity.

In addition, the tools and methods of the invention provide for vaccine development for all three human parainfluenza viruses, HPIV1, HPIV2 and HPIV3 that are most important in human disease. For example, to produce and select effective HPIV3 vaccine agents within the invention, mutations associated with desired phenotypes of biologically deriving HPIV3 candidate vaccines or the attenuated BPIV3 virus, e.g. attenuating mutations, can be identified and incorporated into rPIV. Applying these methods, attenuating mutations from a large menu of candidate mutations are selected and combined to generate rPIV having a desired balance between attenuation and immunogenicity, and which retain the attenuation phenotype following replication in humans.

In the present example, the genetic bases of temperature-sensitive (ts) and in vivo attenuation (att) phenotypes of the PIV3 JS cp45 live-attenuated virus are described. Seven exemplary recombinant PIV3 viruses (three single-, three double-, and one triple-lesioned virus) were recovered from full-length antigenomic cDNA and analyzed for their ts and att phenotypes. These recombinants bore one or more amino acid substitution mutations present in the L gene of JS cp45 (alternatively referred to herein as cp45), adopted within a cDNA clone of the JS wt parent. These three exemplary, biologically derived mutations are all present in a representative strain of JS cp45 grown in Vero cells, designated JS cp45 Vero, deposited on Aug. 21, 1997 under the terms of the Budapest Treaty with the American Type Culture Collection (ATCC) of 12301 Parklawn Drive, Rockville, Md. 20852, U.S.A., and granted the accession number ATCC VR 2588.

L protein positions 942, 992, and 1558, individually and in combination, and (ii) ablating one specific naturally-occurring restriction enzyme site proximal to each codon substitution as a marker [See Table 5].

TABLE 5

Nucleotide substitutions introduced into rPIV3 that encode cp45L protein gene amino acid substitutions and, as markers, ablate naturally-occurring restriction enzyme sites.

| rPIV3 designation | Amino Acid Substitution (wt to cp45) | Sequence of wt[a] | Sequence of Mutant | Restriction Enzyme site Ablated |
|---|---|---|---|---|
| r942 | Tyr-942 to His | 11468-TTACA*TGGC*C*A*T (SEQ ID NO: 25) | 11468-TCACATGGCG*A*T (SEQ ID NO: 26) | Eae I |
| r992 | Leu-992 to Phe | 11618-TTT*T*GA*T*TGGGC (SEQ ID NO: 27) | 11618-TTT*T*GA*T*TGGGC (SEQ ID NO: 28) | Bsr I |
| r1558 | Thr-1558 to Ile | 13307-T*GG*T*CC*TAATACTG (SEQ ID NO: 29) | 13307-TGGG*CC*TAATATCG (SEQ ID NO: 30) | Ava II |

[a]The nucleotide sequence around each of the three mutated regions is shown.
The first nucleotide in each provided sequence is numbered according to its position in the complete antigenomic RNA.
The codon involved in each amino acid substitution is in bold.
Naturally-occurring restriction enzyme sites present in the wt sequence, and which were ablated to mark the mutation, are in italics.
The nucleotides that were mutated to produce an aa substitution or remove a restriction enzyme site are underlined.

Analyses of exemplary PIV recombinants, presented below, demonstrate that each of the three exemplary mutations in L (Tyr$_{942}$ to His, Leu$_{992}$ to Phe, and Thr$_{1558}$ to Ile) contribute to the ts and att phenotypes of cp45 and are useful for generating of recombinant vaccine virus.

Viruses and Cells.

The PIV3 JS wt and cp45 viruses were grown in LLC-MK2 cells as described previously (Hall et al., *Virus Res.* 22:173–184 (1992), incorporated herein by reference). The vTF7-3 recombinant vaccinia virus is described in Fuerst et al., *Virology* 225: 419–422 (1996) and the modified vaccinia virus Ankara (MVA) which expresses the T7 polymerase is described in Wyatt et al., *Virology* 210:202–205 (1995) (each incorporated herein by reference). HEp-2 (ATCC CCL 23) and LLC-MK2 (ATCC CCL 7.1) cells were maintained in OptiMEM (Life Technologies) supplemented with 2% FBS and gentamicin sulfate (50 ug/mL).

Construction of Point Mutations in the L Gene of PIV3.

pUC19 was modified to accept a fragment of the JS wt PIV3 L gene in order to introduce point mutations into the L gene by site-directed mutagenesis. First, a unique Nhe I restriction site was introduced into pUC19 by ligating a pair of complementary oligonucleotides (5' GATCGATGCTAGCCC 3' (SEQ ID NO: 23) and 5' GATCGGGCTAGCATC 3' (SEQ ID NO: 24)) containing an Nhe I restriction site into the Hind III site of pUC19 to create pUC19 (N). The Sph I (PIV3 nt 11317) to Nhe I (PIV3 nt 14087) fragment of pTM(L), which includes the positions where the three coding changes in cp45 occur and which can be directly introduced into the full-length PIV3 cDNA (see below), was cloned into the Sph I and Nhe I site of pUC19 (N) to create pUCL(N-S). Point mutations were introduced into pUCL (N-S) using mutagenic oligonucleotides with the Transformer mutagenesis kit (Clontech, Palo Alto, Calif.) for the purpose of (i) creating exemplary amino acid substitutions at Mutations introduced in pUCL(N-S) derivatives were verified by dideoxynucleotide sequencing of plasmid DNA. The Sph I to BamHI (nt 13733) fragment of pUCL(N-S) containing the cp45 individual L gene mutations was subcloned into the Sph I to BamHI sites of pTM(L) to give pTM(L)-942, -992, -942/992, and -1558; the other double and triple mutations were assembled using the Pin Al and Nhe I sites (FIG. 12). The mutant pTM(L) plasmids were each tested at permissive temperature (32° C.) for the ability to direct the expression of the chloramphenicol acetyl transferase marker gene in a minireplicon system comprising a plasmid-encoded minigenome RNA and the N, P and L proteins (Durbin et al., *Virology* 234:74–78 (1997), incorporated herein by reference). The various mutant L plasmids supported marker gene expression to 75–106% the level of wt L, indicating that each engineered cDNA was free of significant spurious mutation (not shown). The Sph I to Nhe I fragments of each of the mutant pTM(L) plasmids were then subcloned into the Sph I to Nhe I window of the full-length PIV3 JS antigenomic cDNA p3/7(131)2G to create seven full-length PIV3 cDNA clones representing every possible combination of the three substitutions.

Recovery of Recombinant PIV3 (rPIV3) Bearing One, Two or Three cp45 L Protein Substitutions.

Each full-length antigenomic cDNA bearing one or more cp45 L gene mutations, together with the three support plasmids pTM(N), pTM(P) and pTM(L), was transfected into HEp-2 cells on 6-well plates (Costar, Cambridge, Mass.) using LipofectACE (Life Technologies) and MVA-T7 as described above. After incubation at 32° C. for 4 days, the transfection harvest was passaged onto HEp-2 cells on 6-well plates which were incubated at 32° C. for 4 days. Each passage 1 supernatant was harvested and passed onto a T-25 flask of LLC-MK2 cells, which was incubated at 32° C. for 5–6 days. The passage 2 supernatant was harvested and the presence of recombinant virus was initially confirmed by immunoperoxidase staining of virus plaques (Murphy et al., *Vaccine* 8:497–502 (1990), incorporated herein by reference) with anti-HN monoclonal antibody (Mab) 77/5, which binds to both biologically derived and recombinant JS PIV3, and Mab 423/6, which does not bind to cDNA-derived virus because its epitope was ablated to serve as a marker. Virus present in passage 1 was subjected to two or three rounds of plaque purification on LLC-MK2 cells as described previously. Each biologically cloned recombinant virus was amplified twice in LLC-MK2 cells at 32° C. to produce virus for further characterization. Virus was concentrated from clarified medium by polyethylene glycol precipitation, and viral RNA (vRNA) was extracted with Trizol Reagent (Life Technologies). Reverse transcription (RT) was performed on vRNA using the Superscript II kit with random hexamer primers (Life Technologies). The Advantage cDNA PCR kit (Clontech, Palo Alto, Calif.) and sense (5' nt 11190-GCATTATCTAGATGTGTCTTCTGGT-CAGAG 3, nt-11219) (SEQ ID NO: 31) and antisense (5' nt 14140-CCTGAATTATAATAATTAACTGCAGGTCCT 3' nt-14111) (SEQ ID NO: 32) primers specific for the PIV3 L gene were used to amplify the region spanning the Sph I to Nhe I fragment. The PCR fragments were analyzed by digestion with each of the restriction enzymes whose recognition sites had been ablated during insertion of the three cp45 mutations in L (see Table 5).

Efficiency of Plaque Formation (EOP) at Permissive and Restrictive Temperatures of rPIV3 Bearing One, Two or Three cp45 L Protein Amino Acid Substitutions.

The level of temperature sensitivity of plaque formation in vitro of control and recombinant viruses was determined at 32° C., 37° C., 38° C., 39° C., 40° C., and 41° C. in LLC-MK2 monolayer cultures and plaques were enumerated by hemadsorption with guinea pig red blood cells following removal of the methylcellulose overlay. Alternatively, viral plaques present in the monolayer were identified by immunoperoxidase staining with a mixture of two PIV3-specific anti-HN murine mAbs 101/1 and 454/11 diluted 1:500, (Murphy et al., supra, (1990)).

Hamster Studies.

4 to 16 week-old golden Syrian hamsters in groups of six were inoculated intranasally with 0.1 ml OptiMEM1 per animal containing $10^{5.5}$ pfu of rPIV3 JS wt, PIV3 cp45 virus, or one of the rPIV3 containing one or more cp45 L protein substitution(s). On day 4 post-infection, the hamsters were sacrificed, the lungs and nasal turbinates were harvested, and the virus was quantified as described above. The mean $\log_{10}$ $TCID_{50}$/g was calculated for each group of six hamsters.

Results

Introduction of the PIV3 cp45 L Protein Amino Acid Substitutions into wt JS rPIV3.

As noted above, the three amino acid substitutions present in the L protein of cp45 (Table 5) were introduced individually or in selected combinations into the antigenomic cDNA that encodes its wt parent, PIV3 JS strain. Each introduced mutation was engineered to be marked with a silent mutation that ablated a proximal, naturally-occurring restriction enzyme site to facilitate monitoring the mutation in recovered rPIV3 (Table 5, FIG. 12). The coding change at amino acid 1558 was designed to contain two nucleotide changes in r1558, compared to the one nt substitution in cp45, to reduce the chance of reversion at this site during in vitro or in vivo replication.

Seven rPIV3s bearing one, two or all three of the amino acid substitutions from cp45 were recovered in tissue culture by transfection of each antigenomic cDNA together with the pTM(N), pTM(P) and pTM(L) support plasmids and coinfection with the vaccinia virus MVA/T7 pol recombinant (Wyatt et al., supra, (1995)). Each rPIV3 possessed the Mab resistance marker that had been deliberately introduced into the HN gene by engineering the antigenomic cDNA. The rPIV3s were biologically cloned by two or three cycles of plaque to plaque passage to ensure that each virus preparation was genetically homogeneous. This precaution was taken because vaccinia virus can meditate recombination between the antigenomic cDNA and the support plasmids.

To confirm that each of the seven rPIV3 contained the engineered mutation(s) in the L gene, RNA was purified from precipitated virions and was copied into cDNA and amplified by RT-PCR. Control reactions showed that the RT step was required for generation of RT-PCR products, indicating that an RNA template rather than contaminating cDNA was required for the generation of the RT-PCR product. The RT-PCR products were subjected to digestion with the three restriction enzymes whose recognition sequences had been ablated as markers for the inserted coding changes. As expected, the RT-PCR product of JS wt rPIV3 was cleaved the appropriate number of times by each of the three enzymes, whereas r942/992/1558 lacked each of the three sites ablated during creation of the individual cp45 coding changes. Each of the other rPIV3s lacked the appropriate restriction site(s), indicating the presence of the introduced mutations.

Efficiency of Plaque Formation at 32° C., 37° C., 38° C., 39° C., 40° C., and 41° C. of rPIV3 Bearing cp45 L Mutations.

The seven rPIV3s bearing the various combinations of cp45 L protein amino acid substitutions were assayed for their ability to form plaques on LLC-MK2 monolayers at 32° C., 37° C., 38° C., 39° C., 40° C. and 41° C. As shown in Table 6, each rPIV3 bearing a cp45 aa substitution was ts, whereas the JS wt rPIV3 parent was not restricted in plaque formation at any temperature tested. The shut-off temperature of plaque formation of r942, r992 and r1558 was 40° C. r942 manifested a 700-fold reduction of plaque formation at 40° C., indicating that its replication was marginally reduced at this restrictive temperature. However, the plaque size of r942 also was greatly reduced at 40° C., which also indicates that its replication was restricted at this temperature compared to the JS wt. r942 was completely restricted in replication at 41° C. (data not shown). r992 and r1558 were greatly reduced (over a 1,000,000-fold reduction) in plaque formation at 40° C. These results indicate that each of the three cp45 L gene mutations individually specifies the ts phenotype, although that of the r942 mutation is somewhat less restrictive. The double mutant virus r942/1558 and the triple mutant r942/992/1558 had a shut-off temperature of 39° C., while that of r942/992 and cp45 was 38° C. The double mutant, r992/1558, was less ts than the r992 single mutant. r992/1558, like r942, was completely restricted in plaque formation at 41° C. The level of temperature sensitivity exhibited by double or triple results from a rPIVs delicate interplay of the three mutations that cannot be predicted from level of temperature-sensitivity exhibited by the single mutants. Also, since r942/992/1558 was slightly less ts than cp45, other mutations outside of the L gene also likely contribute to the ts phenotype of cp45, therefore representing additional mutations of interest within the invention.

TABLE 6

The efficiency of plaque formation (EOP) at 32° C., 37° C., 38° C., 39° C. and 40° C. of rPIV3 bearing one, two or three cp45 L protein amino acid substitutions.

| Virus[a] | Virus titer (log$_{10}$ pfu/ml) | | | | |
|---|---|---|---|---|---|
| | 32° C. | 37° C. | 38° C. | 39° C. | 40° C. |
| r942 | 6.8 | 6.8[b] | 6.6[b] | 6.5[b] | <u>4.3</u>[b] |
| r992 | 6.9 | 6.8[b] | 6.7[b] | 6.1[b] | <u>0.7</u> |
| r1558 | 6.6[b] | 6.6[b] | 6.4[b] | 5.0[b] | <u>0.7</u> |
| r942/992 | 6.7 | 6.5[b] | <u>4.5</u>[b] | 3.0[b] | <0.7 |
| r942/1558 | 5.2 | 5.0[b] | 4.0[b] | 1.0[b] | <0.7 |
| r992/1558 | 6.7 | 6.7[b] | 6.5[b] | 5.9[a] | 5.1[b] |
| r942/992/1558 | 6.6 | 6.2[b] | 6.2[b] | <u>2.7</u>[b] | <0.7 |
| cp45[b] | 6.6 | 4.8 | <u>4.5</u>[b] | <0.7 | <0.7 |
| rPIV3 JS | 8.3 | 8.4 | 8.5 | 8.5 | 8.3 |

[a]The cp45 virus is a biologically derived virus, and each of the other viruses tested is a recombinant.
[b]Plaques were of pinpoint size.
[c]Underlined numbers represent the shut-off temperature of plaque formation, which is defined as the lowest restrictive temperature at which a 100-fold reduction in titer is observed compared to the titer at 32° C..

Growth in hamsters. Groups of six Golden Syrian hamsters were inoculated intranasally with JS wt rPIV3, biologically-derived cp45, or with rPIV3 containing one or more cp45 L protein amino acid substitutions, and virus replication in the lungs and nasal turbinates was determined. In this experiment [Table 7], each of the rPIV3s bearing a single amino acid substitution was restricted in replication in the upper and lower respiratory tract [Table 7]. However, r942, the least ts virus, was only marginally suppressed in replication in the upper and lower respiratory tract in a second experiment. These data demonstrate that two of the three amino acid substitutions contribute to the att phenotype when present as single-lesioned recombinant viruses. However, the 942 mutation indeed contributes to attenuation (e.g., the r942/992 is more attenuated than r992 alone). Thus, each of the amino acid substitutions in L contribute to the att phenotype either acting alone or in concert with another L amino acid mutation. Each of the double mutants was attenuated indicating that loss of any of the three L gene substitutions following replication in vivo still leaves an attenuated virus. This is a partial explanation for the previously observed high level of stability of the ts phenotype of the cp45 following replication in vivo. The triple mutant r942/992/1558 was as restricted as cp45 for replication in the upper and lower respiratory tract indicating that the three amino acid substitutions in the L protein are the major contributors to the att phenotype of cp45.

TABLE 7

The level of replication in the upper and lower respiratory tract of hamsters of rPIV3 bearing one, two or three cp45 L protein amino acid substitutions, compared to JS wt rPIV3 and cp45a.

| Virus | Mean virus titer (log$_{10}$ TCID$_{50}$/ g ± S.E[b]) | |
|---|---|---|
| | Nasal turbinates | Lungs |
| rPIV3 wt | 7.4 ± .16 | 5.1 ± .49 |
| r942 | 6.6 ± .17 | 3.0 ± .78 |
| r992 | 4.4 ± .16 | 3.1 ± .11 |
| r1558 | 3.8 ± .40 | 4.3 ± .34 |
| r942/992 | <1.5 ± 0 | <1.5 ± 0 |
| r942/1558 | 2.9 ± .23 | 1.8 ± .17 |
| r992/1558 | 5.7 ± .16 | 3.2 ± .57 |
| r942/992/1558 | 3.9 ± .15 | <1.5 ± 0 |
| cp45 | 4.1 ± .27 | 1.6 ± .08 |

[a]Groups of six hamsters each were intranasally administered 10$^{5.5}$ pfu of virus per animal in an 0.1 ml inoculum, and lungs and nasal turbinates were harvested four days later.
[b]Standard Error
[c]cp45 is a biologically derived virus and the others are recombinant.

To summarize the above results, substitutions at L protein amino acid positions 992 and 1558 each specified a 1,000,000-fold reduction in plaque formation in cell culture at 40° C., while the substitution at position 942 specified a 700-fold reduction. Thus, each of the three mutations individually contributes to the ts phenotype. The triple recombinant which possesses all three L mutations is slightly less ts than cp45, suggesting that there are mutations outside of the L gene in cp45 that also might contribute to its ts phenotype. Two of the three individual mutations in L each contributed to restricted replication in the upper or lower respiratory tract of hamsters, which accounts for the observed stability of ts and att phenotypes of cp45 during replication in vivo. Importantly, the level of temperature sensitivity of recombinant vaccine strains in vitro was closely predictive of attenuation in vivo. The recombinant virus possessing all three mutations was as restricted in replication as the cp45 mutant in both the upper and lower respiratory tract of hamsters, indicating that the L gene of the cp45 virus is a major attenuating component of this candidate vaccine strain. While each mutation on its own specifies the ts phenotype, when placed together they are not simply additive but instead somehow influence each other. The effect of the three mutations together in the triple mutant seemed to ameliorate rather than enhance the level of temperature-sensitivity observed in the two double mutants which were evaluated. Interestingly, this should provide an unanticipated selective pressure to maintain at least some of the cp45 L mutations, since the loss by reversion of either the 992 or 1558 substitution would increase rather than decrease the level of temperature sensitivity. Considered together, these findings indicate that the high level of the stability of the ts and att phenotypes of cp45 virus results from the contribution of multiple ts mutations in L to the att phenotype. The identification of these three mutations as the major attenuating mutations of cp45 provides the basis for monitoring virus during all stages of manufacture and following replication in humans.

It is of further interest that the tyrosine to histidine mutation at position 942, arguably the most conservative substitution of the three mutations, was the least temperature sensitive. The L polymerase of PIV3 is a large polypeptide, 2233 aa in length, and is thought to be a multifunctional protein that encodes multiple domains including those required for complex formation with the P protein, RNA binding, RNA polyadenylation, RNA transcription and RNA replication (Collins et al., supra, (1996)). The amino acid substitutions in L at positions 942 and 992 are located near regions that are well-conserved among other members of the Paramyxovirus family (Blumberg et al., *Virology*

164:487–497 (1982); Galinski et al., *Virology* 165:499–510 (1988)). The mutation at position 1558 is in a region of the polymerase which appears to share less sequence identity with other L polymerases. Although the mechanism by which the ts phenotype is conferred by the triple amino acid substitution in L is not known, it is likely that multiple L protein domains and activities are affected, or that a common mechanism involving various activities of L is affected.

EXAMPLE X

Direct Identification, and Reconstitution into Recombinant Vaccine Viruses, of Mutations in a Biologically Derived, Live-Attenuated HPIV Type 3 Virus (cp45) which Specify the Temperature-Sensitive, Cold-Adaptation and Attenuation Phenotypes The above Examples demonstrate that each of the three amino acid substitutions in the L polymerase protein of cp45 confer the temperature-sensitive (ts) and attenuation (att) phenotypes, but not the cold-adaptation (ca) phenotype (see also, Skiadopoulos et al., *J. Virol* 72(3):1762–8, 1998). cp45 contains twelve additional mutations in other proteins (N, C, M, F and HN) or potential cis-acting sequences (the leader region and the transcription gene start {GS} signal of the N gene), and their contribution to these phenotypes has been heretofore undefined. The present Example further characterizes the genetic basis for the ts, ca, and att phenotypes of cp45 to provide yet additional information regarding basis for the observed high level of stability of these phenotypes following replication of cp45 in humans or non-human primates. In one aspect of this study, a recombinant cp45 (rcp45) virus containing all fifteen cp45-specific mutations was constructed, using a reverse genetics system, and was found to be essentially indistinguishable from the biologically-derived virus on the basis of plaque size, level of temperature-sensitivity, cold-adaptation, and level of replication in the upper and lower respiratory tract of hamsters. In addition, recombinant viruses containing: (1) the cp45-specific changes in the C, M, F or HN proteins, (2) the combined leader and N gene mutations, or (3) several combinations of the cp45 mutations were constructed. Analysis of these recombinant viruses showed that multiple cp45 mutations distributed throughout the genome contribute to the ts, Ca, and att phenotypes. The mutations in C and F were not ts at 40° C. but nonetheless conferred the att phenotype, and they, therefore, are non-ts att mutations. The HN mutation did not confer the ca, ts or att phenotypes. Viruses possessing the 3' leader and N mutations were ts, but exhibited only marginal attenuation in the lower respiratory tract of hamsters. Recombinants possessing several combinations of mutations exhibited a greater level of temperature sensitivity than cp45, but the increased level of temperature-sensitivity was not reflected in an increase in attenuation in vivo. These latter findings indicate that the multiple mutations identified in cp45 are interacting to affect replication in vitro. The presence of multiple ts and non-ts attenuating mutations in cp45 likely contributes to its high level of attenuation and phenotypic stability. Knowledge of the phenotypes associated with the various mutations of cp45 provided herein allows for accurate monitoring of biologically derived PIV viruses and ready manipulation of recombinant virus to achieve a large assemblage of useful vaccine recombinants within the invention.

Viruses and Cells.

The rPIV3s, PIV3 JS wt and cp45 viruses described in the present Example were grown in simian LLC-MK2 cells (ATCC CCL 7.1) as described above (see also, Durbin et al., *Virology* 235:323–332, 1997a; Hall et al., *Virus Res.* 22(3): 173–184, 1992; Skiadopoulos et al., *J. Virol* 72(3):1762–8, 1998). The modified vaccinia virus Ankara was provided as described above. HEp-2 (ATCC CCL 23) and LLC-MK2 cells were maintained in OptiMEM I (Life Technologies, Gaithersburg, Md.) supplemented with 2% FBS and gentamicin sulfate (50 ug/mL), or in EMEM supplemented with 10% FBS, gentamicin sulfate (50 ug/mL), and 2 mM glutamine. L-132 cells (ATCC CCL 5) were grown in Earl's MEM (Life Technologies) supplemented with 10% FBS, 2 mM glutamine, 20 mM Hepes, 1 mM non-essential amino acids, and 100 units streptomycin-neomycin/ml.

Construction of Point Mutations in PIV3.

Subgenomic fragments of p3/7(131)2G, the antigenomic cDNA clone of PIV3 JS wt used above to recover infectious virus (see also, Durbin et al., *Virology* 235:323–332, 1997a; Skiadopoulos et al., *J. Virol.* 72(3):1762–8, 1998), were cloned into pUC19 vectors modified to accept these fragments, using standard molecular cloning techniques. Point mutations corresponding to mutations identified in cp45, as well as mutations creating or ablating silent restriction enzyme recognition sequences (Table 8) were introduced using the Transformer Mutagenesis Kit (Clontech, Palo Alto, Calif.) as described previously.

TABLE 8

PIV3 cp45 mutations introduced into rPIV3

| seq id no | region affected | nt position[a] | sequence changes[b] | restriction marker[c] | amino acid substitution[d] |
|---|---|---|---|---|---|
| 1 | 3' | 20 | TTGTCTGGGAAT | none | non-coding |
| 47 | leader | | TTGCCTGGGAAT | | |
| 2 | 3' | 20 | TTGTCTGGGAAT | none | non-coding |
| 48 | leader | | TTGTTTGGGAAT | | |
| 3 | 3' | 20 | TTGTCTGGGAAT | none | non-coding |
| 49 | leader | | TTGTCTGGTAAT | | |
| 4[e] | 3' | 40 | AAC*TTTAAA*TTA | -Dra I | non-coding |
| 51 | leader | | AACTTAAAATTA | | |
| 5[e] | 52 N gene | 60 | TTAAAGACATTG | none | non-coding |
| 53 | start | | TTTAAGACATTG | | |
| 6[e] | 54 N | 390 | GCAGATGTCAAG | none | Val-96 to |
| 55 | | | GCAGATGCCAAG | | Ala |
| 7[e] | 56 N | 1271 | CGAATCTAAAGA | none | Ser-389 to |
| 57 | | | CGAAGCTAAAGA | | Ala |

TABLE 8-continued

PIV3 cp45 mutations introduced into rPIV3

| seq id no | region affected | nt position[a] | sequence changes[b] | restriction marker[c] | amino acid substitution[d] |
|---|---|---|---|---|---|
| 8 58 59 | C | 2076 | GA*A*ATA*TT*GATC<br>GAAACATTGATC | −Ssp I | Ile-96 to Thr |
| 9 60 61 | H | 4341 | TCTCTACCCAAC<br>TC*GTTA*ACCAAC | +Hpa I | Pro-199 to Thr |
| 10[f] 62 63 | F | 6323 | AGTACAATAGGT<br>*AGTAC*TGTGGGT | +Sca I | Ile-420 to Val |
| 11 64 65 | F | 6419 | GCACTTGATCCA<br>ACACT*GG*AT*CC*A | +Bam HI | Ala-450 to Thr |
| 12 66 67 | HN | 7944 | CCATCATTGTTGTTGACAA<br>CC*A*TCATTG*TGGC**TGACAA | +Bst XI | Val-384 to Ala |
| 13 68 69 | L | 11468 | TTACA*TG*GCCA<br>TCACATGGC*GA* | −Eae I | Tyr-942 to His |
| 14 70 71 | L | 11618 | TTTGGAC*TGGG*C<br>TTTTGATTGGGC | −Bsr I | Leu-992 to Phe |
| 15[f] 72 73 | L | 13308 | *GGTCC*TAATACT<br>GGGCCTAATATC | −Ava II | Thr-1558 to Ile |

[a]Position of the first nucleotide in the PIV3 sequence shown.
[b]Wild type sequence is shown above the mutant sequence. Nucleotide changes are underlined. Codon substitutions are in bold font.
[c]Each relevant restriction endonuclease recognition sequence is in italics; (+) indicates addition of new restriction endonuclease recognition sequence; (−) indicates ablation of a naturally occurring restriction endonuclease recognition sequence.
[d]Mutations are indicated as the three letter amino acid assignment of wt, followed by the amino acid position, followed by the cp45 assignment.
[e]These mutations were identified by Joanne Tatem (unpublished observations), the others were from Stokes et al., Virus Res. 30(1): 43–52, 1993.
[f]Two nucleotides were changed in the indicated codon in order to reduce the chance of reversion to wild type sequence.

After mutagenesis, restriction endonuclease fragments were sequenced completely and cloned back into the full-length clone, p3/7(131)2G. The 3' leader and N mutations were amplified by reverse transcription (RT)-PCR directly from PIV3 cp45 virion RNA and were cloned into pLeft+2G (see above), or a modified pUC19 v end of the incubation period, virus was harvested by freeze/thawing. The titer of virus recovered from each well was determined by plaque assay in LLC-MK2 cells at 32° C. using hemadsorption with guinea pig red blood cells to visualize plaques. Two wt and two cp45 reference stocks were used as controls.

Hamster Studies.

5 week-old Golden Syrian hamsters in groups of five were inoculated intranasally with 0.1 ml OptiMEM I per animal containing $10^{6.0}$ pfu of JS wt rPIV3, PIV3 cp45 virus, or one of the mutant rPIV3s. On day 4 post-infection, the hamsters were sacrificed, the lungs and nasal turbinates were harvested, and the virus was quantified as described above. The mean $\log_{10}$ TCID$_{50}$/gram at 32° C. was calculated for each group of hamsters.

Results

Introduction of the PIV3 cp45 Mutations into JS wt rPIV3.

The fifteen mutations in the 3' leader, the N GS signal, and the N, C, M, F, HN and L proteins of cp45 (Table 8) were introduced into the complete PIV3 antigenomic cDNA by site directed mutagenesis or by direct PCR amplification of a segment of cp45 cDNA bearing the desired mutations. The following antigenomic cDNAs were made (see FIG. 13): (i) rcp45 3'N, containing the four point mutations of the leader region, the point mutation in the N GS signal, and the two amino acid changes in the N protein; (ii) rcp45 C, containing the single amino acid change in the C protein; (iii) rcp45 M, containing the single amino acid change in M, (iv) rcp45 F, containing the two amino acid changes in F; (v) rcp45 HN, containing the single amino acid change in HN; (vi) rcp45 L, containing the three amino acid changes in L, as described above; (vii) rcp45 3'NL, containing the mutations from i. and vi. above; (viii) rcp45 3'NCMFHN, containing all of the mutations except for the three in L; and (ix) rcp45, containing all fifteen cp45 mutations listed in Table 8. In most cases, each cp45 change was engineered to be accompanied by one or more nearby silent changes which introduced or removed a restriction enzyme recognition site (Table 8). These served as markers to confirm the presence of the mutation in the cDNA and in recovered virus. Also, two of the amino acid coding changes (mutation numbers 10 and 15 in Table 8) were made using two nucleotide changes rather than the single change found in cp45, reducing the possibility of same-site reversion to wt. The cp45 cDNA, which contains all fifteen of the cp45 changes in Table 8, was assembled from the same mutagenized cDNA subclones as were used to introduce cp45 changes into the other antigenomic cDNAs; it was sequenced in its entirety, and was confirmed to contain only the intended mutations. This indicated that all of the regions which had been subjected to mutagenesis or PCR and had been manipulated by cloning possessed the desired sequences and lacked other unwanted mutations. Each full-length plasmid bearing one or more of the cp45 mutations was transfected into HEp-2 cells along with support plasmids and MVA-T7 to produce recombinant PIV3 as described above. Analysis of RT-PCR fragments encompassing the mutations indicated in Table 8 were amplified from virion RNA of the various recombinant viruses indicated in FIG. 13 confirmed the presence of the introduced mutations, and other unintended mutations were not found.

Plaque Morphology.

Several of the recombinant viruses exhibited distinctive plaque morphologies when tested on LLC-MK2 cells. JS wt rPIV3 plaques averaged 1 mm in size, and were indistinguishable in size from the biologically derived JS wt PIV3. Plaques of the cp45 and rcp45 viruses were larger than wt, averaging two- to three-fold larger in diameter than wt, and were indistinguishable from each other. This demonstrated the comparability of the biologically-derived and recombinant cp45 virus for this phenotype.

Efficiency of Plaque Formation of rPIV3s Bearing the cp45 Mutations in LLC-MK2 Cells at Permissive and Restrictive Temperatures.

The rPIV3s were assayed for their ability to form plaques at permissive and restrictive temperatures ranging from 32° C. to 41° C. (Table 9). Analysis of the ts phenotypes of viruses bearing individual components of cp45 revealed that the rcp45 3'N and rcp45 M viruses had a shutoff temperature of 40° C., and the rcp45 C mutant had a shutoff of 41° C. The shutoff temperature of rcp45 F and rcp45 HN mutants was greater than 41° C. Consistent with the above results, the rcp45 L virus had a shutoff temperature of 39° C. A virus is considered to have a ts phenotype, for example, if its reduction of replication at 40° C. (ie. titer at 32° C. minus titer at 40° C.) is approximately ≧100-fold that of wt virus at 40° C. Applying this definition, the present results indicated that at least two regions of cp45 (3'N, and L) contribute to the ts phenotype.

TABLE 9

The efficiency of plaque formation (EOP) of recombinant and biologically-derived viruses at permissive and restrictive temperatures.

| Virus | Mean Virus Titer[a] ($\log_{10}$ pfu/ml) | | | | | | | | ts phenotype[c] |
|---|---|---|---|---|---|---|---|---|---|
| | 32° C. | 35° C. | 36° C. | 37° C. | 38° C. | 39° C. | 40° C. | 41° C. | |
| rcp45 3'N | 7.1 | — | — | 7.0 | 6.4 | 5.4 | <u>4.2</u> | <3.7 | + |
| rcp45 C | 6.9 | — | — | 7.0 | 6.7 | 6.6 | 5.9 | <u>≦3.7</u> | − |
| rcp45 M | 7.7 | — | — | 7.4 | 7.0 | 6.5 | <u>5.3</u> | <3.7 | − |
| rcp45 F | 7.5 | — | — | 7.2 | 6.0 | 6.6 | 5.9 | 5.7 | − |
| rcp45 HN | 6.4 | — | — | 6.5 | 6.2 | 6.4 | 4.7 | 4.4 | − |
| rcp45 L | 7.3 | — | — | 7.2 | 6.7 | <u>4.0</u> | <0.7 | <0.7 | + |
| rcp45 3'NL | 7.3 | 5.7 | <u>≦0.7</u> | <0.7 | <0.7 | <0.7 | <0.7 | — | + |
| rcp45 3'NCMFHN | 7.2 | 5.6 | <u>≦0.7</u> | 2.0 | 2.4 | <0.7 | <0.7 | — | + |
| rcp45 | 8.5 | 7.5 | 7.1 | 6.4 | <u>6.0</u> | 2.0 | <0.7 | <0.7 | + |

TABLE 9-continued

The efficiency of plaque formation (EOP) of recombinant and biologically-derived viruses at permissive and restrictive temperatures.

| Virus | Mean Virus Titer[a] ($\log_{10}$ pfu/ml) | | | | | | | | ts phenotype[c] |
|---|---|---|---|---|---|---|---|---|---|
| | 32° C. | 35° C. | 36° C. | 37° C. | 38° C. | 39° C. | 40° C. | 41° C. | |
| Cp45[b] | 8.3 | 8.0 | 7.4 | 7.0 | <u>6.2</u> | 2.3 | <0.7 | <0.7 | + |
| rPIV3 wt | 7.3 | 7.3 | 7.0 | 7.4 | 7.6 | 7.7 | 6.8 | 6.0 | − |

[a]Plaques were enumerated by immunoperoxidase staining after incubation for 6 days at the indicated temperature. Values are the mean of two experiments, values in bold are from a single experiment. Underlined values represent the lowest non-permissive temperature at which a 100-fold reduction of plaquing efficiency occurs compared to titer at 32° C., and this is defined as the shutoff temperature of plaque formation.
[b]cp45 is biologically-derived and the other viruses are recombinants.
[c]A virus is defined as bearing the ts phenotype if its reduction of replication at 40° C. (ie. titer at 32° C. minus titer at 400C ) is ≧100-fold that of wt virus at 40° C..

As shown in Table 9, rcp45, containing all of the cp45 mutations, had a shut-off temperature of 38° C., which was identical to that of the biologically-derived cp45. These results show that the ts phenotype of cp45 was successfully reproduced in rcp45. In addition, these results validate the sequence analysis of cp45 and the subsequent reconstruction of mutations into recombinant virus.

The rcp45 3'NCMFHN virus, which is identical to rcp45 except that it lacks the three L mutations, exhibited a shutoff temperature of 36° C. Since the L mutations are known to confer temperature-sensitivity individually and in combination, it is somewhat paradoxical that rcp45 3'NCMFHN was more, rather than less, ts than cp45. This implies that there is an interaction of mutations within cp45 whereby mutations compensate for each other to give a level of temperature-sensitivity which is less than the sum of the individual components.

Virus rcp45 3'NL was constructed to investigate whether the L mutations interact with the leader and/or N mutations, since all of these elements are believed to interact during RNA synthesis. This virus had a shutoff temperature 36° C., compared to 40° C. and 39° C. for rcp45 3'N and rcp45 L, respectively. These results suggest that there is an interaction between the 3'N and L mutations that results in augmentation of temperature-sensitivity. These results also provide another example in which a subset of cp45 mutations specifies a level of temperature sensitivity greater than that observed for rcp45 which contains the entire set of mutations ca Phenotype of rPIV3s Bearing cp45 Mutations.

The rPIV3s were analyzed to determine which genetic elements of cp45 specified the ca phenotype (Table 10). It was demonstrated above that rcp45 L is ts and att, but not ca. This indicates that the genetic elements specifying the greater part of the ca phenotype are located outside L, and this was confirmed in the present study. Each of the rPIVs possessing the 3' leader and N mutations were ca except rcp45 3'NCMFHN, which exhibited an intermediate phenotype. This shows that the ca phenotype is specified mostly within the 3'N region. The finding that the level of ca of viruses containing the 3'N segment is less than that of cp45 or rcp45 indicates that other regions of cp45 contribute to the ca phenotype, even though this is not apparent from analysis of the other regions individually. The rcp45 3'NL virus is more ca than the rcp45 3'N virus, suggesting that the L mutations may make a modest contribution. The biologically-derived cp45 and rcp45 viruses exhibit comparable levels of Ca, indicating that this phenotype, like the plaque size and ts phenotypes, was successfully reproduced in the recombinant cp45 virus provided herein. Therefore, the ca phenotype, like the ts phenotype, is a composite phenotype reflecting individual contributions to the overall phenotype as well as contributions from interacting genetic elements.

TABLE 10

Growth of wt and mutant PIV3s at 20° C. compared to 32° C.[a] (cold adaptation phenotype).

| Virus | 20° C. | 32° C. | ca Phenotype |
|---|---|---|---|
| cp45[b] | 6.72 | 8.49 | + |
| rcp45 | 6.57 | 8.35 | + |
| rcp45 3'NL | 5.02 | 7.23 | + |
| rcp45 3'N | 4.39 | 8.53 | + |
| rcp45 3'NCMFHN | 3.53 | 8.08 | +/– |
| rcp45 L | 3.18 | 7.98 | – |
| rcp45 C | 2.52 | 8.32 | – |
| rcp45 F | 2.47 | 8.10 | – |
| rcp45 EN | 2.11 | 8.01 | – |
| rcp45 M | 1.76 | 8.21 | – |
| PIV3 WT | 2.57 | 8.43 | – |

[a]Virus titer is expressed in $log_{10}$ PFU/mL.
[b]cp45 is biologically-derived and the other viruses are recombinant. The ca phenotype is defined as a greater than 10-fold increase in growth at 20° C. relative to wt.

Growth of the rcp45 Mutant Viruses in Hamsters.

Groups of five Golden Syrian hamsters were inoculated intranasally with $10^6$ $TCID_{50}$ of recombinant or biologically-derived virus, and the level of virus replication in the lungs and nasal turbinates was determined four days later (Table 11). The fourth day post-inoculation has been shown previously to be the peak of virus replication in hamsters for both the wt and cp45 viruses (see, Crookshanks and Belshe, *J. Med Virol* 13(3):243–9, 1984, incorporated herein by reference in its entirety). The rcp45 virus was reduced approximately 40-fold in replication in the nasal turbinates and 1000-fold in the lungs, and thus was as attenuated as the biologically-derived cp45 virus. These results indicate that the attenuation phenotype of cp45 was successfully reproduced in its recombinant version. Since each phenotype of cp45 was fully reproduced in rcp45, the additional five mutations in cp45 that were not included in this Example likely made little contribution to the properties of cp45.

TABLE 11

Level of replication in the upper and lower respiratory tract of hamsters[a] of wt and mutant PIV3s[b].

| Virus | Mean virus titer ($\log_{10}$ TCID$_{50}$/ g ± S.E[c]) in: | |
|---|---|---|
| | Nasal turbinates | Lungs |
| JS wt rPIV3 | 6.9 ± 0.2 | 5.4 ± 0.5 |
| rcp45 3'N | 6.5 ± 0.2 | 3.9 ± 1.1 |
| rcp45 C | 4.8 ± 0.3 | 3.1 ± 0.7 |
| rcp45 M[d] | 6.8 ± 0.2 | 6.7 ± 0.3 |
| rcp45 F | 4.6 ± 0.2 | 3.4 ± 0.6 |
| rcp45 HN | 6.3 ± 0.2 | 5.3 ± 1.0 |
| rcp45L | 4.2 ± 0.1 | 2.1 ± 0.3 |
| rcp45 3'NL | 4.7 ± 0.2 | 2.1 ± 0.3 |
| rcp45 3'NCMFHN | 5.8 ± 0.3 | 2.9 ± 0.9 |
| rcp45 | 5.3 ± 0.1 | 2.4 ± 0.2 |
| cp45 | 4.9 ± 0.4 | 1.9 ± 0.2 |

[a]Groups of five hamsters each were intranasally administered $10^{6.0}$ TCID$_{50}$ of virus per animal in an 0.1 ml inoculum, and lungs and nasal turbinates were harvested four days later.
[b]cp45 is a biologically-derived virus, the other viruses are recombinant.
[c]TCID$_{50}$, 50% tissue infectious dose ± Standard Error.
[d]The virus pool used in this study was found to contain a mixed plaque phenotype. The attenuation phenotype of this mutant will be reassessed using additional virus preparations.

As demonstrated above, the mutations in the L gene of cp45 specify the majority of the attenuation phenotype of this virus. In the present Example, the contribution of the cp45 mutations outside of L as a group was examined. The rcp45 3'NCMFHN mutant was only slightly reduced in replication in the nasal turbinates, but was more than 100-fold reduced in replication in the lungs, which shows that additional attenuating mutations were present outside of the L protein. Importantly, if each of the three mutations in the L gene of rcp45 reverted to wild type sequence, the resulting virus, rcp45 3'NCMFHN, would still retain the attenuation phenotype. The rcp45 M and rcp45 HN mutant viruses were not defective for replication in the respiratory tract of hamsters, and the rcp45 3'N virus showed only a marginal decrease in replication in the lower respiratory tract. This suggests that the mutations present in the 3' leader, in the N gene start site and the N, M and HN proteins are not attenuating in and of themselves. However, these mutations could contribute to the overall attenuation of cp45 in the context of the other cp45 mutations. Also, individual mutations within the 3'N region may have effects which are not apparent when the set of mutations is analyzed together, which can be readily determined according to the present disclosure.

Replication of the rcp45 C and rcp45 F mutant viruses was approximately 100-fold reduced in both the nasal turbinates and the lungs, demonstrating that the mutations present in the C and F proteins of cp45 confer the attenuation phenotype in hamsters, although the level of attenuation is not as great as that conferred by the cp45 L mutations. As described above, the rcp45 F and rcp45 C mutant viruses did not possess the ts phenotype, and therefore, the mutations that occur in the C and F proteins are considered to be non-ts attenuating mutations.

EXAMPLE XI

Recovery of Recombinant, Chimeric PIV3 in which the Hemagglutinin and Fusion Glycoproteins have been Substituted with Corresponding Glycoproteins From PIV1

Within the present example, a chimeric rPIV virus is generated and selected which incorporates one or more heterologous genes or large polynucleotide sequences from one PIV into a different rPIV background. Within this aspect of the invention, individual genes or gene segments of one PIV are substituted by counterpart sequence(s) from a heterologous PIV or other source. In one embodiment described in the present Example, tools and methods are provided for substituting, e.g., the HN and/or F protective antigens of HPIV1 or HPIV2 into a recombinant HPIV3 to yield a chimeric recombinant suitable for developing live-attenuated vaccines.

Viruses and Cells.

The PIV1 strain used in this study, PIV1/Washington/20993/1964 (PIV1/Wash64), was isolated in Washington D.C. in 1964 and was confirmed to be a virulent wild type virus in clinical studies in adult human volunteers (Murphy et al. *Infect. Immun.* 12:62–8 (1975), incorporated herein by reference). It was propagated in LLC-MK2 cells (ATCC CCL 7.1) in Opti-MEM I (Life Technologies) with 50 µg/ml gentamicin sulfate, 2 mM glutamine and 0.75 µg/ml trypsin (Catalog No. 3741, Worthington Biochemical Corp., Freehold, N.J.). The Greer strain of human PIV2 (Catalog No. V-322-001-020, NIAID Repository, Rockville, Md.) used in the hemagglutination-inhibition assay (HAI) was propagated in the same way. The JS strain of human PIV3 virus and its recombinant derivative from cDNA (rPIV3/JS) with wild type phenotype were propagated as described above. The modified vaccinia Ankara (MVA) recombinant that expresses the bacteriophage T7 RNA polymerase is described in Wyatt et al., *Virology* 210:202–205 (1995) (incorporated herein by reference).

HEp-2 cells were obtained from ATCC (ATCC CCL 23) and maintained in Opti-MEM I (Life Technologies) with 2% fetal bovine serum (FBS), 50 µg/ml gentamicin sulfate and 2 mM glutamine.

Construction of a cDNA Encoding a Complete Chimeric PIV3-PIV1 Antigenome.

A cDNA encoding a full-length PIV3 antigenomic RNA in which the PIV3 HN and F ORFs were replaced by their PIV1 counterparts was constructed as shown in FIG. 14. cDNA clones of the HN and F genes of PIV1/Wash64 were prepared from RNA extracted from LLC-MK2 cells which had been infected with PIV1/Wash64 wild type virus. cDNA was generated using the SuperScript Preamplification System using random hexamer primers (Life Technologies). PIV1 F and HN cDNAs were amplified with Vent DNA polymerase (New England Biolabs, Beverly, Mass.) using gene specific primer pairs based on consensus sequences present in GenBank. All primers described below are annotated so that PIV specific sequences are underlined, restriction sites are in italics, nt altered from wild type sequences are in lowercase, and start and stop codons are in bold. The positive sense PIV1 F primer, hybridizing to nt 69–97 upstream of the start codon, was 5'-GGGAAAGAAtCCAGAGACAAGAACGG-3' (SEQ ID NO: 33). The negative-sense PIV1 F primer, hybridizing to nt 36–61 downstream of the F stop codon, was 5'-GGTGAAGTTGTGGATccATTTGATTG-3' (SEQ ID NO: 34). It carries a BamH I site. The positive-sense primer for PIV1 HN was 5'-CAACCTGTAAGGtAcCAGCATCCG-3' (SEQ ID NO: 35). It hybridizes to nt 13–36 upstream the HN start codon and carries a Kpn I site. The negative-sense PIV1 HN primer was 5'-GATATGGTGTTaGGc CTTGATCTGTTC-3' (SEQ ID NO: 36). It hybridizes to the last two nt of the stop codon and 25 nt further downstream and carries a Stu I site. The PIV1 F cDNA was cloned as a BamH I and blunt-end fragment into BamH I-EcoR V digested pLITMUS28 (New England Biolabs), while the PIV1 HN cDNA was cloned as a Kpn I-Stu I fragment into the same vector. The nt sequences of the resulting plasmids, designated as pLit.1HNwt and pLit.1Fwt (GenBanK Accession number: AF016280, AF016279), were determined using the Circumvent Sequencing Kit (New England Biolabs). These two clones were modified (FIG. 14) using mutagenic PCR primers to delete their non-coding regions and to introduce new restriction sites flanking their start and stop codons for the purpose of constructing the PIV3-1 chimeric HN and F genes. The sequences of positive-sense and negative-sense PIV1 F mutagenic primers were 5'-CgccATGgAAAAATCAGAGATCCTCTTCT-3' (SEQ ID NO: 37) and 5'-CtggatcctAATTGGAGTTGTTACCCATGTA-3' (SEQ ID NO: 38), respectively, the introduced restriction sites are Nco I and BamH I. The sequences of positive-sense and negative sense PIV1 HN mutagenic primers were 5'-AACcATGGCTGAAAAAGGGAAAA-3' (SEQ ID NO: 39) and 5'-GGTGAaGCTt AAGATGTGATTTTACATATTTTA-3' (SEQ ID NO: 40), respectively, the introduced restriction sites are Nco I and Hind III.

The second step involved the modification of the PIV3 HN and F genes to serve as acceptors of the PIV1 coding regions generated above. The PIV3 F and HN genes were subcloned in several steps from the full-length clone of PIV3/JS, p3/7(131)2G to generate pLit.PIV3.HN.4 and pLit.PIV3.F.3a (FIG. 14). The PIV3 F or HN coding regions were deleted by PCR mutagenesis and replaced by restriction sites appropriate to accept the PIV1 HN and F cDNA described above. The sequences of the PIV3 F positive sense and negative sense mutagenic primers were 5'-AAATAggatccCTACAGATCATTAGATATTAAAAT-3' (SEQ ID NO: 41) and 5'-CgcCATgGTGTTCAGTGCTTGTTG-3' (SEQ ID NO: 42), respectively, the introduced restriction sites were BamH I and Nco I. The sequences of PIV3 HN positive sense and negative sense mutagenic primers were 5'-CCACAAgCtTAATTAACCATAATATGCATCA-3, (SEQ ID NO: 43) and 5'-TTCCATgg ATTTGGATTTGTCTATTGGGT-3' (SEQ ID NO: 44), respectively, the introduced restriction sites were Hind III and Nco I. The stop codon for the chimeric HN would be regenerated upon ligation with mutagenized PIV1 HN cassette. The PIV1 HN or F cDNAs described above were imported in as a Nco I-Hind III fragment for HN or as a Nco I-BamH I fragment for F, which generated pLit.PIV3-1.HNhc and pLit.PIV3-1.Fhc. These two cDNAs were then joined into pSE.PIV3-1.hc, which was subsequently sequenced in its entirety. Then the BspE I-Sph I fragment was inserted into p3/7(131)2G to generate pFLC.2G+.hc (FIG. 14). The nucleotide sequence of this BspE I-Sph I fragment, containing the chimeric F and HN genes, is in GenBank (Accession No. AF016281). Importantly, the cDNA engineering was designed so that the final rPIV3-1 antigenome conformed to the rule of six (Durbin et al. *Virology* 234:74–78 (1997), incorporated herein by reference). The plasmid pFLC.2G+.hc encoding the rPIV3-1 chimera was deposited on Sep. 17, 1997 under the terms of the Budapest Treaty with the American Type Culture Collection (ATCC) of 12301 Parklawn Drive, Rockville, Md. 20852, U.S.A.

Transfection. HEp-2 cell monolayers were grown to confluence in six-well plates (Costar Corp, Cambridge, Mass.) and transfections were performed as described above. Cell monolayers were infected with MVA-T7 at a multiplicity of infection (MOI) of 3 in 0.8 ml of serum-free Opti-MEM I containing 50 μg/ml gentamicin, and 2 mM glutamine and then transfected with the three support plasmids, 0.4 μg pTM(N), 0.4 μg pTM(P), 0.05 μg pTM(L), and 5 μg the PIV3-1 antigenome cDNA. The plasmids were mixed in 0.2 ml of Opti-MEM I containing 12 μl LipofectACE (Life Technologies) and added to each well. The PIV3/JS cDNA plasmid, p3/7(131)2G, which encodes wild type PIV3/JS antigenomic RNA, was transfected in parallel as a positive control. After incubation at 32° C. for 12 hours, the transfection medium was replaced with 1.5 ml of fresh Opti-MEM I supplemented with 50 μg/ml gentamicin, and cultures were incubated at 32° C. for two additional days. Trypsin was added to a final concentration of 0.75 μg/ml on day 3 post transfection. Cell culture supernatants were harvested on day 4 and passaged (referred to as passage 1) onto fresh LLC-MK2 cell monolayers. After overnight adsorption, the medium was replaced with fresh Opti-MEM I with 0.75 μg/ml trypsin. Passage 1 cultures were incubated at 32° C. for 4 days, and the amplified virus was harvested and further passaged on LLC-MK2 cells (referred to as passage 2) for another 4 days at 32° C. in the presence of 0.75 μg/ml trypsin. The recovered virus was characterized by reaction with rabbit PIV1 antiserum, guinea pig PIV2 antiserum, and two PIV3 HN monoclonal antibodies in a hemagglutination-inhibition (HAI) assay as described previously (van Wyke Coelingh et al., supra, (1985)) with the exception that chicken red blood cells (RBCS) were used for viruses possessing the PIV1 HN glycoproteins, whereas guinea pig RBCs were used for PIV3. The HAI was performed to determine if rPIV3 possessed the monoclonal antibody resistant mutation (MARM) that marked virus recovered from cDNA or if rPIV3-1 possesses the PIV1 HN.

Nucleotide sequence analysis. The chimeric cDNA construct pSE.PIV3-1.hc was sequenced with the Circumvent Sequencing kit (New England Biolabs) before the final assembly into full-length clone pFLC.2G+.hc. For analysis of RNA, the appropriate PIVs were amplified in T75 flasks of LLC-MK2 cells. Virus was harvested on day 5 post-infection and concentrated by polyethylene glycol precipitation (Mbiguino et al., *J. Virol. Methods* 31:161–70 (1991)). Viral RNA was extracted from the viral pellets and used in reverse transcription (RT) with the Superscript Preamplification System (Life Technologies). RT-PCR was performed using the Advantage cDNA synthesis kit (Clontech) and PIV1 or PIV3 specific primer pairs. RT-PCR products were gel purified by electrophoresis onto, and elusion from, strips of NA45 DEAE nitrocellulose membrane (Schleicher & Schnuell, Keene, N.H.), and were sequenced.

Replication of PIVs in LLC-MK2 cells. Plaque enumeration on LLC-MK2 monolayers was performed as previously described except that trypsin was added in the case of the PIV1 and rPIV3-1 viruses (Hall et al. *Virus Res.* 22:173–84 (1992)). Briefly, serially-diluted virus was inoculated onto LLC-MK2 monolayers in six-well plates; virus was adsorbed for 1 hour at 32° C.; the cultures were overlaid with L-15 medium (Life Technologies) containing 0.8% agarose with or without added trypsin and incubated at 32° C. for 6 days; and plaques were identified by hemadsorption (HAD) with guinea pig red blood cells following the removal of the agarose overlay.

Growth of the PIV viruses in tissue culture was evaluated by infecting confluent LLC-MK2 monolayers on twelve-well plates with virus at a MOI of 0.01. After adsorption at 32° C. for 1 hour, the inoculum was replaced with 1.5 ml/well Opti-MEM I supplemented with gentamicin (50 µg/ml) and trypsin (0.75 µg/ml), and further incubated at 32° C. for 6 days. At 24 hour intervals, 0.3 ml medium was removed from each well and 0.3 ml fresh medium with trypsin was added back. The titer of virus was determined at 32° C. by hemadsorption assay on LLC-MK2 cell monolayers using fluid overlay as previously described (Hall et al. Virus Res. 22:173–84 (1992)), and the titers were expressed as $\log_{10}$ TCID$_{50}$/ml.

Replication of PIVs in the respiratory tract of hamsters. Golden Syrian hamsters in groups of 12 were each inoculated intranasally with 0.1 ml of L-15 medium containing $10^5$ pfu of rPIV3/JS, rPIV3-1, or PIV1/Wash64. On days 4 and 5 post-inoculation, six hamsters from each group were sacrificed, and their lungs and nasal turbinates harvested, and homogenized, and virus present in the samples was titered on LLC-MK2 cell monolayers at 32° C. The titers were expressed as mean $\log_{10}$ TCID$_{50}$/g for each group of six hamsters.

Results

Construction of a cDNA Clone Encoding a Full-Length, Chimeric PIV3-1 Antigenomic RNA Yielded Recovery of the Chimeric Virus rPIV3-1.

As noted above, the final construct of the PIV3 and PIV1 chimeric cDNA, in which the ORFs of the JS wild type PIV3 HN and F glycoprotein genes were replaced by those of PIV1/Wash64 coding sequences (FIG. 14) encodes a PIV3-1 chimeric antigenomic RNA of 15,516 nt, which conforms to the rule of six (Durbin et al., Virology 234:74–78 (1997)). The pFLC.2G+.hc cDNA encoding the chimeric PIV3-1 antigenome was transfected onto HEp-2 cells together with the N, P and L support plasmids. The p3/7(131)2G cDNA encoding the JS wt PIV3 antigenome was transfected in parallel to generate a rPIV3 control parental virus. Virus was recovered from each transfection following the second amplification on LLC-MK2 cells, and studies were initiated to confirm that each recombinant virus was derived from cDNA.

Recombinant viruses rPIV3-1 and rPIV3 were first characterized for the presence of the PIV1 or PIV3 HN glycoprotein by HAI assay with serotype-specific anti-HN monoclonal or polyclonal antibodies. As shown in Table 12, rPIV3 reacted with only one of the two PIV3 mAbs as expected, whereas its biologically derived parent PIV3/JS reacted with both. This confirmed that rPIV3 contained the introduced MARM mutation that marks this virus as being derived from cDNA. The rPIV3-1 virus reacted with antibodies specific to the PIV1 HN glycoprotein, but not to ones specific to HN of PIV3 or PIV2, showing that the virus contained the PIV1 HN gene as expected.

TABLE 12 rPIV3-1 possesses the RN glycoprotein of PIV1
Hemagglutination-inhibition titer[a] (reciprocal) of indicated monoclonal antibody or polyclonal antiserum

| Virus | PIV1[b] antiserum | PIV2[b] antiserum | α-PIV3 mAb 423/6[c] | α-PIV3 mAb 77/5[c] |
|---|---|---|---|---|
| PIV1/Wash64 | 256 | 32[d] | ≦50 | ≦50 |
| rPIV3-1 | 64 | ≦2 | ≦50 | ≦50 |
| rPIV3/JS | 4 | ≦2 | ≦50 | 3,200 |
| PIV3/JS | 8 | ≦2 | 12,800 | 6,400 |
| PIV2/Greer | 8 | 512 | ≦50 | ≦50 |

[a]Chick red blood cells (RBC) were used in HA1 assay for PIV1, PIV2, and rPIV3-1 and guinea pig RBCs were used for PIV3/JS and rPIV3/JS.
[b]PIV1 rabbit antiserum was purchased from Denka Seiken Co. Ltd., Japan (Catalog No. 410-701), and PIV2 guinea pig antiserum was obtained from NIAID repository, Rockville, MD (Catalog No. V-322-50-558).
[c]Biologically derived PIV3/JS contains epitopes recognized by both mAb 423/6 and 77/5, whereas rPIV3/JS was engineered to lack reactivity with mAb 423/6.
[d]The PIV2 antiserum had some reactivity with PIV1 virus, and therefore is not completely type specific.

It was next confirmed that the rPIV3-1 virus contained the engineered, chimeric PIV3-1 HN and F genes. As designed, the genetic structure of rPIV3-1 was unique in four junction regions when compared with either of its parents, PIV1/Wash64 or rPIV3/JS (boxed in FIG. 15A). These regions are the transition points at which the sequence switches from the PIV3 non-coding region to the PIV1 coding region and then from the PIV1 coding region back to the PIV3 non-coding region. Using the primer pair A specific to PIV3 M and L genes, or primer pair B specific to the PIV1 M and the very 3'-end of HN gene, RT-PCR products were generated for virion-derived RNAs from rPIV3-1, rPIV3/JS, and PIV1/Wash64. Control reactions showed that the RT step was required for generation of RT-PCR products, indicating that an RNA template, rather than contaminating DNA, was required to produce the RT-PCR product. An early indication that rPIV3-1 was indeed a chimeric virus came from the finding that only the PIV3-specific primer pair A generated the expected 4.6 kb cDNA product that spans the F and HN genes (FIG. 15B). Thus, while rPIV3-1 virus contains only HPIV1-specific HN glycoprotein (See Table 12), the non-coding regions are specific to PIV3. Conversely, the PIV1 specific primer pair B amplified an appropriately sized product from PIV1 control but not from rPIV3-1. Restriction digestion analysis also demonstrated that rPIV3-1 RT-PCR product had unique restriction patterns different from that of rPIV3/JS and PIV1/Wash64 and appropriate for its predicted sequence.

The nt sequence of the 4.6 kb RT-PCR product of rPIV3-1 was determined in its four regions (FIG. 15A) and compared with that of rPIV3/JS and PIV1/Wash64 (FIG. 16). The rPIV3-1 sequence was completely in agreement with the cDNA from which it was derived. Examination of the sequence alignment of the Region I-IV for the three RT-PCR products illustrates that rPIV3-1 contains the PIV1 F and HN glycoprotein ORFs with altered start and stop codons and flanked by the 5' and 3' non-coding regions of PIV3. Examples of sequencing ladders spanning the Region III and IV of rPIV3-1 (FIG. 17), compared in parallel with rPIV3/JS or PIV1/Wash64, were evaluated, and this analysis confirmed that rPIV3-1 is a recombinant chimeric virus whose structure is completely in agreement with the cDNA from which it was generated.

Trypsin-Dependence and Cytopathicity of rPIV3-1 In Vitro.

PIV1, like Sendai virus but contrary to PIV3, requires trypsin for cleavage of its F glycoprotein in order to undergo multicycle replication on continuous lines of tissue culture cells (Frank et al. *J. Clin. Microbiol.* 10:32–6 (1979)). In addition, PIV1 is a non-cytopathic virus whereas PIV3 readily produces extensive CPE (Collins et al. In Fields *Virology*, 3rd ed., 1:1205–43 (1996)). rPIV3-1, rPIV3 and PIV1/Wash64 were compared on the basis of these properties. rPIV3-1, like PIV1/Wash64, had a higher HA titer using chicken, rather than guinea pig (Table 13), RBCs. rPIV3-1, like its PIV1/Wash64 parent, required trypsin for efficient replication in cultures with fluid overlay as well as for efficient plaque formation. rPIV3-1 produced plaques at 32° C., 37° C. or 40° C. with similar efficiency. It is therefore evident that rPIV3-1 possesses the F glycoprotein of the PIV1 parent virus, and it is not temperature sensitive. On the other hand, rPIV3-1 produced CPE, as indicated by the cell rounding and detaching in the virus infected monolayers, almost to the same extent as its PIV3 parent suggesting that this biological property is a function of its PIV3 genes, which lie outside of the HN and F coding regions. Thus, rPIV3-1 possesses biological properties from both parents which is consistent with the findings above demonstrating that it is a chimeric virus. This exemplary recombinant, chimeric virus within the invention was deposited on May 21, 1998 under the terms of the Budapest Treaty with the American Type Culture Collection (ATCC) of 12301 Parklawn Drive, Rockville, Md. 20852, U.S.A.

TABLE 13

Comparison of the HA titer and the infectivity and cytopathicity of parental and chimeric PIVs[a]

| | HA titer using indicated RBC | | CPE Trypsin | | HAD Trypsin | | PFU/ml[c] (Log$_{10}$) Trypsin | |
|---|---|---|---|---|---|---|---|---|
| Virus | Chicken | Guinea Pig | − | + | − | + | − | + |
| PIV1/Wash64 | 16 | 8 | ≦2.5 | ≦2.5 | 4.8[d] | 6.3 | ≦0.7[e] | 5.8 |
| rPIV3-1 | 64 | 16 | ≧2.5 | 5.8 | 5.5[d] | 7.8 | ≦0.7[e] | 7.1 |
| rPIV3/JS | 0 | 8 | | 4.5 | 7.3 | 5.0[d] | 7.5 | 5.0 | 6.2 |

[a]Virus stocks were grown in LLC-MK2 cells which were infected at an MOI of 0.01 and incubated for 6 days in the presence (PIV1/Wash64, rPIV3-1) or absence (rPIV3/JS) of 0.75 μg/ml trypsin. The resulting virus stocks were assayed by the tests below in the presence or absence of trypsin as indicated.
[b]The TCID50 assay was read at 6 days by direct visualization of CPE or by hemadsorption (HAD).
[c]Plaques were visualized by HAD after six days of incubation.
[d]The HAD of PIV3-infected monolayers was grossly apparent whereas that of PIV1 and rPIV3-1 was observable only under the microscope in which single cells with RBC adsorbed were observed.
[e]The lowest level of virus detectable was $10^{0.7}$/ml.

Comparison of the Level of Replication of rPIV3-1 and its Parental Viruses in LLC-MK2 Cells and Hamsters.

The multicycle replication of rPIV3, rPIV3-1, and PIV1 Wash/64 viruses was evaluated following inoculation of LLC-MK2 tissue culture cells at a MOI of 0.01 (FIG. 18). It can be seen that the kinetics and magnitude of replication of the three viruses are very similar. This indicates that the substitution of the HN and F genes of PIV1 for those of PIV3 did not attenuate the virus for replication in vitro. It was next determined whether rPIV3-1 was attenuated in vivo, specifically for replication in the upper and lower respiratory tracts of hamsters (TABLE 14). The observed level of replication of rPIV3-1 was similar to, if not slightly higher than, either parent in the upper and lower respiratory tract of hamsters.

TABLE 14

Level of replication of parental and chimeric PIVs in the upper and lower respiratory tract of hamsters[a]

| | Virus titer (mean log$_{10}$ TCID$_{50}$/gram ± S.E.) in indicated tissue | | | |
|---|---|---|---|---|
| | Nasal Turbinates | | Lungs | |
| Virus | Day 4 | Day 5 | Day 4 | Day 5 |
| PIV1/Wash6 | 5.2 ± .24 | 5.2 ± .12 | 5.0 ± .31 | 5.0 ± .38 |
| rPIV3-1 | 4.9 ± .23 | 6.2 ± .17 | 5.8 ± .15 | 6.0 ± .09 |
| rPIV3/JS | 4.5 ± .09 | 5.0 ± .18 | 5.1 ± .26 | 5.0 ± .32 |

[a]Hamsters were infected intranasally with $10^{5.0}$ TCID$_{50}$ per animal of the indicated virus, and lungs and nasal turbinates were removed on day 4 or 5 after infection. The titers are means of six animals per day and are expressed as mean log$_{10}$TCID$_{50}$/gram ± standard error.

In summary, the present Example demonstrates successful recovery of a rPIV3-1 chimeric virus in which the ORFs of the PIV1 HN and F glycoproteins were substituted for those of rPIV3. This chimeric virus replicated like its wild type PIV1 and PIV3 parental viruses in vitro and in vivo, demonstrating that the substitution of the glycoprotein ORFs did not result in attenuation of rPIV3-1. This successful recovery of a recombinant PIV3 which bears the HN and F glycoproteins of PIV1 is surprising because the two viruses, representing distinct serotypes, are not closely related. In particular, it is remarkable that the chimeric recombinant grows as well as the two parents. Notably, chimeric recombinant viruses possessing a substitution in the glycoprotein gene have also been recovered for vesicular stomatitis virus (VSV) (Lawson et al. *Proc. Natl. Acad. Sci. USA* 92:4477–81 (1995)). Specifically, the VSV G glycoprotein gene of Indiana serotype was replaced by that from New Jersey serotype which share only 50% amino acid sequence identity. In contrast to rPIV3-1, the chimeric recombinant $VSV_{INJ}$ replicates to only 10% the level of recombinant $VSV_I$ or biologically derived, VSV.

In the present Example, the HN and F glycoproteins have 43 and 47% sequence identity, respectively, between PIV1 and PIV3. The transfer of the two glycoproteins together would, of course, obviate glycoprotein-to-glycoprotein incompatibility (Tanabayashi, K. and Compans, R. W. *J. Virol.* 70:6112–18 (1996)). On the other hand, it is generally thought that the glycoproteins interact with the M protein (which is 63% identical between PIV1 and PIV3) through their cytoplasmic (CT) or transmembrane (TM) domains, and that this interaction is important in virion morphogenesis and structure. In this regard, the degree of sequence identity between the HN and F proteins of the two serotypes in the TM and CT domains is low indeed: 30% and 22%, respectively for the TM domain, and 9 and 11% respectively for the CT domain. In light of this low level of sequence relatedness, we have also pursued a parallel strategy of constructing chimeric glycoproteins in which the PIV1 ectodomain of each glycoprotein was fused to the PIV3 TM and CT domains. Regarding possible interaction with the M protein or other internal proteins, it might be that a conserved structure, such as a constellation of charged amino acids, is important rather than a conserved sequence. Alternatively, it might be that interaction of the TM and CT domains of the glycoproteins with internal proteins is not as critical as has been previously thought. It will be possible to examine these factors more closely using the methods and tools provided herein. For example, these factors will be further elucidated by work in progress employing the methods described above to construct a PIV3 virus bearing HN and F of PIV2.

It was expected that rPIV3-1 would require trypsin for efficient replication in tissue culture since this is a property conferred by the PIV1 F glycoprotein, and this was found to be the case. However, it was interesting to observe that rPIV3-1 caused CPE that more closely resembled that of PIV3 parent virus, indicating that a PIV3 gene(s) other than HN or F specifies this phenotype. These roles will also be further elucidated using the methods and tools provided herein to exchange additional gene(s) between the non-cytopathic PIV1 and the cytopathic PIV3.

EXAMPLE XII

Recovery of Live-Attenuated Chimeric Recombinant PIV Encoding the Internal Proteins of PIV Type 3 and the Surface Glycoproteins of PIV Type 1

In the present Example, a derivative of rPIV3-1 carrying the three temperature-sensitive and attenuating amino acid coding changes found in the L gene of the live-attenuated cp45 PIV3 candidate vaccine virus, termed rPIV3-1.cp45L, is shown to exhibit a temperature sensitive phenotype with a shut-off temperature of 38° C., similar to that of the recombinant rPIV3 cp45L which possesses the same three mutations. rPIV3-1.cp45L is attenuated in the respiratory tract of hamsters to the same extent as rPIV3 cp45L. Infection of hamsters with rPIV3-1.cp45L generates a moderate level of hemagglutination-inhibiting antibodies against wt PIV1 and induces complete resistance to challenge with wild type PIV1. This demonstrates that attenuated chimeric PIV according to the invention are capable of inducing a highly effective immune response against PIV1. This disclosure also confirms the above described data demonstrating that the surface glycoproteins of parainfluenza viruses are sufficient to induce a high level of resistance to homologous virus challenge. Unexpectedly, infection with recombinant chimeric virus rPIV3-1.cp45L or rPIV3-1, each bearing the surface glycoprotein genes of PIV1 and the internal genes of PIV3, also induces a moderate level of resistance to replication of PIV3 challenge virus. This indicates that the internal genes of PIV3 can independently induce protective immunity against PIV3 in rodents. Thus, a reverse genetics system for PIV3 as disclosed herein successfully produces live attenuated PIV1 vaccine candidates that are attenuated and protective in accepted model subjects.

Viruses and Cells.

The wt PIV1 strain used in this study is PIV1/Washington/ 20993/1964 (PIV1/Wash64) (see, eg., Murphy et al., Infect. Immun. 12:62, 1975 (incorporated herein by reference in its entirety). Chimeric rPIV3-1, recovered from chimeric PIV3 cDNA in which the PIV3 F and HN ORFs were replaced with those of PIV1/Wash64, as described above and in Tao et al., J. Virol. 72:2955, 1998 (incorporated herein by reference in its entirety). These viruses were propagated in LLC-MK2 cells (ATCC CCL 7.1) in Opti-MEM I (Life Technologies, Gaithersburg, Md.) with 50 µg/ml gentamicin sulfate, and 0.75 µg/ml trypsin (Catalog No. 3741, Worthington Biochemical Corp., Freehold, N.J.). Trypsin is included because the F glycoprotein of PIV1, but not that of PIV3, is dependent on exogenous trypsin for cleavage when grown in cell culture under these conditions. The wt JS strain of human PIV3 virus and its recombinant derivative from cDNA (rPIV3/JS) were propagated as described above and in Durbin et al., Virology 235:323, 1997 (incorporated herein by reference in its entirety). The propagation of cp45, an attenuated derivative of wt PIV3/JS (see above; and Karron et al., J. Infect. Dis. 171:1107, 1995 (incorporated herein by reference in its entirety)), and rPIV3 cp45L, a recombinant PIV3 carrying the three ts mutations found in the L gene of cp45, were propagated as described above and in Skiadopoulos et al., J Virol 72:1762, 1998 (incorporated herein by reference in its entirety). The modified vaccinia Ankara (MVA) recombinant that expresses the bacteriophage T7 RNA polymerase is described in Virology 210: 202, 1995 (incorporated herein by reference in its entirety).

HEp-2 cells, which are used in transfection, were obtained from ATCC (ATCC CCL 23) and maintained in Opti-MEM I with 2% fetal bovine serum (FBS), 50 µg/ml gentamicin sulfate.

Introduction of L Mutations into rPIV3-1 Antigenomic cDNA.

The three L mutations of cp45 present in the pTM(L)942/ 992/1558 plasmid, described above (see also, Skiadopoulos et al., J Virol 72:1762, 1998, were introduced into chimeric cDNA pFLC.2G+.hc (described above; see also, Tao et al., J Virol 72:2955, 1998), as a 2.8 kb SphI-NheI fragment (nt 11313 to 14092 in PIV3 antigenomic cDNA) to generate the full-length pFLC.2G+.hc.cp45L bearing the PIV1 F and HN ORFs and the three cp45 L gene mutations (FIG. 19). The specific mutations present in pTM(L)942/992/1558 are indicated in the legend to FIG. 19.

Transfection. HEp-2 cell monolayers in six-well plates were grown to confluence and transfections were performed as described above (see also, Tao et al., J Virol 72:2955, 1998). Trypsin was added to a final concentration of 0.75 µg/ml on day 3 post transfection prior to harvesting on day 4. Cell culture supernatants were clarified and passaged (referred to as passage 1) onto fresh LLC-MK2 cell monolayers. After overnight adsorption, the medium was replaced with fresh Opti-MEM I with 0.75 µg/ml trypsin. Passage 1 cultures were incubated at 32° C. for 4 days, and the virus present in the supernatant was harvested and passaged again under the same conditions (referred to as passage 2). Virus present in the passage 2 harvest was tested for the presence of the PIV1 HN protein by hemagglutination-inhibition (HAI) assay as described above (see also Tao et al., J Virol 72:2955, 1998).

Replication of PIVs in LLC-MK2 at Various Temperatures.

Plaque enumeration on LLC-MK2 monolayers was performed as described above, with 0.75 µg/ml trypsin added to the agarose overlay in the case of PIV1, rPIV3-1, and rPIV3-1.cp45L (see also, Tao et al., J Virol 72:2955, 1998). After incubation at various temperatures for 6 days, the agarose overlay was removed and plaques were identified by hemadsorption (HAD) with guinea pig erythrocytes (RBCs).

Replication of PIVs in the Respiratory Tract of Hamsters.

Groups of five hamsters were inoculated intranasally with 0.1 ml of L15 medium containing $10^6$ plaque forming units (PFU) of rPIV3/JS, rPIV3 cp45L, cp45, PIV1/Wash64, rPIV3-1, or rPIV3-1.cp45L. Hamsters were sacrificed on day 4 post-infection, and their lungs and nasal turbinates were harvested and homogenized. Virus present in the tissue samples was titered on LLC-MK2 cell monolayers at 32° C. as described above and in Tao et al., J Virol 72:2955, 1998.

The titers are expressed as reciprocal mean $\log_{10}$ TCID$_{50}$/gram of tissue for each group.

Immunization and Challenge Studies in Hamsters.

Groups of ten hamsters were immunized intranasally with $10^6$ PFU of virus per animal, as described above. Serum was collected for HAI assay prior to infection and on day 33. The level of HAI antibodies present in the sera of each group of 10 hamsters was determined using PIV1/Wash64 and PIV3/JS as antigens, and the HAI titers determined are presented as mean $\log_2$ (see also, Tao et al., J Virol 72:2955, 1998).

Thirty-five days post-immunization, five hamsters from each group were challenged intranasally with $10^6$ PFU of either PIV1/Wash64 or rPIV3/JS. Nasal turbinates and lungs of these challenged hamsters were harvested four days post challenge. Virus titers in tissue samples were determined on LLC-MK2 monolayers as described above and in Tao et al., J Virol 72:2955, 1998, and the titers are presented as mean $\log_{10}$ TCID$_{50}$/gram of tissue.

Results

Recovery and Characterization of the Recombinant Chimeric Virus rPIV3-1.cp45L.

As noted above, the cDNA clone pFLC.2G+.hc, a full-length antigenomic cDNA of PIV3 in which the ORFs encoding the F and HN glycoproteins have been replaced by those of PIV1, was modified by introduction of three amino acid coding changes (designated 942, 992 and 1558, according to amino acid position in the L protein) identified in the L gene of cp45 and shown to be independent ts and attenuating mutations (FIG. 19; see also, Skiadopoulos et al., J Virol 72:1762, 1998). Each coding change was marked by the co-introduction of contiguous translationally silent nt substitutions that ablate a naturally-occurring restriction site (FIG. 19; Table 8). The final full-length plasmid construct, pFLC.2G+.hc.cp45L (FIG. 19), encodes a PIV3-1 chimeric antigenomic RNA of 15516 nt in length and conforms to the rule of six (see, Durbin et al., Virology 234:74, 1997, incorporated herein by reference in its entirety). The authenticity of pFLC.2G+.hc.cp45L was confirmed by digestion with appropriate restriction enzymes.

The pFLC.2G+.hc.cp45L cDNA was transfected into HEp-2 cells together with the PIV3 N, P and L support plasmids and infected with MVA-T7 as described above and in Tao et al., J Virol 72:2955, 1998). Virus recovered after two passages on LLC-MK2 cells, termed rPIV3-1.cp45L, was biologically cloned by plaque-to-plaque-to-plaque passage, and amplified virus was analyzed to confirm that it possessed the PIV1 glycoproteins and the three introduced mutations in L. First, the presence of the PIV1 HN protein in rPIV3-1.cp45L was confirmed by reactivity with PIV1 specific antibodies in HAI assay as described above and in Tao et al., J Virol 72:2955, 1998. The presence of the chimeric PIV3-1 HN and F genes as well as the introduced L gene mutations in rPIV3-1.cp45L genomic RNA was confirmed by restriction enzyme digestion or nucleotide sequence analysis of RT-PCR products generated from virion RNA as described above and in Tao et al., J Virol 72:2955, 1998. These data confirmed that rPIV3-1.cp45L is a recombinant chimeric virus bearing the three codon substitutions of the L gene of cp45.

rPIV3-1.cp45L is Temperature Sensitive.

The three L gene mutations of cp45 were shown above to confer the ts phenotype when introduced into wt PIV3 (see also, Skiadopoulos et al., J Virol 72:1762, 1998). To evaluate whether their presence in the chimeric virus would have the same effect, the efficiency of plaque formation of rPIV3-1.cp45L was determined at various temperatures. As shown in Table 15, the three L mutations indeed conferred the ts phenotype to the chimeric virus. The level of temperature sensitivity specified by the cp45 L mutations in the recombinant viruses rPIV3 cp45L and rPIV3-1.cp45L was equivalent (Table 15), indicating that the effect of the mutations is independent of the PIV3 or PIV1 HN and F glycoproteins. The level of temperature sensitivity of rPIV3 cp45L and rPIV3-1.cp45L was comparable to that of the biologically derived cp45 virus, despite the fact that the latter virus possesses mutations outside of L (see, Stokes et al., Virus Res 30:43, 1993, incorporated herein by reference in its entirety).

TABLE 15

The recombinant chimeric rPIV3-1.cp45L candidate vaccine virus is temperature sensitive

| Virus[a] | Virus titer[b] at indicated temperatures ($\log_{10}$PFU/ml) | | | | | |
|---|---|---|---|---|---|---|
| | 32° C. | 36° C. | 37° C. | 38° C. | 39° C. | 40° C. |
| rPIV3/JS | 7.4 | 7.2 | 7.2 | 7.2 | 7.2 | 7.2 |
| PIV1/Wash64[c] | 7.5 | 7.6 | 7.5 | 7.5 | 7.4 | 7.2 |
| rPIV3-1 | 7.5 | 7.5 | 7.5 | 7.2 | 6.0 | 6.1 |
| PIV3cp45[c] | 7.4 | 6.9 | 6.8 | 4.7[d] | <0.7 | <0.7 |
| rPIV3cp45L | 7.9 | 7.4 | 7.7 | 5.3 | 1.2 | <0.7 |
| rPIV3-1.cp45L | 8.2 | 8.0 | 8.2 | 6.1 | <0.7 | <0.7 |

[a]Virus nomenclature: rPIV3/JS, recombinant wt PIV3 strain JS; PIV1/Wash64, biologically-derived wt PIV1; rPIV3-1, recombinant chimeric PIV3 in which the F and HN ORFs have been replaced with those of PIV1/Wash64; PIV3cp45, biologically-derived cp45 candidate vaccine virus; rPIV3cp45L, recombinant PIV3 containing the three L gene mutations of cp45; rPIV3-1.cp4SL, recombinant chimeric rPIV3-1 containing the three L gene mutations of cp45.
[b]Virus titers were determined using LLC-MK2 monolayers in 12-well plates. Titers are the average of two assays.
[c]Biologically-derived viruses. All others are recombinant viruses.
[d]The shut-off temperature, i.e. the lowest restrictive temperature at which a two $\log_{10}$ reduction in virus titer is observed, of each ts virus is indicated in bold.

Level of Replication of rPIV3-1.cp45L in Hamsters.

The three L gene mutations of cp45 were shown above to confer attenuation of virus replication in the upper and lower respiratory tract of hamsters when introduced into wt PIV3 (see also, Skiadopoulos et al., J Virol 72:1762, 1998). Their effect on the chimeric virus was evaluated by intranasal infection of hamsters, as shown in Table 16. These findings indicate that rPIV3-1.cp45L indeed was attenuated at both sites and, furthermore, that its level of attenuation was comparable to that of rPIV3 cp45L. Thus, the ability of the cp45 L mutations to confer attenuation, like temperature sensitivity, is independent of the antigenic specificity of the surface glycoproteins.

TABLE 16

The recombinant chimeric rPIV3-1.cp45L candidate vaccine virus is attenuated in the respiratory tract of hamsters[a]

| Virus | Virus titer in indicated tissue ($\log_{10}$TCID$_{50}$/g ± S.E)[b] | |
|---|---|---|
| | Nasal turbinates | Lungs |
| rPIV3-1.cp45L | 4.6 ± 0.3 | 1.9 ± 0.4 |
| rPIV3-1 | 6.0 ± 0.3 | 6.3 ± 0.4 |

TABLE 16-continued

The recombinant chimeric rPIV3-1.cp45L candidate vaccine virus is attenuated in the respiratory tract of hamsters[a]

| Virus | Virus titer in indicated tissue (log₁₀TCID₅₀/g ± S.E)[b] | |
|---|---|---|
| | Nasal turbinates | Lungs |
| rPIV3cp45L | 3.0 ± 0.3 | <1.2 |
| rPIV3/JS | 5.7 ± 0.3 | 5.0 ± 0.3 |

[a]Groups of five hamsters were infected intranasally with indicated viruses at a dosage of $10^6$ PFU per hamster. On day 4 post infection, the tissue samples were harvested and assayed for virus.
[b]Virus titers are given as $Log_{10}TCID_{50}$ per gram of tissue.

Infection with rPIV3-1 or rPIV3-1.cp45L, Containing the Internal Proteins of PIV3 and the Glycoproteins of PIV1, Confers Resistance to PIV1 Challenge in Hamsters.

The chimeric rPIV3-1 virus and its attenuated rPIV3-1.cp45L derivative were evaluated for immunogenicity and protective efficacy in hamsters. As shown in Table 17, infection with either virus induced HAI antibodies against PIV1, but not PIV3, confirming that these chimeric viruses possess the PIV1 HN glycoprotein and are highly immunogenic. The level of HAI antibodies induced by rPIV3-1.cp45L was two-fold less than that by rPIV3-1, which indicates that its attenuation resulted in a modest decrease in immunogenicity. Similarly, rPIV3 and rPIV3 cp45L induced HAI antibodies against PIV3, but not PIV1, and the level induced by the attenuated virus was approximately two-fold lower. Despite the restricted replication in hamsters of the recombinant viruses bearing the cp45 L mutations, infection with either rPIV3 cp45L or rPIV3-1.cp45L induced complete resistance to replication of challenge virus bearing homologous glycoproteins.

Infection with rPIV3-1.cp45L also Confers Resistance to PIV3.

Information on the role of the non-HN or F glycoproteins of PIVs (i.e., the internal proteins) in resistance is limited. The disclosure and use of rPIV3-1 and rPIV3-1.cp45L herein provides an opportunity to examine the role that internal proteins play in resistance to challenge with PIV3, since the only genes shared by immunizing and challenge viruses are the internal protein genes. PIV3 challenge virus replication was significantly restricted in both the upper and lower respiratory tracts by prior infection of hamsters with rPIV3-1 or rPIV3-1.cp45L (Table 17). Thus, these data indicate that the internal proteins of PIV3, like the HN and F proteins, are capable of inducing partial resistance to replication of the challenge PIV3.

Among the findings demonstrated by the immunogenicity and efficacy studies above a particularly unexpected finding was that infection with wt or attenuated rPIV3 induced a 100-fold reduction in the replication of PIV1 challenge virus in the lungs. Thus, infection with one serotype of PIV provided significant protection against a heterologous serotype. This was unexpected in part because previous studies indicated that infection of animals with one type of human PIV did not induce significant heterologous protection against a PIV belonging to a different human serotype, conforming to a general belief that immunity to human PIV infections was largely type-specific (see, eg., Cook et al., Amer. Jour. Hyg. 77:150, 1963; Ray et al., J. Infect. Dis. 162:746, 1990, each incorporated herein by reference in its entirety).

The present Example demonstrates successful exploitation of novel methods and reagents developed for generating PIV3 vaccines to further provide rapid, rational development of live attenuated candidate vaccines for PIV1. A cDNA encoding infectious PIV3 was modified by substitution of the ORFs encoding the PIV1 HN and F protective antigens for their PIV3 counterparts. Subsequently, attenuating mutations, exemplified by three attenuating mutations present in the L gene of the cp45 PIV3, were incorporated within this modified chimeric PIV3-PIV1 cDNA. From this cDNA, a recombinant virus was recovered bearing the HN and F genes of PIV1, the internal proteins of PIV3, and the PIV3 cp45 L gene mutations. This recombinant, rPIV3-

TABLE 17

The recombinant chimeric rPIV3-1.cp45L candidate vaccine virus induces complete resistance to PIV1 and partial resistance to PIV3 upon challenge in hamsters[a]

| | | Post-immunization HAI titer (log₂Reciprocal ± S.E.) | | Virus Titer in Indicated Tissue[c] (log₁₀TCID₅₀/Gram ± S.E.) | | | |
|---|---|---|---|---|---|---|---|
| | | | | Replication of PIV1 challenge virus | | Replication of PIV3 challenge virus | |
| Virus used for immunization | Origin of glycoproteins | α-PIV1 | α-PIV1 | Nasal Turbinates | Lungs | Nasal Turbinates | Lungs |
| Control[b] | — | ≤1 | ≤1 | 5.0 ± 0.3 | 4.6 ± 0.5 | 5.5 ± 0.4 | 5.0 ± 0.7 |
| rPIV3-1.cp45L | PIV1 | 6.9 ± 0.5 | ≤1 | ≤1.2 | ≤1.2 | 1.9 ± 0.6 | 1.7 ± 0.5 |
| rPIV3-1 | PIV1 | 7.9 ± 0.4 | ≤1 | ≤1.2 | ≤1.2 | 2.9 ± 0.3 | 2.6 ± 0.4 |
| rPIV3cp45L | PIV3 | ≤1 | 9.3 ± 0.2 | 4.6 ± 0.2 | 2.8 ± 0.7 | ≤1.2 | ≤1.2 |
| rPIV3/JS | PIV3 | ≤1 | 10.3 ± 0.3 | 4.6 ± 0.4 | 2.4 ± 0.5 | ≤1.2 | ≤1.2 |
| PIV3cp45[d] | PIV3 | ≤1 | 8.9 ± 0.4 | 4.9 ± 0.2 | 2.5 ± 0.8 | ≤1.2 | ≤1.2 |

[a]Groups of 10 hamsters were immunized intranasally with $10^6$ PFU of indicated viruses. Post-immunization sera were collected on days 33, two days prior to challenge (see [c]).
[b]Hamsters in control group were not inoculated.
[c]Five weeks after immunization, five hamsters from each group were challenged intranasally with $10^6$ PFU of indicated virus. Tissue samples were harvested 4 days post challenge. Viruses present in tissue samples were titered on LLC-MK2 monolayers and the data are presented as $log_{10}TCID_{50}$/gram of tissue ± standard error.
[d]Biologically-derived virus.

1.cp45L, was temperature sensitive, highly attenuated in hamsters, and highly efficacious against PIV1 challenge in hamsters. The level of temperature sensitivity, attenuation, and immunogenicity exhibited by rPIV3-1.cp45L was comparable to that of cp45 PIV3, indicating that the phenotypes specified by the set of cp45 L gene mutations are independent of the HN and F surface glycoproteins. These findings, which represent the first live attenuated PIV1 vaccine candidate generated by reverse genetics, provide a generally successful scheme for developing vaccines against PIV1.

Little information is known concerning the role that internal proteins of parainfluenza viruses play in resistance to reinfection with homologous virus. Infection with vaccinia recombinants expressing N, epitopes within N, or M reportedly induce resistance to replication of challenge virus, but the magnitude of the resistance reported is less than that induced by vaccinia recombinants bearing HN or F glycoproteins (see, eg., Kast et al., *Proc. Natl. Acad. Sci. USA* 88:2283, 1991; Sakaguchi et al., *J. Gen. Virol.* 74:479, 1993; Thomson et al., *J. Immunol.* 157:822, 1996, each incorporated herein by reference in its entirety). These studies suggested that the internal proteins were making only minor contributions to resistance to reinfection. Therefore, the present disclosure presents unexpected results by showing that prior infection of hamsters with rPIV3-1.cp45L or rPIV3-1 induced about 250-to 4000-fold reduction of replication of PIV3 in both the nasal turbinates and lungs. These two chimeric recombinant viruses differ from the PIV3 challenge virus in that they possess the HN and F glycoproteins of PIV1 rather than PIV3, but they share all other genes with the challenge virus. The HN and F glycoproteins of PIV1 share 47% and 43% sequence identity with those of PIV3, respectively. Although it is likely that the shared internal proteins are mediating the observed resistance, it is also possible that shared protein sequences between PIV1 and PIV3 F and HN glycoproteins are contributing to the observed immunity. For example, there are 5 stretches in HN and 2 stretches in F extending at least 9 amino acid residues in length that are shared between PIV1 and PIV3 and have the potential to act as protective CTL epitopes. It is reasonable to consider that the shared internal proteins are contributing to the restriction of replication of wt PIV3 challenge virus, since this level of cross-immunity has not been seen in previous studies (see, eg., Cook et al., *Amer. Jour. Hyg.* 77:150, 1963; Ray et al., *J. Infect. Dis.* 162:746, 1990, incorporated herein by reference in its entirety).

The finding that the internal PIV3 proteins of the rPIV3-1 and rPIV3-1.cp45L chimeras conferred resistance to PIV3 challenge demonstrates that attenuated derivatives of PIV3 can be used as vectors for PIV1 and PIV2 protective antigens. Following the teachings of the invention, immunization with one PIV3-based live-attenuated vaccine virus can restrict the replication of other PIV3-based vaccine viruses administered subsequently, thereby decreasing the immunogenicity of the second virus. Since PIV3, like RSV, induces significant illness in early infancy, a combined RSV-PIV3 vaccine for use in the very young 2- to 4-week old infant is therefore an important aspect of the invention (see, eg., Collins et al., *Fields Virology* 3rd ed. Philadelphia: Lippincott-Raven Publishers, 1205(1), 1996; Reed et al., *J. Infect. Dis.* 175:807, 1997, each incorporated herein by reference in its entirety). According to this aspect of the invention, immunization with a PIV1-PIV2 vaccine will be preferably initiated at about 6 months of age, since most PIV1 and PIV2 disease occurs after the age of six months. In the possible circumstance that immunization with rPIV3 cp45 significantly inhibits replication of a chimeric recombinant PIV3-1 vaccine virus with which it shares internal protein genes, successful immunization with a recombinant PIV3-1 vaccine may be compromised. In this event, a trivalent PIV vaccine will be administered simultaneously rather than sequentially, thereby preventing the above noted inhibition.

The disclosure herein that infection with a vaccine or wt PIV3 would induce a 100-fold reduction of pulmonary virus replication of the heterologous wt PIV1 was clearly unexpected, in part because the human PIV viruses are serologically distinct by neutralization assay, and previous studies in hamsters found that prior infection with one type of PIV failed to induce resistance to challenge with a high dose of a different PIV type (see eg., Cook et al., *Amer. Jour. Hyg.* 77:150, 1963; Ray et al., *J. Infect. Dis.* 162:746, 1990; Cook et al., *Amer. Jour. Hyg.* 69:250, 1959). Furthermore, there is little epidemiological data documenting that prior infection with one PIV significantly modifies subsequent infection with a heterotypic PIV.

In summary, the present Example shows that rPIV3 was successfully converted into a vaccine for PIV1 by substituting the ORFs encoding the F and HN glycoproteins and introducing known attenuating mutations into the PIV3 internal genes. Thus, the extensive methods and reagents provided herein can be applied directly and predictably to attenuating the PIV3 backbone of the rPIV3-1 chimeric virus, as well as for generating live-attenuated PIV2 vaccine viruses.

The foregoing disclosure makes it possible to exploit the reagents and methods provided herein to develop a broad assemblage of PIV and related vaccines. In this context, recovery of live, immunogenic chimeras between PIV3 and PIV2 exemplifies powerful new tools for developing a range of recombinant PIV viruses for vaccine use. In conjunction with this work, identification and characterization of the genetic basis for attenuation of naturally occurring PIV mutants, e.g., cp45 and BPIV3 vaccine candidates, following the teachings of the present disclosure also enables development of a large host of recombinant vaccine viruses and subviral particles. In particular, desired mutations present in biologically derived mutant viruses will be readily identified and selected by their introduction, singly and in combination, into a wild type, partially attenuated, or chimeric PIV background, as shown in the Examples above. These findings will expand the menu of exemplary, attenuating mutations within the invention which can introduced into PIV clones to calibrate the level of attenuation and immunogenicity in vaccine recombinants. Biologically derived mutations can also be introduced within PIV clones having different types of mutations, e.g., mutations involving alterations, deletions, or substitutions of a gene or gene segment. Within this aspect of the invention, recombinant PIV are provided which have a selected gene deletion, addition, or substitution, such as rPIV having a deletion of the C, D or V ORF(s). Such alternatively mutated clones can be further modified according to the present disclosure by introducing one or more mutations specifying a ts, ca or att phenotype adopted from a biologically derived mutant PIV, as exemplified by the PIV recombinants r942, r992, r1558, r942/992, r992/1558, or r942/1558, and r942/992/1558. In additional aspects of the invention, biologically derived mutations will be combined with de novo attenuating mutations not found in nature, as exemplified by attenuating gene deletions, e.g., of the C, D and/or V ORFs. Other types of mutations disclosed herein conferring desired phenotypic characteristics will also be combined with biologically derived, attenuating mutations, similar to the range of combinatorial mutations disclosed for recombinant RSV vaccine strains in U.S. patent application Ser. No. 08/892,403, filed Jul. 15, 1997 (incorporated herein by reference). Comparable mutations can be readily introduced, e.g., into a chimeric virus, to achieve a desired levels of attenuation and immunogenicity in a chimeric vaccine strain. In this manner, a large menu of mutations are provided within the invention that are useful to engineer a wide assemblage of live attenuated rPIV vaccines having a desired balance of attenuation and immunogenicity, along with other desired phenotypic characteristics.

Although the foregoing invention has been described in some detail by way of illustration and example for purposes of clarity of understanding, it will be obvious that certain changes and modifications may be practiced within the scope of the appended claims.

What is claimed is:

1. An isolated polynucleotide molecule comprising an operably linked i) transcriptional promoter operative in a mammalian cell or operative in vitro, ii) a polynucleotide sequence encoding a partial or complete human PIV genome, said polynucleotide comprising at least one sequence selected from the group consisting of the complement of nucleotide sequences of SEQ ID NOS: 61, 63, 65, 67, 69, 71 and 73, or a polynucleotide encoding a partial or complete human PIV antigenome said polynucleotide comprising at least one nucleotide sequence selected from the group consisting of SEQ ID NOS: 61, 63, 65, 67, 69, 71 and 73, and iii) a transcriptional terminator operative in a mammalian cell or operative in vitro.

2. The isolated polynucleotide molecule of claim 1, in which the polynucleotide ii) encodes a human PIV3 genome or antigenome.

3. An isolated polynucleotide molecule comprising an operably linked i) transcriptional promoter operative in a mammalian cell or operative in vitro, ii) a polynucleotide sequence encoding a partial or complete human PIV genome said polynucleotide comprising the complement of nucleotide sequences of SEQ ID NOS: 69, 71 and 73, or a polynucleotide encoding a partial or complete human PIV antigenome said polynucleotide comprising the nucleotide sequences of SEQ ID NOS: 69, 71 and 73, and iii) a transcriptional terminator operative in a mammalian cell or operative in vitro.

4. The isolated polynucleotide of claim 3, in which the polynucleotide ii) is a polynucleotide sequence encoding a partial or complete human PIV3 genome and comprising the complement of nucleotide sequences of SEQ ID NOS: 69, 71 and 73, or is a polynucleotide encoding a partial or complete human PIV3 antigenome and comprising the nucleotide sequences of SEQ ID NOS: 69, 71 and 73.

5. An isolated polynucleotide molecule comprising an operably linked transcriptional promoter operative in a mammalian cell or operative in vitro, a polynucleotide sequence encoding a chimeric partial or complete PIV genome or antigenome comprising said chimeric partial or complete partial or complete PIV genome or antigenome, and a transcriptional terminator operative in a mammalian cell or operative in vitro, wherein said polynucleotide sequence encoding said chimeric partial or complete PIV genome or antigenome comprises a polynucleotide sequence of a background partial or complete PIV genome or antigenome and at least one heterologous PIV sequence selected from a HPIV 1 sequence, a HPIV 2 sequence, a HPIV 3 sequence, a BPIV sequence or a MPIV sequence, and wherein said polynucleotide sequence encoding said chimeric partial or complete PIV genome or antigenome comprises a polynucleotide encoding the L protein of the wild-type of said background PIV or of said heterologous PIV.

6. The isolated polynucleotide of claim 5, in which the polynucleotide sequence encoding the background partial or complete PIV genome or antigenome further includes at least one mutation at a position corresponding to a position in the genome of HPIV3 selected from the group consisting of Val96 of the N protein, Ser389 of the N protein, Ile96 of the C protein, Pro199 of the M protein, Ile420 of the F protein, Ala450 of the F protein, Val384 of the HN protein, nucleotide 23 of the 3' leader sequence, nucleotide 24 of the 3' leader sequence, nucleotide 28 of the 3' leader sequence, nucleotide 45 of the 3' leader sequence and nucleotide 62 in the N gene start sequence.

7. The isolated polynucleotide of claim 5, in which the chimeric partial or complete PIV genome or antigenome comprises a heterologous PIV sequence that encodes an open reading frame of a HN glycoprotein or of a F glycoprotein.

8. The isolated polynucleotide of claim 6, in which the chimeric partial or complete PIV genome or antigenome comprises a heterologous PIV sequence that encodes an open reading frame of a HN glycoprotein or of a F glycoprotein.

9. The isolated polynucleotide of claim 6, in which the heterologous PIV sequence is from HPIV1.

10. The isolated polynucleotide of claim 7, in which the heterologous PIV sequence is from HPIV1.

11. The isolated polynucleotide of claim 5, that comprises a heterologous PIV sequence that encodes an open reading frame of a HN glycoprotein and a heterologous PIV sequence that encodes an open reading frame of a F glycoprotein.

12. The isolated polynucleotide of claim 6, that comprises a heterologous PIV sequence that encodes an open reading frame of a HN glycoprotein and a heterologous PIV sequence that encodes an open reading frame of a F glycoprotein.

13. The isolated polynucleotide of claim 11, in which both of the heterologous PIV sequences are from HPIV1.

14. The isolated polynucleotide of claim 12, in which both of the heterologous PIV sequences are from HPIV1.

15. The isolated polynucleotide of claim 11, in which the heterologous PIV sequence is a gene segment encoding a portion of an open reading frame of a HN or F glycoprotein comprising an antigenic domain or epitope or the cytoplasmic tail portion of said HN or F glycoprotein and replaces the counterpart gene segment of said background PIV sequence to form an open reading frame encoding a chimeric glycoprotein.

16. An isolated polynucleotide molecule comprising an operably linked transcriptional promoter operative in a mammalian cell or operative in vitro, a polynucleotide sequence encoding a chimeric partial or complete PIV genome or antigenome that includes at least one point mutation comprising said partial or complete PIV genome or antigenome, and a transcriptional terminator operative in a mammalian cell or operative in vitro, wherein said polynucleotide sequence encoding said partial or complete PIV genome or antigenome comprises a polynucleotide sequence of a background partial or complete PIV genome or antigenome and at least one heterologous PIV sequence selected from a HPIV 1 sequence, a HPIV 2 sequence, a HPIV 3 sequence a BPIV sequence or a MPIV sequence, and wherein said polynucleotide sequence encoding said partial or complete PIV genome or antigenome comprises a polynucleotide encoding the L protein of the wild-type of said background PIV or of said heterologous PIV.

17. The isolated polynucleotide of claim 16, in which the chimeric partial or complete PIV genome or antigenome comprises a heterologous PIV sequence that encodes an open reading frame of a HN glycoprotein or of a F glycoprotein.

18. The isolated polynucleotide of claim 16, in which the heterologous PIV sequence is from HPIV1.

19. The isolated polynucleotide of claim 17, in which the heterologous PIV sequence is from HPIV1.

20. The isolated polynucleotide of claim 16, that comprises a heterologous PIV sequence that encodes an open reading frame of a HN glycoprotein and a heterologous PIV sequence that encodes a F glycoprotein.

21. The isolated polynucleotide of claim 20, in which both of the heterologous PIV sequences are from HPIV1.

22. An isolated polynucleotide molecule comprising an operably linked transcriptional promoter operative in a mammalian cell or operative in vitro, a polynucleotide sequence encoding a chimeric partial or complete PIV genome or antigenome, and a transcriptional terminator operative in a mammalian cell or operative in vitro, wherein said polynucleotide sequence encoding said chimeric partial or complete PIV genome or antigenome comprises a polynucleotide sequence encoding a background partial or complete PIV genome or antigenome and at least one heterologous PIV polynucleotide sequence selected from a HPIV 1 sequence, a HPIV 2 sequence, a HPIV 3 sequence, a BPIV sequence or a MPIV sequence, wherein said heterologous PIV polynucleotide sequence comprises a transcription unit comprising a polynucleotide sequence encoding an open reading frame of a protein of said heterologous PIV or portion thereof providing an antigenic determinant that is inserted between a gene start sequence and a gene end sequence of the PIV of the background.

23. The isolated polynucleotide of claim 22, in which the heterologous PIV polynucleotide sequence replaces an open reading frame of a gene of the background PIV.

24. The isolated polynucleotide of claim 22, in which the heterologous PIV nucleotide sequence is added to the genome or antigenome of the background PIV.

25. The isolated polynucleotide of claim 22, in which the polynucleotide sequence encoding the background partial or complete PIV genome or antigenome further includes at least one mutation at a position corresponding to a position in the genome of HPIV3 selected from the group consisting of Val96 of the N protein, Ser389 of the N protein, Ile96 of the C protein, Pro199 of the M protein, Ile420 of the F protein, Ala450 of the F protein, Val384 of the HN protein, Tyr942 of the L protein, Leu992 of the L protein, Thr1558 of the L protein, nucleotide 23 of the 3' leader sequence, nucleotide 24 of the 3' leader sequence, nucleotide 28 of the 3' leader sequence, nucleotide 45 of the 3' leader sequence and nucleotide 62 in the N gene start sequence.

26. The isolated polynucleotide of claim 22, in which the polynucleotide sequence encoding the background partial or complete PIV genome or antigenome further includes mutations at positions corresponding to a position in the genome of HPIV3 of Tyr942 of the L protein, Leu992 of the L protein and Thr1558 of the L protein.

27. The isolated polynucleotide of claim 22, in which the polynucleotide sequence that encodes the background partial or complete PIV genome comprises at least one nucleotide sequence that is the complement of a sequence selected from the group consisting of SEQ ID NOS: 51, 53, 55, 57, 59, 61, 63, 65, 67, 69, 71 and 73, or in which the polynucleotide sequence that encodes the background PIV antigenome comprises at least one nucleotide sequence selected from the group consisting of SEQ ID NOS: 51, 53, 55, 57, 59, 61, 63, 65, 67, 69, 71 and 73.

28. The isolated polynucleotide of claim 23, in which the polynucleotide sequence that encodes the background partial or complete PIV genome comprises the complement of nucleotide sequences of SEQ ID NOS: 69, 71 and 73, or in which the polynucleotide sequence that encodes the background PIV antigenome comprises nucleotide sequences of SEQ ID NOS: 69, 71 and 73.

29. The isolated polynucleotide of claim 24, in which the polynucleotide sequence that encodes the background partial or complete PIV genome comprises the complement of nucleotide sequences of SEQ ID NOS: 69, 71 and 73, or in which the polynucleotide sequence that encodes the background PIV antigenome comprises nucleotide sequences of SEQ ID NOS: 69, 71 and 73.

30. The isolated polynucleotide of claim 23, in which the chimeric partial or complete PIV genome or antigenome comprises a heterologous PIV sequence that encodes an open reading frame of a HN glycoprotein or of a F glycoprotein.

31. The isolated polynucleotide of claim 30, in which the heterologous PIV sequence is from HPIV1.

32. The isolated polynucleotide of claim 22, that comprises a heterologous PIV sequence that encodes an open reading frame of a HN glycoprotein and a heterologous PIV sequence that encodes an open reading frame of a F glycoprotein.

33. The isolated polynucleotide of claim 32, in which both of the heterologous PIV sequences are from HPIV1.

34. The isolated polynucleotide of claim 22, in which the heterologous PIV sequence is a gene segment encoding a portion of an open reading frame of a HN or F glycoprotein comprising an antigenic domain or epitope or the cytoplasmic tail portion, of said HN or F glycoprotein and replaces the counterpart gene segment of said background PIV sequence to form an open reading frame encoding a chimeric glycoprotein.

35. An infectious parainfluenza virus (PIV) comprising a major nucleocapsid (N) protein, a nucleocapsid phosphoprotein (P), a large polymerase protein (L), and a partial or complete human PIV genome comprising at least one sequence selected from the group consisting of the complement of nucleotide sequences of SEQ ID NOS: 61, 63, 65, 67, 69, 71 and 73, or a partial or complete human PIV antigenome comprising at least one nucleotide sequence selected from the group consisting of SEQ ID NOS: 61, 63, 65, 67, 69, 71 and 73.

36. The infectious PIV of claim 35, in which the human partial or complete PIV genome or antigenome is a human PIV3 genome or antigenome.

37. An infectious parainfluenza virus (PIV) comprising a major nucleocapsid (N) protein, a nucleocapsid phosphoprotein (P), a large polymerase protein (L), and a human partial or complete PIV genome comprising the complement of nucleotide sequences of SEQ ID NOS: 69, 71, and 73, or a partial or complete human PIV antigenome comprising the nucleotide sequences of SEQ ID NOS: 69, 71, and 73.

38. The infectious PIV of claim 37, in which the human partial or complete PIV genome or antigenome is a human PIV3 genome comprising the complement of nucleotide sequences of SEQ ID NOS: 69, 71 and 73, or a partial or complete human PIV3 antigenome comprising the nucleotide sequences of SEQ ID NOS: 69, 71 and 73.

39. An infectious chimeric parainfluenza virus (PIV) comprising a major nucleocapsid (N) protein, a nucleocapsid phosphoprotein (P), a large polymerase protein (L), and a chimeric partial or complete PIV genome or antigenome comprising a a background partial or complete PIV genome or antigenome and at least one heterologous PIV sequence selected from a HPIV 1 sequence, a HPIV 2 sequence, a HPIV 3 sequence a BPIV sequence or a MPIV sequence, wherein said chimeric partial or complete PIV genome or antigenome comprises a polynucleotide encoding the L protein of the wild-type of said background PIV or of said heterologous PIV.

40. The infectious chimeric PIV of claim 39, in which the background partial or complete PIV genome or antigenome further includes at least one mutation at a position corresponding to a position in the genome of HPIV3 selected from the group consisting of Val96 of the N protein, Ser389 of the N protein, Pro199 of the M protein, Ile96 of the C protein, Ile420 of the F protein, Ala450 of the F protein, Val384 of the HN protein, nucleotide 23 of the 3' leader sequence, nucleotide 24 of the 3' leader sequence, nucleotide 28 of the 3' leader sequence, nucleotide 45 of the 3' leader sequence and nucleotide 62 in the N gene start sequence.

41. The infectious chimeric PIV of claim 39, in which the chimeric partial or complete PIV genome or antigenome comprises a heterologous PIV sequence that encodes an open reading frame of a HN glycoprotein or of a F glycoprotein.

42. The infectious chimeric PIV of claim 40, in which the chimeric partial or complete PIV genome or antigenome comprises a heterologous PIV sequence that encodes an open reading frame of a HN glycoprotein or of a F glycoprotein.

43. The infectious chimeric PIV of claim 40, in which the heterologous PIV sequence is from HPIV1.

44. The infectious chimeric PIV of claim 41, in which the heterologous PIV sequence is from HPIV1.

45. The infectious chimeric PIV of claim 39, in which the chimeric partial or complete PIV genome or antigenome comprises a heterologous PIV sequence that encodes an open reading frame of a HN glycoprotein and a heterologous PIV sequence that encodes an open reading frame of a F glycoprotein.

46. The infectious chimeric PIV of claim 40, in which the chimeric partial or complete PIV genome or antigenome comprises a heterologous PIV sequence that encodes an open reading frame of a HN glycoprotein and a heterologous PIV sequence that encodes an open reading frame of a F glycoprotein.

47. The infectious chimeric PIV of claim 45, in which both of the heterologous PIV sequences are from HPIV1.

48. The infectious chimeric PIV of claim 46, in which both of the heterologous PIV sequences are from HPIV1.

49. The infectious chimeric PIV of claim 45, in which the heterologous PIV sequence is a gene segment encoding a portion of an open reading frame of a HN or F glycoprotein comprising an antigenic domain or epitope or the cytoplasmic tail portion of said HN or F glycoprotein and replaces the counterpart gene segment of said background PIV sequence to form an open reading frame encoding a chimeric glycoprotein.

50. An infectious chimeric PIV virus comprising a chimeric partial or complete PIV genome or antigenome that includes at least one point mutation comprising said chimeric partial or complete PIV genome or antigenome,
wherein said chimieric partial or complete PIV genome or antigenome comprises a polynucleotide sequence of a background partial or complete PIV genome or antigenome and at least one heterologous PIV sequence selected from a HPIV 1 sequence, a HPIV 2 sequence, a HPIV 3 sequence a BPIV sequence or a MPIV sequence,
and wherein said polynucleotide sequence encoding said partial or complete PIV genome or antigenome comprises a polynucleotide encoding the L protein of the wild-type of said background PIV or of said heterologous PIV.

51. The infectious chimeric PIV of claim 50, in which the chimeric partial or complete PIV genome or antigenome comprises a heterologous PIV sequence that encodes an open reading frame of a HN glycoprotein or of a F glycoprotein.

52. The infectious chimeric PIV of claim 50, in which the heterologous PIV sequence is from HPIV1.

53. The infectious chimeric PIV of claim 51, in which the heterologous PIV sequence is from HPIV1.

54. The infectious chimeric PIV of claim 50, in which the chimeric partial or complete PIV genome or antigenome comprises a heterologous PIV sequence that encodes an open reading frame of a HN glycoprotein and a heterologous PIV sequence that encodes a F glycoprotein.

55. The infectious chimeric PIV of claim 54, in which both of the heterologous PIV sequences are from HPIV1.

56. An infectious chimeric PIV comprising a chimeric partial or complete PIV genome or antigenome,
wherein said chimeric partial or complete PIV genome or antigenome comprises a background partial or complete PIV genome or antigenome and at least one heterologous PIV polynucleotide sequence selected from a HPIV 1 sequence, a HPIV 2 sequence, a HPIV 3 sequence a BPIV sequence or a MPIV sequence,
wherein said heterologous PIV polynucleotide sequence comprises a transcription unit comprising a polynucleotide sequence encoding an open reading frame of a protein of said heterologous PIV or portion thereof providing an antigenic determinant that is inserted between a gene start sequence and a gene end sequence of the PIV of the background.

57. The infectious chimeric PIV of claim 56, in which the heterologous PIV polynucleotide sequence replaces an open reading frame of a gene of the background PIV.

58. The infectious chimeric PIV of claim 56, in which the heterologous PIV nucleotide sequence is added to the genome or antigenome of the background PIV.

59. The infectious chimeric PIV of claim 56, in which the background partial or complete PIV genome or antigenome further includes at least one mutation at a position corresponding to a position in the genome of HPIV3 selected from the group consisting of Val96 of the N protein, Ser389 of the N protein, Ile96 of the C protein, Pro199 of the M protein, Ile420 of the F protein, Ala450 of the F protein, Val384 of the HN protein, Tyr942 of the L protein, Leu992 of the L protein, Thr1558 of the L protein, nucleotide 23 of the 3' leader sequence, nucleotide 24 of the 3' leader sequence, nucleotide 28 of the 3' leader sequence, nucleotide 45 of the 3' leader sequence and nucleotide 62 in the N gene start sequence.

60. The infectious chimeric PIV of claim 56, in which the background partial or complete PIV genome or antigenome further includes mutations at positions corresponding to a position in the genome of HPIV3 of Tyr942 of the L protein, Leu992 of the L protein and Thr1558 of the L protein.

61. The infectious chimeric PIV of claim 56, in which the background partial or complete PIV genome comprises at least one nucleotide sequence that is the complement of a sequence selected from the group consisting of SEQ ID NOS: 51, 53, 55, 57, 59, 61, 63, 65, 67, 69, 71 and 73
or in which the background PIV antigenome comprises at least one nucleotide sequence selected from the group consisting of SEQ ID NOS: 51, 53, 55, 57, 59, 61, 63, 65, 67, 69, 71 and 73.

62. The infectious chimeric PIV of claim 57, in which background partial or complete PIV genome comprises the complement of nucleotide sequences of SEQ ID NOS: 69, 71 and 73,
or in which the background PIV antigenome comprises nucleotide sequences of SEQ ID NOS: 69, 71 and 73.

63. The infectious chimeric PIV of claim 58, in which the background partial or complete PIV genome comprises the complement of nucleotide sequences of SEQ ID NOS: 69, 71 and 73,
or in which the background PIV antigenome comprises nucleotide sequences of SEQ ID NOS: 69, 71 and 73.

64. The infectious chimeric PIV of claim 57, in which the chimeric partial or complete PIV genome or antigenome comprises a heterologous PIV sequence that encodes an open reading frame of a HN glycoprotein or of a F glycoprotein.

65. The infectious chimeric PIV of claim 64, in which the heterologous PIV sequence is from HPIV1.

66. The infectious chimeric PIV of claim 56, in which the chimeric partial or complete PIV genome or antigenome comprises a heterologous PIV sequence that encodes an open reading frame of a HN glycoprotein and a heterologous PIV sequence that encodes an open reading frame of a F glycoprotein.

67. The infectious chimeric PIV of claim 66, in which both of the heterologous PIV sequences are from HPIV1.

68. The infectious chimeric PIV of claim 56, in which the heterologous PIV sequence is a gene segment encoding a portion of an open reading frame of a HN or F glycoprotein comprising an antigenic domain or epitope or the cytoplasmic tail portion of said HN or F glycoprotein and replaces the counterpart gene segment of said background PIV sequence to form an open reading frame encoding a chimeric glycoprotein.

69. An immunogenic composition comprising the infectious PIV of any one of claims 65–46 and 47–68.

70. A method for making a PIV, comprising expressing the isolated polynucleotide of any one of claims 1–12 and 13–34 in a cell or in a cell-free lysate, said cell or cell-free lysate comprising a major nucleocapsid (N) protein, a nucleocapsid phosphoprotein (P) and a large polymerase protein (L) of a human or bovine PIV.

* * * * *